US012188067B2

(12) United States Patent
Pauthenier et al.

(10) Patent No.: US 12,188,067 B2
(45) Date of Patent: Jan. 7, 2025

(54) METHOD FOR BIOSYNTHESISING DIOSMETIN AND/OR HESPERETIN IN A MICROORGANISM

(71) Applicant: ABOLIS BIOTECHNOLOGIES, Evry (FR)

(72) Inventors: Cyrille Pauthenier, Juvisy-sur-Orge (FR); André Le Jeune, Draveil (FR); Hélène Scornec, Longjumeau (FR); Célia Roussel, Saintry sur Seine (FR); Laetitia Joubert, Palaiseau (FR)

(73) Assignee: ABOLIS BIOTECHNOLOGIES, Evry (FR)

( * ) Notice: Subject to any disclaimer, the term of this patent is extended or adjusted under 35 U.S.C. 154(b) by 283 days.

(21) Appl. No.: 17/429,463

(22) PCT Filed: Feb. 11, 2020

(86) PCT No.: PCT/EP2020/053493
§ 371 (c)(1),
(2) Date: Aug. 9, 2021

(87) PCT Pub. No.: WO2020/165182
PCT Pub. Date: Aug. 20, 2020

(65) Prior Publication Data
US 2021/0355517 A1    Nov. 18, 2021

(30) Foreign Application Priority Data
Feb. 11, 2019 (EP) ...................... 19305162

(51) Int. Cl.
C12P 17/06 (2006.01)
C12N 1/18 (2006.01)
C12N 9/10 (2006.01)
C12R 1/865 (2006.01)

(52) U.S. Cl.
CPC .............. *C12P 17/06* (2013.01); *C12N 1/185* (2021.05); *C12N 9/1007* (2013.01); *C12R 2001/865* (2021.05); *C12Y 201/01042* (2013.01)

(58) Field of Classification Search
None
See application file for complete search history.

(56) References Cited

U.S. PATENT DOCUMENTS 10,435,673 B2    10/2019    Wessjohann et al.

FOREIGN PATENT DOCUMENTS

JP      2015 077072       4/2015
WO   WO 2016/050656      4/2016

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession T06006. Apr. 30, 1999. (Year: 1999).*
Accession P21964. Aug. 1, 1991 (Year: 1991).*
Accession A5A219. May 29, 2007 (Year: 2007).*
Accession T09757. Jul. 16, 1999 (Year: 1999).*
Accession F4YYF2. Jun. 28, 2011 (Year: 2011).*
Cao, Y. et al. "Computational Studies of the Regioselectivities of COMT-Catalyzed Meta-/Para-O Methylations of Luteolin and Quercetin" *The Journal of Physical Chemistry B*, 2014, pp. 470-481, vol. 118, No. 2.
Chen, Z.-J. et al. "Luteolin is a rare substrate of human catechol-O-methyltransferase favoring a para-methylation" *Mol. Nutr. Food Res.*, 2013, pp. 877-885, vol. 57.
Pandey, R. P. et al. "Microbial production of natural and non-natural flavonoids: Pathway engineering, directed evolution and systems/synthetic biology" *Biotechnology Advances*, 2016, pp. 634-662, vol. 34, No. 5.
Shimizu, T. et al. "Draft Sequencing of the Heterozygous Diploid Genome of Satsuma (*Citrus unshiu* Marc.) Using a Hybrid Assembly Approach" *Frontiers in Genetics*, Dec. 6, 2017, pp. 1-19, vol. 8, Article 180.
Database Uniprot [Online] Accession No. A0A2H5QCN9, SubName: Full=Uncharacterized protein {ECO:0000313|EMBL:GAY62410. 1}; Feb. 28, 2018, p. 1, XP002798583.
Written Opinion in International Application No. PCT/EP2020/053493, Jun. 23, 2020, pp. 1-11.

* cited by examiner

*Primary Examiner* — Christian L Fronda
(74) *Attorney, Agent, or Firm* — SALIWANCHIK, LLOYD & EISENSCHENK

(57) ABSTRACT

The present invention relates to a recombinant microorganism which is modified to be capable of producing diosmetin and/or hesperetin and to the use thereof for producing diosmetin and/or hesperetin.

19 Claims, 23 Drawing Sheets

Specification includes a Sequence Listing.

[Figure 1]
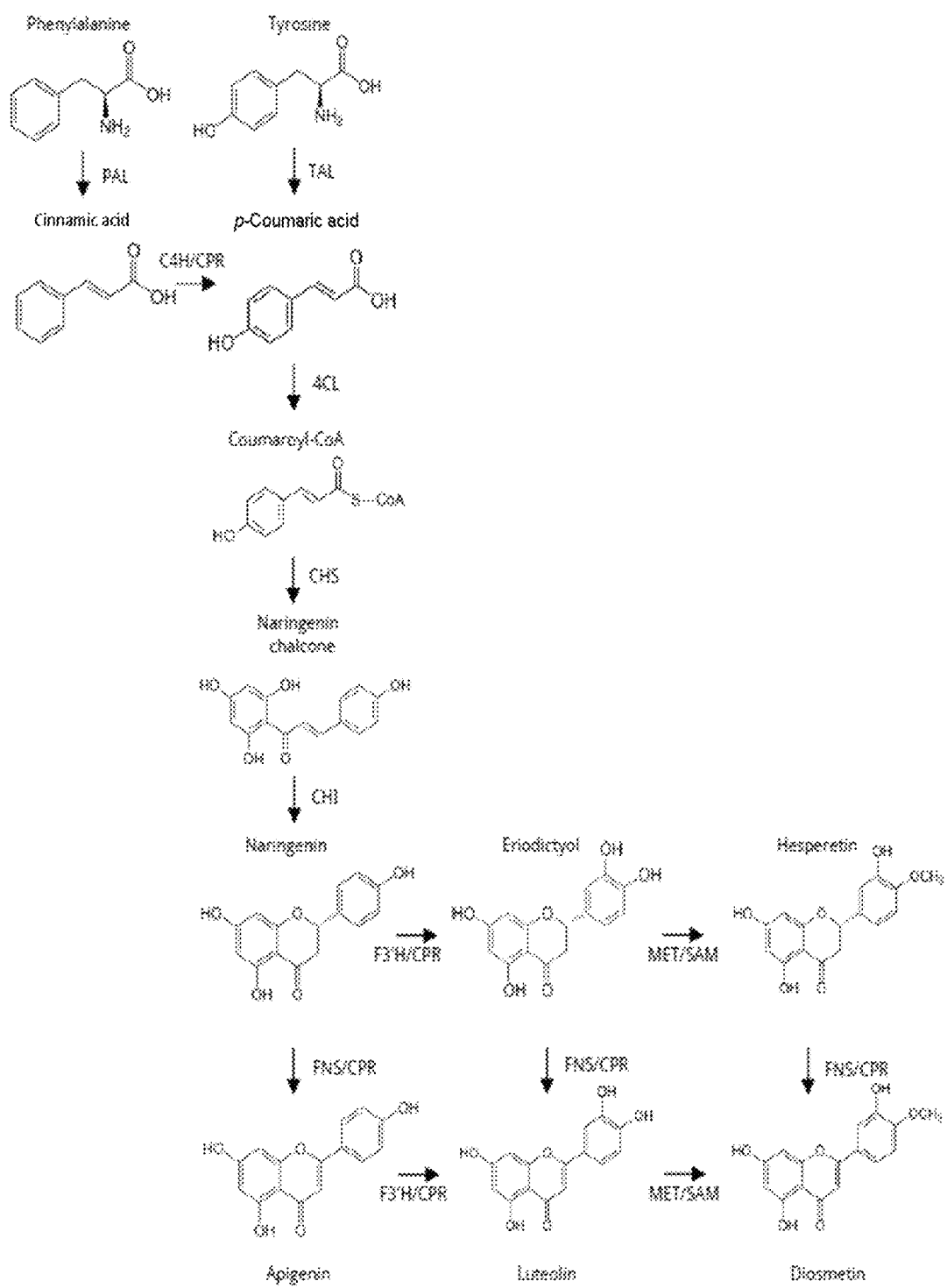

[Figure 2]
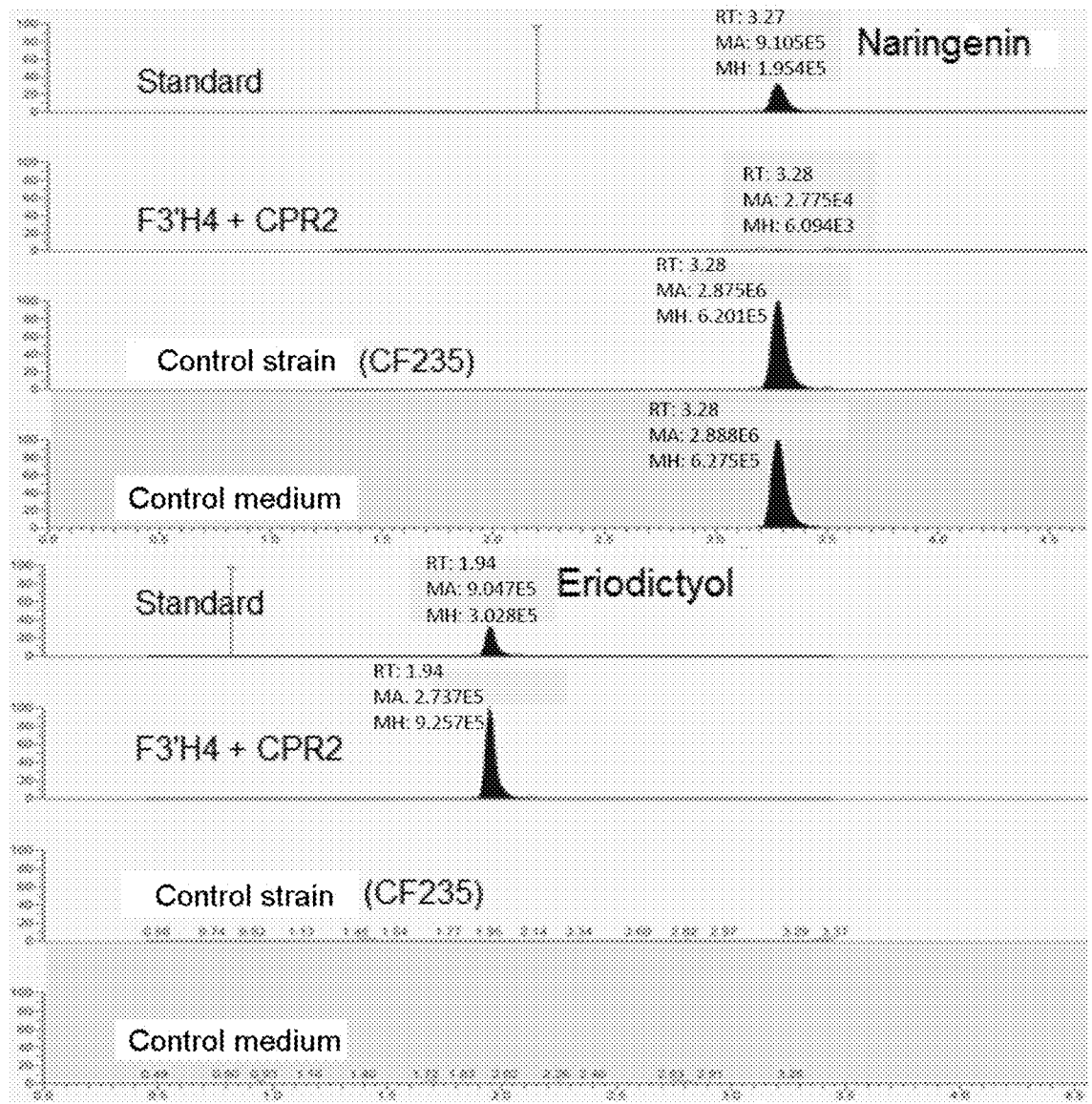

[Figure 3]
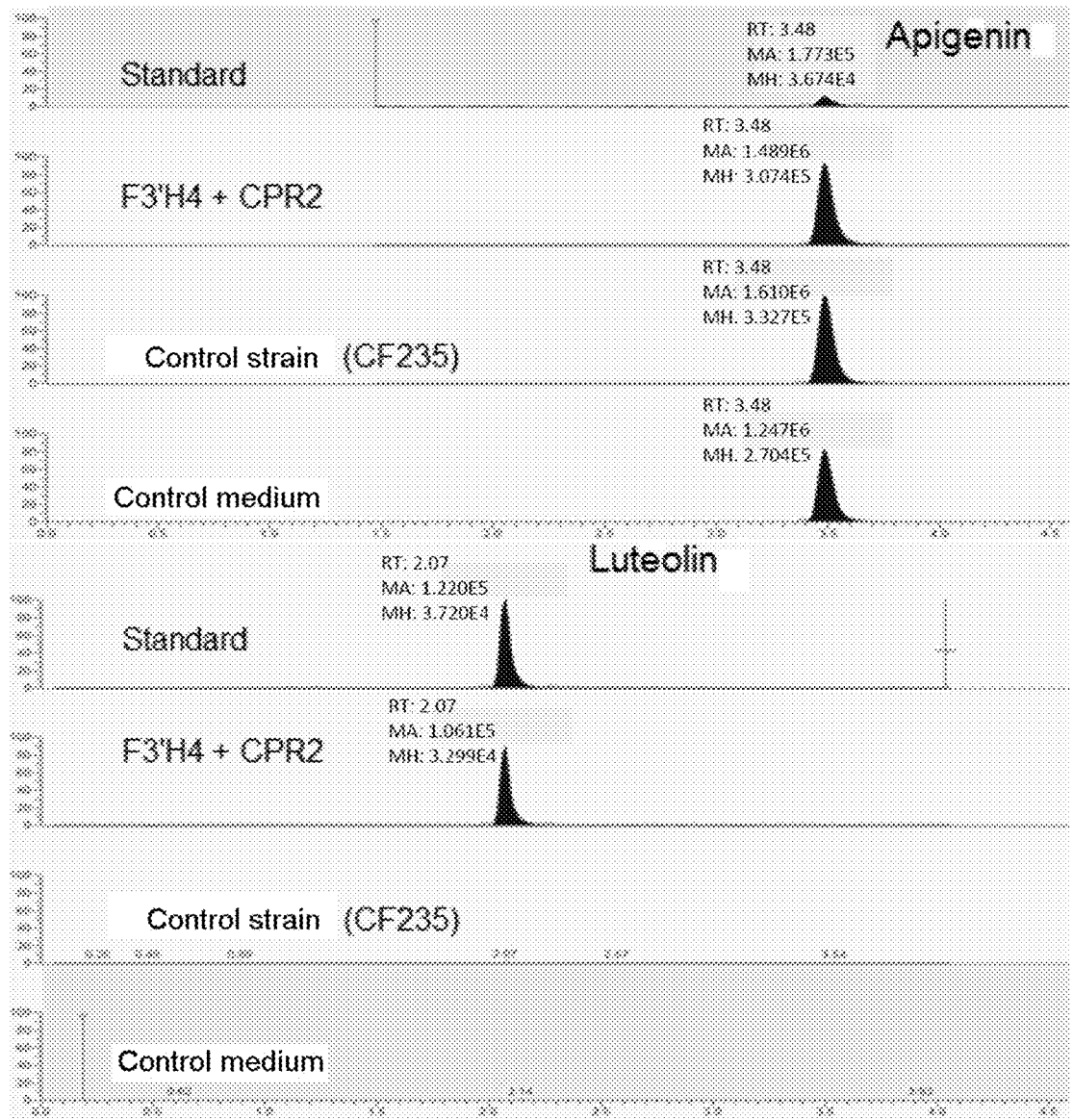

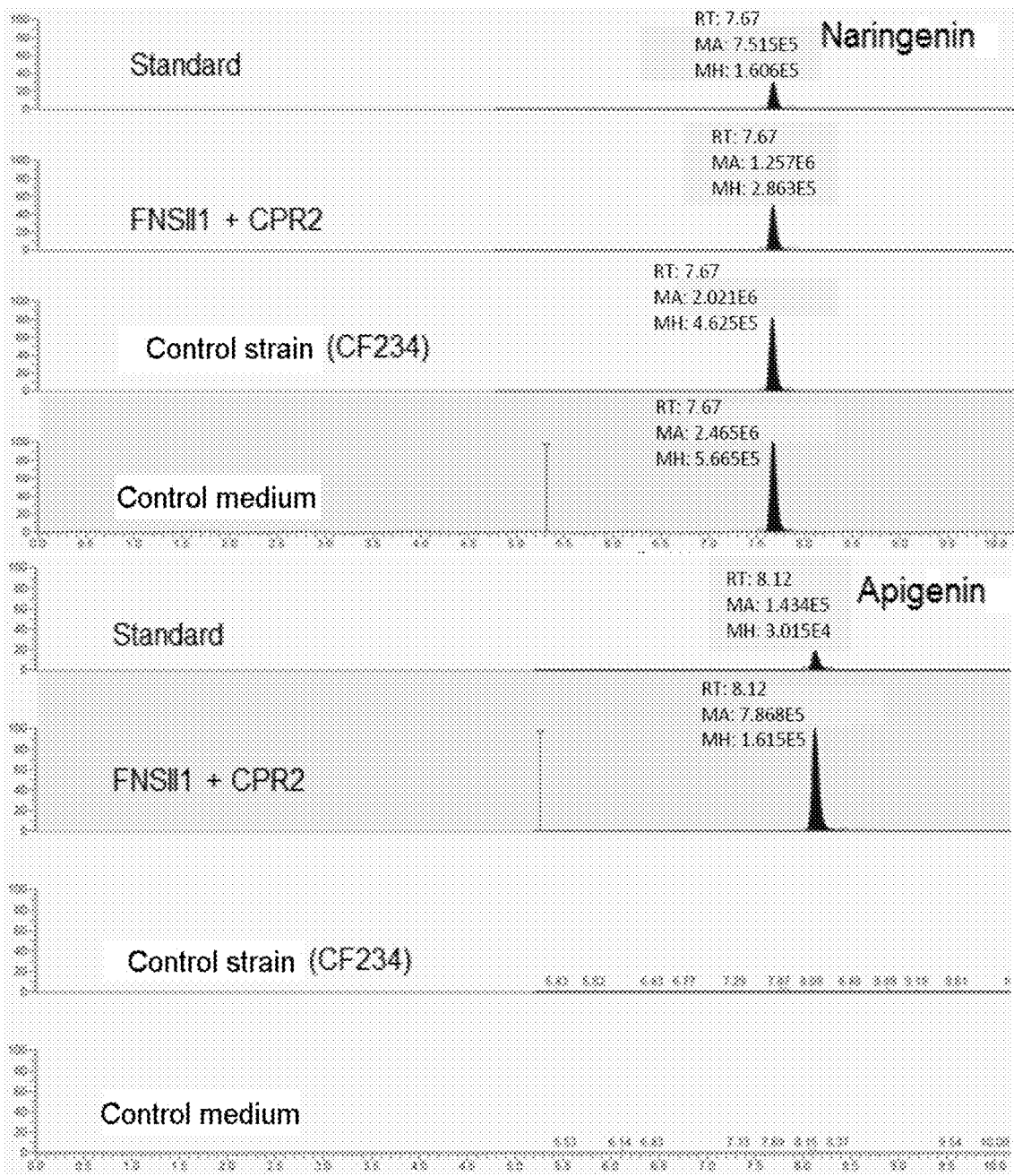
[Figure 4]

[Figure 5]
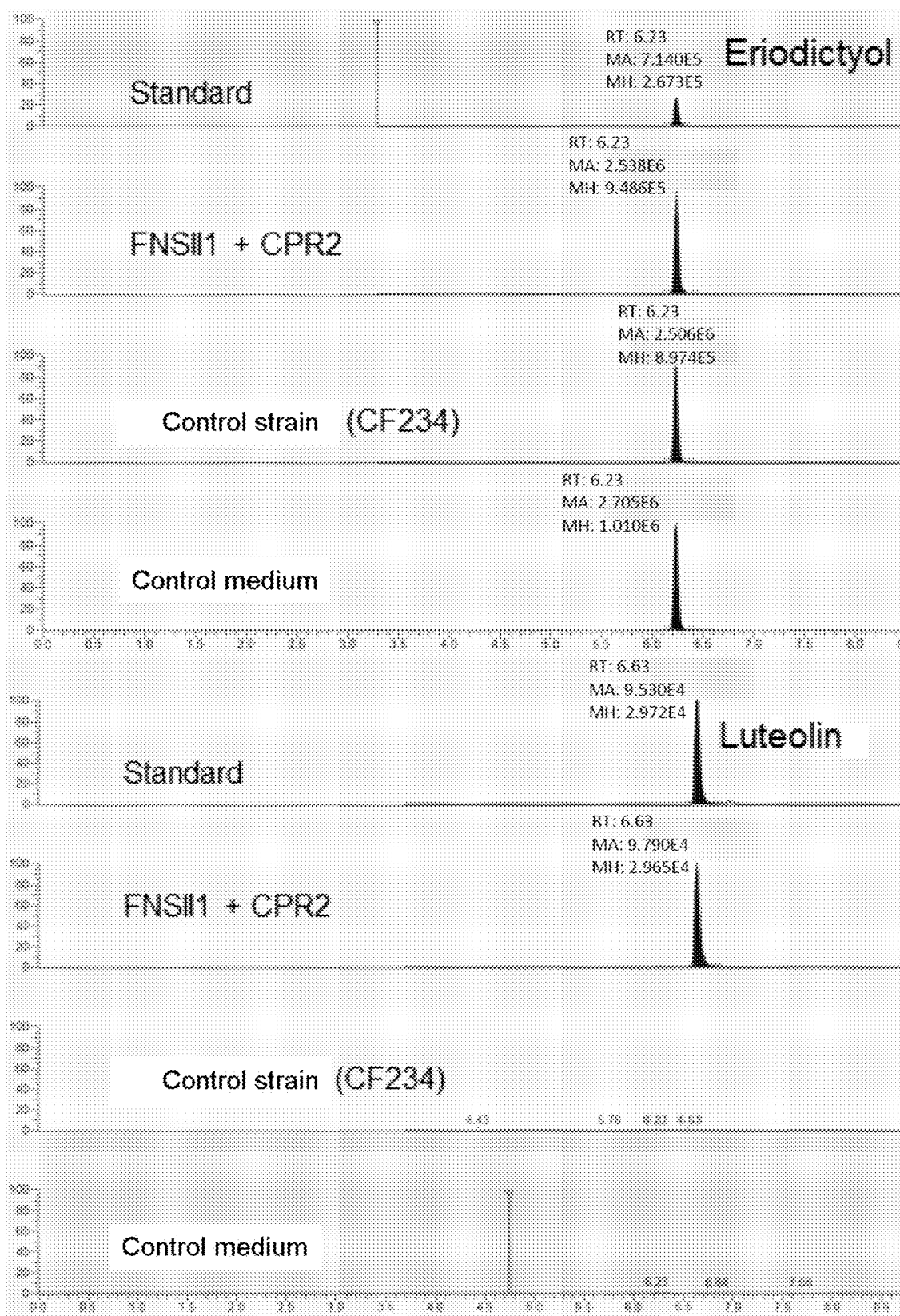

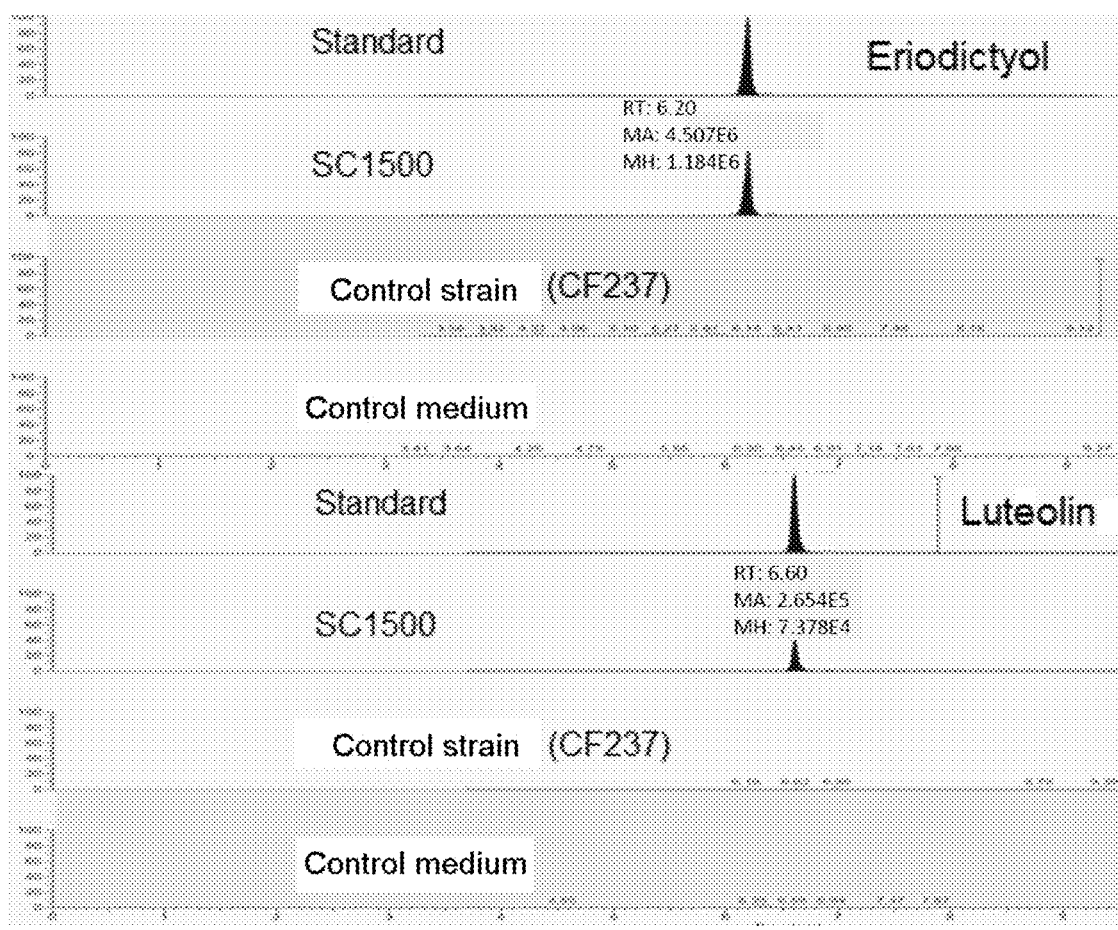
[Figure 6]

[Figure 7]
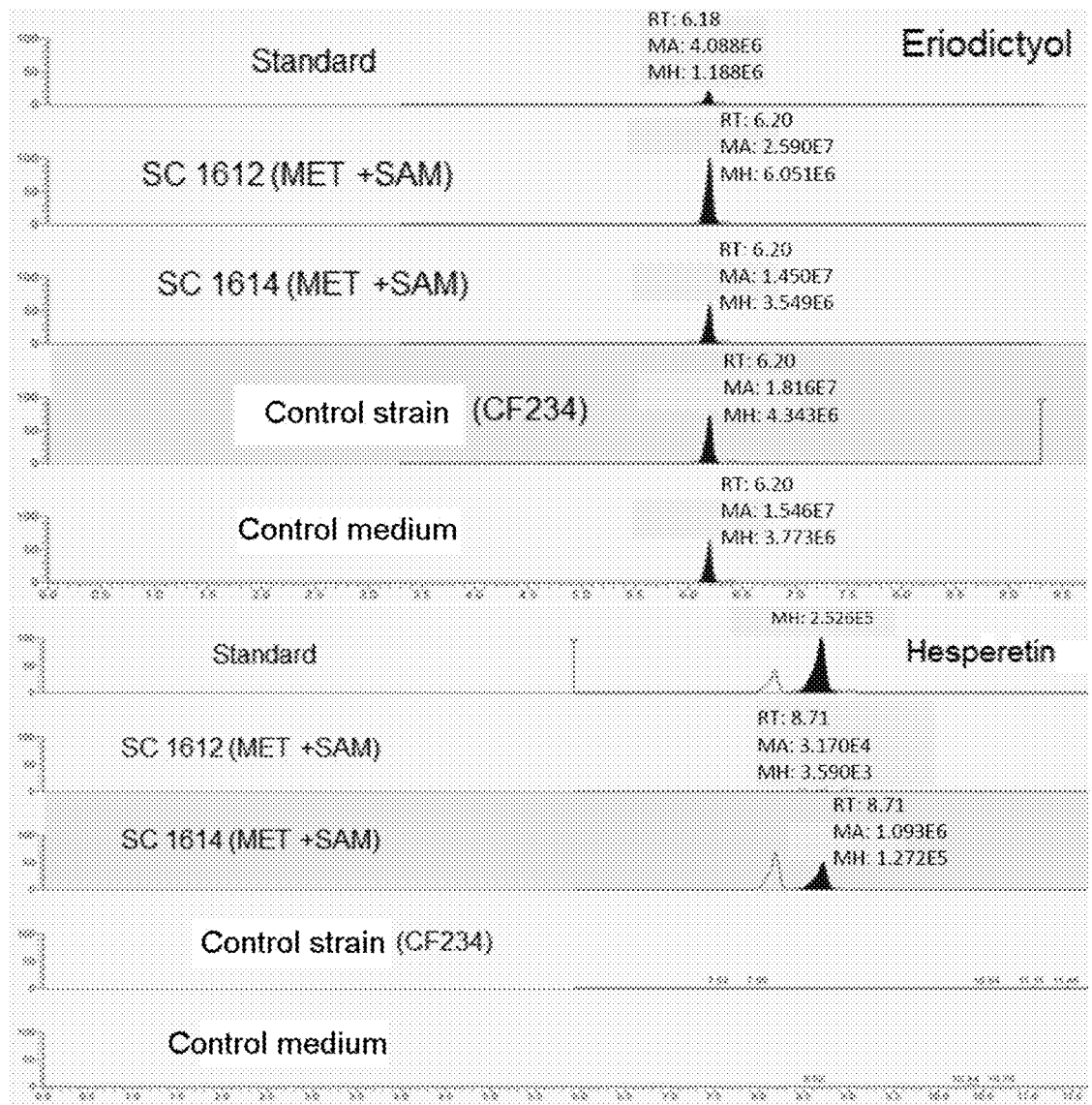

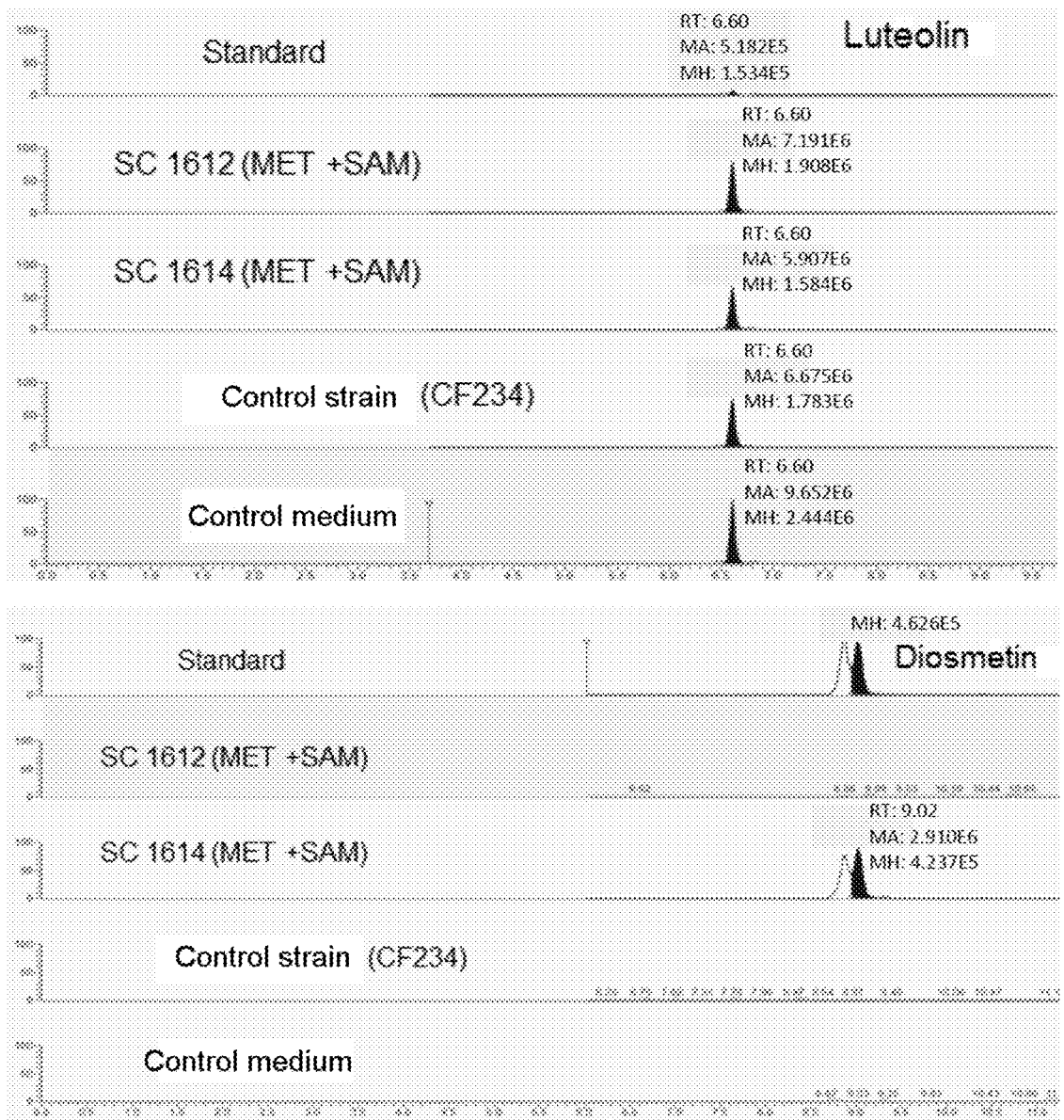
[Figure 8]

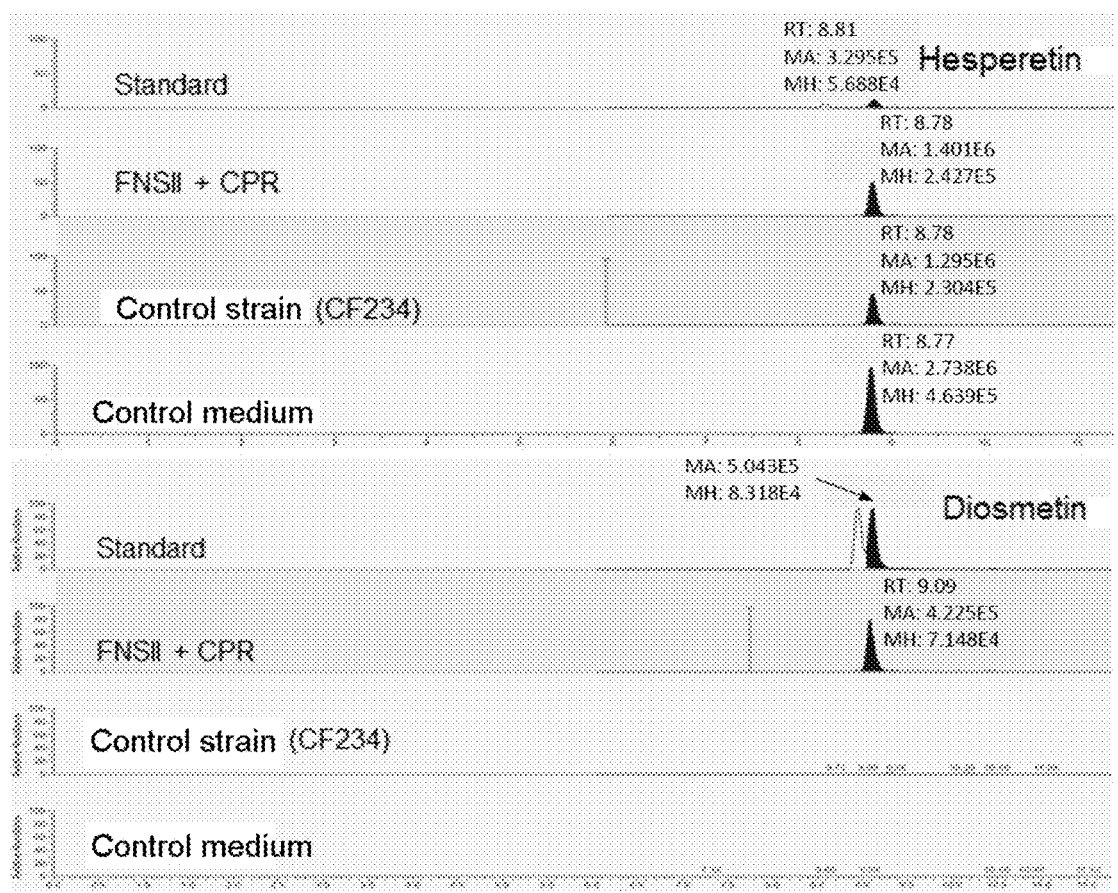
[Figure 9]

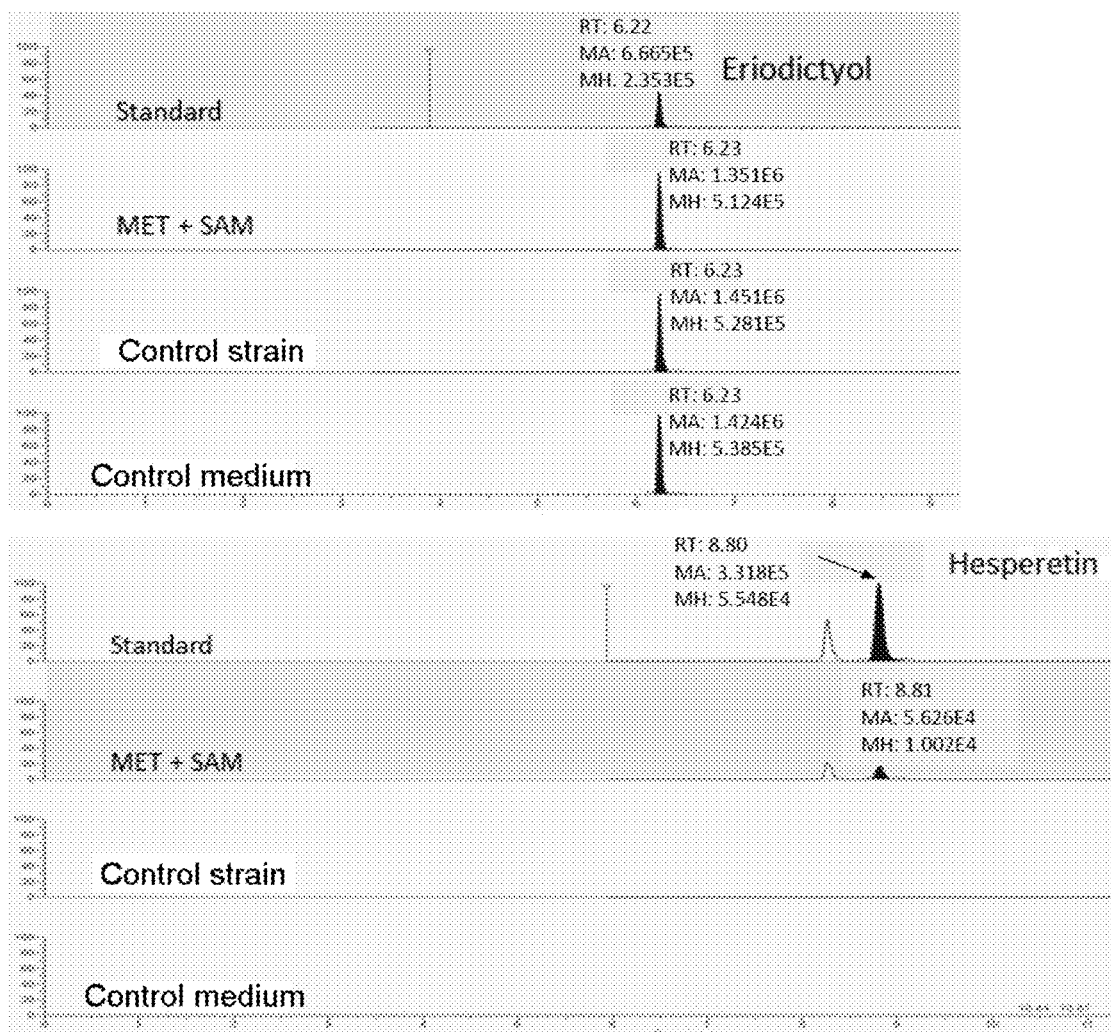
[Figure 10]

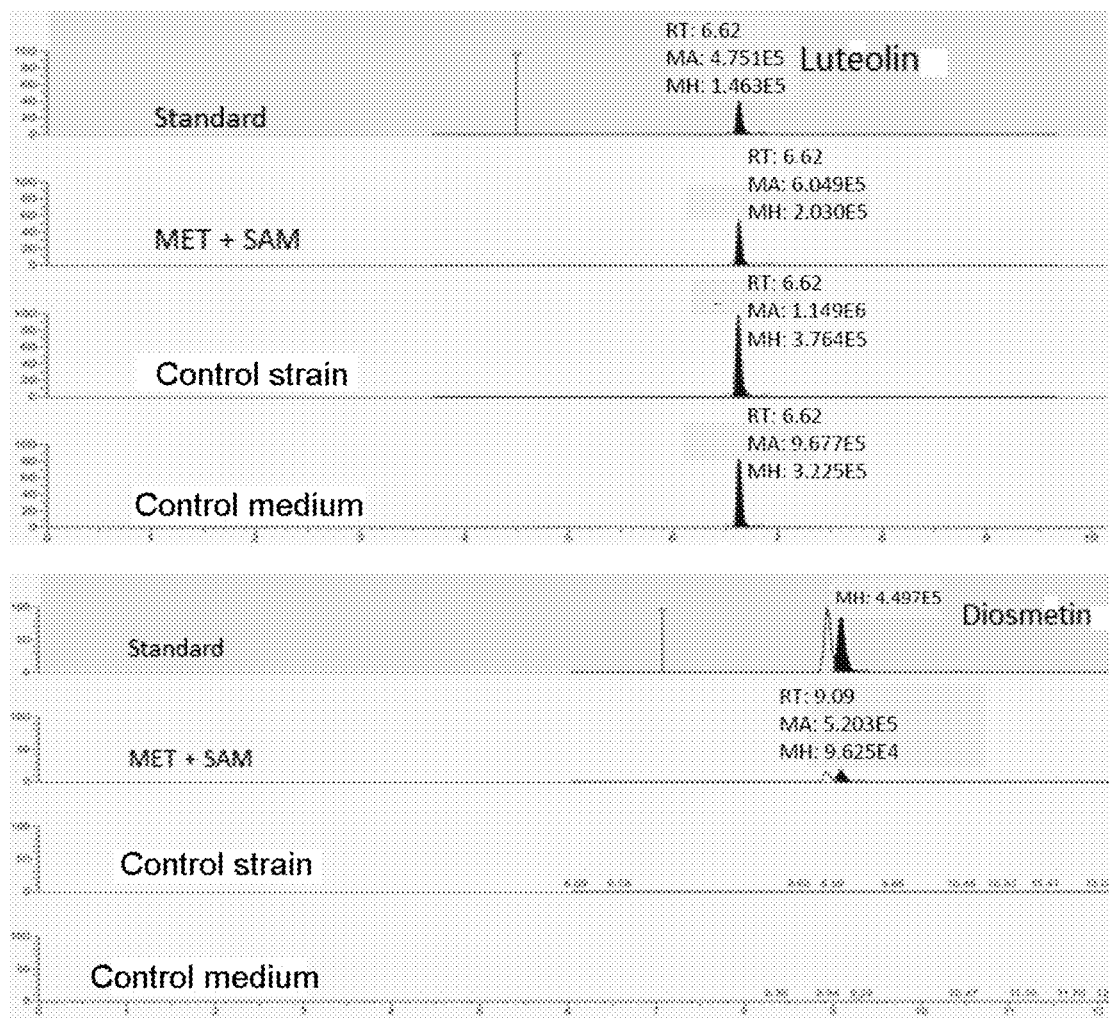
[Figure 11]

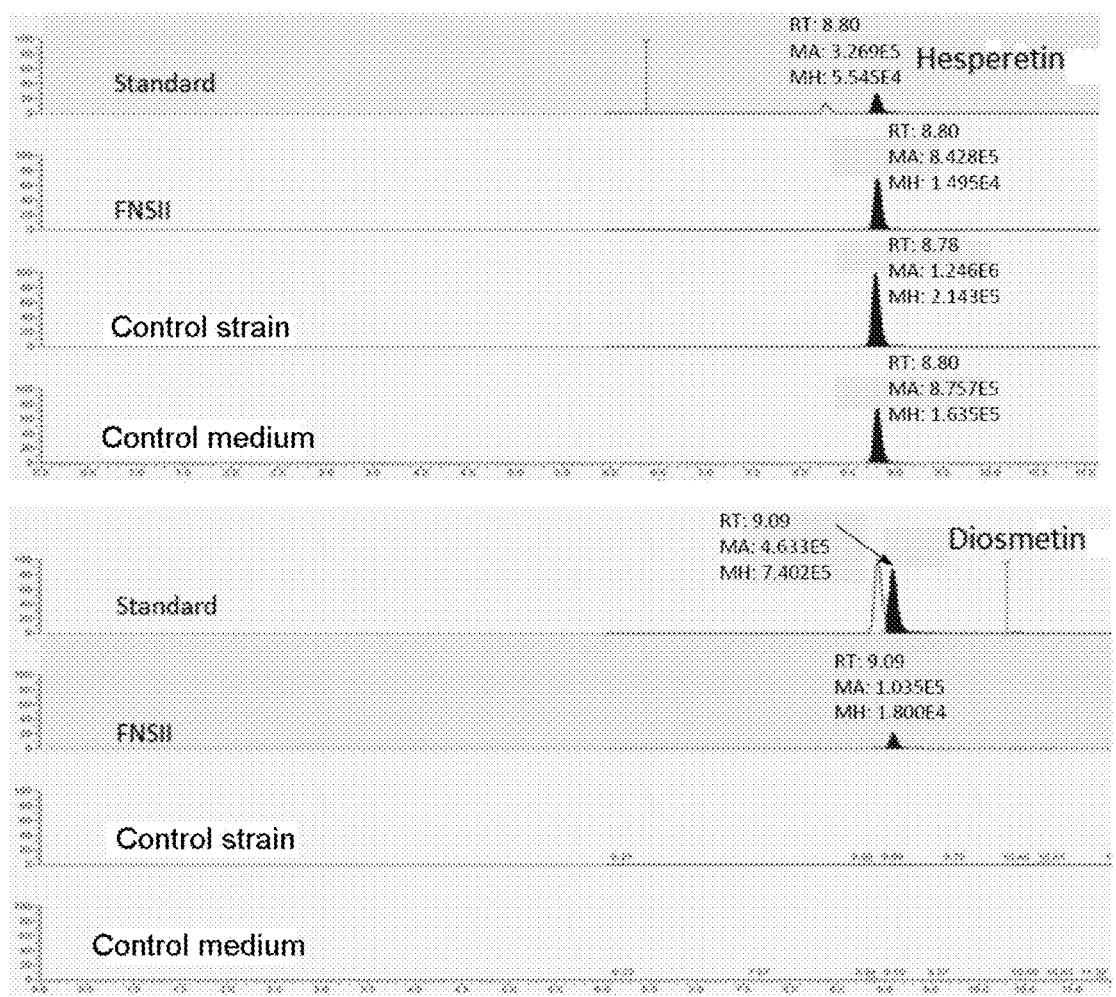
[Figure 12]

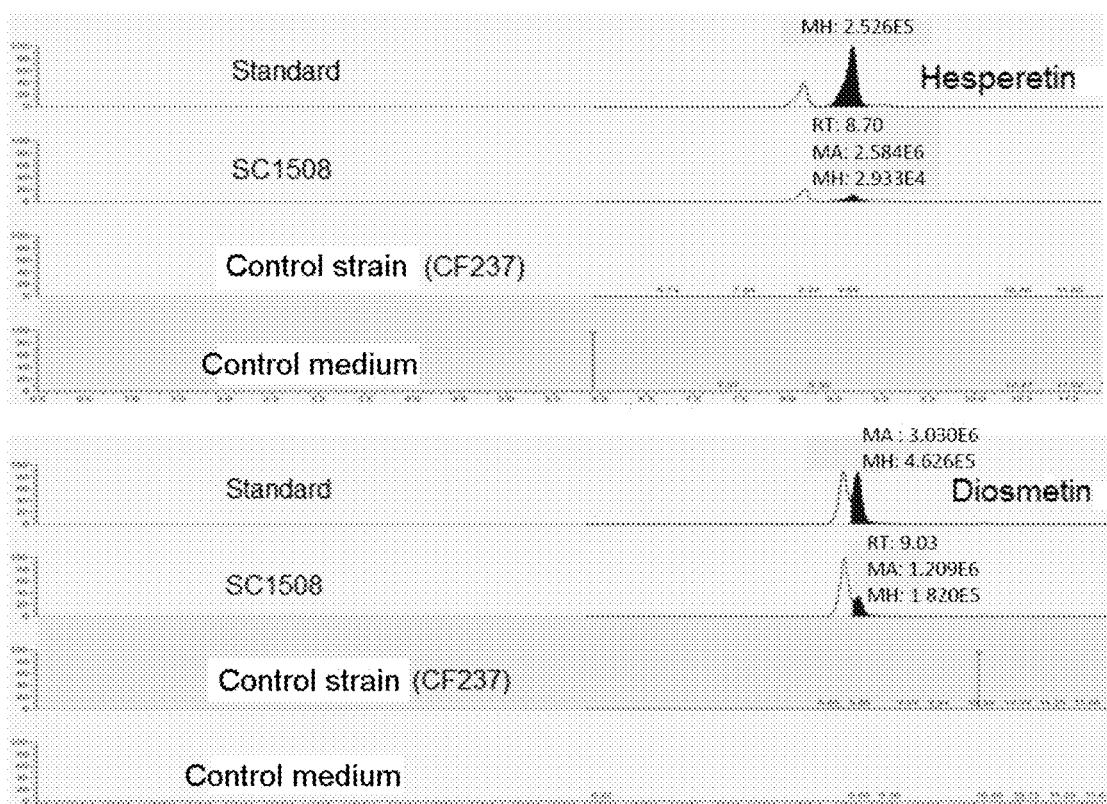
[Figure 13]

[Figure 14]
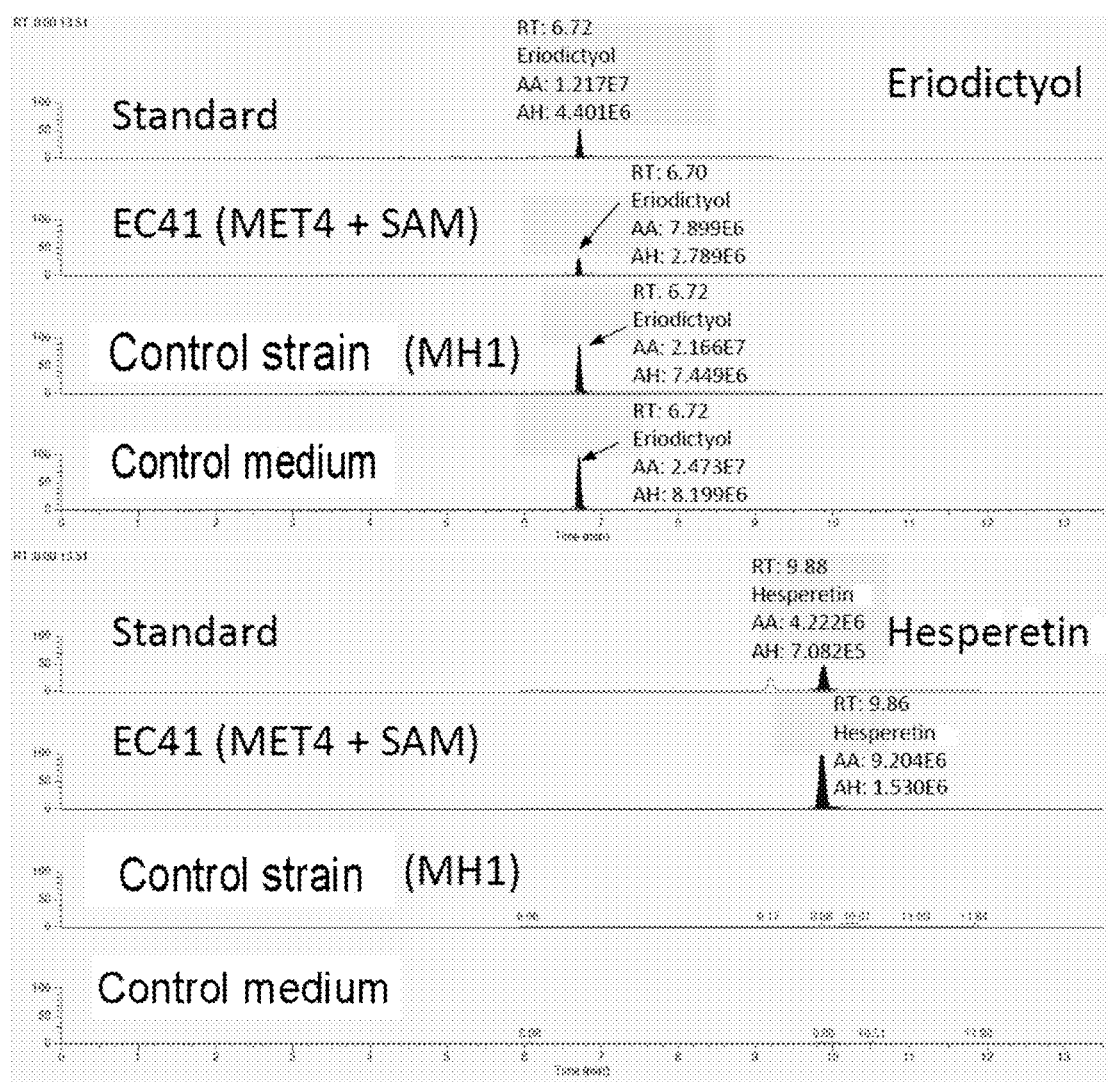

[Figure 15]
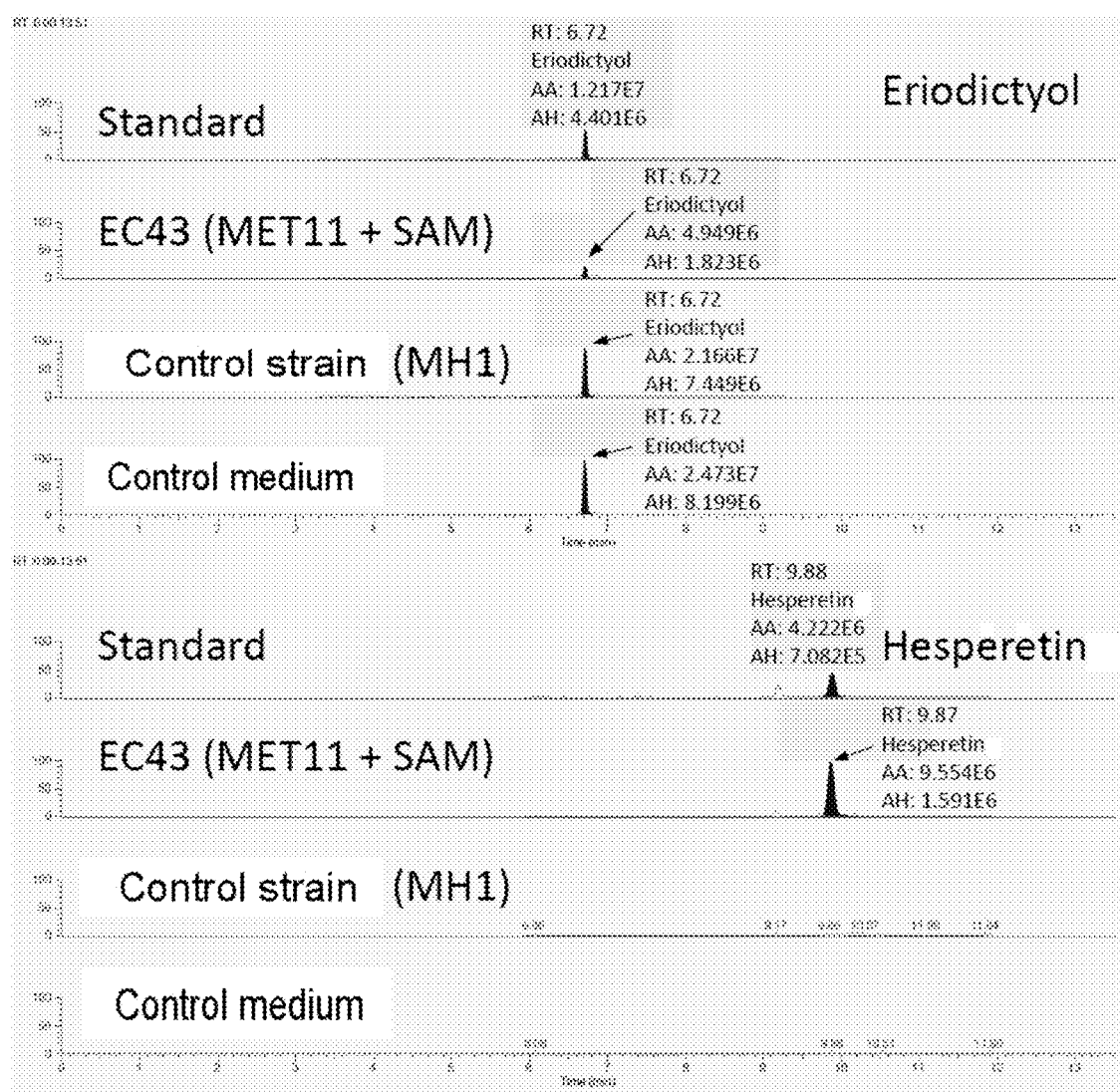

[Figure 16]
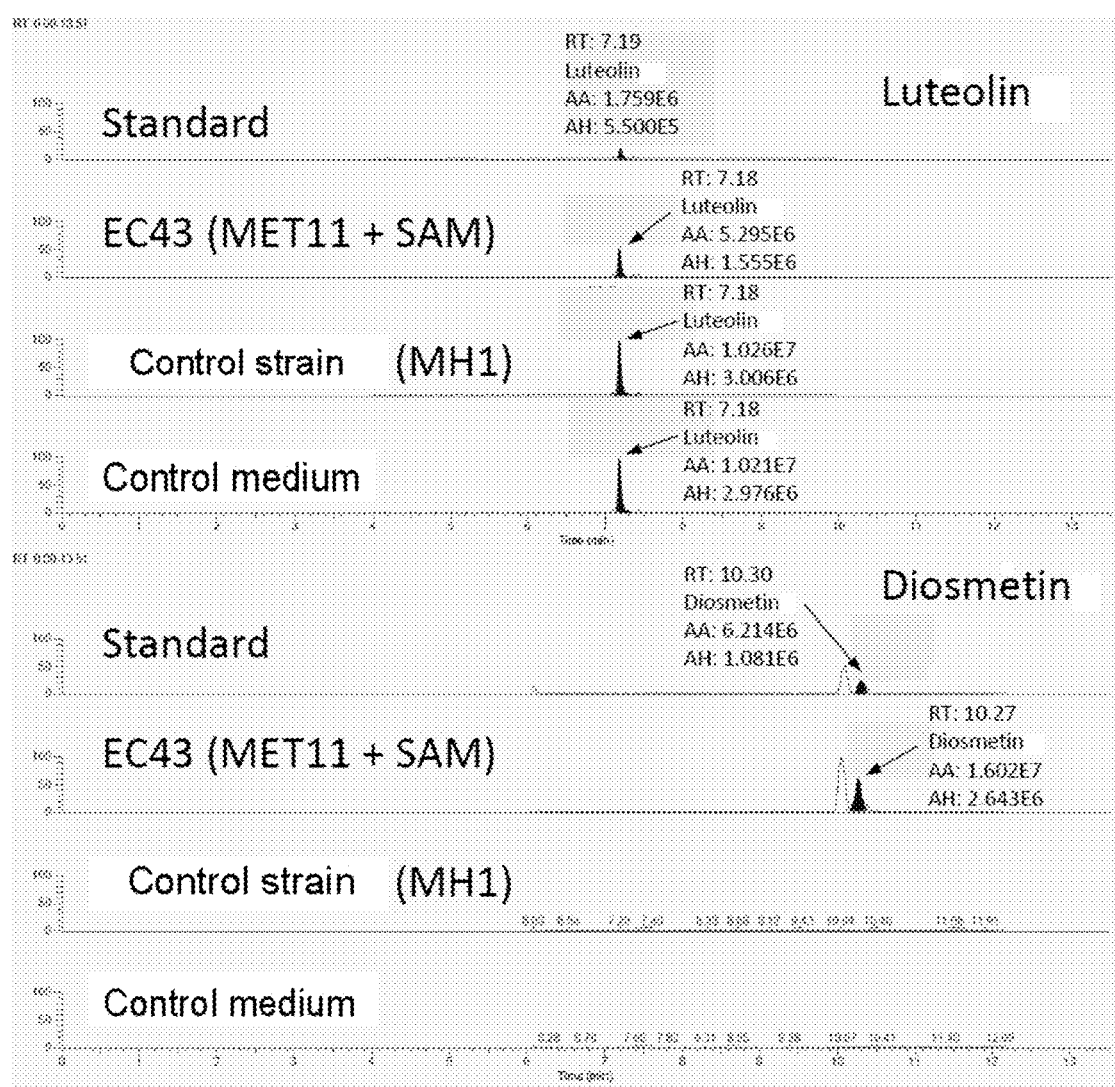

[Figure 17]
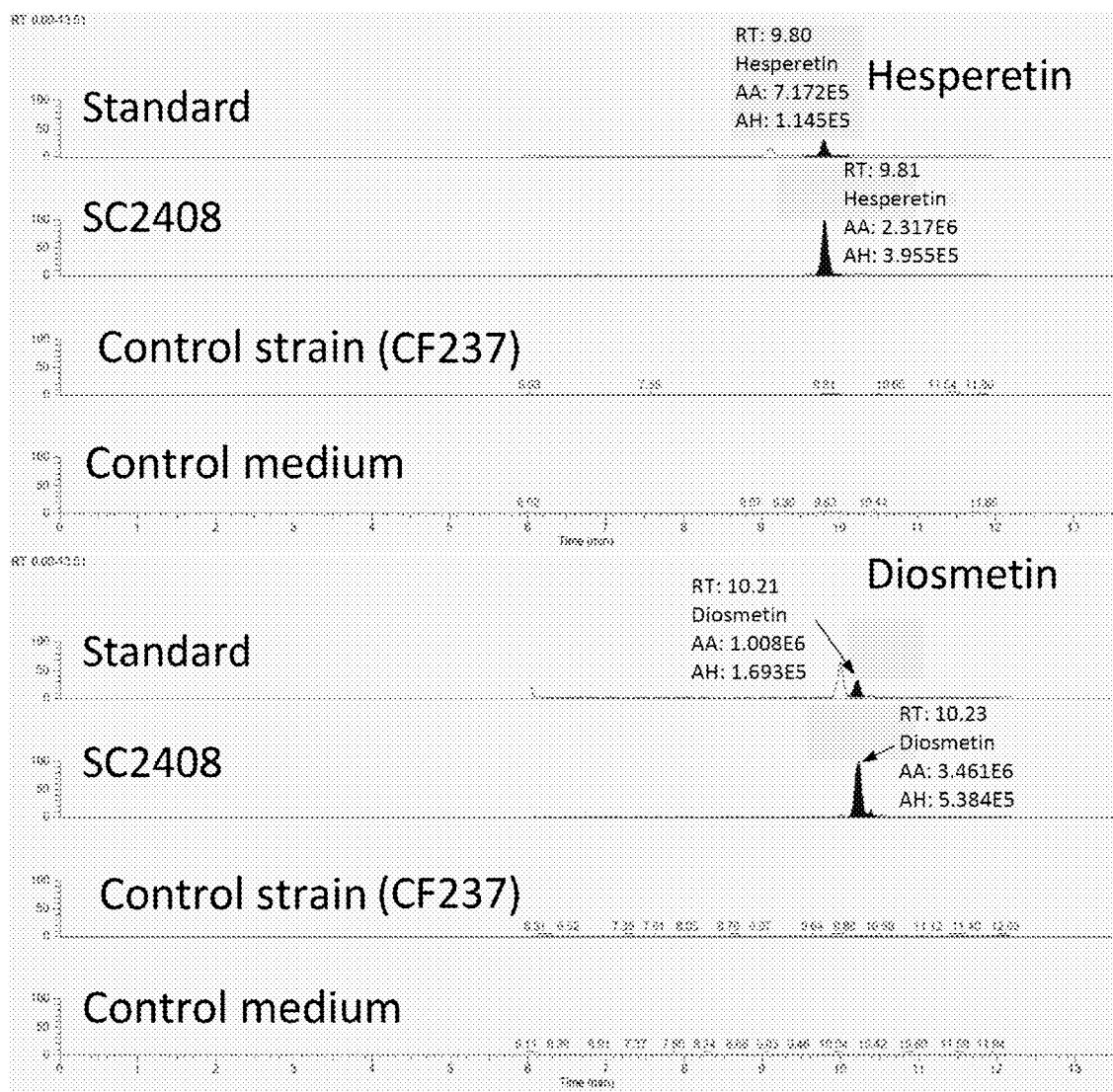

[Figure 18]
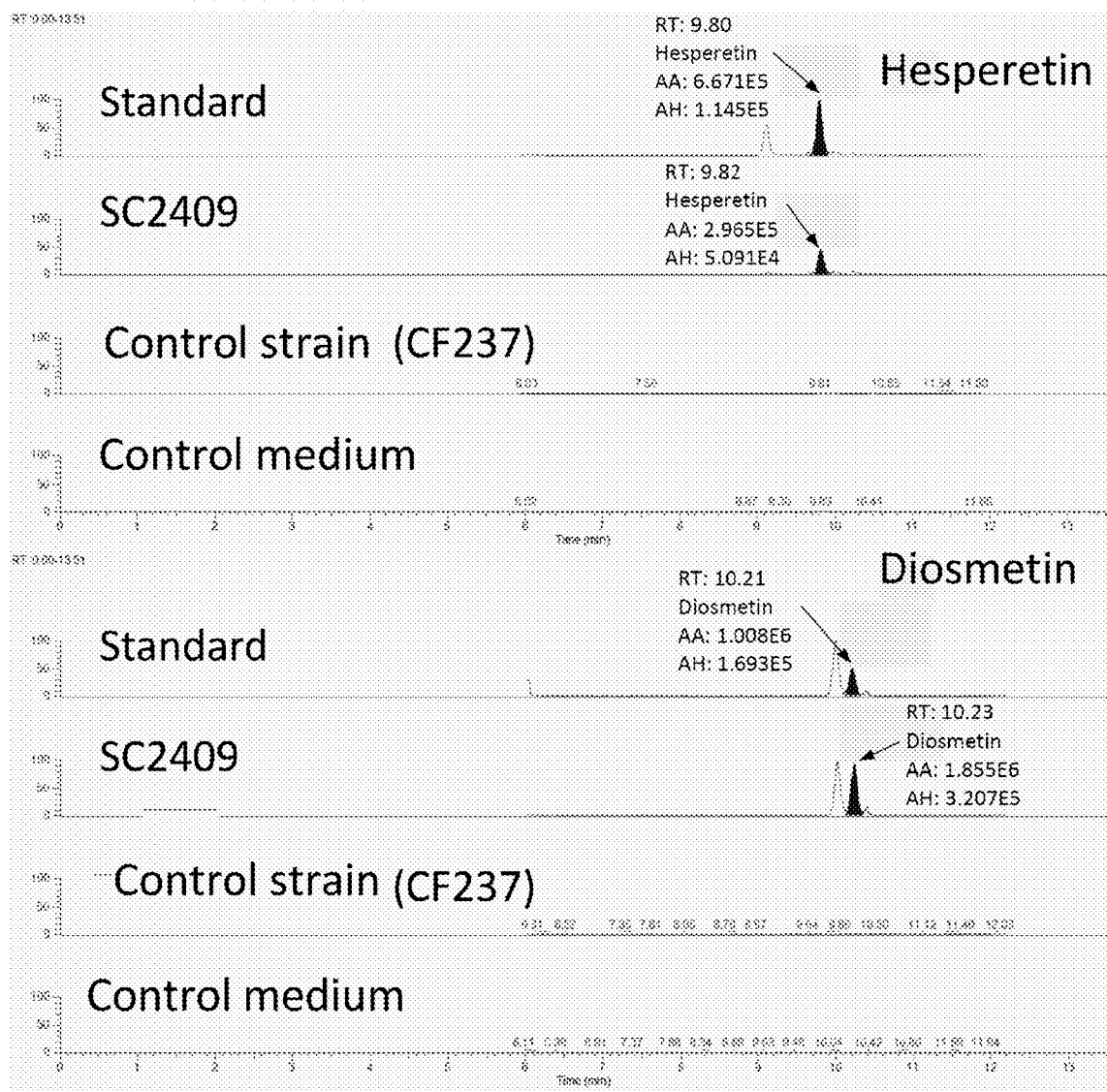

[Figure 19]
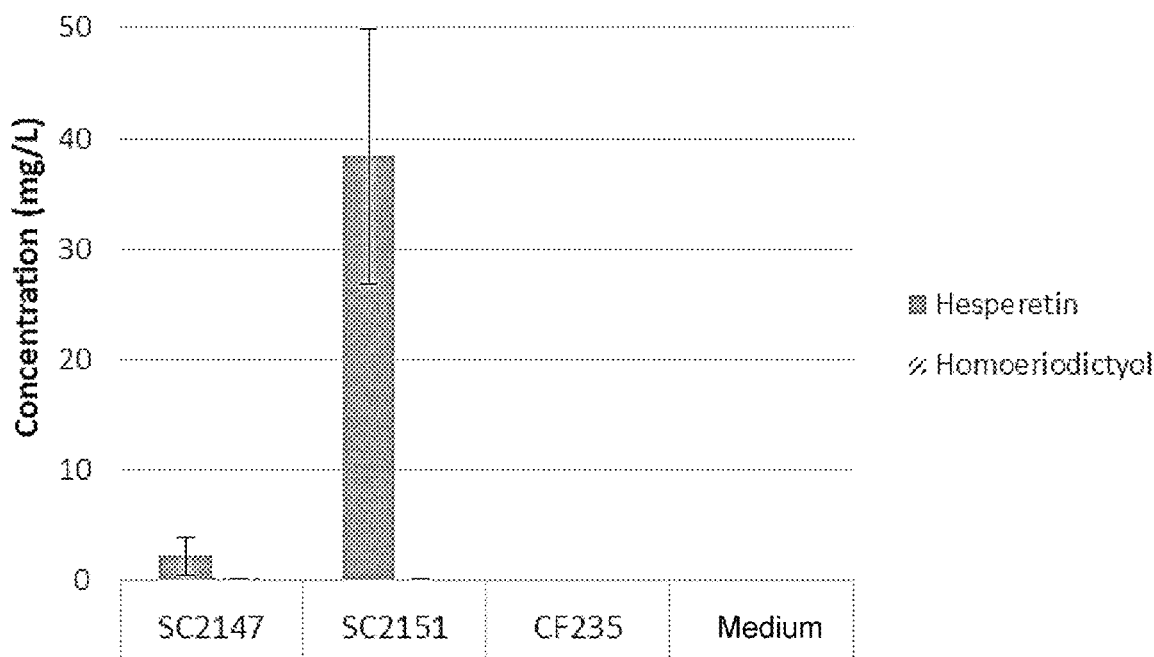
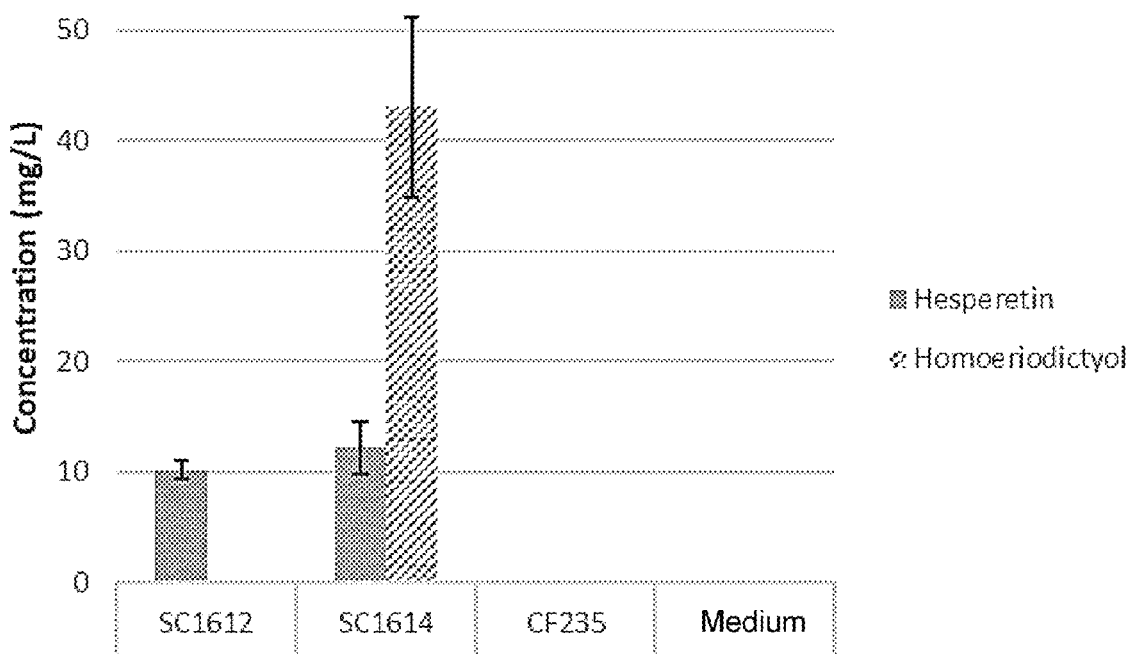

[Figure 20]
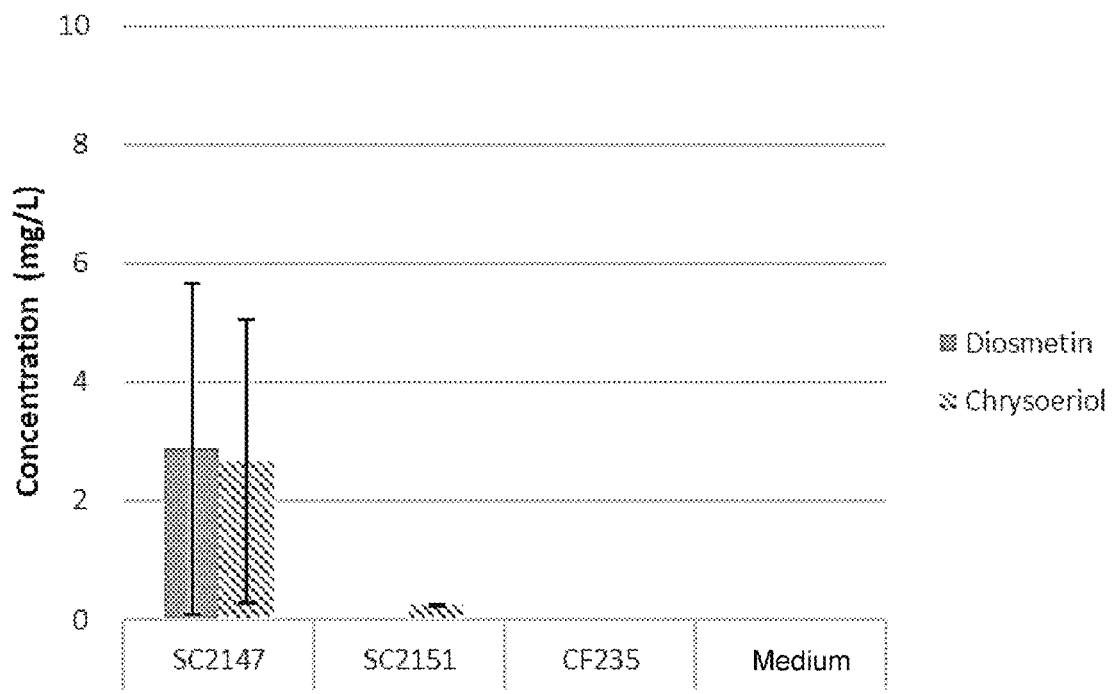
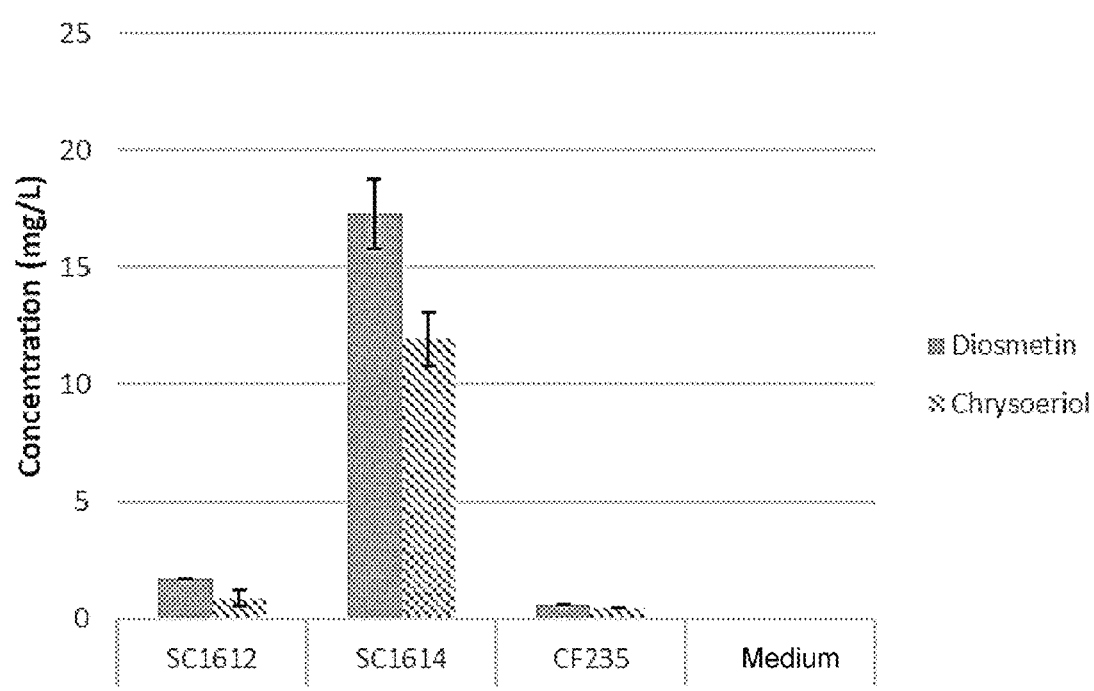

[Figure 21]
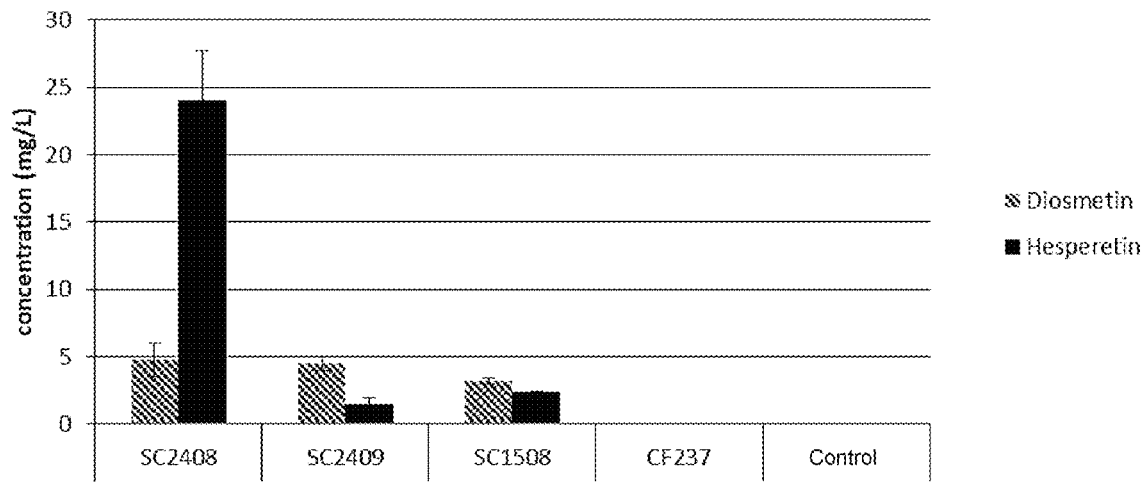
[Figure 22]
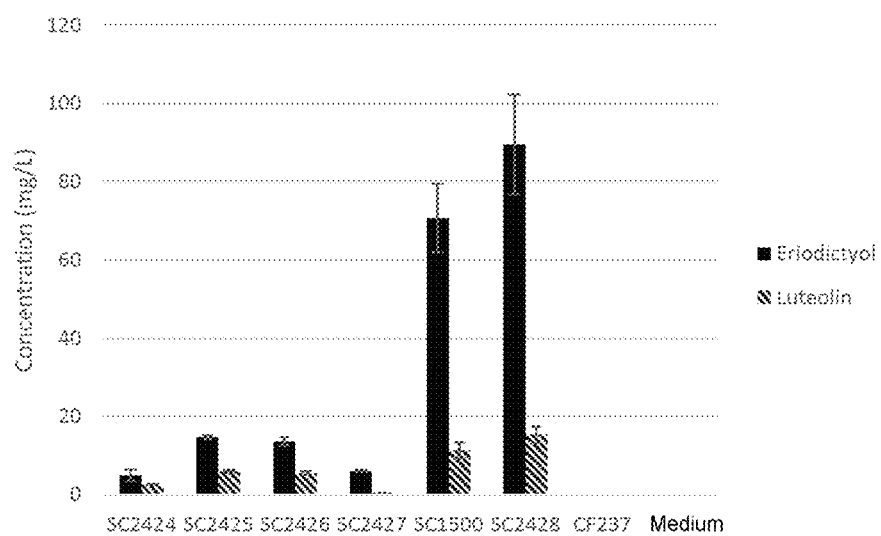

[Figure 23]
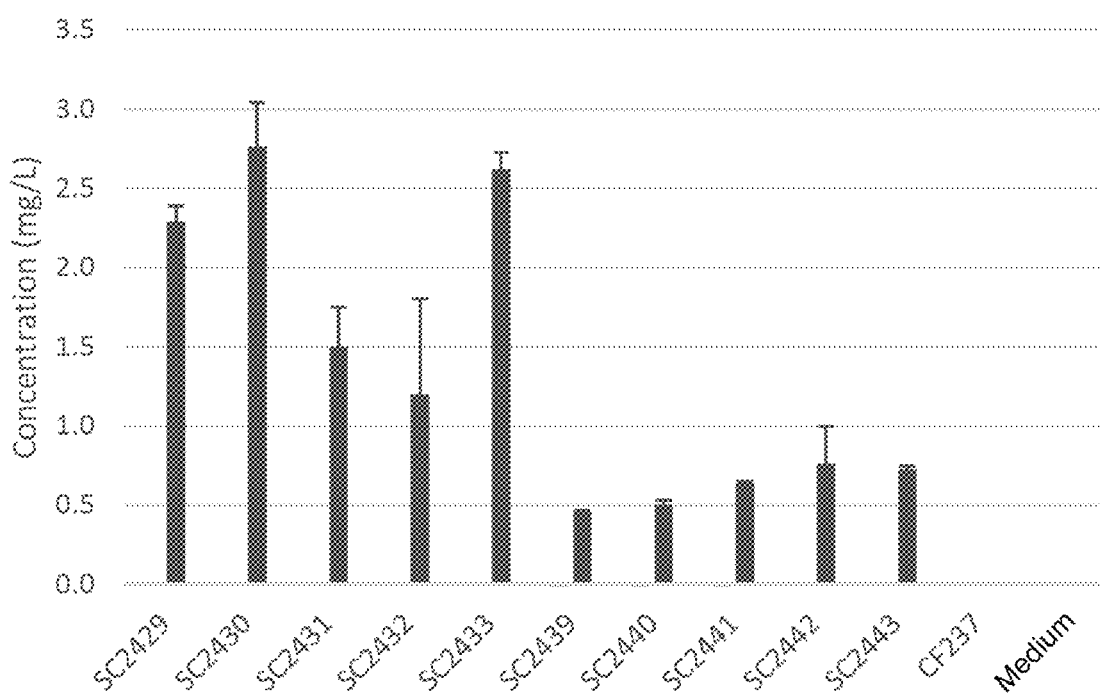
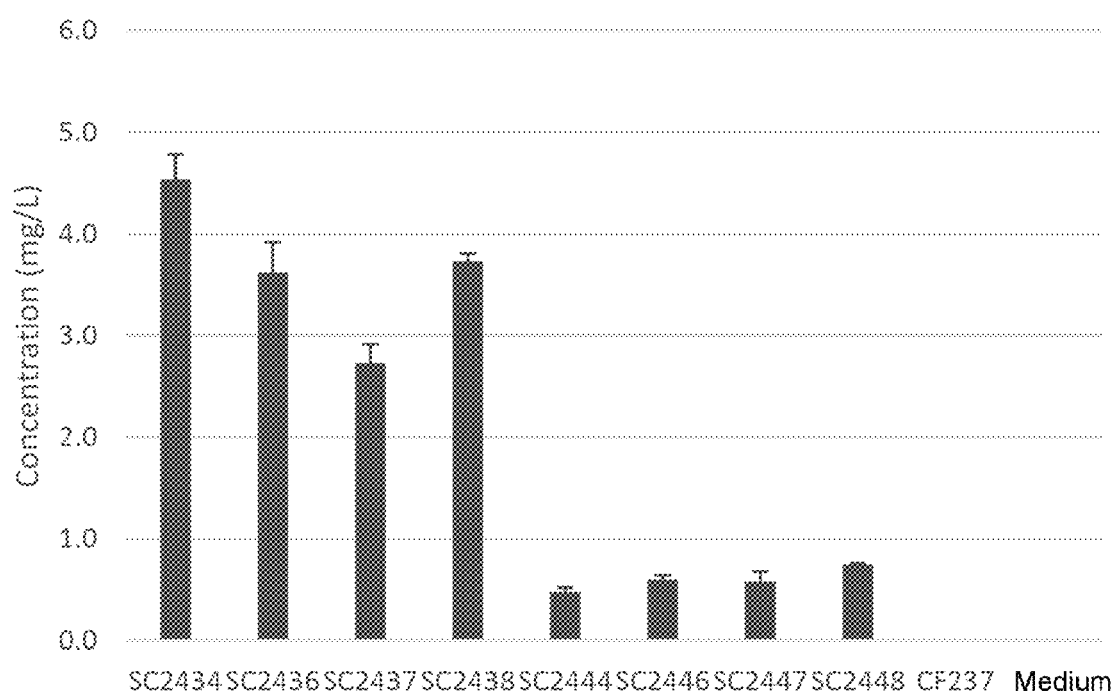

[Figure 23 continued]
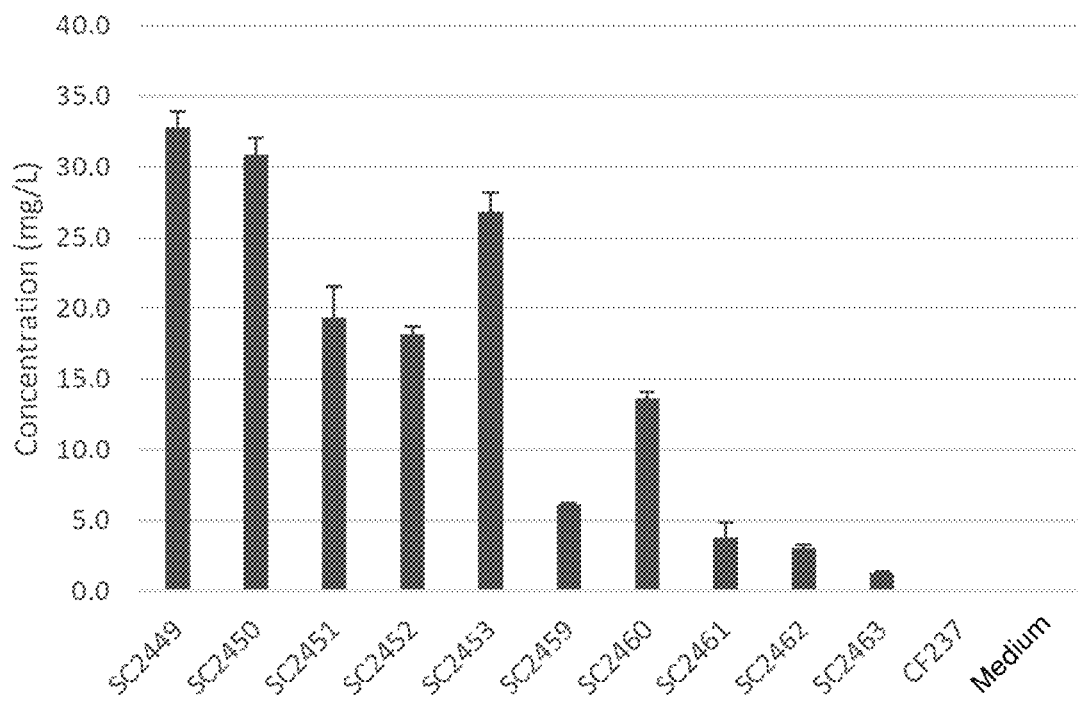
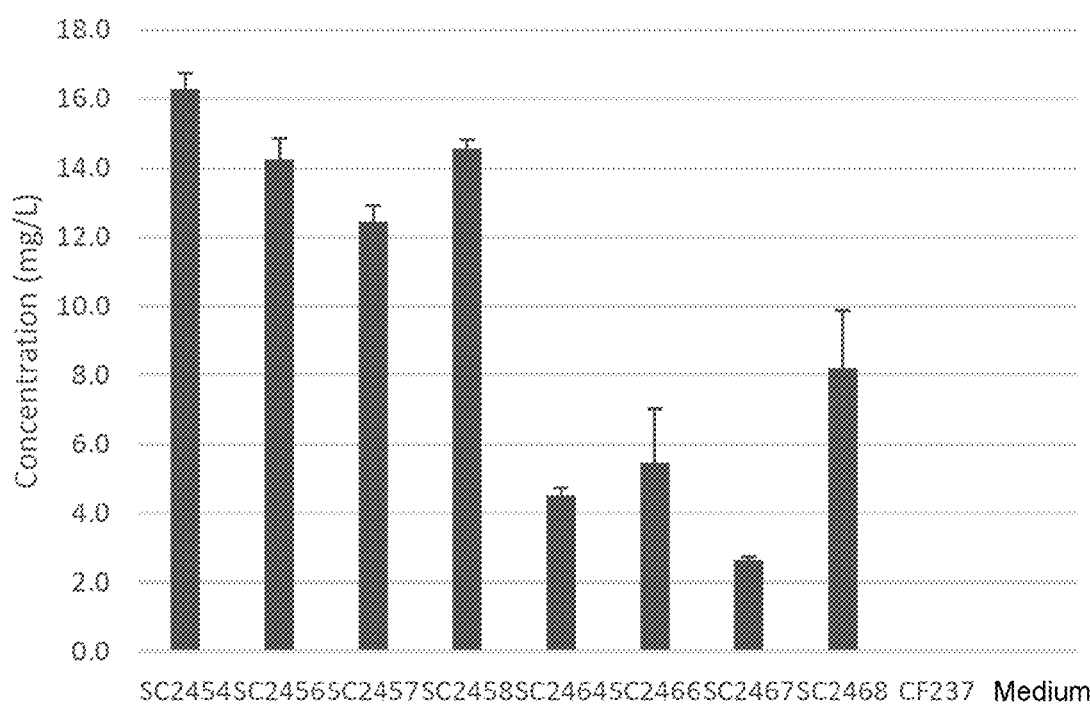

SEQUENCE LISTING

```
<160> NUMBER OF SEQ ID NOS: 134

<210> SEQ ID NO 1
<211> LENGTH: 524
<212> TYPE: PRT
<213> ORGANISM: Perilla frutescens

<400> SEQUENCE: 1

Met Ser Ile Ser Ala Ala Val Ser Leu Ile Ile Cys Thr Ser Ile Leu
1               5                   10                  15

Gly Val Leu Val Tyr Phe Leu Phe Leu Arg Arg Gly Gly Gly Ser Asn
```

```
                  20                  25                  30
Gly Arg Pro Leu Pro Gly Pro Arg Pro Trp Pro Ile Val Gly Asn
                35                  40                  45
Leu Pro Gln Leu Gly Pro Lys Pro His Gln Ser Met Ala Ala Leu Ala
    50                  55                  60
Arg Val His Gly Pro Leu Met His Leu Lys Met Gly Phe Val His Val
65                  70                  75                  80
Val Val Ala Ala Ser Ala Thr Val Ala Glu Lys Phe Leu Lys Val His
                85                  90                  95
Asp Thr Asn Phe Leu Ser Arg Pro Pro Asn Ser Gly Ala Glu His Ile
                    100                 105                 110
Ala Tyr Asn Tyr Asn Asp Leu Val Phe Ala Pro His Gly Pro Arg Trp
                    115                 120                 125
Arg Leu Leu Arg Lys Ile Cys Ala Leu His Leu Phe Ser Ser Lys Ala
                    130                 135                 140
Leu Asp Asp Phe Arg His Val Arg Glu Glu Val Gly Ile Leu Ile
145                 150                 155                 160
Arg Asn Leu Ala Ser Val Gly Glu Met Pro Ala Ser Ile Gly Gln Met
                    165                 170                 175
Met Tyr Val Cys Ala Thr Asn Ala Ile Ser Arg Val Met Leu Gly Arg
                    180                 185                 190
His Val Leu Gly Asp Glu His Arg Gly Ala Ala Gly Gly Asp Thr
        195                 200                 205
Thr Ala Glu Glu Phe Lys Ala Met Val Val Glu Leu Met Ala Leu Ala
        210                 215                 220
Gly Val Phe Asn Val Gly Asp Phe Ile Pro Leu Lys Gly Leu Asp
225                 230                 235                 240
Leu Gln Gly Val Val Ala Lys Met Lys Lys Leu His Gln Arg Phe Asp
                    245                 250                 255
Ala Phe Phe Ser Gly Ile Leu Asp His Lys Ile Asn Gly Ser Asn
                260                 265                 270
Ala Ala Glu Gly His Val Asp Leu Leu Thr Thr Leu Ile Ser Leu Lys
                    275                 280                 285
Asp Val Asp Asn Asn Gly Glu Gly Lys Leu Thr Asp Thr Glu Ile
            290                 295                 300
Lys Ala Leu Leu Leu Asn Leu Phe Thr Ala Gly Thr Asp Thr Thr Ser
305                 310                 315                 320
Ser Thr Val Glu Trp Ala Ile Thr Glu Leu Ile Arg Asn Pro Asn Ile
                        325                 330                 335
Leu Ala Arg Val Arg Lys Glu Leu Asp Leu Ile Val Gly Lys Asp Lys
                    340                 345                 350
Leu Val Lys Glu Ser Asp Leu Gly Gln Leu Thr Tyr Leu Gln Ala Val
                    355                 360                 365
Ile Lys Glu Asn Phe Arg Leu His Pro Ser Thr Pro Leu Ser Leu Pro
            370                 375                 380
Arg Val Ala Gln Glu Ser Cys Glu Ile Asn Gly Tyr Tyr Ile Pro Lys
385                 390                 395                 400
Asp Ser Thr Leu Leu Val Asn Val Trp Ala Ile Gly Arg Asp Pro Asn
                    405                 410                 415
Val Trp Pro Asp Pro Leu Glu Phe Arg Pro Glu Arg Phe Leu Met Gly
                420                 425                 430
Gly Glu Lys Pro Asn Val Asp Val Arg Gly Asn Asp Phe Glu Leu Ile
                    435                 440                 445
```

```
Pro Phe Gly Ser Gly Arg Arg Ile Cys Ala Gly Met Asn Leu Gly Ile
            450                 455                 460

Arg Met Val Gln Leu Leu Ile Ala Thr Met Val His Ala Phe Asp Phe
465                 470                 475                 480

Glu Leu Ala Asn Gly Gln Leu Ala Lys Asp Leu Asn Met Glu Glu Ala
                485                 490                 495

Tyr Gly Ile Thr Leu Gln Arg Ala Asp Pro Leu Val Val His Pro Arg
                500                 505                 510

Pro Arg Leu Ala Arg His Val Tyr Gln Ala Gln Val
            515                 520

<210> SEQ ID NO 2
<211> LENGTH: 1575
<212> TYPE: DNA
<213> ORGANISM: artificial sequence
<220> FEATURE:
<223> OTHER INFORMATION: coding sequence for SEQ ID NO: 1

<400> SEQUENCE: 2
atgtccatct ctgccgccgt ttctttgatc atctgtactt ccattttggg tgttttggtt      60
tacttcttgt tcttgagaag aggtggtggt tctaacggta gaccattgcc accaggtcca     120
agaccatggc caattgtcgg taacttgcca caattgggtc aaagccaca ccaatctatg      180 gctgccttgg ccagagttca cggtccattg atgcacttga gatgggtttt cgttcacgtt     240
gttgttgccg cctccgccac cgttgctgaa aagttcttga aggttcacga caccaacttc     300
ttgtctagac caccaaactc cggtgccgaa cacattgctt acaactacaa cgacttggtt     360
ttcgctccac acggtccaag atggagattg ttgagaaaga tttgtgcctt gcacttgttc     420
tcctccaagg ccttggatga cttcagacac gttagaagaa agaagttgg tatcttgatt     480 agaaacttgg cttctgttgg tgaaatgcca gcttctatcg tcaaatgat gtacgtttgt     540 gccactaacg ctatctctag agtcatgttg ggtagacacg ttttgggtga cgaacacaga     600
ggtgccgccg gtggtggtga taccactgct gaagaattca aggctatggt tgttgaattg     660 atggcttttgg ccggtgtttt caacgttggt gatttcattc caccattgaa gggttttggac    720 ttgcaaggtg ttgttgctaa gatgaagaag ttgcaccaaa gattcgacgc tttcttctct     780
ggtatcttgc acgatcacaa gatcaacggt tctaacgccg ctgaaggtca cgttgacttg     840
ttgactactt tgatttcttt gaaggacgtt gacaacaacg gtgaaggtgg taagttgacc     900
gatactgaaa ttaaggcttt gttgttgaac ttgttcactg ctggtactga cactacttct    960
tctactgttg aatgggccat cactgaattg atcagaaacc caaacatttt ggctagagtt    1020
agaaaggaat tggacttgat cgttggtaag gataagttgg ttaaggaatc cgatttgggt    1080
caattgacct acttgcaagc cgttatcaag gaaaacttca gattgcaccc atctactcca    1140
ttgtctttgc caagagtcgc tcaagaatct tgtgaaatca acggttacta catcccaaag    1200
gattctacct tgttggtcaa cgtttgggcc atcggtagag atccaaacgt ttggccagat    1260
ccattggaat tcagaccaga aagattcttg atgggtggtg aaaagccaaa cgttgatgtt    1320
agaggtaacg atttcgaatt gattccattc ggttctggta agaatttg tgctggtatg      1380 aacttgggta ttagaatggt tcaattgttg attgctacta tggttcacgc tttcgatttc    1440
gaattggcta acggtcaatt ggccaaggac ttgaacatgg aagaagctta cggtattact    1500
ttgcaaagag ccgacccatt ggttgtccac ccaagaccaa gattggccag acacgtttac    1560
caagctcaag tttaa                                                    1575
```

<210> SEQ ID NO 3
<211> LENGTH: 627
<212> TYPE: PRT
<213> ORGANISM: Phanerochaete chrysosporium

<400> SEQUENCE: 3

Met Ser Pro Leu Leu Ser Ala Val Pro Ala Ala Leu Pro Leu Leu
1               5                   10                  15

Ala Ala Ala Met Tyr Val Leu Trp Thr Phe Leu Ala Leu Leu Val Arg
            20                  25                  30

Gln Ala Arg Ser Pro Leu Arg His Leu Arg Gly Pro Pro Ser Pro Ser
        35                  40                  45

Phe Leu Val Gly Asn Leu Arg Glu Met His Asp Gln Glu Asn Thr Ala
    50                  55                  60

Leu Phe Ala Arg Trp Glu His Arg Tyr Gly Ser Thr Phe Val Tyr His
65                  70                  75                  80

Gly Phe Leu Gly Gly Ala Arg Leu Leu Thr Thr Asp Pro Val Ala Val
                85                  90                  95

Ala His Ile Leu Ala His Gly Tyr Asp Phe Pro Lys Pro Glu Phe Ile
            100                 105                 110

Arg Asp Ala Leu Ala Ser Met Ala Ala Gly His Glu Gly Leu Leu Val
        115                 120                 125

Val Glu Gly Asp Gly His Arg Arg Gln Arg Lys Ile Leu Ser Pro Ala
    130                 135                 140

Phe Ala Thr Pro His Ile Lys Ser Leu Ser Pro Ile Ile Trp Ser Lys
145                 150                 155                 160

Ala Thr Gln Leu Arg Asp Val Trp Ile Asp Leu Ala Ser Ser Pro Ser
                165                 170                 175

Leu Thr Pro Ala Ala Thr Pro Ser Asp Pro Leu Ala His Ala Glu Glu
            180                 185                 190

Gln Pro Ala Arg Ala Ser Gly Phe Leu Pro Asn Pro Phe Ser Ser Phe
        195                 200                 205

Leu Ser Ser Lys Ala His Pro Arg Ser Ala Leu Pro Arg Ala Glu Ala
    210                 215                 220

His Pro Glu Asp Arg Met Ser Ser Pro Gly Thr Lys Val Asp Val Leu
225                 230                 235                 240

Ala Trp Leu Ala Arg Ala Thr Leu Asp Val Ile Gly Glu Ala Gly Phe
                245                 250                 255

Gly Tyr Ala Phe Asn Ser Val Arg Ala Ala Ala Cys Pro Gly Asp Ala
            260                 265                 270

Ala Glu Asp Glu Leu Ala Arg Ala Phe Ala Val Ile Phe Ser Thr Ala
        275                 280                 285

Arg Lys Phe Arg Leu Ile Thr Val Leu Gln Val Trp Phe Pro Phe Leu
    290                 295                 300

Arg Arg Phe Arg Arg Asn Ser Ala Ala Glu Asp His Ala Arg Ala Thr
305                 310                 315                 320

Met Arg Arg Ile Gly Leu Ala Leu Ile Ala Glu Arg Arg Gln Glu Val
                325                 330                 335

Leu Asp Asp Lys Ala His Ala Ser Gln Glu Ala Met Asp Gly Lys Asp
            340                 345                 350

Leu Leu Thr Val Met Ile Lys Ser Ser Leu Ser Ser Asp Pro Ser Gln
        355                 360                 365

Gln Leu Ser Thr Asn Glu Met Leu Cys Gln Ile Ala Thr Phe Leu Ala

```
                370             375             380
Ala Gly His Glu Thr Ser Ala Ser Ala Leu Ser Trp Ala Leu Tyr Ala
385             390             395             400
Leu Ala Arg Ala Pro Ala Cys Gln His Thr Leu Arg Arg Glu Leu Arg
            405             410             415
Ala Leu Thr Leu Pro Ala Asp Pro Ser Ala Ala Asp Leu Gln Ala Val
            420             425             430
Leu Ala Leu Pro Tyr Leu Asp Ala Val Val Arg Glu Thr Leu Arg Val
            435             440             445
His Ala Pro Val Thr Ser Thr Met Arg Val Ala His Asp Ala Ala
            450             455             460
Val Pro Val Gly Thr Pro Phe Arg Asp Ala His Gly Ala Gln His Ala
465             470             475             480
Ala Ile Arg Leu Arg Ala Gly Asp Val Val Thr Leu Pro Leu Gln Ala
            485             490             495
Met Asn Lys Ala Arg Ala Leu Trp Gly Ala Asp Ala Ala Cys Phe Arg
            500             505             510
Pro Glu Arg Trp Leu Ala His Gly Asp Ala Pro Arg Glu Pro Arg Gly
            515             520             525
Leu Trp Gly Gly Val Met Thr Phe Gly Thr Gly Val Val Ala Asn Gly
530             535             540
Asn Arg Ser Cys Ile Gly Tyr Arg Phe Ala Val Asn Glu Ile Lys Leu
545             550             555             560
Phe Leu Tyr Ala Leu Val Arg Asp Ile Glu Phe Thr Ile Asp Pro Trp
            565             570             575
Ile Glu Ile Glu Lys Arg Val Asn Val Val Thr Arg Pro Cys Val Lys
            580             585             590
Ser Glu Pro His Leu Gly Asn Gln Met Pro Leu Arg Leu Arg Arg Val
            595             600             605
Ala Val Glu Glu Thr Val Gly Asp Ser Ser Gly Asp Gly Ala Pro Arg
            610             615             620
Thr Val Ser
625

<210> SEQ ID NO 4
<211> LENGTH: 1884
<212> TYPE: DNA
<213> ORGANISM: artificial
<220> FEATURE:
<223> OTHER INFORMATION: coding sequence for SEQ ID NO: 3

<400> SEQUENCE: 4
atgtccccat tgttgtctgc cgttccagcc gccgctttgc cattgttggc cgccgctatg      60
tacgttttgt ggactttctt ggctttgttg gttagacaag ccagatcccc attgagacac     120
ttgagaggtc caccatctcc atctttcttg gtcggtaact tgagagaaat gcacgaccaa     180
gaaaacaccg ctttgttcgc tagatgggaa cacagatacg ttctaccttc gtctaccac     240 ggtttcttgg gtggtgccag attgttgacc accgacccag tcgccgtcgc ccacatcttg     300
gcccacggtt acgacttccc aaagccagaa ttcatcagag atgccttggc ttctatggcc     360
gccggtcacg aaggtttgtt ggtcgtcgaa ggtgacggtc acaggagaca agaaagatc      420 ttgtccccag ctttcgccac tccacacatc aagtctttgt ctccaatcat ctggtctaag     480
gctactcaat tgagagatgt tggattgac ttggcctctt ctccatcctt gactccagct      540
gctaccccat ccgacccatt ggctcacgct gaagaacaac cagctagagc ttctggtttc     600
```

```
ttgccaaacc cattctcttc tttcttgtca tctaaggctc acccaagatc cgctttgcca      660
agagctgaag ctcacccaga agatagaatg tcctctccag gtaccaaggt cgacgttttg      720
gcttggttgg ctagagccac tttggacgtc atcggtgaag ccggtttcgg ttacgctttc      780
aactctgtca gagccgctgc ttgtccaggt gacgccgctg aagatgaatt ggctagagct      840
ttcgctgtca tcttctctac tgctagaaag ttcagattga tcactgtctt gcaagtttgg      900
ttcccattct tgagaagatt cagaagaaac tctgctgctg aagatcacgc tagagctact      960
atgagaagaa tcggtttggc tttgatcgct gaaaggagac aagaagtctt ggacgacaag     1020
gctcacgcct ctcaagaagc tatggatggt aaggacttgt tgactgtcat gatcaagtca     1080
tctttgtcat ccgatccatc tcaacaattg tctactaacg aaatgttgtg tcaaatcgct     1140
actttcttgg ctgctggtca cgaaacctct gcttctgctt tgtcttgggc cttgtacgcc     1200
ttggctagag ctccagcttg tcaacacact ttgagaagag aattgagagc tttgactttg     1260
ccagctgacc catctgccgc tgacttgcaa gctgttttgg cttttgccata cttggacgcc     1320 gtcgttagag aaactttgag agttcacgct ccagttactt ctactatgag agtcgctgct     1380
cacgacgccg ctgttccagt cggtactcca ttcagagatg ctcacggtgc tcaacacgcc     1440
gctatcagat tgagagctgg tgacgtcgtc actttgccat gcaagctat gaacaaggcc     1500 agagctttgt ggggtgccga cgccgcttgt ttcagaccag aaagatggtt ggctcacggt     1560
gacgccccaa gagaaccaag aggtttgtgg ggtggtgtca tgactttcgg taccggtgtc     1620
gtcgctaacg gtaacagatc ttgtattggt tacagattcg ctgttaacga aatcaagttg     1680
ttcttgtacg ccttggttag agacatcgaa ttcactatcg acccatggat cgaaatcgaa     1740
aagagagtta acgtcgtcac cagaccatgt gtcaagtccg aaccacactt gggtaaccaa     1800
atgccattga gattgagaag agtcgctgtt gaagaaactg ttggtgattc ttctggtgac     1860
ggtgctccaa gaactgtttc ttaa                                             1884
```

<210> SEQ ID NO 5
<211> LENGTH: 513
<212> TYPE: PRT
<213> ORGANISM: Petunia x hybrida

<400> SEQUENCE: 5

```
Met Ser Glu Ile Leu Ser Leu Ile Leu Tyr Thr Val Ile Phe Ser Phe
1               5                   10                  15

Leu Leu Gln Phe Ile Leu Arg Ser Phe Phe Arg Lys Arg Tyr Pro Leu
            20                  25                  30

Pro Leu Pro Pro Gly Pro Lys Pro Trp Pro Ile Ile Gly Asn Leu Val
        35                  40                  45

His Leu Gly Pro Lys Pro His Gln Ser Thr Ala Ala Met Ala Gln Thr
    50                  55                  60

Tyr Gly Pro Leu Met Tyr Leu Lys Met Gly Phe Val Asp Val Val
65                  70                  75                  80

Ala Ala Ser Ala Ser Val Ala Ala Gln Phe Leu Lys Thr His Asp Ala
                85                  90                  95

Asn Phe Ser Ser Arg Pro Pro Asn Ser Gly Ala Glu His Met Ala Tyr
            100                 105                 110

Asn Tyr Gln Asp Leu Val Phe Ala Pro Tyr Gly Pro Arg Trp Arg Met
        115                 120                 125

Leu Arg Lys Ile Cys Ser Val His Leu Phe Ser Thr Lys Ala Leu Asp
    130                 135                 140
```

```
Asp Phe Arg His Val Arg Gln Asp Glu Val Lys Thr Leu Thr Arg Ala
145                 150                 155                 160

Leu Ala Ser Ala Gly Gln Lys Pro Val Lys Leu Gly Gln Leu Leu Asn
            165                 170                 175

Val Cys Thr Thr Asn Ala Leu Ala Arg Val Met Leu Gly Lys Arg Val
        180                 185                 190

Phe Ala Asp Gly Ser Gly Asp Val Asp Pro Gln Ala Ala Glu Phe Lys
    195                 200                 205

Ser Met Val Val Glu Met Met Val Val Ala Gly Val Phe Asn Ile Gly
210                 215                 220

Asp Phe Ile Pro Gln Leu Asn Trp Leu Asp Ile Gln Gly Val Ala Ala
225                 230                 235                 240

Lys Met Lys Lys Leu His Ala Arg Phe Asp Ala Phe Leu Thr Asp Ile
                245                 250                 255

Leu Glu Glu His Lys Gly Lys Ile Phe Gly Glu Met Lys Asp Leu Leu
            260                 265                 270

Ser Thr Leu Ile Ser Leu Lys Asn Asp Ala Asp Asn Asp Gly Gly
        275                 280                 285

Lys Leu Thr Asp Thr Glu Ile Lys Ala Leu Leu Leu Asn Leu Phe Val
            290                 295                 300

Ala Gly Thr Asp Thr Ser Ser Ser Thr Val Glu Trp Ala Ile Ala Glu
305                 310                 315                 320

Leu Ile Arg Asn Pro Lys Ile Leu Ala Gln Ala Gln Gln Glu Ile Asp
                325                 330                 335

Lys Val Val Gly Arg Asp Arg Leu Val Gly Glu Leu Asp Leu Ala Gln
            340                 345                 350

Leu Thr Tyr Leu Glu Ala Ile Val Lys Glu Thr Phe Arg Leu His Pro
        355                 360                 365

Ser Thr Pro Leu Ser Leu Pro Arg Ile Ala Ser Glu Ser Cys Glu Ile
    370                 375                 380

Asn Gly Tyr Phe Ile Pro Lys Gly Ser Thr Leu Leu Leu Asn Val Trp
385                 390                 395                 400

Ala Ile Ala Arg Asp Pro Asn Ala Trp Ala Asp Pro Leu Glu Phe Arg
                405                 410                 415

Pro Glu Arg Phe Leu Pro Gly Gly Glu Lys Pro Lys Val Asp Val Arg
            420                 425                 430

Gly Asn Asp Phe Glu Val Ile Pro Phe Gly Ala Gly Arg Arg Ile Cys
        435                 440                 445

Ala Gly Met Asn Leu Gly Ile Arg Met Val Gln Leu Met Ile Ala Thr
    450                 455                 460

Leu Ile His Ala Phe Asn Trp Asp Leu Val Ser Gly Gln Leu Pro Glu
465                 470                 475                 480

Met Leu Asn Met Glu Glu Ala Tyr Gly Leu Thr Leu Gln Arg Ala Asp
                485                 490                 495

Pro Leu Val Val His Pro Arg Pro Arg Leu Glu Ala Gln Ala Tyr Ile
            500                 505                 510

Gly

<210> SEQ ID NO 6
<211> LENGTH: 1542
<212> TYPE: DNA
<213> ORGANISM: artificial
<220> FEATURE:
<223> OTHER INFORMATION: coding sequence for SEQ ID NO: 5
```

<400> SEQUENCE: 6

```
atgtccgaaa tcttgtcttt gattttgtac accgtcattt tctctttctt gttgcaattc      60
attttgagat ctttcttcag aaagagatac ccattgccat tgccaccagg tccaaagcca     120
tggccaatta tcggtaactt ggtccacttg ggtccaaagc cacaccaatc tactgctgcc     180
atggctcaaa cttacggtcc attgatgtac ttgaagatgg gtttcgttga cgttgttgtt     240
gctgcctctg cttctgttgc tgctcaattc ttaaagactc acgatgctaa cttctcttct     300
agaccaccaa actctggtgc tgaacacatg gcttacaact accaagattt ggttttcgct     360
ccatacggtc aagatggag aatgttgaga aagatttgtt ctgttcactt gttctctacc     420
aaggctttgg atgacttcag acacgtcaga caagatgaag ttaagacttt gactagagct     480
ttggcttctg ctggtcaaaa gccagtcaag ttgggtcaat tgttgaacgt tgtactact    540
aacgctttgg ctagagttat gttgggtaag agagttttcg ccgacggttc tggtgatgtt     600
gatccacaag ctgctgaatt caagtctatg gttgttgaaa tgatggttgt cgccggtgtt     660
ttcaacattg gtgatttcat tccacaattg aactggttgg atattcaagg tgttgccgct     720
aagatgaaga agttgcacgc tagattcgac gctttcttga ctgatatctt ggaagaacac     780
aagggtaaga ttttcggtga atgaaggat tgttgtcta ctttgatctc tttgaagaac     840
gatgatgctg ataacgatgg tggtaagttg actgatactg aaattaaggc tttgttgttg     900
aacttgttcg ttgctggtac tgacacttct tcttctactg ttgaatgggc cattgctgaa     960
ttgattagaa acccaaagat cttggcccaa gcccaacaag aaatcgacaa ggtcgttggt    1020
agagacagat tggttggtga attggacttg gcccaattga cttacttgga agctatcgtc    1080
aaggaaacct tcagattgca cccatctacc ccattgtctt tgccaagaat tgcttctgaa    1140
tcttgtgaaa tcaacggtta cttcattcca agggttcta ctttgttgtt gaacgtttgg    1200
gccattgcta gagatccaaa cgcttgggct gatccattgg aattcagacc agaaagattc    1260
ttgccaggtg gtgaaaagcc aaaggttgat gtcagaggta cgacttcga agtcatccca    1320
ttcggtgctg gtagaagaat ttgtgctggt atgaacttgg gtatcagaat ggtccaattg    1380
atgattgcta ctttgatcca cgctttcaac tgggatttgg tatctggtca attgccagaa    1440
atgttgaaca tggaagaagc ttacggtttg accttgcaaa gagctgatcc attggttgtt    1500
cacccaagac caagattgga agcccaagct tacattggtt aa                       1542
```

<210> SEQ ID NO 7
<211> LENGTH: 519
<212> TYPE: PRT
<213> ORGANISM: Callistephus chinensis

<400> SEQUENCE: 7

```
Met Ser Thr Ile Leu Pro Phe Ile Phe Tyr Thr Cys Ile Thr Ala Leu
1               5                   10                  15

Val Leu Tyr Val Leu Leu Asn Leu Leu Thr Arg Asn Pro Asn Arg Leu
            20                  25                  30

Pro Pro Gly Pro Thr Pro Trp Pro Ile Val Gly Asn Leu Pro His Leu
        35                  40                  45

Gly Met Ile Pro His His Ser Leu Ala Ala Leu Ala Gln Lys Tyr Gly
    50                  55                  60

Pro Leu Met His Leu Arg Leu Gly Phe Val Asp Val Val Val Ala Ala
65                  70                  75                  80

Ser Ala Ser Val Ala Ala Gln Phe Leu Lys Thr His Asp Ala Asn Phe
```

```
                       85                  90                  95
Ala Ser Arg Pro Pro Asn Ser Gly Ala Lys His Ile Ala Tyr Asn Tyr
                100                 105                 110

Gln Asp Leu Val Phe Ala Pro Tyr Gly Pro Arg Trp Arg Met Leu Arg
            115                 120                 125

Lys Ile Cys Ser Val His Leu Phe Ser Thr Lys Ala Leu Asp Asp Phe
        130                 135                 140

Arg His Val Arg Glu Glu Val Ala Ile Leu Thr Arg Val Leu Val
145                 150                 155                 160

His Ala Gly Glu Ser Ala Val Lys Leu Gly Gln Leu Leu Asn Val Cys
                165                 170                 175

Thr Thr Asn Ala Leu Ala Arg Val Met Leu Gly Arg Arg Val Phe Ala
            180                 185                 190

Asp Gly Ser Glu Gly Arg Gly Val Asp Pro Lys Ala Asp Glu Phe Lys
        195                 200                 205

Asp Met Val Val Glu Leu Met Glu Leu Ala Gly Glu Phe Asn Ile Gly
210                 215                 220

Asp Phe Ile Pro Pro Leu Asp Cys Leu Asp Leu Gln Gly Ile Thr Lys
225                 230                 235                 240

Lys Met Lys Lys Leu His Ala Arg Phe Asp Lys Phe Leu Asn Ile Ile
                245                 250                 255

Leu Asp Asp His Lys Ile Glu Lys Gly Ala Ala Gly Arg Arg His Ser
            260                 265                 270

Asp Leu Leu Thr Thr Leu Ile Ser Leu Lys Asp Val Asp Ala Ala Asp
        275                 280                 285

Asp Asp Glu Glu Gly Lys Leu Ser Asp Ile Glu Ile Lys Ala Leu Leu
        290                 295                 300

Leu Asn Leu Phe Ala Ala Gly Thr Asp Thr Ser Ser Ser Thr Val Glu
305                 310                 315                 320

Trp Ala Val Ala Glu Leu Ile Arg His Pro Glu Leu Leu Lys Gln Ala
                325                 330                 335

Arg Glu Glu Met Asp Ile Val Val Gly Arg Asp Arg Leu Val Thr Glu
            340                 345                 350

Leu Asp Leu Ser Arg Leu Thr Phe Leu Gln Ala Ile Val Lys Glu Thr
        355                 360                 365

Phe Arg Leu His Pro Ser Thr Pro Leu Ser Leu Pro Arg Met Ala Ser
370                 375                 380

Glu Ser Cys Glu Val Asp Gly Tyr Tyr Ile Pro Lys Gly Ser Thr Leu
385                 390                 395                 400

Leu Val Asn Val Trp Ala Ile Ala Arg Asp Pro Lys Met Trp Thr Asn
                405                 410                 415

Pro Leu Glu Phe Arg Pro Ser Arg Phe Leu Pro Gly Gly Glu Lys Pro
            420                 425                 430

Asp Ala Asp Ile Lys Gly Asn Asp Phe Glu Val Ile Pro Phe Gly Ala
        435                 440                 445

Gly Arg Arg Ile Cys Ala Gly Met Ser Leu Gly Met Arg Met Val Gln
        450                 455                 460

Leu Leu Ile Ala Thr Leu Val Gln Thr Phe Asp Trp Glu Leu Ala Asn
465                 470                 475                 480

Gly Leu Asp Pro Glu Lys Leu Asn Met Glu Glu Ala Tyr Gly Leu Thr
                485                 490                 495

Leu Gln Arg Ala Glu Pro Leu Met Val His Pro Arg Pro Arg Leu Ser
            500                 505                 510
```

Pro His Val Tyr Glu Ser Arg
          515

<210> SEQ ID NO 8
<211> LENGTH: 1560
<212> TYPE: DNA
<213> ORGANISM: artificial
<220> FEATURE:
<223> OTHER INFORMATION: coding sequence for SEQ ID NO: 7

<400> SEQUENCE: 8

| | | | | | |
|---|---|---|---|---|---|
| atgtccacca | ttttgccatt | cattttctac | acttgtatca | ctgccttggt | tttgtacgtt | 60 |
| ttgttgaact | tgttgaccag | aaacccaaac | agattgccac | caggtccaac | cccatggcca | 120 |
| atcgttggta | acttgccaca | cttgggtatg | atcccacacc | actctttggc | tgccttggcc | 180 |
| caaaagtacg | gtccattgat | gcacttgaga | ttgggtttcg | ttgacgttgt | cgttgccgct | 240 |
| tctgcttccg | ttgctgctca | attcttaaag | actcacgacg | ctaacttcgc | ttctagacca | 300 |
| ccaaactctg | gtgccaagca | cattgcctac | aactaccaag | atttggtttt | cgctccatac | 360 |
| ggtccaagat | ggagaatgtt | gagaaagatt | tgttctgttc | acttgttctc | cactaaggct | 420 |
| ttggacgact | tcagacacgt | tagagaagaa | gaagttgcta | tcttgactag | agttttggtc | 480 |
| cacgctggtg | aatctgctgt | taagttgggt | caattgttga | acgtttgtac | cactaacgct | 540 |
| ttggctagag | ttatgttggg | tagaagagtt | ttcgctgacg | gttctgaagg | tagaggtgtc | 600 |
| gacccaaagg | ctgatgaatt | caaggacatg | gttgttgaat | tgatggaatt | ggccggtgaa | 660 |
| ttcaacatcg | gtgacttcat | cccaccattg | gactgtttgg | atttgcaagg | tatcaccaag | 720 |
| aagatgaaga | agttgcacgc | tagattcgac | aagttcttga | acatcatctt | ggacgaccac | 780 |
| aagatcgaaa | agggtgctgc | cggtagaagg | cactctgact | tgttgaccac | tttgatttct | 840 |
| ttgaaggatg | ttgatgctgc | tgatgatgat | gaagaaggta | agttgtctga | cattgaaatc | 900 |
| aaggctttgt | tgttgaactt | gttcgctgct | ggtactgaca | cttcttcttc | taccgttgaa | 960 |
| tgggctgttg | ccgaattgat | tagacaccca | gaattgttga | agcaagctag | agaagaaatg | 1020 |
| gatatcgttg | ttggtagaga | cagattggtt | accgaattgg | acttgtctag | attgacttct | 1080 |
| ttgcaagcca | ttgttaagga | aaccttcaga | ttgcacccat | ctactccatt | gtccttgcca | 1140 |
| agaatggctt | ctgaatcttg | tgaagttgat | ggttactaca | ttccaaaggg | ttccactttg | 1200 |
| ttggttaacg | tttgggccat | cgccagagat | ccaaagatgt | ggactaaccc | attggaattc | 1260 |
| agaccatcta | gattcttgcc | aggtggtgaa | aagccagatg | ctgatatcaa | gggtaacgat | 1320 |
| ttcgaagtca | tcccattcgg | tgccggtaga | agaatctgtg | ctggtatgtc | tttgggtatg | 1380 |
| agaatggtcc | aattgttgat | tgctactttg | gtccaaacct | tcgattggga | attggctaac | 1440 |
| ggtttggacc | agaaaaagtt | gaacatggaa | gaagcttacg | gtttgacctt | gcaaagagct | 1500 |
| gaaccattga | tggttcaccc | aagaccaaga | ttgtctccac | acgtttacga | atctagataa | 1560 |

<210> SEQ ID NO 9
<211> LENGTH: 511
<212> TYPE: PRT
<213> ORGANISM: Callistephus chinensis

<400> SEQUENCE: 9

Met Ser Ser Ile Leu Ser Leu Leu Val Tyr Phe Cys Ile Ser Leu Leu
1               5                   10                  15

Val Ile Ile Ala Leu Val Asn Met Phe Ile Thr Arg His Thr Asn Arg
            20                  25                  30

```
Leu Pro Pro Gly Pro Ala Pro Trp Pro Val Val Gly Asn Leu Pro His
            35                  40                  45

Leu Gly Ala Ile Pro His His Thr Leu Ala Ala Leu Ala Thr Lys Tyr
 50                  55                  60

Gly Pro Leu Val Tyr Leu Arg Leu Gly Phe Val His Val Val Ala
 65                  70                  75                  80

Ser Ser Pro Ser Val Ala Ala Gln Phe Leu Lys Val His Asp Leu Lys
                85                  90                  95

Phe Ala Ser Arg Pro Pro Asn Ser Gly Ala Lys His Ile Ala Tyr Asn
                100                 105                 110

Tyr Gln Asp Met Val Phe Ala Pro Tyr Gly Pro Gln Trp Thr Met Phe
            115                 120                 125

Arg Lys Ile Cys Lys Asp His Leu Phe Ser Ser Lys Ala Leu Asp Asp
            130                 135                 140

Phe Arg His Val Arg Gln Glu Glu Val Ala Ile Leu Ala Arg Gly Leu
145                 150                 155                 160

Ala Gly Ala Gly Arg Ser Lys Val Asn Leu Gly Gln Gln Leu Asn Met
                165                 170                 175

Cys Thr Ala Asn Thr Leu Ala Arg Met Met Leu Asp Lys Arg Val Phe
            180                 185                 190

Gly Asn Glu Ser Gly Gly Asp Asp Pro Lys Ala Asn Glu Phe Lys Glu
            195                 200                 205

Met Ala Thr Glu Leu Met Phe Leu Ala Gly Gln Phe Asn Ile Gly Asp
    210                 215                 220

Tyr Ile Pro Val Leu Asp Trp Leu Asp Leu Gln Gly Ile Val Lys Lys
225                 230                 235                 240

Met Lys Lys Leu His Thr Arg Phe Asp Lys Phe Leu Asp Val Ile Leu
                245                 250                 255

Asp Glu His Lys Val Ile Ala Ser Gly His Ile Asp Met Leu Ser Thr
            260                 265                 270

Leu Ile Ser Leu Lys Asp Asp Thr Ser Val Asp Gly Arg Lys Pro Ser
            275                 280                 285

Asp Ile Glu Ile Lys Ala Leu Leu Leu Glu Leu Phe Val Ala Gly Thr
    290                 295                 300

Asp Thr Ser Ser Asn Thr Val Glu Trp Ala Ile Ala Glu Leu Ile Arg
305                 310                 315                 320

Gln Pro His Leu Leu Lys Arg Ala Gln Glu Glu Met Asp Ser Val Val
                325                 330                 335

Gly Gln Asn Arg Leu Val Thr Glu Met Asp Leu Ser Gln Leu Thr Phe
            340                 345                 350

Leu Gln Ala Ile Val Lys Glu Ala Phe Arg Leu His Pro Ser Thr Pro
            355                 360                 365

Leu Ser Leu Pro Arg Ile Ala Ser Glu Ser Cys Glu Val Asp Gly Tyr
    370                 375                 380

Tyr Ile Pro Lys Gly Ser Thr Leu Leu Val Asn Ile Trp Ala Ile Gly
385                 390                 395                 400

Arg His Pro Glu Val Trp Thr Asp Pro Leu Glu Phe Arg Pro Thr Arg
                405                 410                 415

Phe Leu Pro Gly Gly Glu Lys Pro Gly Ile Val Val Lys Val Asn Asp
            420                 425                 430

Phe Glu Val Leu Pro Phe Gly Ala Gly Arg Arg Ile Cys Ala Gly Met
    435                 440                 445
```

```
Ser Leu Ala Leu Arg Thr Val Gln Leu Leu Met Gly Thr Leu Val Gln
    450                 455                 460

Ala Phe Asp Trp Glu Leu Ala Asn Gly Ile Lys Pro Glu Lys Leu Asn
465                 470                 475                 480

Met Asp Glu Ala Phe Gly Leu Ser Val Gln Arg Ala Glu Pro Leu Val
                485                 490                 495

Val His Pro Arg Pro Arg Leu Pro Pro His Val Tyr Lys Ser Gly
                500                 505                 510

<210> SEQ ID NO 10
<211> LENGTH: 1536
<212> TYPE: DNA
<213> ORGANISM: artificial
<220> FEATURE:
<223> OTHER INFORMATION: coding sequence for SEQ ID NO: 9

<400> SEQUENCE: 10
atgtcctcta ttttgtcttt gttggtctac ttctgtatct ctttgttggt tatcattgct      60
ttggttaaca tgttcatcac cagacacacc aacagattgc caccaggtcc agccccatgg     120
ccagtcgtcg gtaacttgcc acacttgggt gctattccac accacacttt ggctgctttg     180
gctactaagt acggtccatt ggtttacttg agattgggtt tcgttcacgt tgttgttgcc     240
tcttctccat ccgttgctgc tcaattcttg aaggttcacg acttgaagtt cgcctctaga     300
ccaccaaact ctggtgctaa gcacatcgct acaactacc aagatatggt tttcgctcca     360
tacggtccac aatggactat gttcagaaag atttgtaagg atcacttgtt ctcttctaag     420
gctttggatg atttcagaca cgttagacaa gaagaagttg ctatcttggc tagaggtttg     480
gctggtgctg gtagatctaa ggttaacttg ggtcaacaat tgaacatgtg taccgctaac     540
actttggcta aatgatgtt ggacaagaga gttttcggta cgaatctgg tggtgatgat     600 ccaaaggcta acgaattcaa ggaaatggct actgaattga tgttcttggc tggtcaattc     660
aacattggtg actacatccc agttttggac tggttggact gcaaggtat tgttaagaag     720 atgaagaagt tgcacactag attcgataag ttcttggacg ttatcttgga tgaacacaag     780
gttatcgctt ctggtcacat cgacatgttg tctactttga ttctttgaa ggatgatacc     840 tctgttgacg gtagaaagcc atccgacatc gaaatcaagg ctttgttgtt ggaattgttc     900
gttgctggta ctgacacttc ttctaacacc gttaatggg ctatcgctga attgattaga     960
caaccacact tgttgaagag agcccaagaa gaaatggact ctgttgttgg tcaaaacaga    1020
ttggttaccg aaatggactt gtctcaattg actttcttgc aagccattgt taaggaagcc    1080
ttcagattgc acccatctac tccattgtcc ttgccaagaa ttgcttccga atcttgtgaa    1140
gttgatggtt actacatccc aaagggttcc actttgttgg ttaacatctg gccattggt     1200 agacacccag aagtttggac cgacccattg gaattcagac aactagatt cttgccaggt    1260 ggtgaaaagc caggtattgt cgtcaaggtt aacgatttcg aagtcttgcc attcggtgcc    1320
ggtagaagaa tctgtgctgg tatgtctttg gccttgaaga ctgtccaatt gttgatgggt    1380
actttggtcc aagccttcga ttgggaattg ctaacggta tcaagccaga aaagttgaac    1440
atggacgaag ccttcggttt gtctgttcaa agagctgaac cattggttgt tcacccaaga    1500
ccaagattgc caccacacgt ttacaagtct ggttaa                             1536

<210> SEQ ID NO 11
<211> LENGTH: 513
<212> TYPE: PRT
<213> ORGANISM: Gerbera hybrida
```

<400> SEQUENCE: 11

```
Met Ser Thr Pro Leu Thr Leu Leu Ile Gly Thr Cys Val Thr Gly Leu
1               5                   10                  15

Phe Leu Tyr Val Leu Leu Asn Arg Cys Thr Arg Asn Pro Asn Arg Leu
            20                  25                  30

Pro Pro Gly Pro Thr Pro Trp Pro Val Val Gly Asn Leu Pro His Leu
        35                  40                  45

Gly Thr Ile Pro His His Ser Leu Ala Ala Met Ala Lys Lys Tyr Gly
    50                  55                  60

Pro Leu Met His Leu Arg Leu Gly Phe Val Asp Val Val Ala Ala
65                  70                  75                  80

Ser Ala Ser Val Ala Ala Gln Phe Leu Lys Thr His Asp Ala Asn Phe
                85                  90                  95

Ala Asp Arg Pro Pro Asn Ser Gly Ala Lys His Ile Ala Tyr Asn Tyr
            100                 105                 110

Gln Asp Leu Val Phe Ala Pro Tyr Gly Pro Arg Trp Arg Met Leu Arg
            115                 120                 125

Lys Ile Cys Ser Val His Leu Phe Ser Thr Lys Ala Leu Asp Asp Phe
    130                 135                 140

Arg His Val Arg Gln Glu Glu Val Ala Ile Leu Ala Arg Ala Leu Val
145                 150                 155                 160

Gly Ala Gly Lys Ser Pro Val Lys Leu Gly Gln Leu Leu Asn Val Cys
                165                 170                 175

Thr Thr Asn Ala Leu Ala Arg Val Met Leu Gly Arg Arg Val Phe Asp
            180                 185                 190

Ser Gly Asp Ala Gln Ala Asp Glu Phe Lys Asp Met Val Val Glu Leu
        195                 200                 205

Met Val Leu Ala Gly Glu Phe Asn Ile Gly Asp Phe Ile Pro Val Leu
    210                 215                 220

Asp Trp Leu Asp Leu Gln Gly Val Thr Lys Met Lys Lys Leu His
225                 230                 235                 240

Ala Lys Phe Asp Ser Phe Leu Asn Thr Ile Leu Glu Glu His Lys Thr
            245                 250                 255

Gly Ala Gly Asp Gly Val Ala Ser Gly Lys Val Asp Leu Leu Ser Thr
            260                 265                 270

Leu Ile Ser Leu Lys Asp Asp Ala Asp Gly Glu Gly Lys Leu Ser
    275                 280                 285

Asp Ile Glu Ile Lys Ala Leu Leu Leu Asn Leu Phe Thr Ala Gly Thr
    290                 295                 300

Asp Thr Ser Ser Ser Thr Ile Glu Trp Ala Ile Ala Glu Leu Ile Arg
305                 310                 315                 320

Asn Pro Gln Leu Leu Asn Gln Ala Arg Lys Glu Met Asp Thr Ile Val
            325                 330                 335

Gly Gln Asp Arg Leu Val Thr Glu Ser Asp Leu Gly Gln Leu Thr Phe
            340                 345                 350

Leu Gln Ala Ile Ile Lys Glu Thr Phe Arg Leu His Pro Ser Thr Pro
        355                 360                 365

Leu Ser Leu Pro Arg Met Ala Leu Glu Ser Cys Glu Val Gly Gly Tyr
    370                 375                 380

Tyr Ile Pro Lys Gly Ser Thr Leu Leu Val Asn Val Trp Ala Ile Ser
385                 390                 395                 400

Arg Asp Pro Lys Ile Trp Ala Asp Pro Leu Glu Phe Gln Pro Thr Arg
```

```
                   405                 410                 415
Phe Leu Pro Gly Gly Glu Lys Pro Asn Thr Asp Ile Lys Gly Asn Asp
            420                 425                 430

Phe Glu Val Ile Pro Phe Gly Ala Gly Arg Arg Ile Cys Val Gly Met
        435                 440                 445

Ser Leu Gly Leu Arg Met Val Gln Leu Leu Thr Ala Thr Leu Ile His
    450                 455                 460

Ala Phe Asp Trp Glu Leu Ala Asp Gly Leu Asn Pro Lys Lys Leu Asn
465                 470                 475                 480

Met Glu Glu Ala Tyr Gly Leu Thr Leu Gln Arg Ala Ala Pro Leu Val
                485                 490                 495

Val His Pro Arg Pro Arg Leu Ala Pro His Val Tyr Glu Thr Thr Lys
            500                 505                 510

Val

<210> SEQ ID NO 12
<211> LENGTH: 1542
<212> TYPE: DNA
<213> ORGANISM: artificial
<220> FEATURE:
<223> OTHER INFORMATION: coding sequence for SEQ ID NO:11

<400> SEQUENCE: 12
atgtccactc cattgacttt gttgatcggt acctgtgtca ctggtttgtt cttgtacgtt      60
ttgttgaaca gatgtaccag aaacccaaac agattgccac caggtccaac tccatggcca     120
gtcgtcggta acttgccaca cttgggtact atcccacacc actctttggc tgctatggct     180
aagaagtacg gtccattgat gcacttgaga ttgggtttcg tcgacgtcgt tgttgccgcc     240
tccgcctccg tcgccgctca attcttaaag actcacgacg ctaacttcgc cgatagacca     300
ccaaactccg gtgccaagca catcgcttac aactaccaag atttggtttt cgctccatac     360
ggtccaagat ggagaatgtt gagaaagatt gttctgttc acttgttctc caccaaggct      420
ttggatgatt tcagacacgt cagacaagaa gaagttgcta tcttggctag gctttggtc      480 ggtgccggta gtctccagt taagttgggt caattgttga cgtttgtac cactaacgct       540 ttggctagag ttatgttggg tagaagagtt ttcgactccg gtgatgctca agctgatgaa     600
ttcaaggaca tggttgttga attgatggtt ttggccggtg aattcaacat cggtgacttc     660
atcccagttt ggactggtt ggacttgcaa ggtgttacta agaagatgaa gaagttgcac      720
gctaagttcg actctttctt gaacactatc ttggaagaac acaagaccgg tgccggtgac     780
ggtgtcgctt ctggtaaggt tgacttgttg tctactttga tttctttgaa ggatgacgct     840
gatggtgaag gtggtaagtt gtctgacatt gaaatcaagg ctttgttgtt gaacttgttc     900
actgctggta ctgacacttc ttcttctact attgaatggg ctatcgctga attgattaga     960
aacccacaat gttgaaccaa gccagaaag gaaatggaca ccatcgttgg tcaagacaga    1020
ttggttaccg aatctgactt gggtcaattg actttcttgc aagccattat caaggaaact    1080
ttcagattgc acccatctac cccattgtct ttgccaagaa tggctttgga atcttgtgaa    1140
gttggtggtt actacatccc aaagggttcc actttgttgg ttaacgtttg gccatttct     1200 agagatccaa agatttgggc cgatccattg gaattccaac aactagatt cttgccaggt     1260 ggtgaaaagc caaacactga tatcaagggt aacgatttcg aagtcatccc attcggtgcc    1320
ggtagaagaa tttgtgtcgg tatgtctttg ggtttgagaa tggtccaatt gttgactgct    1380
accttgatcc acgccttcga ttgggaattg gctgatggtt tgaacccaaa gaagttgaac    1440
```

```
atggaagaag cttacggttt gaccttgcaa agagccgctc cattggttgt tcacccaaga    1500
ccaagattgg ccccacacgt ttacgaaact actaaggtct aa                      1542
```

<210> SEQ ID NO 13
<211> LENGTH: 515
<212> TYPE: PRT
<213> ORGANISM: Osteospermum hybrid cultivar

<400> SEQUENCE: 13

```
Met Ser Thr Ile Leu Pro Leu Val Leu Tyr Ser Cys Ile Thr Gly Leu
1               5                   10                  15

Val Ile Tyr Val Leu Leu Asn Leu Arg Thr Arg His Ser Asn Arg Leu
            20                  25                  30

Pro Pro Gly Pro Thr Pro Trp Pro Ile Val Gly Asn Leu Pro His Leu
        35                  40                  45

Gly Val Val Pro His His Ser Leu Ala Ala Met Ala Glu Lys Tyr Gly
    50                  55                  60

Pro Leu Met His Leu Arg Leu Gly Phe Val Asp Val Val Ala Ala
65                  70                  75                  80

Ser Ala Val Ala Ala Gln Phe Leu Lys Val His Asp Ala Asn Phe
            85                  90                  95

Ala Ser Arg Pro Pro Asn Ser Gly Ala Lys His Ile Ala Tyr Asn Tyr
            100                 105                 110

Gln Asp Leu Val Phe Ala Pro Tyr Tyr Gly Pro Arg Trp Arg Met Leu
            115                 120                 125

Arg Lys Ile Cys Ser Val His Leu Phe Ser Ser Lys Ala Leu Asp Asp
        130                 135                 140

Phe Arg His Val Arg Gln Glu Glu Val Ala Ile Leu Thr Arg Ala Leu
145                 150                 155                 160

Ile Gly Ala Gly Asp Ser Pro Val Lys Leu Gly Gln Leu Leu Asn Val
                165                 170                 175

Cys Thr Thr Asn Ala Leu Ala Arg Val Met Leu Gly Lys Arg Val Phe
            180                 185                 190

Gly Asp Arg Ser Gly Gly Gly Asp Pro Lys Ala Asp Glu Phe Lys Asp
        195                 200                 205

Met Val Glu Val Met Glu Leu Ala Gly Glu Phe Asn Ile Gly Asp
    210                 215                 220

Phe Ile Pro Val Leu Asp Ser Leu Asp Leu Gln Gly Ile Ala Lys Lys
225                 230                 235                 240

Met Lys Glu Leu His Val Arg Phe Asp Ser Phe Leu Gly Lys Ile Leu
                245                 250                 255

Glu Glu His Lys Thr Gly Asn Gly Gly Ala Ser Ser Gln His Thr Asp
            260                 265                 270

Leu Leu Thr Thr Leu Ile Ser Leu Lys Asp Asp Thr Asp Glu Glu Gly
        275                 280                 285

Gly Lys Leu Ser Asp Ile Glu Ile Lys Ala Leu Leu Leu Asn Leu Phe
    290                 295                 300

Thr Ala Gly Thr Asp Thr Ser Ser Ser Thr Val Glu Trp Ala Ile Ala
305                 310                 315                 320

Glu Leu Ile Arg His Pro Gln Leu Leu Lys Gln Ala Gln Glu Glu Ile
                325                 330                 335

Asp Asn Val Val Gly Arg Asp His Leu Val Thr Glu Leu Asp Leu Thr
            340                 345                 350
```

```
Gln Leu Pro Phe Leu Gln Ala Ile Val Lys Glu Thr Phe Arg Leu His
            355                 360                 365
Pro Ser Thr Pro Leu Ser Leu Pro Arg Ile Ala Ser Glu Ser Cys Glu
        370                 375                 380
Val Asn Gly Tyr His Ile Pro Lys Gly Ser Thr Leu Leu Val Asn Val
385                 390                 395                 400
Trp Ala Ile Ala Arg Asp Pro Lys Met Trp Ser Glu Pro Leu Glu Phe
                405                 410                 415
Arg Pro Ala Arg Phe Leu Pro Gly Gly Glu Lys Pro Asp Ala Asp Val
            420                 425                 430
Lys Gly Asn Asp Phe Glu Val Ile Pro Phe Gly Ala Gly Arg Arg Ser
        435                 440                 445
Cys Ala Gly Met Ser Leu Gly Leu Arg Met Val Gln Leu Leu Val Ala
    450                 455                 460
Thr Leu Val Gln Thr Phe Asp Trp Glu Leu Ala Asn Gly Leu Lys Pro
465                 470                 475                 480
Glu Lys Leu Asn Met Glu Glu Ala Tyr Gly Leu Thr Leu Gln Arg Ala
                485                 490                 495
Ala Pro Leu Leu Val His Pro Lys Pro Arg Leu Ala Pro His Val Tyr
            500                 505                 510
Gly Ser Asn
        515

<210> SEQ ID NO 14
<211> LENGTH: 1548
<212> TYPE: DNA
<213> ORGANISM: artificial
<220> FEATURE:
<223> OTHER INFORMATION: coding sequence for SEQ ID NO: 13

<400> SEQUENCE: 14
atgtccacca ttttgccatt ggttttgtac tcttgtatca ctggtttggt tatctacgtt      60
ttgttgaact tgagaaccag acactctaac agattgccac caggtccaac tccatggcca     120
atcgtcggta acttgccaca cttgggtgtt gttccacacc actctttggc tgctatggct     180
gaaaagtacg gtccattgat gcacttgaga ttgggtttcg ttgacgttgt tgttgctgct     240
tctgctgccg ttgctgctca attcttgaag gttcacgatg ctaacttcgc ttctagacca     300
ccaaactccg gtgctaagca catcgcttac aactaccaag acttggtttt cgctccatac     360
tacggtccaa gatggagaat gttgagaaag atttgttccg ttcacttgtt ctcttctaag     420
gctttggatg atttcagaca cgtcagacaa gaagaagttg ctatcttgac tagagctttg     480
atcggtgccg gtgactctcc agttaagttg ggtcaattgt gaacgtttg tactactaac     540 gctttggcta gagttatgtt gggtaagaga gttttcggtg acagatctgg tggtggtgat     600
ccaaaggctg atgaattcaa ggatatggtt gttgaagtta tggaattggc cggtgaattc     660
aacatcggtg atttcatccc agttttggat tctttggatt gcaaggtat cgctaagaag     720 atgaaggaat gcacgttag attcgattct ttcttgggta gatcttgga agaacacaag     780 accggtaacg tggtgcttc ttctcaacac actgacttgt tgactacctt gatttctttg     840
aaggatgata ctgatgaaga aggtggtaag ttgtctgaca ttgaaatcaa ggctttgttg     900
ttgaacttgt tcactgctgg tactgacact tcttcttcta ccgttgaatg ggctatcgcc     960
gaattgatta gacacccaca attgttgaag caagccaag aagaaatcga caacgttgtt    1020
ggtagagatc acttggttac cgaattggac ttgacccaat tgccattctt gcaagccatt    1080
```

-continued

```
gttaaggaaa ccttcagatt gcacccatct actccattgt ctttgccaag aattgcttcc    1140
gaatcttgtg aagtcaacgg ttaccacatc ccaaagggtt ccactttgtt ggttaacgtt    1200
tgggccatcg ccagagatcc aaagatgtgg tccgaaccat tggaattcag accagccaga    1260
ttcttgccag gtggtgaaaa gccagatgct gatgttaagg gtaacgattt cgaagtcatc    1320
ccattcggtg ccggtagaag atcttgtgct ggtatgtctt tgggtttgag aatggttcaa    1380
ttgttggttg ctactttggt tcaaaccttc gactgggaat tggctaacgg tttgaagcca    1440
gaaaagttga acatggaaga agcttacggt ttgactttgc aaagagctgc tccattgttg    1500
gttcacccaa agccaagatt ggctccacac gtttacggtt ctaactaa              1548
```

<210> SEQ ID NO 15
<211> LENGTH: 539
<212> TYPE: PRT
<213> ORGANISM: Citrus clementina

<400> SEQUENCE: 15

```
Met Ser Gln Pro Leu Val Arg Leu Leu Val Pro Phe Leu Arg Phe Leu
1               5                   10                  15

Trp Glu Thr Lys Gln Arg Ala Met Ser Thr Leu Pro Leu Leu Ile Leu
            20                  25                  30

Tyr Thr Ser Leu Leu Ala Ile Val Ile Ser Phe Leu Phe Ser Leu Leu
        35                  40                  45

Arg Asn Arg Arg Arg His Ser Ser His Arg Leu Pro Pro Gly Pro Lys
    50                  55                  60

Pro Trp Pro Ile Val Gly Asn Leu Pro His Leu Gly Pro Met Pro His
65                  70                  75                  80

Gln Ser Ile Ala Gly Leu Ala Arg Thr His Gly Pro Leu Met Tyr Leu
                85                  90                  95

Arg Leu Gly Phe Val Asp Val Val Ala Ala Ser Ala Ser Val Ala
            100                 105                 110

Ala Gln Phe Leu Lys Ile His Asp Ser Asn Phe Ser Asn Arg Pro Pro
        115                 120                 125

Asn Ser Gly Ala Lys His Ile Ala Tyr Asn Tyr Gln Asp Ile Val Phe
    130                 135                 140

Arg Pro Tyr Gly Pro Arg Trp Arg Met Leu Arg Lys Ile Ser Ser Val
145                 150                 155                 160

His Leu Phe Ser Gly Lys Ala Leu Asp Asp Tyr Arg His Val Arg Gln
                165                 170                 175

Glu Glu Met Ala Val Leu Thr Arg Ala Leu Ala Ser Ala Gly Thr Glu
            180                 185                 190

Pro Val Asn Leu Ala Gln Arg Leu Asn Leu Cys Val Val Asn Ala Leu
        195                 200                 205

Gly Arg Val Met Leu Gly Phe Arg Val Phe Gly Asp Gly Thr Gly Gly
    210                 215                 220

Ser Asp Pro Arg Ala Asp Glu Phe Lys Ser Met Val Val Glu Leu Met
225                 230                 235                 240

Val Leu Ala Gly Val Phe Asn Val Gly Asp Phe Val Pro Ala Leu Glu
                245                 250                 255

Arg Leu Asp Leu Gln Gly Val Ala Arg Lys Met Lys Lys Leu His Lys
            260                 265                 270

Arg Phe Asp Val Phe Leu Ser Asp Ile Leu Glu Glu Arg Lys Met Asn
        275                 280                 285

Gly Arg Asp Gly Gly Asn Lys Leu Thr Asp Leu Leu Gly Thr Leu Ile
```

290                 295                 300
Ser Leu Met Asp Asp Ala Asn Gly Glu Glu Lys Leu Thr Glu Thr Glu
305                 310                 315                 320

Ile Lys Ala Leu Leu Leu Asn Met Phe Thr Ala Gly Thr Asp Thr Ser
                325                 330                 335

Ser Ser Thr Ile Glu Trp Ala Ile Ala Glu Leu Ile Arg His Pro Lys
                340                 345                 350

Val Trp Ala Gln Val Gln Gln Glu Leu Asp Ser Val Val Gly Arg Asp
                355                 360                 365

Arg Leu Val Thr Glu Leu Asp Leu Pro Gln Leu Thr Tyr Leu Gln Ala
            370                 375                 380

Val Ile Lys Glu Ile Phe Arg Leu His Pro Ser Thr Pro Leu Ser Leu
385                 390                 395                 400

Pro Arg Ala Ala Ser Glu Ser Cys Lys Ile Asn Gly Tyr Asp Ile Pro
                405                 410                 415

Lys Gly Ser Thr Leu Leu Val Asn Ile Trp Ala Ile Ala Arg Asp Pro
                420                 425                 430

Asn Glu Trp Ala Asp Pro Leu Glu Phe Arg Pro Glu Arg Phe Leu Pro
                435                 440                 445

Gly Gly Glu Lys Tyr Asn Val Asp Val Lys Gly Asn Asp Tyr Glu Leu
            450                 455                 460

Ile Pro Phe Gly Ala Gly Arg Arg Ile Cys Ala Gly Leu Ser Trp Gly
465                 470                 475                 480

Leu Arg Met Val Gln Leu Gly Thr Ala Thr Leu Ala His Ala Phe Asn
                485                 490                 495

Trp Glu Leu Pro Gly Gly Leu Lys Pro Glu Lys Leu Asn Met Asp Glu
                500                 505                 510

Ala Tyr Gly Leu Thr Leu Gln Arg Ala Ala Pro Leu Val Val His Pro
            515                 520                 525

Arg Pro Arg Leu Ser Pro Asn Ala Tyr Gln Ala
    530                 535

<210> SEQ ID NO 16
<211> LENGTH: 1620
<212> TYPE: DNA
<213> ORGANISM: artificial
<220> FEATURE:
<223> OTHER INFORMATION: coding sequence for SEQ ID NO: 15

<400> SEQUENCE: 16
atgtcccaac cattggttag attgttggtt ccattcttga gattcttgtg ggaaactaag     60
caaagagcta tgtctacttt gccattgttg atcttgtaca cttctttgtt ggctattgtc    120
atttctttct tgttctcttt gttgagaaac agaaggagac actcctccca cagattgcca    180
ccaggtccaa agccatggcc aatcgtcggt aacttgccac acttgggtcc aatgccacac    240
caatccatcg ctggtttggc cagaacccac ggtccattga tgtacttgag attgggtttc    300
gttgacgtcg tcgttgccgc ttccgcttcc gttgctgccc aattcttgaa gatccacgat    360
tccaacttct ccaacagacc accaaactcc ggtgccaagc acatcgctta caactaccaa    420
gacatcgttt tcagaccata cggtccaaga tggagaatgt tgagaaagat ctcttccgtt    480
cacttgttct ccggtaaggc cttggatgac tacagacacg ttagacaaga gaaatggct    540 gttttgacta gagctttggc ttctgctggt actgaaccag ttaacttggc tcaaagattg    600
aacttgtgtg ttgttaacgc cttgggtaga gttatgttgg gtttcagagt tttcggtgac    660

```
ggtaccggtg gttctgaccc aagagctgac gaattcaagt ctatggttgt tgaattgatg    720
gttttggctg gtgttttcaa cgtcggtgat tcgtcccag ccttggaaag attggacttg    780
caaggtgttg ctagaaagat gaagaagttg cacaagagat tcgatgtttt cttgtctgat    840
atcttggaag aaagaaagat gaacggtaga gatggtggta acaagttgac tgacttgttg    900
ggtaccttga tttctttgat ggatgatgct aacggtgaag aaaagttgac tgaaactgaa    960
atcaaggctt tgttgttgaa catgttcact gctggtaccg acacttcttc ttctactatc   1020
gaatgggcca ttgctgaatt gatcagacac ccaaaggtct gggcccaagt ccaacaagaa   1080
ttggattctg ttgttggtag agatagattg gtcaccgaat tggacttgcc acaattgact   1140
tacttgcaag ccgttatcaa ggaaatcttc agattgcacc atctactcc attgtctttg    1200 ccaagagctg cttccgaatc ttgtaagatc aacggttacg atattccaaa gggttccact   1260 tgttggtca acatctgggc cattgctaga gatccaaacg aatgggccga cccattggaa   1320
ttcagaccag aaagattctt gccaggtggt gaaaagtaca acgttgatgt taagggtaac   1380
gattacgaat tgatcccatt cggtgccggt agaagaattt gtgctggttt gtcttggggt   1440
ttgagaatgg ttcaattggg tactgctact ttggcccacg ctttcaactg gaattgcca    1500 ggtggtttga agccagaaaa gttgaacatg gacgaagctt acggtttgac cttgcaaaga   1560
gctgctccat ggttgttca cccaagacca agattgtctc caaacgctta ccaagcttaa   1620
```

<210> SEQ ID NO 17
<211> LENGTH: 517
<212> TYPE: PRT
<213> ORGANISM: Citrus sinensis

<400> SEQUENCE: 17

```
Met Ser Ser Thr Leu Pro Leu Leu Ile Leu Tyr Thr Ser Leu Leu Ala
1               5                   10                  15

Ile Val Ile Ser Phe Leu Phe Ser Leu Leu Arg Asn Arg Arg Arg His
            20                  25                  30

Ser Ser His Arg Leu Pro Pro Gly Pro Lys Pro Trp Pro Ile Val Gly
        35                  40                  45

Asn Leu Pro His Leu Gly Pro Met Pro His Gln Ser Ile Ala Gly Leu
    50                  55                  60

Ala Arg Thr His Gly Pro Leu Met Tyr Leu Arg Leu Gly Phe Val Asp
65                  70                  75                  80

Val Val Val Ala Ala Ser Ala Ser Val Ala Ala Gln Phe Leu Lys Ile
                85                  90                  95

His Asp Ser Asn Phe Ser Asn Arg Pro Pro Asn Ser Gly Ala Lys His
            100                 105                 110

Ile Ala Tyr Asn Tyr Gln Asp Ile Val Phe Arg Pro Tyr Gly Pro Arg
        115                 120                 125

Trp Arg Met Leu Arg Lys Ile Ser Ser Val His Leu Phe Ser Gly Lys
    130                 135                 140

Ala Leu Asp Asp Tyr Arg His Val Arg Gln Glu Met Ala Val Leu
145                 150                 155                 160

Ala Arg Ala Leu Ala Ser Ala Gly Thr Glu Pro Val Asn Leu Ala Gln
                165                 170                 175

Arg Leu Asn Leu Cys Val Val Asn Ala Leu Gly Arg Val Met Leu Gly
            180                 185                 190

Phe Arg Val Phe Gly Asp Gly Thr Gly Gly Ser Asp Pro Arg Ala Asp
        195                 200                 205
```

```
Glu Phe Lys Ser Met Val Val Glu Leu Met Val Leu Ala Gly Val Phe
210                 215                 220

Asn Val Gly Asp Phe Val Pro Ala Leu Glu Arg Leu Asp Leu Gln Gly
225                 230                 235                 240

Val Ala Arg Lys Met Lys Lys Leu His Lys Arg Phe Asp Val Phe Leu
                245                 250                 255

Ser Asp Ile Leu Glu Glu Arg Lys Met Asn Gly Arg Asp Gly Gly Asn
                260                 265                 270

Lys His Thr Asp Leu Leu Gly Thr Leu Ile Ser Leu Met Asp Asp Ala
                275                 280                 285

Asn Gly Glu Glu Lys Leu Thr Glu Thr Glu Ile Lys Ala Leu Leu Leu
290                 295                 300

Asn Met Phe Thr Ala Gly Thr Asp Thr Ser Ser Thr Ile Glu Trp
305                 310                 315                 320

Ala Ile Ala Glu Leu Ile Arg His Pro Lys Val Arg Ala Gln Val Gln
                325                 330                 335

Gln Glu Leu Asp Ser Val Val Gly Arg Asp Arg Leu Val Thr Glu Leu
                340                 345                 350

Asp Leu Pro Gln Leu Thr Tyr Leu Gln Ala Val Ile Lys Glu Ile Phe
                355                 360                 365

Arg Leu His Pro Ser Thr Pro Leu Ser Leu Pro Arg Ala Ala Ser Glu
370                 375                 380

Ser Cys Lys Ile Asn Gly Tyr Asp Ile Pro Lys Gly Ser Thr Leu Leu
385                 390                 395                 400

Val Asn Ile Trp Ala Ile Ala Arg Asp Pro Asn Glu Trp Ala Asp Pro
                405                 410                 415

Leu Glu Phe Arg Pro Glu Arg Phe Leu Pro Gly Gly Glu Lys Tyr Asn
                420                 425                 430

Val Asp Val Lys Gly Asn Asp Tyr Glu Leu Ile Pro Phe Gly Ala Gly
                435                 440                 445

Arg Arg Ile Cys Ala Gly Leu Ser Trp Gly Leu Arg Met Val Gln Leu
                450                 455                 460

Gly Thr Ala Thr Leu Ala His Ala Phe Asn Trp Glu Leu Pro Gly Gly
465                 470                 475                 480

Leu Lys Pro Glu Lys Leu Ser Met Asp Glu Ala Tyr Gly Leu Thr Leu
                485                 490                 495

Gln Arg Ala Ala Pro Leu Val Val His Pro Arg Pro Arg Leu Ser Pro
                500                 505                 510

Asn Ala Tyr Gln Ala
        515

<210> SEQ ID NO 18
<211> LENGTH: 1554
<212> TYPE: DNA
<213> ORGANISM: artificial
<220> FEATURE:
<223> OTHER INFORMATION: coding sequence for SEQ ID NO: 17

<400> SEQUENCE: 18
atgtcctcta ctttgccatt gttgatcttg tacacttctt gttggctat tgtcatttct      60 ttcttgttct ctttgttgag aaacagaagg agacactcct cccacagatt gccaccaggt     120
ccaaagccat ggccaatcgt cggtaacttg ccacacttgg gtccaatgcc acaccaatcc     180
atcgctggtt ggccagaaac ccacggtcca ttgatgtact tgagattggg ttcgttgac     240 gtcgtcgttg ccgcttctgc ttccgttgct gccaattct tgaagatcca cgattccaac     300
```

```
ttctccaaca gaccaccaaa ctccggtgcc aagcacatcg cttacaacta ccaagacatc      360
gttttcagac catacggtcc aagatggaga atgttgagaa agatctcttc cgttcacttg      420
ttctccggta aggccttgga tgactacaga cacgttagac aagaagaaat ggctgttttg      480
gctagagctt tggcttctgc tggtactgaa ccagttaact tggctcaaag attgaacttg      540
tgtgttgtta acgccttggg tagagttatg ttgggtttca gagttttcgg tgacggtacc      600
ggtggttctg acccaagagc tgacgaattc aagtctatgg ttgttgaatt gatggttttg      660
gctggtgttt tcaacgtcgg tgacttcgtc ccagccttgg aaagattgga cttgcaaggt      720
gttgctagaa agatgaagaa gttgcacaag agattcgatg ttttcttgtc tgatatcttg      780
gaagaaagaa agatgaacgg tagagatggt ggtaacaagc acactgactt gttgggtacc      840
ttgatttctt tgatggatga tgctaacggt gaagaaaagt tgactgaaac tgaaatcaag      900
gctttgttgt tgaacatgtt cactgctggt accgacactt cttcttctac tatcgaatgg      960
gccattgctg aattgatcag acacccaaag gtcagagccc aagtccaaca agaattggat     1020
tctgttgttg gtagagatag attggtcacc gaattggact tgccacaatt gacttacttg     1080
caagccgtta tcaaggaaat cttcagattg cacccatcta ctccattgtc tttgccaaga     1140
gctgcttccg aatcttgtaa gatcaacggt tacgatattc caaagggttc cactttgttg     1200
gtcaacatct gggccattgc tagagatcca aacgaatggg ccgacccatt ggaattcaga     1260
ccagaaagat tcttgccagg tgtgaaaag tacaacgttg atgttaaggg taacgattac     1320
gaattgatcc cattcggtgc cggtagaaga atttgtgctg gtttgtcttg ggtttgaga     1380
atggttcaat tgggtactgc tactttggcc cacgctttca ctgggaatt gccaggtggt     1440
ttgaagccag aaaagttgtc tatggacgaa gcttacggtt tgaccttgca aagagctgct     1500
ccattggttg ttcacccaag accaagattg tctccaaacg cttaccaagc ttaa           1554
```

<210> SEQ ID NO 19
<211> LENGTH: 513
<212> TYPE: PRT
<213> ORGANISM: Pilosella officinarum

<400> SEQUENCE: 19

```
Met Ser Thr Leu Leu Ser Leu Ile Ile Tyr Leu Cys Ile Thr Gly Val
1               5                   10                  15

Thr Ala Tyr Val Leu Val Asn Leu Arg Thr Arg Ala Asn Arg Leu
            20                  25                  30

Pro Pro Gly Pro Thr Pro Trp Pro Ile Val Gly Asn Leu Pro His Leu
        35                  40                  45

Gly Thr Ile Pro His His Ser Leu Ala Asp Leu Ala Thr Arg Tyr Gly
    50                  55                  60

Pro Leu Met His Leu Arg Leu Gly Phe Val Asp Val Val Ala Ala
65                  70                  75                  80

Ser Ala Ser Val Ala Ala Gln Phe Leu Lys Thr His Asp Ala Asn Phe
                85                  90                  95

Ala Ser Arg Pro Pro Asn Ser Gly Ala Lys His Met Ala Tyr Asn Tyr
            100                 105                 110

Gln Asp Leu Val Phe Ala Pro Tyr Gly Pro Arg Trp Arg Met Leu Arg
        115                 120                 125

Lys Ile Cys Ser Val His Leu Phe Ser Ala Lys Ser Leu Asp Asp Phe
    130                 135                 140

Arg His Val Arg Gln Glu Glu Val Ala Ile Leu Thr Arg Ala Leu Val
```

```
            145                 150                 155                 160
        Gly Ala Gly Lys Ser Thr Val Lys Leu Gly Gln Leu Leu His Val Cys
                        165                 170                 175

Thr Thr Asn Ala Leu Val Arg Val Met Leu Gly Arg Arg Val Phe Gly
                        180                 185                 190

Asp Gly Ser Gly Gly Gly Asp Pro Lys Ala Asp Glu Phe Lys Asn Met
                        195                 200                 205

Val Ile Glu Met Met Val Leu Ala Gly Glu Phe Asn Leu Gly Asp Phe
        210                 215                 220

Ile Pro Val Leu Asp Leu Leu Asp Leu Gln Gly Val Thr Lys Lys Met
        225                 230                 235                 240

Lys Lys Leu His Thr Arg Phe Asp Ser Phe Leu Asn Ser Ile Leu Glu
                        245                 250                 255

Glu His Arg Thr Ser Ser Gly Gly Ala Ser Gly His Val Asp Leu Leu
                        260                 265                 270

Ser Thr Leu Ile Ser Leu Lys Asp Glu Ala Asp Gly Glu Gly Gly Lys
                        275                 280                 285

Leu Thr Asp Thr Glu Ile Lys Ala Leu Leu Leu Asn Leu Phe Val Ala
                        290                 295                 300

Gly Thr Asp Thr Ser Ser Ser Thr Val Glu Trp Ala Ile Ala Glu Leu
        305                 310                 315                 320

Ile Arg Asn Pro Gln Leu Leu Lys Gln Ala Gln Gln Glu Leu Asp Thr
                        325                 330                 335

Val Val Gly Gln Gly Arg Leu Val Asn Glu Ser Asp Leu Ser Gln Leu
                        340                 345                 350

Thr Phe Leu Gln Ala Ile Val Lys Glu Thr Phe Arg Leu His Pro Ser
                        355                 360                 365

Thr Pro Leu Ser Leu Pro Arg Ile Ala Ser Glu Ser Cys Glu Ile Asn
                        370                 375                 380

Gly Tyr Asn Ile Pro Lys Gly Ser Thr Leu Leu Val Asn Val Trp Ala
        385                 390                 395                 400

Ile Ala Arg Asp Pro Lys Met Trp Thr Glu Pro Leu Glu Phe Arg Pro
                        405                 410                 415

Ser Arg Phe Leu Pro Asp Gly Glu Lys Pro Asn Ala Asp Val Lys Gly
                        420                 425                 430

Asn Asp Phe Glu Val Ile Pro Phe Gly Ala Gly Arg Arg Ile Cys Ala
                        435                 440                 445

Gly Met Ser Leu Gly Leu Arg Met Val Gln Leu Leu Thr Ala Thr Leu
        450                 455                 460

Ile Gln Ala Phe Asp Trp Glu Leu Ala Asn Gly Leu Glu Pro Arg Asn
        465                 470                 475                 480

Leu Asn Met Glu Glu Ala Tyr Gly Leu Thr Leu Gln Arg Ala Gln Pro
                        485                 490                 495

Leu Met Val His Pro Arg Pro Arg Leu Ala Pro His Val Tyr Gly Thr
                        500                 505                 510

Gly

<210> SEQ ID NO 20
<211> LENGTH: 1542
<212> TYPE: DNA
<213> ORGANISM: artificial
<220> FEATURE:
<223> OTHER INFORMATION: coding sequence for SEQ ID NO: 19

<400> SEQUENCE: 20
```

```
atgtccacct tgttgtcctt gatcatctac ttgtgtatca ctggtgttac tgcctacgtt      60
ttggttaact tgagaactag aagagctaac agattgccac caggtccaac cccatggcca     120
atcgtcggta acttgccaca cttgggtact attccacacc actctttggc tgatttggct     180
actagatacg gtccattgat gcacttgaga ttgggtttcg ttgacgttgt tgttgccgcc     240
tctgcttccg tcgctgctca attcttaaag actcacgacg ctaacttcgc ttctagacca     300
ccaaactctg gtgctaagca catggcttac aactaccaag atttggtttt cgctccatac     360
ggtccaagat ggagaatgtt gagaaagatt tgttccgttc acttgttctc tgccaagtct     420
ttggatgatt tcagacacgt tagacaagaa gaagttgcta tcttgactag agctttggtc     480
ggtgccggta agtctactgt taagttgggt caattgttgc acgtttgtac cactaacgct     540
ttggttagag ttatgttggg tagaagagtt ttcggtgatg gttctggtgg tggtgatcca     600
aaggctgatg aattcaagaa catggttatt gaaatgatgg ttttggccgg tgaattcaac     660
ttgggtgatt tcatcccagt tttggatttg tggacttgc aaggtgttac taagaagatg      720
aagaagttgc acactagatt cgattctttc ttgaactcta tcttggaaga cacagaact      780
tcttctggtg gtgcttctgg tcacgtcgat ttgttgtcta ctttgatttc tttgaaggat     840
gaagccgatg gtgaaggtgg taagttgact gacactgaaa ttaaggcttt gttgttgaac     900
ttgttcgttg ctggtactga cacttcttct tctaccgttg aatgggctat cgctgaattg     960
attagaaacc cacaattgtt gaagcaagcc caacaagaat tggacactgt tgttggtcaa    1020
ggtagattgg ttaacgaatc tgacttgtct caattgaccc tcttgcaagc cattgttaag    1080
gaaactttca gattgcaccc atctactcca ttgtccttgc caagaatcgc ttccgaatct    1140
tgtgaaatca acggttacaa cattccaaag ggttccactt tgttggttaa cgtttgggcc    1200
atcgctagag atccaaagat gtggaccgaa ccattggaat tcagaccatc cagattcttg    1260
ccagacggtg aaaagccaaa cgctgatgtt aagggtaacg atttcgaagt catcccattc    1320
ggtgctggta agaatttg tgctggtatg tctttgggtt tgagaatggt ccaattgttg      1380
accgctactt tgattcaagc cttcgattgg gaattggcta acggtttgga accaagaaac    1440
ttgaacatgg aagaagccta cggtttgacc ttgcaaagag ctcaaccatt gatggttcac    1500
ccaagaccaa gattggcccc acacgtttac ggtactggtt aa                       1542
```

<210> SEQ ID NO 21
<211> LENGTH: 406
<212> TYPE: PRT
<213> ORGANISM: Streptomyces avermitilis

<400> SEQUENCE: 21

```
Met Ser Ala Ala Ala Phe Asp Leu Ala Phe Asp Pro Trp Asp Pro Ala
1               5                   10                  15

Phe Leu Ala Asp Pro Tyr Pro Ala Tyr Ala Asp Leu Arg Ala Lys Gly
            20                  25                  30

Arg Val His Tyr Tyr Glu Pro Thr Asn Gln Trp Leu Val Pro His His
        35                  40                  45

Ala Asp Val Ser Ala Leu Leu Arg Asp Arg Arg Leu Gly Arg Ala Tyr
    50                  55                  60

Gln His Arg Tyr Thr His Glu Asp Phe Gly Arg Thr Ala Pro Pro Ala
65                  70                  75                  80

Glu His Glu Pro Phe His Thr Leu Asn Asp His Gly Met Leu Asp Leu
                85                  90                  95
```

```
Glu Pro Pro Asp His Thr Arg Ile Arg Arg Leu Val Ser Lys Ala Phe
                100                 105                 110

Thr Pro Arg Thr Val Glu Gln Leu Lys Pro Tyr Val Ala Lys Leu Ala
            115                 120                 125

Gly Glu Leu Val Asp Arg Leu Val Ala Ala Gly Gly Asp Leu Leu
        130                 135                 140

Ala Asp Val Ala Glu Pro Leu Pro Val Ala Val Ile Ala Glu Met Leu
145                 150                 155                 160

Gly Ile Pro Glu Ser Asp Arg Ala Pro Leu Arg Pro Trp Ser Ala Asp
                165                 170                 175

Ile Cys Gly Met Tyr Glu Leu Asn Pro Pro Lys Asp Val Ala Ala Lys
            180                 185                 190

Ala Val Arg Ala Ser Val Glu Phe Ser Asp Tyr Leu Arg Glu Leu Ile
        195                 200                 205

Ala Glu Arg Arg Lys Glu Pro Gly Asp Asp Leu Ile Ser Gly Leu Ile
    210                 215                 220

Ala Ala His Asp Glu Gly Asp Arg Leu Thr Glu Gln Glu Met Ile Ser
225                 230                 235                 240

Thr Cys Val Leu Leu Leu Asn Ala Gly His Glu Ala Thr Val Asn Ala
                245                 250                 255

Thr Val Asn Gly Trp Tyr Ala Leu Phe Arg Asn Pro Asp Gln Leu Ala
            260                 265                 270

Ala Leu Arg Ala Asp His Ser Leu Val Pro Ala Ala Val Glu Glu Leu
        275                 280                 285

Met Arg Tyr Asp Thr Pro Leu Gln Leu Phe Glu Arg Trp Val Leu Asp
    290                 295                 300

Glu Ile Glu Ile Asp Gly Thr Thr Val Pro Arg Gly Ala Glu Ile Ala
305                 310                 315                 320

Met Leu Phe Gly Ser Ala Asn His Asp Pro Glu Val Phe Arg Asn Pro
                325                 330                 335

Glu Lys Leu Asp Leu Thr Arg Glu Asp Asn Pro His Ile Ser Phe Ser
            340                 345                 350

Ala Gly Ile His Tyr Cys Ile Gly Ala Pro Leu Ala Arg Ile Glu Leu
        355                 360                 365

Ala Ala Ser Met Thr Ala Leu Leu Glu Lys Ala Pro Thr Leu Gly Leu
    370                 375                 380

Val Ala Glu Pro Lys Arg Lys Pro Asn Phe Val Ile Arg Gly Leu Glu
385                 390                 395                 400

Gly Leu Ser Val Ala Val
                405

<210> SEQ ID NO 22
<211> LENGTH: 1221
<212> TYPE: DNA
<213> ORGANISM: artificial
<220> FEATURE:
<223> OTHER INFORMATION: coding sequence for SEQ ID NO: 21

<400> SEQUENCE: 22
atgtccgctg ctgctttcga cttggccttc gacccatggg acccagcttt cttggccgac      60
ccatacccag cctacgccga tttgagagcc aagggtagag ttcactacta cgaaccaact     120
aaccaatggt tggttccaca ccacgctgac gtttctgctt tgttgagaga cagaagattg     180
ggtagagctt accaacacag atacactcac gaagatttcg gtagaaccgc tccaccagct     240
gaacacgaac cattccacac cttgaacgac cacggtatgt tggacttgga accaccagac     300
```

-continued

```
cacaccagaa tcagaagatt ggtttctaag gctttcactc caagaaccgt tgaacaattg    360
aagccatacg ttgccaagtt ggccggtgaa ttggttgaca gattggtcgc tgctggtggt    420
ggtgatttgt tggctgatgt cgccgaacca ttgccagttg ccgtcatcgc gaaatgttg     480
ggtatcccag aatccgacag agccccatta agaccatggt ctgctgacat ctgtggtatg    540
tacgaattga acccaccaaa ggacgttgct gctaaggctg ttagagcttc tgttgaattc    600
tccgactact tgagagaatt gatcgccgaa agaagaaagg aaccaggtga cgatttgatc    660
tctggtttga tcgccgccca cgacgaaggt gacagattga ccgaacaaga aatgatctcc    720
acctgtgtct tgttgttgaa cgctggtcac gaagccaccg tcaacgccac tgtcaacggt    780
tggtacgcct tgttcagaaa cccagaccaa ttggccgcct gagagccga ccactctttg     840
gttccagccg ccgttgaaga attgatgaga tacgacactc cattgcaatt gttcgaaaga    900
tgggtcttgg acgaaatcga atcgacggt actactgtcc aagaggtgc tgaaatcgcc      960
atgttgttcg gttccgccaa ccacgaccca gaagttttca gaaacccaga aaagttggac   1020
ttgaccagag aagataaccc acacatttcc ttctctgctg gtatccacta ctgtatcggt   1080
gctccattgg ctagaatcga attggctgct tctatgactg ccttgttgga aaaggcccca   1140
actttgggtt tggttgctga accaaagaga aagccaaact tcgttatcag aggtttggaa   1200
ggtttgtctg tcgctgtcta a                                             1221
```

<210> SEQ ID NO 23
<211> LENGTH: 715
<212> TYPE: PRT
<213> ORGANISM: Catharanthus roseus

<400> SEQUENCE: 23

```
Met Ser Asp Ser Ser Glu Lys Leu Ser Pro Phe Glu Leu Met Ser
1               5                   10                  15

Ala Ile Leu Lys Gly Ala Lys Leu Asp Gly Ser Asn Ser Ser Asp Ser
            20                  25                  30

Gly Val Ala Val Ser Pro Ala Val Met Ala Met Leu Leu Glu Asn Lys
        35                  40                  45

Glu Leu Val Met Ile Leu Thr Thr Ser Val Ala Val Leu Ile Gly Cys
    50                  55                  60

Val Val Val Leu Ile Trp Arg Arg Ser Gly Ser Gly Lys Lys Val
65                  70                  75                  80

Val Glu Pro Pro Lys Leu Ile Val Pro Lys Ser Val Val Glu Pro Glu
                85                  90                  95

Glu Ile Asp Glu Gly Lys Lys Lys Phe Thr Ile Phe Gly Thr Gln
            100                 105                 110

Thr Gly Thr Ala Glu Gly Phe Ala Lys Ala Leu Ala Glu Glu Ala Lys
        115                 120                 125

Ala Arg Tyr Glu Lys Ala Val Ile Lys Val Ile Asp Ile Asp Asp Tyr
    130                 135                 140

Ala Ala Asp Asp Glu Glu Tyr Glu Glu Lys Phe Arg Lys Glu Thr Leu
145                 150                 155                 160

Ala Phe Phe Ile Leu Ala Thr Tyr Gly Asp Gly Glu Pro Thr Asp Asn
                165                 170                 175

Ala Ala Arg Phe Tyr Lys Trp Phe Val Glu Gly Asn Asp Arg Gly Asp
            180                 185                 190

Trp Leu Lys Asn Leu Gln Tyr Gly Val Phe Gly Leu Gly Asn Arg Gln
        195                 200                 205
```

```
Tyr Glu His Phe Asn Lys Ile Ala Lys Val Val Asp Glu Lys Val Ala
    210                 215                 220
Glu Gln Gly Gly Lys Arg Ile Val Pro Leu Val Leu Gly Asp Asp Asp
225                 230                 235                 240
Gln Cys Ile Glu Asp Asp Phe Ala Ala Trp Arg Glu Asn Val Trp Pro
                245                 250                 255
Glu Leu Asp Asn Leu Leu Arg Asp Glu Asp Thr Thr Val Ser Thr
                260                 265                 270
Thr Tyr Thr Ala Ala Ile Pro Glu Tyr Arg Val Val Phe Pro Asp Lys
    275                 280                 285
Ser Asp Ser Leu Ile Ser Glu Ala Asn Gly His Ala Asn Gly Tyr Ala
290                 295                 300
Asn Gly Asn Thr Val Tyr Asp Ala Gln His Pro Cys Arg Ser Asn Val
305                 310                 315                 320
Ala Val Arg Lys Glu Leu His Thr Pro Ala Ser Asp Arg Ser Cys Thr
                325                 330                 335
His Leu Asp Phe Asp Ile Ala Gly Thr Gly Leu Ser Tyr Gly Thr Gly
                340                 345                 350
Asp His Val Gly Val Tyr Cys Asp Asn Leu Ser Glu Thr Val Glu Glu
            355                 360                 365
Ala Glu Arg Leu Leu Asn Leu Pro Pro Glu Thr Tyr Phe Ser Leu His
370                 375                 380
Ala Asp Lys Glu Asp Gly Thr Pro Leu Ala Gly Ser Ser Leu Pro Pro
385                 390                 395                 400
Pro Phe Pro Pro Cys Thr Leu Arg Thr Ala Leu Thr Arg Tyr Ala Asp
                405                 410                 415
Leu Leu Asn Thr Pro Lys Lys Ser Ala Leu Leu Ala Leu Ala Ala Tyr
                420                 425                 430
Ala Ser Asp Pro Asn Glu Ala Asp Arg Leu Lys Tyr Leu Ala Ser Pro
                435                 440                 445
Ala Gly Lys Asp Glu Tyr Ala Gln Ser Leu Val Ala Asn Gln Arg Ser
450                 455                 460
Leu Leu Glu Val Met Ala Glu Phe Pro Ser Ala Lys Pro Pro Leu Gly
465                 470                 475                 480
Val Phe Phe Ala Ala Ile Ala Pro Arg Leu Gln Pro Arg Phe Tyr Ser
                485                 490                 495
Ile Ser Ser Ser Pro Arg Met Ala Pro Ser Arg Ile His Val Thr Cys
                500                 505                 510
Ala Leu Val Tyr Glu Lys Thr Pro Gly Gly Arg Ile His Lys Gly Val
            515                 520                 525
Cys Ser Thr Trp Met Lys Asn Ala Ile Pro Leu Glu Glu Ser Arg Asp
530                 535                 540
Cys Ser Trp Ala Pro Ile Phe Val Arg Gln Ser Asn Phe Lys Leu Pro
545                 550                 555                 560
Ala Asp Pro Lys Val Pro Val Ile Met Ile Gly Pro Gly Thr Gly Leu
                565                 570                 575
Ala Pro Phe Arg Gly Phe Leu Gln Glu Arg Leu Ala Leu Lys Glu Glu
                580                 585                 590
Gly Ala Glu Leu Gly Thr Ala Val Phe Phe Gly Cys Arg Asn Arg
            595                 600                 605
Lys Met Asp Tyr Ile Tyr Glu Asp Glu Leu Asn His Phe Leu Glu Ile
610                 615                 620
```

```
Gly Ala Leu Ser Glu Leu Leu Val Ala Phe Ser Arg Glu Gly Pro Thr
625                 630                 635                 640

Lys Gln Tyr Val Gln His Lys Met Ala Glu Lys Ala Ser Asp Ile Trp
                645                 650                 655

Arg Met Ile Ser Asp Gly Ala Tyr Val Tyr Val Cys Gly Asp Ala Lys
            660                 665                 670

Gly Met Ala Arg Asp Val His Arg Thr Leu His Thr Ile Ala Gln Glu
        675                 680                 685

Gln Gly Ser Met Asp Ser Thr Gln Ala Glu Gly Phe Val Lys Asn Leu
    690                 695                 700

Gln Met Thr Gly Arg Tyr Leu Arg Asp Val Trp
705                 710                 715

<210> SEQ ID NO 24
<211> LENGTH: 2148
<212> TYPE: DNA
<213> ORGANISM: artificial
<220> FEATURE:
<223> OTHER INFORMATION: coding sequence for SEQ ID NO: 23

<400> SEQUENCE: 24
atgtccgatt cttcttctga aaagttgtct ccattcgaat gatgtctgc tatcttgaag      60 ggtgctaagt tggatggttc taactcttct gattctggtg ttgctgtttc tccagctgtt    120
atggctatgt tgttggaaaa caaggaattg ttatgatttt gactacttc tgttgctgtt    180 ttgatcggtt gtgtcgttgt tttgatctgg agaagatctt ccggttctgg taagaaggtc    240
gttgaaccac caaagttgat cgttccaaag tctgttgttg aaccagaaga aattgatgaa    300
ggtaagaaga agttcaccat cttcttcggt actcaaactg gtactgctga aggtttcgct    360
aaggctttgg ctgaagaagc caaggctaga tacgaaaagg ctgttatcaa ggttattgat    420
atcgatgatt acgctgctga tgatgaagaa tacgaagaaa agttcagaaa ggaaaccttg    480
gctttcttca tcttggccac ttacggtgat ggtgaaccaa ccgacaacgc tgctagattc    540
tacaagtggt tcgttgaagg taacgataga ggtgactggt tgaagaactt gcaatacggt    600
gttttcggtt tgggtaacag acaatacgaa cacttcaaca agattgctaa ggttgttgat    660
gaaaaggttg ctgaacaagg tggtaagaga attgttccat tggttttggg tgacgatgac    720
caatgtattg aagatgactt cgctgcttgg agagaaaacg tttggccaga attggataac    780
ttgttgagag atgaagatga tactactgtt tctactacct acactgctgc tattccagaa    840
tacagagttt ttttcccaga caagtctgat tctttgattt ctgaagctaa cggtcacgcc    900
aacggttacg ctaacggtaa caccgtttac gatgcccaac cccatgtag atctaacgtt    960 gctgttagaa aggaattgca cactccagct tctgatagat cttgtaccca cttggatttc   1020
gacattgctg gtactggttt gtcttacggt actggtgatc acgttggtgt ttactgtgat   1080
aacttgtctg aaaccgttga agaagctgaa agattgttga acttgccacc agaaacttac   1140
ttctctttgc acgctgataa ggaagatggt accccattgg ctggttcttc tttgccacca   1200
ccattcccac catgtacttt gagaaccgcc ttgactagat acgctgattt gttgaacact   1260
ccaaagaagt ctgctttgtt ggctttggct gcttacgctt ctgatccaaa cgaagccgat   1320
agattgaagt acttggcttc tccagccggt aaggatgaat acgctcaatc tttggttgct   1380
aaccaaagat ctttgttgga agtcatggct gaattcccat ctgctaagcc accattgggt   1440
gttttcttcg ctgctattgc tccaagattg caaccaagat ctactctat ctcttcttct   1500 ccaagaatgg ctccatctag aattcacgtc acttgtgctt tggtttacga aaagactcca   1560
```

```
ggtggtagaa ttcacaaggg tgtttgttct acttggatga agaacgccat tccattggaa    1620
gaatctagag actgttcttg ggctccaatc ttcgtcagac aatctaactt caagttgcca    1680
gccgatccaa aggttccagt tatcatgatc ggtccaggta ctggtttggc tccattcaga    1740
ggtttcttgc aagaaagatt ggctttgaag gaagaaggtg ctgaattggg tactgctgtt    1800
ttcttcttcg ttgtagaaa cagaaagatg gattacatct acgaagatga attgaaccac     1860
ttcttggaaa ttggtgcttt gtccgaattg ttggttgctt tctctagaga aggtccaact    1920
aagcaatacg ttcaacacaa gatggctgaa aaggcttctg atatttggag aatgatttct    1980
gatggtgctt acgtttacgt ctgtggtgat gccaagggta tggccagaga tgtccacaga    2040
actttgcaca ccattgctca agaacaaggt tctatggatt ctactcaagc tgaaggtttc    2100
gttaagaact tgcaaatgac cggtagatac ttgagagatg tctggtaa                 2148
```

<210> SEQ ID NO 25
<211> LENGTH: 692
<212> TYPE: PRT
<213> ORGANISM: Saccharomyces cerevisiae

<400> SEQUENCE: 25

```
Met Ser Pro Phe Gly Ile Asp Asn Thr Asp Phe Thr Val Leu Ala Gly
1               5                   10                  15

Leu Val Leu Ala Val Leu Leu Tyr Val Lys Arg Asn Ser Ile Lys Glu
            20                  25                  30

Leu Leu Met Ser Asp Asp Gly Asp Ile Thr Ala Val Ser Ser Gly Asn
        35                  40                  45

Arg Asp Ile Ala Gln Val Val Thr Glu Asn Asn Lys Asn Tyr Leu Val
    50                  55                  60

Leu Tyr Ala Ser Gln Thr Gly Thr Ala Glu Asp Tyr Ala Lys Lys Phe
65                  70                  75                  80

Ser Lys Glu Leu Val Ala Lys Phe Asn Leu Asn Val Met Cys Ala Asp
                85                  90                  95

Val Glu Asn Tyr Asp Phe Glu Ser Leu Asn Asp Val Pro Val Ile Val
            100                 105                 110

Ser Ile Phe Ile Ser Thr Tyr Gly Glu Gly Asp Phe Pro Asp Gly Ala
        115                 120                 125

Val Asn Phe Glu Asp Phe Ile Cys Asn Ala Glu Ala Gly Ala Leu Ser
    130                 135                 140

Asn Leu Arg Tyr Asn Met Phe Gly Leu Gly Asn Ser Thr Tyr Glu Phe
145                 150                 155                 160

Phe Asn Gly Ala Ala Lys Lys Ala Glu Lys His Leu Ser Ala Ala Gly
                165                 170                 175

Ala Ile Arg Leu Gly Lys Leu Gly Glu Ala Asp Asp Gly Ala Gly Thr
            180                 185                 190

Thr Asp Glu Asp Tyr Met Ala Trp Lys Asp Ser Ile Leu Glu Val Leu
        195                 200                 205

Lys Asp Glu Leu His Leu Asp Glu Gln Glu Ala Lys Phe Thr Ser Gln
    210                 215                 220

Phe Gln Tyr Thr Val Leu Asn Glu Ile Thr Asp Ser Met Ser Leu Gly
225                 230                 235                 240

Glu Pro Ser Ala His Tyr Leu Pro Ser His Gln Leu Asn Arg Asn Ala
                245                 250                 255

Asp Gly Ile Gln Leu Gly Pro Phe Asp Leu Ser Gln Pro Tyr Ile Ala
            260                 265                 270
```

```
Pro Ile Val Lys Ser Arg Glu Leu Phe Ser Ser Asn Asp Arg Asn Cys
    275                 280                 285

Ile His Ser Glu Phe Asp Leu Ser Gly Ser Asn Ile Lys Tyr Ser Thr
    290                 295                 300

Gly Asp His Leu Ala Val Trp Pro Ser Asn Pro Leu Glu Lys Val Glu
305                 310                 315                 320

Gln Phe Leu Ser Ile Phe Asn Leu Asp Pro Glu Thr Ile Phe Asp Leu
                325                 330                 335

Lys Pro Leu Asp Pro Thr Val Lys Val Pro Phe Pro Thr Pro Thr Thr
                340                 345                 350

Ile Gly Ala Ala Ile Lys His Tyr Leu Glu Ile Thr Gly Pro Val Ser
                355                 360                 365

Arg Gln Leu Phe Ser Ser Leu Ile Gln Phe Ala Pro Asn Ala Asp Val
    370                 375                 380

Lys Glu Lys Leu Thr Leu Leu Ser Lys Asp Lys Asp Gln Phe Ala Val
385                 390                 395                 400

Glu Ile Thr Ser Lys Tyr Phe Asn Ile Ala Asp Ala Leu Lys Tyr Leu
                405                 410                 415

Ser Asp Gly Ala Lys Trp Asp Thr Val Pro Met Gln Phe Leu Val Glu
                420                 425                 430

Ser Val Pro Gln Met Thr Pro Arg Tyr Tyr Ser Ile Ser Ser Ser Ser
                435                 440                 445

Leu Ser Glu Lys Gln Thr Val His Val Thr Ser Ile Val Glu Asn Phe
    450                 455                 460

Pro Asn Pro Glu Leu Pro Asp Ala Pro Pro Val Gly Val Thr Thr
465                 470                 475                 480

Asn Leu Leu Arg Asn Ile Gln Leu Ala Gln Asn Asn Val Asn Ile Ala
                485                 490                 495

Glu Thr Asn Leu Pro Val His Tyr Asp Leu Asn Gly Pro Arg Lys Leu
                500                 505                 510

Phe Ala Asn Tyr Lys Leu Pro Val His Val Arg Arg Ser Asn Phe Arg
    515                 520                 525

Leu Pro Ser Asn Pro Ser Thr Pro Val Ile Met Ile Gly Pro Gly Thr
    530                 535                 540

Gly Val Ala Pro Phe Arg Gly Phe Ile Arg Glu Arg Val Ala Phe Leu
545                 550                 555                 560

Glu Ser Gln Lys Lys Gly Gly Asn Asn Val Ser Leu Gly Lys His Ile
                565                 570                 575

Leu Phe Tyr Gly Ser Arg Asn Thr Asp Asp Phe Leu Tyr Gln Asp Glu
                580                 585                 590

Trp Pro Glu Tyr Ala Lys Lys Leu Asp Gly Ser Phe Glu Met Val Val
                595                 600                 605

Ala His Ser Arg Leu Pro Asn Thr Lys Lys Val Tyr Val Gln Asp Lys
    610                 615                 620

Leu Lys Asp Tyr Glu Asp Gln Val Phe Glu Met Ile Asn Asn Gly Ala
625                 630                 635                 640

Phe Ile Tyr Val Cys Gly Asp Ala Lys Gly Met Ala Lys Gly Val Ser
                645                 650                 655

Thr Ala Leu Val Gly Ile Leu Ser Arg Gly Lys Ser Ile Thr Thr Asp
                660                 665                 670

Glu Ala Thr Glu Leu Ile Lys Met Leu Lys Thr Ser Gly Arg Tyr Gln
                675                 680                 685
```

Glu Asp Val Trp
    690

<210> SEQ ID NO 26
<211> LENGTH: 2079
<212> TYPE: DNA
<213> ORGANISM: artificial
<220> FEATURE:
<223> OTHER INFORMATION: coding sequence for SEQ ID NO: 25

<400> SEQUENCE: 26

| | | | | | |
|---|---|---|---|---|---|
| atgtccccgt | ttggaataga | caacaccgac | ttcactgtcc | tggcggggct | agtgcttgcc | 60 |
| gtgctactgt | acgtaaagag | aaactccatc | aaggaactgc | tgatgtccga | tgacggagat | 120 |
| atcacagctg | tcagctcggg | caacagagac | attgctcagg | tggtgaccga | aaacaacaag | 180 |
| aactacttgg | tgttgtatgc | gtcgcagact | gggactgccg | aggattacgc | caaaaagttt | 240 |
| tccaaggagc | tggtggccaa | gttcaaccta | acgtgatgt | gcgcagatgt | tgagaactac | 300 |
| gactttgagt | cgctaaacga | tgtgcccgtc | atagtctcga | tttttatctc | tacatatggt | 360 |
| gaaggagact | tccccgacgg | ggcggtcaac | tttgaggact | ttatttgtaa | tgcggaagcg | 420 |
| ggtgcactat | cgaacctgag | gtataatatg | tttggtctgg | gaaattctac | ttatgaattc | 480 |
| tttaatggtg | ccgccaagaa | ggccgagaag | catctctccg | ccgcgggcgc | tatcagacta | 540 |
| ggcaagctcg | gtgaagctga | tgatggtgca | ggaactacag | acgaagatta | catggcctgg | 600 |
| aaggactcca | tcctggaggt | tttgaaagac | gaactgcatt | tggacgaaca | ggaagccaag | 660 |
| ttcacctctc | aattccagta | cactgtgttg | aacgaaatca | ctgactccat | gtcgcttggt | 720 |
| gaaccctctg | ctcactattt | gccctcgcat | cagttgaacc | gcaacgcaga | cggcatccaa | 780 |
| ttgggtccct | cgatttgtc | tcaaccgtat | attgcaccca | tcgtgaaatc | tcgcgaactg | 840 |
| ttctcttcca | atgaccgtaa | ttgcatccac | tctgaatttg | acttgtccgg | ctctaacatc | 900 |
| aagtactcca | ctggtgacca | tcttgctgtt | tggccttcca | acccattgga | aaaggtcgaa | 960 |
| cagttcttat | ccatattcaa | cctggaccct | gaaaccattt | ttgacttgaa | gcccctggat | 1020 |
| cccaccgtca | aagtgccctt | cccaacgcca | actactattg | gcgctgctat | taaacactat | 1080 |
| ttggaaatta | caggacctgt | ctccagacaa | ttgttttcat | ctttgattca | gttcgccccc | 1140 |
| aacgctgacg | tcaaggaaaa | attgactctg | ctttcgaaag | acaaggacca | attgccgtc | 1200 |
| gagataacct | ccaaatattt | caacatcgca | gatgctctga | atatttgtc | tgatggcgcc | 1260 |
| aaatgggaca | ccgtacccat | gcaattcttg | gtcgaatcag | ttccccaaat | gactcctcgt | 1320 |
| tactactcta | tctcttcctc | ttctctgtct | gaaaagcaaa | ccgtccatgt | cacctccatt | 1380 |
| gtggaaaact | ttcctaaccc | agaattgcct | gatgctcctc | cagttgttgg | tgttacgact | 1440 |
| aacttgttaa | gaaacattca | attggctcaa | acaatgtta | acattgccga | aactaaccta | 1500 |
| cctgttcact | acgatttaaa | tggcccacgt | aaacttttcg | ccaattacaa | attgcccgtc | 1560 |
| cacgttcgtc | gttctaactt | cagattgcct | tccaaccctt | ccaccccagt | tatcatgatc | 1620 |
| ggtccaggta | ccggtgttgc | cccattccgt | gggtttatca | gagagcgtgt | cgcgttcctc | 1680 |
| gaatcacaaa | agaagggcgg | taacaacgtt | tcgctaggta | agcatatact | gttttatgga | 1740 |
| tcccgtaaca | ctgatgattt | cttgtaccag | gacgaatggc | agaatacgc | caaaaaattg | 1800 |
| gatggttcgt | tcgaaatggt | cgtggcccat | tccaggttgc | caaacaccaa | aaaagtttat | 1860 |
| gttcaagata | aattaaagga | ttacgaggac | caagtatttg | aaatgattaa | caacggtgca | 1920 |
| tttatctacg | tctgtggtga | tgcaaagggt | atggccaagg | gtgtgtcaac | cgcattggtt | 1980 |

-continued

```
ggcatcttat cccgtggtaa atccattacc actgatgaag caacagagct aatcaagatg    2040
ctcaagactt caggtagata ccaagaagat gtctggtaa                            2079
```

<210> SEQ ID NO 27
<211> LENGTH: 658
<212> TYPE: PRT
<213> ORGANISM: artificial
<220> FEATURE:
<223> OTHER INFORMATION: chimeric cytochrome P450 reductase

<400> SEQUENCE: 27

```
Met Ser Pro Phe Gly Ile Asp Asn Thr Asp Phe Thr Val Leu Ala Gly
1               5                   10                  15

Leu Val Leu Ala Val Leu Leu Tyr Val Lys Arg Asn Ser Ile Lys Glu
            20                  25                  30

Leu Leu Met Ser Asp Asp Gly Asp Ile Thr Ala Val Ser Ser Gly Asn
        35                  40                  45

Arg Asp Ile Ala Gln Val Val Thr Glu Asn Asn Lys Asn Tyr Leu Val
    50                  55                  60

Leu Tyr Ala Ser Gln Thr Gly Thr Ala Glu Asp Tyr Ala Lys Lys Phe
65                  70                  75                  80

Ser Lys Glu Leu Val Ala Lys Phe Asn Leu Asn Val Met Cys Ala Asp
                85                  90                  95

Val Glu Asn Tyr Asp Phe Glu Ser Leu Asn Asp Val Pro Val Ile Val
            100                 105                 110

Ser Ile Phe Ile Ser Thr Tyr Gly Glu Gly Asp Phe Pro Asp Gly Ala
        115                 120                 125

Val Asn Phe Glu Asp Phe Ile Cys Asn Ala Glu Ala Gly Ala Leu Ser
    130                 135                 140

Asn Leu Arg Tyr Asn Met Phe Gly Leu Gly Asn Ser Thr Tyr Glu Phe
145                 150                 155                 160

Phe Asn Gly Ala Ala Lys Lys Ala Glu Lys His Leu Ser Ala Ala Gly
                165                 170                 175

Ala Ile Arg Leu Gly Lys Leu Gly Glu Ala Asp Asp Gly Ala Gly Thr
            180                 185                 190

Thr Asp Glu Asp Tyr Met Ala Trp Lys Asp Ser Ile Leu Glu Val Leu
        195                 200                 205

Lys Asp Glu Leu Gly Val Glu Ala Thr Gly Glu Glu Ser Ser Ile Arg
    210                 215                 220

Gln Tyr Glu Leu Val Val His Thr Asp Ile Asp Ala Ala Lys Val Tyr
225                 230                 235                 240

Met Gly Glu Met Gly Arg Leu Lys Ser Tyr Glu Asn Gln Lys Pro Pro
                245                 250                 255

Phe Asp Ala Lys Asn Pro Phe Leu Ala Ala Val Thr Thr Asn Arg Lys
            260                 265                 270

Leu Asn Gln Gly Thr Glu Arg His Leu Met His Leu Glu Leu Asp Ile
        275                 280                 285

Ser Asp Ser Lys Ile Arg Tyr Glu Ser Gly Asp His Val Ala Val Tyr
    290                 295                 300

Pro Ala Asn Asp Ser Ala Leu Val Asn Gln Leu Gly Lys Ile Leu Gly
305                 310                 315                 320

Ala Asp Leu Asp Val Val Met Ser Leu Asn Asn Leu Asp Glu Glu Ser
                325                 330                 335

Asn Lys Lys His Pro Phe Pro Cys Pro Thr Ser Tyr Arg Thr Ala Leu
            340                 345                 350
```

```
Thr Tyr Tyr Leu Asp Ile Thr Asn Pro Pro Arg Thr Asn Val Leu Tyr
        355                 360                 365

Glu Leu Ala Gln Tyr Ala Ser Glu Pro Ser Glu Gln Glu Leu Leu Arg
    370                 375                 380

Lys Met Ala Ser Ser Gly Glu Gly Lys Glu Leu Tyr Leu Ser Trp
385                 390                 395                 400

Val Val Glu Ala Arg Arg His Ile Leu Ala Ile Leu Gln Asp Cys Pro
                405                 410                 415

Ser Leu Arg Pro Pro Ile Asp His Leu Cys Glu Leu Leu Pro Arg Leu
            420                 425                 430

Gln Ala Arg Tyr Tyr Ser Ile Ala Ser Ser Ser Lys Val His Pro Asn
        435                 440                 445

Ser Val His Ile Cys Ala Val Val Glu Tyr Glu Thr Lys Ala Gly
    450                 455                 460

Arg Ile Asn Lys Gly Val Ala Thr Asn Trp Leu Arg Ala Lys Glu Pro
465                 470                 475                 480

Ala Gly Glu Asn Gly Gly Arg Ala Leu Val Pro Met Phe Val Arg Lys
                485                 490                 495

Ser Gln Phe Arg Leu Pro Phe Lys Ala Thr Thr Pro Val Ile Met Val
            500                 505                 510

Gly Pro Gly Thr Gly Val Ala Pro Phe Ile Gly Phe Ile Gln Glu Arg
        515                 520                 525

Ala Trp Leu Arg Gln Gln Gly Lys Glu Val Gly Glu Thr Leu Leu Tyr
    530                 535                 540

Tyr Gly Cys Arg Arg Ser Asp Glu Asp Tyr Leu Tyr Arg Glu Glu Leu
545                 550                 555                 560

Ala Gln Phe His Arg Asp Gly Ala Leu Thr Gln Leu Asn Val Ala Phe
                565                 570                 575

Ser Arg Glu Gln Ser His Lys Val Tyr Val Gln His Leu Leu Lys Gln
            580                 585                 590

Asp Arg Glu His Leu Trp Lys Leu Ile Glu Gly Gly Ala His Ile Tyr
        595                 600                 605

Val Cys Gly Asp Ala Arg Asn Met Ala Arg Asp Val Gln Asn Thr Phe
    610                 615                 620

Tyr Asp Ile Val Ala Glu Leu Gly Ala Met Glu His Ala Gln Ala Val
625                 630                 635                 640

Asp Tyr Ile Lys Lys Leu Met Thr Lys Gly Arg Tyr Ser Leu Asp Val
                645                 650                 655

Trp Ser

<210> SEQ ID NO 28
<211> LENGTH: 1977
<212> TYPE: DNA
<213> ORGANISM: artificial
<220> FEATURE:
<223> OTHER INFORMATION: coding sequence for SEQ ID NO: 27

<400> SEQUENCE: 28
atgtccccat tcggtatcga caacaccgac ttcactgtct ggctggtttt ggttttggcc    60
gttttgttgt acgttaagag aaactccatc aaggaattgt tgatgtccga tgacggtgat   120
atcactgctg tctcttctgg taacagagac attgctcaag ttgttaccga aaacaacaag   180
aactacttgg ttttgtacgc ttctcaaact ggtactgccg aagattacgc caagaagttc   240
tccaaggaat tggttgccaa gttcaacttg aacgttatgt gtgctgatgt tgaaaactac   300
```

```
gacttcgaat ctttgaacga tgttccagtc atcgtatcta ttttcatctc tacttacggt   360
gaaggtgact tcccagacgg tgctgtcaac ttcgaagatt tcatttgtaa cgctgaagct   420
ggtgctttgt ctaacttgag atacaacatg ttcggtttgg gtaactctac ttacgaattc   480
ttcaacggtg ccgccaagaa ggccgaaaag cacttgtccg ccgctggtgc tatcagattg   540
ggtaagttgg gtgaagctga tgatggtgct ggtactactg acgaagatta catggcctgg   600
aaggactcca tcttggaagt tttgaaggac gaattgggtg ttgaagccac tggtgaagaa   660
tcctctatta gacaatacga attggttgtc cacaccgaca tcgatgctgc aaggtttac    720
atgggtgaaa tgggtagatt gaagtcttac gaaaaccaaa agccaccatt cgatgccaag   780
aacccattct ggctgctgt caccaccaac agaaagttga accaaggtac cgaaagacac    840
ttgatgcact ggaattgga catctctgac tccaagatca gatacgaatc tggtgaccac    900
gttgctgttt acccagccaa cgactctgct ttggtcaacc aattgggtaa gatcttgggt   960
gccgacttgg acgtcgtcat gtccttgaac aacttggatg aagaatccaa caagaagcac  1020
ccattcccat gtccaacttc ctacagaact gccttgacct actacttgga catcaccaac  1080
ccaccaagaa ccaacgtttt gtacgaattg gctcaatacg cctctgaacc atctgaacaa  1140
gaattgttga aaagatggc ctcctcctcc ggtgaaggta aggaattgta cttgtcttgg   1200
gttgttgaag ccaggagaca catcttggcc atcttgcaag actgtccatc cttaagacca  1260
ccaatcgacc acttgtgtga attgttgcca agattgcaag ccagatacta ctccatcgcc  1320
tcttcctcca aggtccaccc aaactctgtt cacatctgtg ctgttgttgt tgaatacgaa  1380
accaaggctg gtagaatcaa caagggtgtt gccaccaact ggttgagagc caaggaacca  1440
gccggtgaaa acggtggtag agctttggtt ccaatgttcg ttagaaagtc ccaattcaga  1500
ttgccattca aggccaccac tccagtcatc atggttggtc caggtaccgg tgttgctcca  1560
ttcatcggtt tcatccaaga aagagcctgg ttgagacaac aaggtaagga agttggtgaa  1620
actttgttgt actacggttg tagaagatct gatgaagatt acttgtacag agaagaattg  1680
gctcaattcc acagagatgg tgctttgacc caattgaacg ttgccttctc cagagaacaa  1740
tcccacaagg tctacgtcca acacttgttg aagcaagaca gagaacactt gtggaagttg  1800
atcgaaggtg gtgcccacat ctacgtctgt ggtgatgcta aaacatggc cagagatgtt  1860
caaaacacct tctacgacat cgttgctgaa ttgggtgcca tggaacacgc tcaagctgtt  1920
gactacatca agaagttgat gaccaagggt agatactcct ggacgtttg gtcttaa     1977
```

<210> SEQ ID NO 29
<211> LENGTH: 693
<212> TYPE: PRT
<213> ORGANISM: Arabidopsis thaliana

<400> SEQUENCE: 29

Met Ser Thr Ser Ala Leu Tyr Ala Ser Asp Leu Phe Lys Gln Leu Lys
1               5                   10                  15

Ser Ile Met Gly Thr Asp Ser Leu Ser Asp Asp Val Val Leu Val Ile
            20                  25                  30

Ala Thr Thr Ser Leu Ala Leu Val Ala Gly Phe Val Val Leu Leu Trp
        35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Leu Asp Leu Gly
65                  70                  75                  80

```
Ser Gly Lys Thr Arg Val Ser Ile Phe Phe Gly Thr Gln Thr Gly Thr
                85                  90                  95

Ala Glu Gly Phe Ala Lys Ala Leu Ser Glu Ile Lys Ala Arg Tyr
            100                 105                 110

Glu Lys Ala Ala Val Lys Val Ile Asp Leu Asp Asp Tyr Ala Ala Asp
            115                 120                 125

Asp Asp Gln Tyr Glu Glu Lys Leu Lys Lys Glu Thr Leu Ala Phe Phe
130                 135                 140

Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
            195                 200                 205

Ala Lys Arg Leu Ile Glu Val Gly Leu Gly Asp Asp Asp Gln Ser Ile
            210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Lys Ser Val Ala Thr Pro Tyr Thr
                245                 250                 255

Ala Val Ile Pro Glu Tyr Arg Val Val Thr His Asp Pro Arg Phe Thr
                260                 265                 270

Thr Gln Lys Ser Met Glu Ser Asn Val Ala Asn Gly Asn Thr Thr Ile
            275                 280                 285

Asp Ile His His Pro Cys Arg Val Asp Val Ala Val Gln Lys Glu Leu
            290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
            355                 360                 365

Ser Pro Leu Glu Ser Ala Val Pro Pro Pro Phe Pro Gly Pro Cys Thr
370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
                405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
            435                 440                 445

Ala Phe Pro Ser Ala Lys Pro Pro Leu Gly Val Phe Phe Ala Ala Ile
450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495
```

Thr Pro Thr Gly Arg Ile His Lys Gly Val Cys Ser Thr Trp Met Lys
                500                 505                 510

Asn Ala Val Pro Ala Glu Lys Ser His Glu Cys Ser Gly Ala Pro Ile
            515                 520                 525

Phe Ile Arg Ala Ser Asn Phe Lys Leu Pro Ser Asn Pro Ser Thr Pro
        530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
                565                 570                 575

Ser Leu Leu Phe Phe Gly Cys Arg Asn Arg Gln Met Asp Phe Ile Tyr
            580                 585                 590

Glu Asp Glu Leu Asn Asn Phe Val Asp Gln Gly Val Ile Ser Glu Leu
        595                 600                 605

Ile Met Ala Phe Ser Arg Glu Gly Ala Gln Lys Glu Tyr Val Gln His
        610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
        675                 680                 685

Leu Arg Asp Val Trp
    690

<210> SEQ ID NO 30
<211> LENGTH: 2082
<212> TYPE: DNA
<213> ORGANISM: artificial
<220> FEATURE:
<223> OTHER INFORMATION: coding sequence for SEQ ID NO: 29

<400> SEQUENCE: 30
atgtccactt ctgctttgta cgcttccgat ttgttcaagc aattgaagtc tattatgggt      60
actgattctt tgtccgacga tgttgttttg gttattgcta ctacttcttt ggctttggtt    120
gctggtttcg ttgttttgtt gtggaagaaa actactgctg atagatctgg tgaattgaag    180
ccattgatga tcccaaagtc tttgatggct aaggacgaag atgatgattt ggatttgggt    240
tccggtaaga ctagagtctc tatcttcttc ggtactcaaa ctggtactgc tgaaggtttc    300
gctaaggctt tgtccgaaga aatcaaggct agatacgaaa aggctgctgt caaggtcatt    360
gacttggatg actacgctgc cgatgatgac caatacgaag aaaagttgaa gaaggaaact    420
ttggctttct tctgtgttgc tacttacggt gatggtgaac caactgacaa cgctgccaga    480
ttctacaagt ggtcactga agaaaacgaa agagatatca gttgcaaca attggcttac    540 ggtgttttcg ctttgggtaa cagacaatac gaacacttca caagatcgg tatcgttttg    600 gatgaagaat gtgtaagaa gggtgctaag agattgattg aagtcggttt gggtgatgat    660
gatcaatcta ttgaagatga tttcaacgcc tggaaggaat ctttgtggtc tgaattggac    720
aagttgttga aggacgaaga tgataagtct gttgctactc catacactgc tgttattcca    780
gaatacagag ttgttactca cgatccaaga ttcactactc aaaagtctat ggaatctaac    840
gttgccaacg gtaacactac tattgacatt caccacccat gtagagttga tgttgctgtt    900

-continued

```
caaaaggaat tgcacactca cgaatctgat agatcttgta ttcacttgga attcgacatc    960
tccagaactg gtattactta cgaaactggt gaccacgttg gtgtttacgc tgaaaaccac   1020
gttgaaatcg ttgaagaagc tggtaagttg ttgggtcact ctttggattt ggttttctcc   1080
atccacgctg acaaggaaga tggttcccca ttggaatctg ctgttccacc accattccca   1140
ggtccatgta ctttgggtac tggtttggct agatacgctg acttgttgaa cccaccaaga   1200
aagtctgctt tggttgcctt ggctgcctac gccactgaac catctgaagc cgaaaagttg   1260
aagcacttga cttctccaga tggtaaggat gaatactctc aatggattgt tgcttctcaa   1320
agatctttgt tggaagttat ggctgctttc ccatctgcta agccaccatt gggtgttttc   1380
ttcgctgcta tcgctccaag attgcaacca agatactact ccatctcttc ctctccaaga   1440
ttggctccat ctagagttca cgttacttcc gctttggttt acggtccaac tccaactggt   1500
agaatccaca agggtgtttg ttctacttgg atgaagaacg ctgttccagc tgaaaagtct   1560
cacgaatgtt ctggtgcccc aatcttcatt agagcttcta acttcaagtt gccatccaac   1620
ccatctactc caatcgttat ggttggtcca ggtactggtt tggctccatt cagaggtttc   1680
ttgcaagaaa aatggctttt gaaggaagat ggtgaagaat tgggttcttc tttgttgttc   1740
ttcggttgta gaaacagaca aatggacttc atctacgaag atgaattgaa caacttcgtt   1800
gatcaaggtg ttatctctga attgatcatg gctttctcca gagaaggtgc tcaaaaggaa   1860
tacgttcaac acaagatgat ggaaaaggct gctcaagttt gggatttgat caaggaagaa   1920
ggttacttgt acgtttgtgg tgatgctaag ggtatggcta gagatgtcca cagaactttg   1980
cacaccattg ttcaagaaca agaaggtgtt tcttcttctg aagctgaagc tatcgttaag   2040
aagttgcaaa ccgaaggtag atacttgaga gatgtctggt aa                     2082
```

<210> SEQ ID NO 31
<211> LENGTH: 712
<212> TYPE: PRT
<213> ORGANISM: Arabidopsis thaliana

<400> SEQUENCE: 31

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn

```
              165                 170                 175
Ala Ala Arg Phe Tyr Lys Trp Phe Thr Glu Gly Asn Asp Arg Gly Glu
                180                 185                 190

Trp Leu Lys Asn Leu Lys Tyr Gly Val Phe Gly Leu Gly Asn Arg Gln
                195                 200                 205

Tyr Glu His Phe Asn Lys Val Ala Lys Val Val Asp Ile Leu Val
        210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
                260                 265                 270

Pro Tyr Thr Ala Ala Val Leu Glu Tyr Arg Val Ser Ile His Asp Ser
                275                 280                 285

Glu Asp Ala Lys Phe Asn Asp Ile Asn Met Ala Asn Gly Asn Gly Tyr
                290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
                340                 345                 350

Gly Val Leu Cys Asp Asn Leu Ser Glu Thr Val Asp Glu Ala Leu Arg
                355                 360                 365

Leu Leu Asp Met Ser Pro Asp Thr Tyr Phe Ser Leu His Ala Glu Lys
                370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
                420                 425                 430

Thr Glu Ala Glu Arg Leu Lys His Leu Ala Ser Pro Ala Gly Lys Val
                435                 440                 445

Asp Glu Tyr Ser Lys Trp Val Val Glu Ser Gln Arg Ser Leu Leu Glu
                450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
                500                 505                 510

Tyr Glu Lys Met Pro Thr Gly Arg Ile His Lys Gly Val Cys Ser Thr
                515                 520                 525

Trp Met Lys Asn Ala Val Pro Tyr Glu Lys Ser Glu Asn Cys Ser Ser
                530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
                580                 585                 590
```

```
Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710
```

<210> SEQ ID NO 32
<211> LENGTH: 2139
<212> TYPE: DNA
<213> ORGANISM: artificial
<220> FEATURE:
<223> OTHER INFORMATION: coding sequence for SEQ ID NO: 31

<400> SEQUENCE: 32

```
atgtcctctt cttcttcttc ttctacctcc atgatcgatt tgatggctgc tatcatcaag    60
ggtgaaccag ttattgtctc cgacccagct aacgcctccg cttacgaatc cgttgctgct   120
gaattgtcct ctatgttgat cgaaaacaga caattcgcca tgattgttac cacttccatt   180
gctgttttga ttggttgtat cgttatgttg gtttggagaa gatccggttc tggtaactct   240
aagagagtcg aaccattgaa gccattggtt attaagccaa gagaagaaga aattgatgat   300
ggtagaaaga aggttaccat cttcttcggt actcaaactg gtactgctga aggtttcgct   360
aaggctttgg gtgaagaagc taaggctaga tacgaaaaga ccagattcaa gatcgttgat   420
ttggatgatt acgctgctga tgatgatgaa tacgaagaaa agttgaagaa ggaagatgtt   480
gctttcttct tcttggccac ttacggtgat ggtgaaccaa ccgacaacgc tgctagattc   540
tacaagtggt tcaccgaagg taacgacaga ggtgaatggt tgaagaactt gaagtacggt   600
gttttcggtt tgggtaacag acaatacgaa cacttcaaca aggttgccaa ggttgttgat   660
gacattttgg tcgaacaagg tgctcaaaga ttggttcaag ttggtttggg tgatgatgac   720
caatgtattg aagatgactt caccgcttgg agagaagctt gtggccagat tggatact    780
atcttgagag aagaaggtga tactgctgtt gccactccat acactgctgc tgttttggaa   840
tacagagttt ctattcacga ctctgaagat gccaagttca cgatatcaa catggctaac   900
ggtaacggtt acactgtttt cgatgctcaa cacccataca aggctaacgt cgctgttaag   960
agagaattgc acactccaga atctgataga tcttgtatcc acttggaatt cgacattgct  1020
ggttctggtt tgacttacga aactggtgat cacgttggtg ttttgtgtga taacttgtct  1080
gaaactgttg atgaagcttt gagattgttg gatatgtctc cagatactta cttctctttg  1140
cacgctgaaa aggaagatgg tactccaatc tcttcttctt tgccaccacc attcccacca  1200
tgtaacttga aactgctttt gactagatac gcttgtttgt tgtcatctcc aaagaagtct  1260
gctttggttg ctttggctgc tcacgcttct gatccaaccg aagctgaaag attgaagcac  1320
```

-continued

```
ttggcttctc cagctggtaa ggttgatgaa tactctaagt gggttgttga atctcaaaga   1380
tctttgttgg aagttatggc cgaattccca tctgccaagc caccattggg tgttttcttc   1440
gctggtgttg ctccaagatt gcaaccaaga ttctactcta tctcttcttc tccaaagatt   1500
gctgaaacta gaattcacgt cacttgtgct ttggtttacg aaaagatgcc aactggtaga   1560
attcacaagg gtgtttgttc cacttggatg aagaacgctg ttccatacga aaagtctgaa   1620
aactgttcct ctgctccaat cttcgttaga caatccaact tcaagttgcc atctgattct   1680
aaggttccaa tcatcatgat cggtccaggt actggtttgg ctccattcag aggtttcttg   1740
caagaaagat tggctttggt tgaatctggt gttgaattgg gtccatctgt tttgttcttc   1800
ggttgtagaa acagaagaat ggatttcatc tacgaagaag aattgcaaag attcgttgaa   1860
tctggtgctt tggctgaatt gtctgtcgcc ttctctagag aaggtccaac caaggaatac   1920
gttcaacaca agatgatgga caaggcttct gatatctgga acatgatctc tcaaggtgct   1980
tacttgtacg tttgtggtga cgccaagggt atggctagag atgttcacag atctttgcac   2040
actatcgctc aagaacaagg ttctatggat tctactaagg ctgaaggttt cgttaagaac   2100
ttgcaaactt ctggtagata cttgagagat gtttggtaa                          2139
```

<210> SEQ ID NO 33
<211> LENGTH: 522
<212> TYPE: PRT
<213> ORGANISM: Lonicera japonica

<400> SEQUENCE: 33

```
Met Ser Trp Ile Phe Asp Leu Thr Ile Ser Phe Thr Thr Leu Leu Phe
1               5                   10                  15

Leu Ile Phe Thr Thr Ala Leu Leu Leu Leu Lys Val Phe Lys Lys
            20                  25                  30

Asn His Lys Leu Arg Pro Pro Ser Pro Phe Thr Leu Pro Ile Ile
        35                  40                  45

Gly His Leu His Leu Leu Gly Pro Leu Ile His Gln Ser Phe His Arg
    50                  55                  60

Leu Ser Thr Leu Tyr Gly Pro Leu Ile Gln Leu Lys Ile Gly Tyr Ile
65                  70                  75                  80

Pro Cys Val Val Ala Ser Thr Pro Glu Leu Ala Lys Glu Phe Leu Lys
                85                  90                  95

Thr His Glu Leu Ala Phe Ser Ser Arg Lys His Ser Ala Ala Ile Lys
            100                 105                 110

Leu Leu Thr Tyr Asp Val Ser Phe Ala Phe Ser Pro Tyr Gly Pro Tyr
        115                 120                 125

Trp Lys Phe Ile Lys Lys Thr Cys Thr Phe Glu Leu Leu Gly Thr Arg
    130                 135                 140

Asn Met Asn His Phe Leu Pro Ile Arg Thr Asn Glu Ile Arg Arg Phe
145                 150                 155                 160

Leu Gln Val Met Leu Glu Lys Ala Lys Ala Ser Glu Gly Val Asn Val
                165                 170                 175

Thr Glu Glu Leu Ile Lys Leu Thr Asn Asn Val Ile Ser Gln Met Met
            180                 185                 190

Phe Ser Thr Arg Ser Ser Gly Thr Glu Gly Glu Ala Glu Glu Met Arg
        195                 200                 205

Thr Leu Val Arg Glu Val Thr Gln Ile Phe Gly Glu Phe Asn Val Ser
    210                 215                 220

Asp Phe Ile Lys Leu Cys Lys Asn Ile Asp Ile Gly Gly Phe Lys Lys
```

```
              225                 230                 235                 240
    Arg Ser Lys Asp Ile Gln Lys Arg Tyr Asp Ala Leu Leu Glu Lys Ile
                    245                 250                 255

Ile Ser Glu Arg Glu Ser Glu Arg Ala Arg Arg Gly Lys Asn Arg Glu
                260                 265                 270

Thr Leu Gly Glu Glu Gly Gly Lys Asp Phe Leu Asp Met Met Leu Asp
                275                 280                 285

Thr Met Glu Asp Gly Lys Cys Glu Val Glu Ile Thr Arg Asp His Ile
            290                 295                 300

Lys Ala Leu Val Leu Asp Phe Leu Thr Ala Ala Thr Asp Thr Thr Ala
    305                 310                 315                 320

Ile Ala Val Glu Trp Thr Leu Ala Glu Leu Ile Ser Asn Pro Glu Val
                    325                 330                 335

Phe Asp Lys Ala Arg Glu Glu Ile Asp Lys Val Val Gly Lys His Arg
                340                 345                 350

Leu Val Thr Glu Leu Asp Thr Pro Asn Leu Pro Tyr Ile His Ala Ile
                355                 360                 365

Ile Lys Glu Ser Phe Arg Leu His Pro Pro Ile Pro Leu Leu Ile Arg
            370                 375                 380

Lys Ser Val Gln Asp Cys Thr Val Gly Gly Tyr His Ile Ser Ala Asn
    385                 390                 395                 400

Thr Ile Leu Phe Val Asn Ile Trp Ala Ile Gly Arg Asn Pro Lys Tyr
                    405                 410                 415

Trp Glu Ser Pro Met Lys Phe Trp Pro Glu Arg Phe Leu Glu Ser Asn
                420                 425                 430

Gly Pro Gly Pro Val Gly Ser Met Asp Ile Lys Gly His His Tyr Glu
                435                 440                 445

Leu Leu Pro Phe Gly Ser Gly Arg Arg Gly Cys Pro Gly Met Ala Leu
            450                 455                 460

Ala Met Gln Glu Leu Pro Val Val Leu Ala Ala Met Ile Gln Cys Phe
    465                 470                 475                 480

Asn Trp Lys Pro Val Thr Leu Asp Gly Glu Glu Leu Asp Met Ser Glu
                    485                 490                 495

Arg Pro Gly Leu Thr Ala Pro Arg Ala His Asp Leu Val Cys Val Pro
                500                 505                 510

Ser Ala Arg Ile Asn Ser Phe Asp Asn Phe
                515                 520

<210> SEQ ID NO 34
<211> LENGTH: 1569
<212> TYPE: DNA
<213> ORGANISM: artificial
<220> FEATURE:
<223> OTHER INFORMATION: coding sequence for SEQ ID NO: 33

<400> SEQUENCE: 34
atgtcctgga tcttcgactt gactatctct ttcaccactt tgttgttctt gatcttcacc      60
accgccttgt tgttgttgtt gaaggttttc aagaagaacc acaagttaag accaccacca     120
tctccattca ccttgccaat catcggtcac ttgcacttgt gggtccatt gatccaccaa      180 tccttccaca gattgtccac cttgtacggt ccattgatcc aattgaagat cggttacatc     240
ccatgtgttg ttgcctctac tccagaattg gctaaggaat tcttaaagac tcacgaattg     300
gctttctcct ctagaaagca ctccgctgcc attaagttgt gacctacga tgtttctttc      360 gctttctctc catacggtcc atactggaag ttcatcaaaa agacttgtac cttcgaattg     420
```

```
ttgggtacta gaaacatgaa ccacttcttg ccaattagaa ccaacgaaat tagaagattc    480
ttgcaagtta tgttggaaaa ggccaaggct tctgaaggtg ttaacgttac tgaagaattg    540
atcaagttga ctaacaacgt tatctctcaa atgatgttct ctactagatc ttctggtacc    600
gaaggtgaag ctgaagaaat gagaactttg gttagagaag ttactcaaat cttcggtgaa    660
ttcaacgttt ctgatttcat caagttgtgt aagaacattg atattggtgg tttcaagaag    720
agatctaagg atatccaaaa gagatacgat gctttgttgg aaaagatcat ctctgaaaga    780
gaatctgaaa gagctagaag aggtaagaac agagaaactt ggggtgaaga aggtggtaag    840
gatttcttgg atatgatgtt ggatactatg aagatggta agtgtgaagt tgaaatcact    900
agagatcaca ttaaggcctt ggttttggat ttcttgactg ctgccactga tactactgct    960
attgctgttg aatggacttt ggccgaattg atctctaacc agaagttttt cgataaggct   1020
agagaagaaa tcgataaggt cgttggtaag cacagattgg tcactgaatt ggacactcca   1080
aacttgccat acatccacgc tatcatcaag gaatctttca gattgcaccc accaattcca   1140 tgttgatca gaaagtctgt ccaagattgt actgttggtg gttaccacat ctctgctaac   1200
accatcttgt tcgtcaacat ttgggccatc ggtagaaaac caaagtactg gaatctcca   1260 atgaagttct ggccagaaag attcttggaa tccaacggtc caggtccagt tggttctatg   1320
gatattaagg gtcaccacta cgaattgttg ccattcggtt ctggtagaag aggttgtcca   1380
ggtatggctt tggccatgca agaattgcca gttgttttgg ccgccatgat ccaatgtttc   1440
aactggaagc cagttacttt ggacggtgaa gaattggata tgtctgaaag accaggtttg   1500
actgctccaa gagcccacga tttggtttgt gttccatccg ctagaattaa ctctttcgat   1560
aacttctaa                                                            1569
```

<210> SEQ ID NO 35
<211> LENGTH: 520
<212> TYPE: PRT
<213> ORGANISM: Lonicera macranthoides

<400> SEQUENCE: 35

```
Met Ser Leu Ile Phe Asp Leu Thr Ile Ser Phe Thr Thr Leu Leu Phe
1               5                   10                  15

Leu Ile Phe Thr Thr Ala Leu Leu Lys Val Phe Lys Lys Asn His
            20                  25                  30

Lys Leu Gln Pro Pro Ser Pro Phe Thr Leu Pro Ile Ile Gly His
        35                  40                  45

Leu His Leu Leu Gly Pro Leu Ile His Gln Ser Phe His Arg Leu Ser
    50                  55                  60

Thr Leu Tyr Gly Pro Leu Ile Gln Leu Lys Ile Gly Tyr Ile Pro Cys
65                  70                  75                  80

Val Val Ala Ser Thr Pro Glu Leu Ala Lys Glu Phe Leu Lys Thr His
                85                  90                  95

Glu Leu Ala Phe Ser Ser Arg Lys His Ser Ala Ala Ile Lys Leu Leu
            100                 105                 110

Thr Tyr Asp Val Ser Phe Ala Phe Ala Pro Tyr Gly Pro Tyr Trp Lys
        115                 120                 125

Phe Ile Lys Lys Thr Cys Thr Phe Glu Leu Leu Gly Thr Arg Asn Met
    130                 135                 140

Asn His Phe Leu Pro Ile Arg Thr Asn Glu Ile Arg Arg Phe Leu Gln
145                 150                 155                 160
```

```
Val Met Leu Glu Lys Ala Lys Ala Ser Glu Gly Val Asn Val Thr Glu
            165                 170                 175
Glu Leu Ile Lys Leu Thr Asn Asn Val Ile Ser Gln Met Met Phe Ser
        180                 185                 190
Thr Arg Ser Ser Gly Thr Glu Gly Glu Ala Glu Glu Val Arg Thr Leu
    195                 200                 205
Val Arg Glu Val Thr Gln Ile Phe Gly Glu Phe Asn Val Ser Asp Phe
210                 215                 220
Ile Lys Leu Cys Lys Asn Ile Asp Ile Gly Phe Lys Lys Arg Ser
225                 230                 235                 240
Glu Asp Ile Gln Lys Arg Tyr Asp Ala Leu Leu Glu Lys Ile Ile Ser
                245                 250                 255
Glu Arg Glu Ser Glu Arg Ala Arg Gly Lys Asn Arg Glu Thr Leu
            260                 265                 270
Gly Glu Glu Gly Gly Lys Asp Phe Leu Asp Met Met Leu Asp Thr Met
        275                 280                 285
Glu Asp Gly Lys Cys Glu Val Glu Ile Thr Arg Asp His Ile Lys Ala
    290                 295                 300
Leu Val Leu Asp Phe Leu Thr Ala Ala Thr Asp Thr Thr Ala Ile Ala
305                 310                 315                 320
Val Glu Trp Thr Leu Ala Glu Leu Ile Ser Asn Pro Glu Val Phe Asp
                325                 330                 335
Lys Ala Arg Glu Glu Ile Asp Lys Val Val Gly Lys His Arg Leu Val
            340                 345                 350
Thr Glu Leu Asp Thr Pro Asn Leu Pro Tyr Ile His Ala Ile Ile Lys
        355                 360                 365
Glu Ser Phe Arg Leu His Pro Pro Ile Pro Leu Val Ile Arg Lys Ser
    370                 375                 380
Val Gln Asp Cys Thr Val Gly Gly Tyr His Ile Ser Ala Asn Thr Ile
385                 390                 395                 400
Leu Phe Ile Asn Ile Trp Ala Ile Gly Arg Asn Pro Lys Tyr Trp Glu
                405                 410                 415
Ser Pro Met Lys Phe Trp Pro Glu Arg Phe Leu Glu Ser Asn Glu Pro
            420                 425                 430
Gly Ser Val Gly Ser Thr Asp Ile Lys Gly His His Tyr Glu Leu Leu
        435                 440                 445
Pro Phe Gly Ser Gly Arg Arg Gly Cys Pro Gly Met Ala Leu Ala Met
    450                 455                 460
Gln Glu Leu Pro Val Val Leu Ala Ala Met Ile Gln Cys Phe Asn Trp
465                 470                 475                 480
Lys Pro Val Thr Leu Asp Gly Glu Glu Leu Asp Met Ser Glu Arg Pro
                485                 490                 495
Gly Leu Thr Ala Pro Arg Ala His Asp Leu Val Cys Val Pro Ser Ala
            500                 505                 510
Arg Ile Asn Ser Phe Asp Asn Phe
            515                 520

<210> SEQ ID NO 36
<211> LENGTH: 1563
<212> TYPE: DNA
<213> ORGANISM: artificial
<220> FEATURE:
<223> OTHER INFORMATION: coding sequence for SEQ ID NO: 35

<400> SEQUENCE: 36
```

```
atgtccttga tcttcgactt gactatctct ttcaccactt tgttgttctt gatcttcacc    60
accgccttgt tgttgaaggt tttcaagaag aaccacaagt tgcaaccacc accatctcca   120
ttcaccttgc caatcatcgg tcacttgcac ttgttgggtc cattgatcca ccaatccttc   180
cacagattgt ccaccttgta cggtccattg atccaattga agatcggtta catcccatgt   240
gttgttgctt ctactccaga attggctaag gaattcttaa agactcacga attggctttc   300
tcctctagaa agcactccgc tgccattaag ttgttgacct acgatgtttc tttcgctttc   360
gctccatacg gtccatactg aagttcatc aaaaagactt gtaccttcga attgttgggt   420
actagaaaca tgaaccactt cttgccaatt agaaccaacg aaattagaag attcttgcaa   480
gttatgttgg aaaaggccaa ggcttctgaa ggtgttaacg ttactgaaga attgatcaag   540
ttgactaaca acgttatctc tcaaatgatg ttctctacta gatcttctgg taccgaaggt   600
gaagctgaag aagttagaac tttggttaga gaagttactc aaatcttcgg tgaattcaac   660
gtttctgatt tcatcaagtt gtgtaagaac attgatattg gtggtttcaa gaagagatct   720
gaagatatcc aaaagagata cgatgctttg ttggaaaaga tcatctctga agagaatct   780
gaaagagcta agagaggtaa gaacagagaa actttgggtg aagaaggtgg taaggatttc   840
ttggacatga tgttggatac tatggaagat ggtaagtgtg aagttgaaat cactagagat   900
cacattaagg ccttggtttt ggatttcttg actgctgcca ctgatactac tgctattgct   960
gttgaatgga ctttggctga attgatctct aacccagaag ttttcgataa ggctagagaa  1020
gaaatcgata aggtcgttgg taagcacaga ttggtcactg aattggacac tccaaacttg  1080
ccatacatcc acgctatcat caaggaatct ttcagattgc acccaccaat tccattggtc  1140
atcagaaagt ctgtccaaga ttgtactgtt ggtggttacc acatctctgc taacactatc  1200
ttgttcatca acatttgggc catcggtaga aacccaaagt actgggaatc tccaatgaag  1260
ttctggccag aaagattctt ggaatccaac gaaccaggtt ctgttggttc tactgatatt  1320
aagggtcacc actacgaatt gttgccattc ggttctggta aagaggttg tccaggtatg  1380
gctttggcca tgcaagaatt gccagttgtt ttggccgcca tgatccaatg tttcaactgg  1440
aagccagtta ctttggacgg tgaagaattg gatatgtctg aaagaccagg tttgactgct  1500
ccaagagccc acgatttggt ttgtgttcca tccgctagaa ttaactcttt cgataacttc  1560
taa                                                               1563
```

<210> SEQ ID NO 37
<211> LENGTH: 366
<212> TYPE: PRT
<213> ORGANISM: Petroselinum crispum

<400> SEQUENCE: 37

```
Met Ser Ala Pro Thr Thr Ile Thr Ala Leu Ala Lys Glu Lys Thr Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Ile Pro Ile Ile Ser Leu Ala Gly Leu Asp
        35                  40                  45

Asp Asp Ser Asp Gly Arg Arg Pro Glu Ile Cys Arg Lys Ile Val Lys
    50                  55                  60

Ala Cys Glu Asp Trp Gly Ile Phe Gln Val Val Asp His Gly Ile Asp
65                  70                  75                  80

Ser Gly Leu Ile Ser Glu Met Thr Arg Leu Ser Arg Glu Phe Phe Ala
                85                  90                  95
```

Leu Pro Ala Glu Glu Lys Leu Glu Tyr Asp Thr Thr Gly Gly Lys Arg
            100                 105                 110

Gly Gly Phe Thr Ile Ser Thr Val Leu Gln Gly Asp Asp Ala Met Asp
            115                 120                 125

Trp Arg Glu Phe Val Thr Tyr Phe Ser Tyr Pro Ile Asn Ala Arg Asp
        130                 135                 140

Tyr Ser Arg Trp Pro Lys Lys Pro Glu Gly Trp Arg Ser Thr Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Glu Lys Gly Asp Leu Thr Lys Ala Cys
            180                 185                 190

Val Asp Met Glu Gln Lys Val Leu Ile Asn Tyr Tyr Pro Thr Cys Pro
        195                 200                 205

Gln Pro Asp Leu Thr Leu Gly Val Arg Arg His Thr Asp Pro Gly Thr
    210                 215                 220

Ile Thr Ile Leu Leu Gln Asp Met Val Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
            260                 265                 270

Arg Asn Ala Asp His Gln Ala Val Val Asn Ser Thr Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Cys Met Thr Lys His Ile Glu Val Ala
                325                 330                 335

Thr Arg Lys Lys Leu Ala Lys Glu Lys Arg Leu Gln Asp Glu Lys Ala
            340                 345                 350

Lys Leu Glu Met Lys Ser Lys Ser Ala Asp Glu Asn Leu Ala
        355                 360                 365

<210> SEQ ID NO 38
<211> LENGTH: 1101
<212> TYPE: DNA
<213> ORGANISM: artificial
<220> FEATURE:
<223> OTHER INFORMATION: coding sequence for SEQ ID NO: 37

<400> SEQUENCE: 38
atgtccgctc caactactat caccgctttg gccaaggaaa agactttgaa cttggacttc     60
gttagagatg aagatgaaag accaaaggtt gcttacaacc aattctctaa cgaaattcca    120
attatttctt tggccggttt ggatgacgat tctgatggta aaggccaga aatctgtaga    180 aagatcgtta aggcttgtga agattggggt attttccaag ttgttgatca cggtattgac    240
tctggtttga tttccgaaat gactagattg tctagagaat tcttcgcttt gccagctgaa    300
gaaaagttgg aatacgatac tactggtggt aagagaggtg gtttcactat ctccactgtt    360
ttgcaaggtg acgacgctat ggattggaga gaattcgtta cttacttctc ttacccaatc    420
aacgctagag actactctag atggccaaag aagccagaag ttggagatc taccactgaa    480 gtttactctg aaaagttgat ggttttgggt gccaagttgt tggaagtttt gtctgaagcc    540

-continued

```
atgggtttgg aaaagggtga tttgactaag gcttgtgttg atatggaaca aaaggttttg    600
attaactact acccaacttg tccacaacca gacttgactt tgggtgtcag gagacacact    660
gatccaggta ctattaccat tttgttgcaa gacatggttg gtggtttgca agccaccaga    720
gatggtggta agacttggat tactgttcaa ccagttgaag gtgctttcgt tgtcaacttg    780
ggtgatcacg gtcactactt gtctaacggt agattcagaa acgctgacca ccaagctgtt    840
gttaactcta cctcttctag attgtctatt gctactttcc aaaacccagc tcaaaacgct    900
atcgtttacc cattgaagat cagagaaggt gaaaaggcta ttttggatga agccatcacc    960
tacgctgaaa tgtacaagaa gtgtatgact aagcacattg aagttgctac tagaaagaag    1020
ttggccaagg aaaagagatt gcaagacgaa aaggccaagt tggaaatgaa gtccaagtct    1080
gctgatgaaa acttggctta a                                              1101
```

<210> SEQ ID NO 39
<211> LENGTH: 507
<212> TYPE: PRT
<213> ORGANISM: Flavobacterium johnsoniae

<400> SEQUENCE: 39

```
Met Ser Asn Thr Ile Asn Glu Tyr Leu Ser Leu Glu Glu Phe Glu Ala
1               5                   10                  15

Ile Ile Phe Gly Asn Gln Lys Val Thr Ile Ser Asp Val Val Val Asn
                20                  25                  30

Arg Val Asn Glu Ser Phe Asn Phe Leu Lys Glu Phe Ser Gly Asn Lys
            35                  40                  45

Val Ile Tyr Gly Val Asn Thr Gly Phe Gly Pro Met Ala Gln Tyr Arg
        50                  55                  60

Ile Lys Glu Ser Asp Gln Ile Gln Leu Gln Tyr Asn Leu Ile Arg Ser
65                  70                  75                  80

His Ser Ser Gly Thr Gly Lys Pro Leu Ser Pro Val Cys Ala Lys Ala
                85                  90                  95

Ala Ile Leu Ala Arg Leu Asn Thr Leu Ser Leu Gly Asn Ser Gly Val
                100                 105                 110

His Pro Ser Val Ile Asn Leu Met Ser Glu Leu Ile Asn Lys Asp Ile
            115                 120                 125

Thr Pro Leu Ile Phe Glu His Gly Gly Val Gly Ala Ser Gly Asp Leu
        130                 135                 140

Val Gln Leu Ser His Leu Ala Leu Val Leu Ile Gly Glu Gly Glu Val
145                 150                 155                 160

Phe Tyr Lys Gly Glu Arg Arg Pro Thr Pro Glu Val Phe Glu Ile Glu
                165                 170                 175

Gly Leu Lys Pro Ile Gln Val Glu Ile Arg Glu Gly Leu Ala Leu Ile
            180                 185                 190

Asn Gly Thr Ser Val Met Thr Gly Ile Gly Val Val Asn Val Tyr His
        195                 200                 205

Ala Lys Lys Leu Leu Asp Trp Ser Leu Lys Ser Ser Cys Ala Ile Asn
    210                 215                 220

Glu Leu Val Gln Ala Tyr Asp Asp His Phe Ser Ala Glu Leu Asn Gln
225                 230                 235                 240

Thr Lys Arg His Lys Gly Gln Gln Glu Ile Ala Leu Lys Met Arg Gln
                245                 250                 255

Asn Leu Ser Asp Ser Thr Leu Ile Arg Lys Arg Glu Asp His Leu Tyr
            260                 265                 270
```

```
Ser Gly Glu Asn Thr Glu Glu Ile Phe Lys Glu Lys Val Gln Glu Tyr
    275                 280                 285

Tyr Ser Leu Arg Cys Val Pro Gln Ile Leu Gly Pro Val Leu Glu Thr
    290                 295                 300

Ile Asn Asn Val Ala Ser Ile Leu Glu Asp Glu Phe Asn Ser Ala Asn
305                 310                 315                 320

Asp Asn Pro Ile Ile Asp Val Lys Asn Gln His Val Tyr His Gly Gly
                325                 330                 335

Asn Phe His Gly Asp Tyr Ile Ser Leu Glu Met Asp Lys Leu Lys Ile
            340                 345                 350

Val Ile Thr Lys Leu Thr Met Leu Ala Glu Arg Gln Leu Asn Tyr Leu
        355                 360                 365

Leu Asn Ser Lys Ile Asn Glu Leu Leu Pro Pro Phe Val Asn Leu Gly
    370                 375                 380

Thr Leu Gly Phe Asn Phe Gly Met Gln Gly Val Gln Phe Thr Ala Thr
385                 390                 395                 400

Ser Thr Thr Ala Glu Ser Gln Met Leu Ser Asn Pro Met Tyr Val His
                405                 410                 415

Ser Ile Pro Asn Asn Asn Asp Asn Gln Asp Ile Val Ser Met Gly Thr
            420                 425                 430

Asn Ser Ala Val Ile Thr Ser Lys Val Ile Glu Asn Ala Phe Glu Val
        435                 440                 445

Leu Ala Ile Glu Met Ile Thr Ile Val Gln Ala Ile Asp Tyr Leu Gly
    450                 455                 460

Gln Lys Asp Lys Ile Ser Ser Val Ser Lys Lys Trp Tyr Asp Glu Ile
465                 470                 475                 480

Arg Asn Ile Ile Pro Thr Phe Lys Glu Asp Gln Val Met Tyr Pro Phe
                485                 490                 495

Val Gln Lys Val Lys Asp His Leu Ile Asn Asn
            500                 505

<210> SEQ ID NO 40
<211> LENGTH: 1524
<212> TYPE: DNA
<213> ORGANISM: artificial
<220> FEATURE:
<223> OTHER INFORMATION: coding sequence for SEQ ID NO: 39

<400> SEQUENCE: 40
atgtccaaca ctattaacga atacttgtct ttggaagaat cgaagccat catcttcggt      60 aaccaaaagg ttactatttc tgacgttgtc gttaacagag ttaacgaatc tttcaacttc     120
ttgaaggaat tctctggtaa caaggttatt tacggtgtta acactggttt cggtccaatg     180
gctcaataca gaattaagga atctgatcaa attcaattgc aatacaactt gattagatct     240
cactcttctg gtaccggtaa gccattgtct ccagtttgtg ctaaggctgc tattttggct     300
agattgaaca ctttgtcttt gggtaactct ggtgttcacc atctgttat caacttgatg     360 tctgaattga tcaacaagga tattaccca ttgatcttcg aacacggtgg tgttggtgcc     420
tctggtgact ggttcaatt gtctcacttg gctttggttt tgattggtga aggtgaagtt     480
ttctacaagg gtgaaagaag gccaactcca gaagttttcg aaattgaagg tttgaagcca     540
attcaagttg aaattagaga aggttttggct tgattaacg gtacttctgt tatgactggt     600
attggtgttg ttaacgttta ccacgctaag aagttgttgg actggtcttt gaatcttct     660 tgtgctatta cgaattggt tcaagcttac gacgatcact tctctgctga attgaaccaa     720
```

```
actaagagac acaagggtca acaagaaatt gctttgaaga tgagacaaaa cttgtctgac      780
tctactttga tcagaaagag agaagatcac ttgtactctg gtgaaaacac cgaagaaatc      840
ttcaaggaaa aggttcaaga atactactct ttgagatgtg ttccacaaat tttgggtcca      900
gttttggaaa ctattaacaa cgttgcttct attttggaag atgaattcaa ctctgctaac      960
gataacccaa ttatcgatgt taagaaccaa cacgtttacc acggtggtaa cttccacggt     1020
gattacattt ctttggaaat ggataagttg aagattgtta ttaccaagtt gactatgttg     1080
gctgaaagac aattgaacta cttgttgaac tctaagatca cgaattgtt gccaccattc      1140 gttaacttgg gtactttggg tttcaacttc ggtatgcaag tgttcaatt cactgctact      1200 tctactactg ctgaatctca aatgttgtct aacccaatgt acgttcactc tattccaaac     1260
aacaacgaca accaagatat cgtttctatg ggtactaact ctgctgttat tacctctaag     1320
gttatcgaaa acgctttcga agttttggct atcgaaatga ttactatcgt tcaagctatt     1380
gattacttgg gtcaaaagga caagatttct tctgtttcta agaagtggta cgatgaaatt     1440
agaaacatca ttccaacttt caaggaagat caagttatgt acccattcgt tcaaaaggtt     1500
aaggatcact tgatcaacaa ctaa                                             1524
```

<210> SEQ ID NO 41
<211> LENGTH: 694
<212> TYPE: PRT
<213> ORGANISM: Rhodotorula glutinis

<400> SEQUENCE: 41

```
Met Ser Ala Pro Arg Pro Thr Ser Gln Ser Gln Ala Arg Thr Cys Pro
1               5                   10                  15

Thr Thr Gln Val Thr Gln Val Asp Ile Val Glu Lys Met Leu Ala Ala
            20                  25                  30

Pro Thr Asp Ser Thr Leu Glu Leu Asp Gly Tyr Ser Leu Asn Leu Gly
        35                  40                  45

Asp Val Val Ser Ala Ala Arg Lys Gly Arg Pro Val Arg Val Lys Asp
    50                  55                  60

Ser Asp Glu Ile Arg Ser Lys Ile Asp Lys Ser Val Glu Phe Leu Arg
65                  70                  75                  80

Ser Gln Leu Ser Met Ser Val Tyr Gly Val Thr Thr Gly Phe Gly Gly
                85                  90                  95

Ser Ala Asp Thr Arg Thr Glu Asp Ala Ile Ser Leu Gln Lys Ala Leu
            100                 105                 110

Leu Glu His Gln Leu Cys Gly Val Leu Pro Ser Ser Phe Asp Ser Phe
        115                 120                 125

Arg Leu Gly Arg Gly Leu Glu Asn Ser Leu Pro Leu Glu Val Val Arg
    130                 135                 140

Gly Ala Met Thr Ile Arg Val Asn Ser Leu Thr Arg Gly His Ser Ala
145                 150                 155                 160

Val Arg Leu Val Val Leu Glu Ala Leu Thr Asn Phe Leu Asn His Gly
                165                 170                 175

Ile Thr Pro Ile Val Pro Leu Arg Gly Thr Ile Ser Ala Ser Gly Asp
            180                 185                 190

Leu Ser Pro Leu Ser Tyr Ile Ala Ala Ala Ile Ser Gly His Pro Asp
        195                 200                 205

Ser Lys Val His Val Val His Glu Gly Lys Glu Lys Ile Leu Tyr Ala
    210                 215                 220
```

-continued

```
Arg Glu Ala Met Ala Leu Phe Asn Leu Glu Pro Val Val Leu Gly Pro
225                 230                 235                 240
Lys Glu Gly Leu Gly Leu Val Asn Gly Thr Ala Val Ser Ala Ser Met
                245                 250                 255
Ala Thr Leu Ala Leu His Asp Ala His Met Leu Ser Leu Leu Ser Gln
            260                 265                 270
Ser Leu Thr Ala Met Thr Val Glu Ala Met Val Gly His Ala Gly Ser
        275                 280                 285
Phe His Pro Phe Leu His Asp Val Thr Arg Pro His Pro Thr Gln Ile
    290                 295                 300
Glu Val Ala Gly Asn Ile Arg Lys Leu Leu Glu Gly Ser Arg Phe Ala
305                 310                 315                 320
Val His His Glu Glu Val Lys Val Lys Asp Asp Glu Gly Ile Leu
                325                 330                 335
Arg Gln Asp Arg Tyr Pro Leu Arg Thr Ser Pro Gln Trp Leu Gly Pro
                340                 345                 350
Leu Val Ser Asp Leu Ile His Ala His Ala Val Leu Thr Ile Glu Ala
        355                 360                 365
Gly Gln Ser Thr Thr Asp Asn Pro Leu Ile Asp Val Glu Asn Lys Thr
370                 375                 380
Ser His His Gly Gly Asn Phe Gln Ala Ala Ala Val Ala Asn Thr Met
385                 390                 395                 400
Glu Lys Thr Arg Leu Gly Leu Ala Gln Ile Gly Lys Leu Asn Phe Thr
                405                 410                 415
Gln Leu Thr Glu Met Leu Asn Ala Gly Met Asn Arg Gly Leu Pro Ser
            420                 425                 430
Cys Leu Ala Ala Glu Asp Pro Ser Leu Ser Tyr His Cys Lys Gly Leu
        435                 440                 445
Asp Ile Ala Ala Ala Tyr Thr Ser Glu Leu Gly His Leu Ala Asn
    450                 455                 460
Pro Val Thr Thr His Val Gln Pro Ala Glu Met Ala Asn Gln Ala Val
465                 470                 475                 480
Asn Ser Leu Ala Leu Ile Ser Ala Arg Arg Thr Thr Glu Ser Asn Asp
                485                 490                 495
Val Leu Ser Leu Leu Leu Ala Thr His Leu Tyr Cys Val Leu Gln Ala
            500                 505                 510
Ile Asp Leu Arg Ala Ile Glu Phe Glu Phe Lys Lys Gln Phe Gly Pro
        515                 520                 525
Ala Ile Val Ser Leu Ile Asp Gln His Phe Gly Ser Ala Met Thr Gly
    530                 535                 540
Ser Asn Leu Arg Asp Glu Leu Val Glu Lys Val Asn Lys Thr Leu Ala
545                 550                 555                 560
Lys Arg Leu Glu Gln Thr Asn Ser Tyr Asp Leu Val Pro Arg Trp His
                565                 570                 575
Asp Ala Phe Ser Phe Ala Ala Gly Thr Val Val Glu Val Leu Ser Ser
            580                 585                 590
Thr Ser Leu Ser Leu Ala Ala Val Asn Ala Trp Lys Val Ala Ala Ala
        595                 600                 605
Glu Ser Ala Ile Ser Leu Thr Arg Gln Val Arg Glu Thr Phe Trp Ser
    610                 615                 620
Ala Ala Ser Thr Ser Ser Pro Ala Leu Ser Tyr Leu Ser Pro Arg Thr
625                 630                 635                 640
Gln Ile Leu Tyr Ala Phe Val Arg Glu Glu Leu Gly Val Lys Ala Arg
```

```
                    645                 650                 655
Arg Gly Asp Val Phe Leu Gly Lys Gln Glu Val Thr Ile Gly Ser Asn
                660                 665                 670

Val Ser Lys Ile Tyr Glu Ala Ile Lys Ser Gly Arg Ile Asn Asn Val
            675                 680                 685

Leu Leu Lys Met Leu Ala
        690

<210> SEQ ID NO 42
<211> LENGTH: 2085
<212> TYPE: DNA
<213> ORGANISM: artificial
<220> FEATURE:
<223> OTHER INFORMATION: coding sequence for SEQ ID NO: 41

<400> SEQUENCE: 42
```

| | | | | | |
|---|---|---|---|---|---|
| atgtccgctc | caagaccaac | ttctcaatct | caagccagaa | cttgtccaac | cacccaagtt | 60 |
| acccaagttg | atatcgttga | aaagatgttg | gctgctccaa | ctgattctac | cttggaattg | 120 |
| gacggttact | ctttgaactt | gggtgatgtt | gtttctgctg | ctagaaaggg | tagaccagtt | 180 |
| agagttaagg | attctgatga | aatcagatct | aagatcgaca | gtctgttgaa | attcttgaga | 240 |
| tctcaattgt | ctatgtctgt | ttacggtgtt | accaccggtt | tcggtggttc | cgctgacacc | 300 |
| agaaccgaag | atgctatttc | tttgcaaaag | gctttgttgg | aacaccaatt | gtgtggtgtt | 360 |
| ttgccatctt | ctttcgactc | tttcagattg | ggtagaggtt | tggaaaactc | tttgccattg | 420 |
| gaagttgtta | gaggtgctat | gaccattaga | gttaactctt | tgaccagagg | tcactctgct | 480 |
| gttagattgg | ttgttttgga | agctttgacc | aacttcttga | ccacggtat | accccaatt | 540 |
| gttccattga | gaggtaccat | ctccgcttct | ggtgatttgt | ctccattgtc | ttacattgct | 600 |
| gctgctattt | ctggtcaccc | agattctaag | gttcacgttt | tcacgaagg | taaggaaaag | 660 |
| atcttgtacg | ctagagaagc | tatggctttg | ttcaacttgg | aaccagttgt | tttgggtcca | 720 |
| aaggaaggtt | tgggtttggt | taacggtacc | gctgtttccg | cttctatggc | taccttggct | 780 |
| ttgcacgacg | ctcacatgtt | gtctttgttg | tctcaatctt | tgaccgctat | gaccgttgaa | 840 |
| gctatggttg | gtcacgctgg | ttctttccac | ccattcttgc | acgatgttac | cagaccacac | 900 |
| ccaacccaaa | tcgaagttgc | tggtaacatt | agaaagttgt | tggaaggttc | tagattcgct | 960 |
| gttcaccacg | aagaagaagt | taaggttaag | gatgatgaag | gtattttgag | acaagataga | 1020 |
| tacccattga | gaacctctcc | acaatggttg | ggtccattgg | tttccgactt | gattcacgct | 1080 |
| cacgccgttt | tgaccatcga | agctggtcaa | tctaccaccg | ataaaccatt | gatcgatgtt | 1140 |
| gaaaacaaga | cctctcacca | cggtggtaac | ttccaagctg | ctgctgttgc | caacactatg | 1200 |
| gaaaagacca | gattgggttt | ggcccaaatc | ggtaagttga | acttcacca | attgaccgaa | 1260 |
| atgttgaacg | ctggtatgaa | cagaggtttg | ccatcttgtt | tggctgctga | agatccatcc | 1320 |
| ttgtcttacc | actgtaaggg | tttggacatt | gctgctgctg | cttacacctc | tgaattgggt | 1380 |
| cacttggcta | acccagttac | cacccacgtt | caaccagctg | aaatggctaa | ccaagctgtt | 1440 |
| aactctttgg | ctttgatttc | tgctagaaga | accaccgaat | ctaacgacgt | tttgtccttg | 1500 |
| ttgttggcta | cccacttgta | ctgtgttttg | caagctatcg | acttgagagc | tattgaattc | 1560 |
| gaattcaaga | agcaattcgg | tccagccatt | gtttctttga | tcgaccaaca | cttcggttct | 1620 |
| gctatgaccg | ttctaacttt | gagagatgaa | ttggttgaaa | aggttaacaa | gactttggcc | 1680 |
| aagagattgg | aacaaaccaa | ctcttacgat | ttggttccaa | gatggcacga | cgctttctct | 1740 |

-continued

```
ttcgctgctg gtactgttgt tgaagttttg tcctctacct ctttgtcttt ggctgccgtt    1800
aacgcttgga aggttgctgc tgccgaatct gctatctcct tgaccagaca agttagagaa    1860
accttctggt ccgctgcttc tacctcctct ccagctttgt cttacttgtc tccaagaacc    1920
caaatcttgt acgctttcgt tagagaagaa ttgggtgtta aggccagaag aggtgacgtt    1980
ttcttgggta agcaagaagt taccatcggt tctaacgttt ctaagattta cgaagccatc    2040
aagtctggta gaatcaacaa cgttttgttg aagatgttgg cttaa                    2085
```

<210> SEQ ID NO 43
<211> LENGTH: 562
<212> TYPE: PRT
<213> ORGANISM: Arabidopsis thaliana

<400> SEQUENCE: 43

```
Met Ser Ala Pro Gln Glu Gln Ala Val Ser Gln Val Met Glu Lys Gln
1               5                   10                  15

Ser Asn Asn Asn Ser Asp Val Ile Phe Arg Ser Lys Leu Pro Asp
            20                  25                  30

Ile Tyr Ile Pro Asn His Leu Ser Leu His Asp Tyr Ile Phe Gln Asn
        35                  40                  45

Ile Ser Glu Phe Ala Thr Lys Pro Cys Leu Ile Asn Gly Pro Thr Gly
    50                  55                  60

His Val Tyr Thr Tyr Ser Asp Val His Val Ile Ser Arg Gln Ile Ala
65                  70                  75                  80

Ala Asn Phe His Lys Leu Gly Val Asn Gln Asn Asp Val Val Met Leu
                85                  90                  95

Leu Leu Pro Asn Cys Pro Glu Phe Val Leu Ser Phe Leu Ala Ala Ser
            100                 105                 110

Phe Arg Gly Ala Thr Ala Thr Ala Ala Asn Pro Phe Phe Thr Pro Ala
        115                 120                 125

Glu Ile Ala Lys Gln Ala Lys Ala Ser Asn Thr Lys Leu Ile Ile Thr
    130                 135                 140

Glu Ala Arg Tyr Val Asp Lys Ile Lys Pro Leu Gln Asn Asp Asp Gly
145                 150                 155                 160

Val Val Ile Val Cys Ile Asp Asp Asn Glu Ser Val Pro Ile Pro Glu
                165                 170                 175

Gly Cys Leu Arg Phe Thr Glu Leu Thr Gln Ser Thr Thr Glu Ala Ser
            180                 185                 190

Glu Val Ile Asp Ser Val Glu Ile Ser Pro Asp Asp Val Val Ala Leu
        195                 200                 205

Pro Tyr Ser Ser Gly Thr Thr Gly Leu Pro Lys Gly Val Met Leu Thr
    210                 215                 220

His Lys Gly Leu Val Thr Ser Val Ala Gln Gln Val Asp Gly Glu Asn
225                 230                 235                 240

Pro Asn Leu Tyr Phe His Ser Asp Asp Val Ile Leu Cys Val Leu Pro
                245                 250                 255

Met Phe His Ile Tyr Ala Leu Asn Ser Ile Met Leu Cys Gly Leu Arg
            260                 265                 270

Val Gly Ala Ala Ile Leu Ile Met Pro Lys Phe Glu Ile Asn Leu Leu
        275                 280                 285

Leu Glu Leu Ile Gln Arg Cys Lys Val Thr Val Ala Pro Met Val Pro
    290                 295                 300

Pro Ile Val Leu Ala Ile Ala Lys Ser Ser Glu Thr Glu Lys Tyr Asp
305                 310                 315                 320
```

Leu Ser Ser Ile Arg Val Val Lys Ser Gly Ala Ala Pro Leu Gly Lys
            325                 330                 335

Glu Leu Glu Asp Ala Val Asn Ala Lys Phe Pro Asn Ala Lys Leu Gly
                340                 345                 350

Gln Gly Tyr Gly Met Thr Glu Ala Gly Pro Val Leu Ala Met Ser Leu
            355                 360                 365

Gly Phe Ala Lys Glu Pro Phe Pro Val Lys Ser Gly Ala Cys Gly Thr
        370                 375                 380

Val Val Arg Asn Ala Glu Met Lys Ile Val Asp Pro Asp Thr Gly Asp
385                 390                 395                 400

Ser Leu Ser Arg Asn Gln Pro Gly Glu Ile Cys Ile Arg Gly His Gln
                405                 410                 415

Ile Met Lys Gly Tyr Leu Asn Asn Pro Ala Ala Thr Ala Glu Thr Ile
            420                 425                 430

Asp Lys Asp Gly Trp Leu His Thr Gly Asp Ile Gly Leu Ile Asp Asp
        435                 440                 445

Asp Asp Glu Leu Phe Ile Val Asp Arg Leu Lys Glu Leu Ile Lys Tyr
    450                 455                 460

Lys Gly Phe Gln Val Ala Pro Ala Glu Leu Glu Ala Leu Leu Ile Gly
465                 470                 475                 480

His Pro Asp Ile Thr Asp Val Ala Val Val Ala Met Lys Glu Glu Ala
                485                 490                 495

Ala Gly Glu Val Pro Val Ala Phe Val Val Lys Ser Lys Asp Ser Glu
            500                 505                 510

Leu Ser Glu Asp Asp Val Lys Gln Phe Val Ser Lys Gln Val Val Phe
        515                 520                 525

Tyr Lys Arg Ile Asn Lys Val Phe Phe Thr Glu Ser Ile Pro Lys Ala
    530                 535                 540

Pro Ser Gly Lys Ile Leu Arg Lys Asp Leu Arg Ala Lys Leu Ala Asn
545                 550                 555                 560

Gly Leu

<210> SEQ ID NO 44
<211> LENGTH: 1689
<212> TYPE: DNA
<213> ORGANISM: artificial
<220> FEATURE:
<223> OTHER INFORMATION: coding sequence for SEQ ID NO: 43

<400> SEQUENCE: 44
atgtccgctc acaagaaca agctgtttct caagttatgg aaaagcaatc taacaacaac      60
aactctgacg tcattttcag atctaagttg ccagatattt catcccaaa ccacttgtct     120 ttgcacgact acatcttcca aaacatctcc gaattcgcca ctaagccatg tttgatcaac     180
ggtccaaccg tcacgttta cacttactcc gacgtccacg tcatctccag acaaatcgcc     240
gccaacttcc acaagttggg tgttaaccaa acgacgtcg tcatgttgtt gttgccaaac     300
tgtccagaat tcgtcttgtc tttcttggcc gcctccttca gaggtgctac cgccaccgcc     360
gctaacccat tcttcactcc agctgaaatc gctaagcaag ccaaggcctc caacaccaag     420
ttgatcatca ccgaagctag atacgtcgac aagatcaagc cattgcaaaa cgacgacggt     480
gttgtcatcg tctgtatcga cgacaacgaa tccgttccaa tcccagaagg ttgtttgaga     540
ttcaccgaat tgactcaatc tactaccgaa gcttctgaag tcatcgactc tgttgaaatt     600
tctccagacg acgttgttgc tttgccatac tcctctggta ctactggttt gccaaagggt     660

-continued

```
gttatgttga ctcacaaggg tttggtcact tctgttgctc aacaagtcga cggtgaaaac    720
ccaaacttgt acttccactc tgatgacgtc atcttgtgtg ttttgccaat gttccacatc    780
tacgctttga actctatcat gttgtgtggt ttgagagttg gtgctgctat tttgatcatg    840
ccaaagttcg aaatcaactt gttgttggaa ttgatccaaa gatgtaaggt tactgttgct    900
ccaatggttc caccaattgt tttggccatt gctaaatctt ctgaaactga aaagtacgat    960
ttatcttcta tcagagttgt taagtctggt gctgctccat gggtaaggaa ttggaagat   1020 gccgttaacg ccaagttccc aaacgccaag ttgggtcaag ttacggtat gactgaagct   1080 ggtccagttt ggctatgtc tttgggtttc gctaaggaac cattcccagt taagtctggt   1140
gcttgtggta ctgttgttag aaacgctgaa atgaagatcg ttgatccaga caccggtgat   1200
tctttgtcta gaaaccaacc aggtgaaatt tgtattagag gtcaccaaat catgaagggt   1260
tacttgaaca acccagctgc tactgctgaa accattgata aggacggttg gttgcacact   1320
ggtgatattg gtttgatcga tgacgatgac gaattgttca tcgttgatag attgaaggaa   1380
ttgatcaagt acaagggttt ccaagttgct ccagctgaat ggaagctttt gttgatcggt   1440
cacccagaca ttactgatgt tgctgttgtc gctatgaagg aagaagctgc tggtgaagtt   1500
ccagttgctt tcgttgttaa gtctaaggat tctgaattgt ctgaagatga tgttaagcaa   1560
ttcgtttcta gcaagttgt tttctacaag agaatcaaca aggttttctt cactgaatcc   1620
attccaaagg ctccatctgg taagatcttg agaaaggatt tgagagctaa gttggctaac   1680
ggtttgtaa                                                           1689
```

<210> SEQ ID NO 45
<211> LENGTH: 545
<212> TYPE: PRT
<213> ORGANISM: Petroselinum crispum

<400> SEQUENCE: 45

```
Met Ser Gly Asp Cys Val Ala Pro Lys Glu Asp Leu Ile Phe Arg Ser
1               5                   10                  15

Lys Leu Pro Asp Ile Tyr Ile Pro Lys His Leu Pro Leu His Thr Tyr
                20                  25                  30

Cys Phe Glu Asn Ile Ser Lys Val Gly Asp Lys Ser Cys Leu Ile Asn
            35                  40                  45

Gly Ala Thr Gly Glu Thr Phe Thr Tyr Ser Gln Val Glu Leu Leu Ser
        50                  55                  60

Arg Lys Val Ala Ser Gly Leu Asn Lys Leu Gly Ile Gln Gln Gly Asp
65                  70                  75                  80

Thr Ile Met Leu Leu Leu Pro Asn Ser Pro Glu Tyr Phe Phe Ala Phe
                85                  90                  95

Leu Gly Ala Ser Tyr Arg Gly Ala Ile Ser Thr Met Ala Asn Pro Phe
            100                 105                 110

Phe Thr Ser Ala Glu Val Ile Lys Gln Leu Lys Ala Ser Gln Ala Lys
        115                 120                 125

Leu Ile Ile Thr Gln Ala Cys Tyr Val Asp Lys Val Lys Asp Tyr Ala
    130                 135                 140

Ala Glu Lys Asn Ile Gln Ile Ile Cys Ile Asp Asp Ala Pro Gln Asp
145                 150                 155                 160

Cys Leu His Phe Ser Lys Leu Met Glu Ala Asp Glu Ser Glu Met Pro
                165                 170                 175

Glu Val Val Ile Asn Ser Asp Asp Val Val Ala Leu Pro Tyr Ser Ser
```

```
                180                 185                 190
Gly Thr Thr Gly Leu Pro Lys Gly Val Met Leu Thr His Lys Gly Leu
                    195                 200                 205
Val Thr Ser Val Ala Gln Gln Val Asp Gly Asp Asn Pro Asn Leu Tyr
        210                 215                 220
Met His Ser Glu Asp Val Met Ile Cys Ile Leu Pro Leu Phe His Ile
225                 230                 235                 240
Tyr Ser Leu Asn Ala Val Leu Cys Cys Gly Leu Arg Ala Gly Val Thr
                245                 250                 255
Ile Leu Ile Met Gln Lys Phe Asp Ile Val Pro Phe Leu Glu Leu Ile
            260                 265                 270
Gln Lys Tyr Lys Val Thr Ile Gly Pro Phe Val Pro Pro Ile Val Leu
        275                 280                 285
Ala Ile Ala Lys Ser Pro Val Val Asp Lys Tyr Asp Leu Ser Ser Val
        290                 295                 300
Arg Thr Val Met Ser Gly Ala Ala Pro Leu Gly Lys Glu Leu Glu Asp
305                 310                 315                 320
Ala Val Arg Ala Lys Phe Pro Asn Ala Lys Leu Gly Gln Gly Tyr Gly
                325                 330                 335
Met Thr Glu Ala Gly Pro Val Leu Ala Met Cys Leu Ala Phe Ala Lys
                340                 345                 350
Glu Pro Tyr Glu Ile Lys Ser Gly Ala Cys Gly Thr Val Val Arg Asn
                355                 360                 365
Ala Glu Met Lys Ile Val Asp Pro Glu Thr Asn Ala Ser Leu Pro Arg
        370                 375                 380
Asn Gln Arg Gly Glu Ile Cys Ile Arg Gly Asp Gln Ile Met Lys Gly
385                 390                 395                 400
Tyr Leu Asn Asp Pro Glu Ser Thr Arg Thr Thr Ile Asp Glu Glu Gly
                405                 410                 415
Trp Leu His Thr Gly Asp Ile Gly Phe Ile Asp Asp Asp Asp Glu Leu
                420                 425                 430
Phe Ile Val Asp Arg Leu Lys Glu Ile Ile Lys Tyr Lys Gly Phe Gln
            435                 440                 445
Val Ala Pro Ala Glu Leu Glu Ala Leu Leu Leu Thr His Pro Thr Ile
        450                 455                 460
Ser Asp Ala Ala Val Val Pro Met Ile Asp Glu Lys Ala Gly Glu Val
465                 470                 475                 480
Pro Val Ala Phe Val Val Arg Thr Asn Gly Phe Thr Thr Thr Glu Glu
                485                 490                 495
Glu Ile Lys Gln Phe Val Ser Lys Gln Val Val Phe Tyr Lys Arg Ile
                500                 505                 510
Phe Arg Val Phe Phe Val Asp Ala Ile Pro Lys Ser Pro Ser Gly Lys
            515                 520                 525
Ile Leu Arg Lys Asp Leu Arg Ala Arg Ile Ala Ser Gly Asp Leu Pro
        530                 535                 540
Lys
545

<210> SEQ ID NO 46
<211> LENGTH: 1638
<212> TYPE: DNA
<213> ORGANISM: artificial
<220> FEATURE:
<223> OTHER INFORMATION: coding sequence for SEQ ID NO: 45
```

<400> SEQUENCE: 46

```
atgtccggtg attgtgttgc tccaaaggaa gatttgattt tcagatctaa gttgccagat     60
atttacatcc caaagcactt gccattgcac acttactgtt tcgaaaacat ctctaaggtt    120
ggtgacaagt cctgtttgat caacggtgct actggtgaaa cttcactta ctctcaagtt    180
gaattgttgt ccagaaaggt tgcttctggt ttgaacaagt tgggtattca acaaggtgat    240
accatcatgt tgttgttgcc aaactcccca gaatacttct tcgctttctt gggtgcttct    300
tacagaggtg ctatttctac tatggccaac ccattcttca cttctgctga agttatcaag    360
caattgaagg cttcccaagc taagttgatc attactcaag cttgttacgt tgacaaggtt    420
aaggactacg ctgctgaaaa gaacatccaa atcatttgta tcgatgatgc tccacaagat    480
tgtttgcact ctccaagtt gatggaagct gatgaatctg aaatgccaga agttgttatc    540
aactctgacg atgtcgtcgc tttgccatac tcttctggta ctactggttt gccaaagggt    600
gttatgttga ctcacaaggg tttggttact tctgttgctc aacaagttga tggtgacaac    660
ccaaacttgt acatgcactc tgaagatgtt atgatctgta tcttgccatt gttccacatt    720
tactctttga cgctgttttt gtgttgtggt ttgagagctg gtgttactat cttgattatg    780
caaaagttcg atattgttcc attcttggaa ttgatccaaa agtacaaggt tactattggt    840
ccattcgttc caccaattgt tttggctatt gctaagtctc cagttgttga taagtacgac    900
ttatcttctg ttagaactgt tatgtctggt gctgctccat gggtaagga attggaagat    960
gctgttagag ctaagttccc aaacgccaag ttgggtcaag gttacggtat gactgaagct   1020
ggtccagttt tggctatgtg tttggctttc gctaaggaac catacgaaat caagtctggt   1080
gcctgtggta ctgttgttag aaacgctgaa atgaagattg ttgatccaga aaccaacgcc   1140
tctttgccaa gaaaccaaag aggtgaaatt tgtattagag gtgaccaaat tatgaaggg   1200
tacttgaacg atccagaatc tactagaact actatcgacg aagaaggttg gttgcacact   1260
ggtgatatcg gtttcattga cgacgatgat gaattgttca ttgttgatag attgaaggaa   1320
atcatcaagt acaagggttt ccaagttgcc ccagctgaat tggaagcttt tgttgttgact   1380
cacccaacca tttccgatgc tgctgttgtt ccaatgatcg atgaaaaggc tggtgaagtt   1440
ccagttgctt tcgttgttag aactaacggt ttcaccacca ctgaagaaga atcaagcaa   1500
ttcgtttcta gcaagttgt tttctacaag agaatcttca gagttttctt cgttgatgct   1560
attccaaagt ctccatctgg taagattttg agaaaggact tgagagctag aatcgcttcc   1620
ggtgatttgc caaagtaa                                                  1638
```

<210> SEQ ID NO 47
<211> LENGTH: 545
<212> TYPE: PRT
<213> ORGANISM: Petroselinum crispum

<400> SEQUENCE: 47

```
Met Ser Gly Asp Cys Val Ala Pro Lys Glu Asp Leu Ile Phe Arg Ser
1               5                   10                  15

Lys Leu Pro Asp Ile Tyr Ile Pro Lys His Leu Pro Leu His Thr Tyr
                20                  25                  30

Cys Phe Glu Asn Ile Ser Lys Val Gly Asp Lys Ser Cys Leu Ile Asn
            35                  40                  45

Gly Ala Thr Gly Glu Thr Phe Thr Tyr Ser Gln Val Glu Leu Leu Ser
        50                  55                  60

Arg Lys Val Ala Ser Gly Leu Asn Lys Leu Gly Ile Gln Gln Gly Asp
```

```
            65                  70                  75                  80
Thr Ile Met Leu Leu Pro Asn Ser Pro Glu Tyr Phe Phe Ala Phe
                85                  90                  95

Leu Gly Ala Ser Tyr Arg Gly Ala Ile Ser Thr Met Ala Asn Pro Phe
            100                 105                 110

Phe Thr Ser Ala Glu Val Ile Lys Gln Leu Lys Ala Ser Leu Ala Lys
            115                 120                 125

Leu Ile Ile Thr Gln Ala Cys Tyr Val Asp Lys Val Lys Asp Tyr Ala
        130                 135                 140

Ala Glu Lys Asn Ile Gln Ile Ile Cys Ile Asp Asp Ala Pro Gln Asp
145                 150                 155                 160

Cys Leu His Phe Ser Lys Leu Met Glu Ala Asp Glu Ser Glu Met Pro
                165                 170                 175

Glu Val Val Ile Asp Ser Asp Asp Val Ala Leu Pro Tyr Ser Ser
            180                 185                 190

Gly Thr Thr Gly Leu Pro Lys Gly Val Met Leu Thr His Lys Gly Leu
        195                 200                 205

Val Thr Ser Val Ala Gln Gln Val Asp Gly Asp Asn Pro Asn Leu Tyr
    210                 215                 220

Met His Ser Glu Asp Val Met Ile Cys Ile Leu Pro Leu Phe His Ile
225                 230                 235                 240

Tyr Ser Leu Asn Ala Val Leu Cys Cys Gly Leu Arg Ala Gly Val Thr
                245                 250                 255

Ile Leu Ile Met Gln Lys Phe Asp Ile Val Pro Phe Leu Glu Leu Ile
            260                 265                 270

Gln Lys Tyr Lys Val Thr Ile Gly Pro Phe Val Pro Pro Ile Val Leu
        275                 280                 285

Ala Ile Ala Lys Ser Pro Val Val Asp Lys Tyr Asp Leu Ser Ser Val
    290                 295                 300

Arg Thr Val Met Ser Gly Ala Ala Pro Leu Gly Lys Glu Leu Glu Asp
305                 310                 315                 320

Ala Val Arg Ala Lys Phe Pro Asn Ala Lys Leu Gly Gln Gly Tyr Gly
                325                 330                 335

Met Thr Glu Ala Gly Pro Val Leu Ala Met Cys Leu Ala Phe Ala Lys
            340                 345                 350

Glu Pro Tyr Glu Ile Lys Ser Gly Ala Cys Gly Thr Val Val Arg Asn
        355                 360                 365

Ala Glu Met Lys Ile Val Asp Pro Glu Thr Asn Ala Ser Leu Pro Arg
    370                 375                 380

Asn Gln Arg Gly Glu Ile Cys Ile Arg Gly Asp Gln Ile Met Lys Gly
385                 390                 395                 400

Tyr Leu Asn Asp Pro Glu Ser Thr Arg Thr Thr Ile Asp Glu Glu Gly
                405                 410                 415

Trp Leu His Thr Gly Asp Ile Gly Phe Ile Asp Asp Asp Glu Leu
            420                 425                 430

Phe Ile Val Asp Arg Leu Lys Glu Ile Ile Lys Tyr Lys Gly Phe Gln
        435                 440                 445

Val Ala Pro Ala Glu Leu Glu Ala Leu Leu Leu Thr His Pro Thr Ile
    450                 455                 460

Ser Asp Ala Ala Val Val Pro Met Ile Asp Glu Lys Ala Gly Glu Val
465                 470                 475                 480

Pro Val Ala Phe Val Val Arg Thr Asn Gly Phe Thr Thr Glu Glu
                485                 490                 495
```

```
Glu Ile Lys Gln Phe Val Ser Lys Gln Val Val Phe Tyr Lys Arg Ile
            500                 505                 510

Phe Arg Val Phe Phe Val Asp Ala Ile Pro Lys Ser Pro Ser Gly Lys
            515                 520                 525

Ile Leu Arg Lys Asp Leu Arg Ala Lys Ile Ala Ser Gly Asp Leu Pro
            530                 535                 540

Lys
545

<210> SEQ ID NO 48
<211> LENGTH: 1638
<212> TYPE: DNA
<213> ORGANISM: artificial
<220> FEATURE:
<223> OTHER INFORMATION: coding sequence for SEQ ID NO: 47

<400> SEQUENCE: 48
atgtccggtg actgtgttgc tccaaaggaa gatttgattt tcagatctaa gttgccagat      60
atttacatcc aaagcacttg ccattgcac acttactgtt tcgaaaacat ctctaaggtt     120
ggtgacaagt cctgtttgat caacggtgct actggtgaaa cttcactta ctctcaagtt     180 gaattgttgt ccagaaaggt tgcttctggt ttgaacaagt gggtattca acaaggtgat     240 accatcatgt tgttgttgcc aaactcccca gaatacttct tcgctttctt gggtgcttct     300
tacagaggtg ctatttctac tatggccaac ccattcttca cttctgctga gttatcaag     360 caattgaagg cttccttggc taagttgatc attactcaag cttgttacgt tgacaaggtt     420
aaggactacg ctgctgaaaa gaacatccaa atcatttgta tcgatgatgc tccacaagat     480
tgtttgcact ctccaagtt gatggaagct gatgaatctg aaatgccaga agttgttatc     540
gattctgacg atgtcgtcgc tttgccatac tcttctggta ctactggttt gccaaagggt     600
gttatgttga cccacaaggg tttggttact tctgttgctc aacaagttga tggtgacaac     660
ccaaacttgt acatgcactc tgaagatgtt atgatctgta tcttgccatt gttccacatt     720 tactcttga acgctgtttt tgttgtggt ttgagagctg tgttactat cttgattatg     780 caaaagttcg atattgttcc attcttggaa ttgatccaaa agtacaaggt tactattggt     840
ccattcgttc caccaattgt tttggctatt gctaagtctc cagttgttga taagtacgac     900
ttatcttctg ttagaactgt tatgtctggt gctgctccat gggtaagga attggaagat     960 gctgttagag ctaagttccc aaacgccaag ttgggtcaag ttacggtat gactgaagct    1020 ggtccagttt tggctatgtg tttggctttc gctaaggaac catacgaaat caagtctggt    1080
gcctgtggta ctgttgttag aaacgctgaa atgaagattg ttgatccaga accaacgcc    1140 tctttgccaa gaaccaaag aggtgaaatt tgtattagag gtgaccaaat tatgaagggt    1200
tacttgaacg atccagaatc tactagaact actatcgacg aagaaggttg gttgcacact    1260
ggtgatatcg gtttcattga cgacgatgat gaattgttca ttgttgatag attgaaggaa    1320
atcatcaagt acaagggttt ccaagttgcc ccagctgaat ggaagctttt gttgttgact    1380
cacccaacca tttccgatgc tgctgttgtt ccaatgatcg atgaaaaggc tggtgaagtt    1440
ccagttgctt cgttgttag aactaacggt ttcaccacca ctgaagaaga atcaagcaa    1500 ttcgtttcta gcaagttgt tttctacaag agaatcttca gagttttctt cgttgatgct    1560
attccaaagt ctccatctgg taagattttg agaaaggact tgagagctaa gatcgcttcc    1620
ggtgatttgc caaagtaa                                                 1638
```

<210> SEQ ID NO 49
<211> LENGTH: 579
<212> TYPE: PRT
<213> ORGANISM: Streptomyces clavuligerus

<400> SEQUENCE: 49

Met Ser Ala Ser Thr Pro Ser Pro Gly Pro Ser Gly Thr Pro Ser Gly
1               5                   10                  15

Thr Pro Pro Ser Gly Pro Ser Gly Thr Pro Ser Pro Gly Pro Ala Gly
            20                  25                  30

Ala Gly Thr Ala Pro Val Phe Arg Ser Arg Tyr Pro Asp Ile Glu Pro
        35                  40                  45

Val Ser Glu Pro Leu His Glu Ala Val Leu Gly Arg Ala Ala Gly Tyr
    50                  55                  60

Gly Ser Glu Pro Ala Leu Val Asp Gly Leu Thr Gly Ala Val Val Ser
65                  70                  75                  80

Tyr Ala Arg Leu Asp Arg Asp His Arg Arg Ile Ala Ala Ala Leu Ala
                85                  90                  95

Ala Ala Gly Val Arg Lys Gly Asp Val Val Ala Leu His Ser Pro Asn
            100                 105                 110

Ser Thr Gly Tyr Pro Ala Val Leu Tyr Gly Ala Leu Arg Ala Gly Ala
        115                 120                 125

Thr Val Thr Thr Ala His Pro Leu Ala Thr Ala Glu Glu Leu Ala Arg
    130                 135                 140

Gln Leu Arg Asp Ser Ala Ala Arg Trp Ile Val Thr Ala Ala Pro Cys
145                 150                 155                 160

Leu Glu Thr Ala Arg Arg Ala Ala Glu Leu Thr Pro Gly Ile Gly Glu
                165                 170                 175

Ile Phe Val Phe Asp Arg Ala Glu Gly His Thr Gly Val Ala Ala Met
            180                 185                 190

Leu Asp Ser Thr Ala Pro Glu Pro Ala Val Pro Val Asp Pro Asp Gln
        195                 200                 205

Asp Val Ala Leu Leu Pro Tyr Ser Ser Gly Thr Thr Gly Thr Pro Lys
    210                 215                 220

Gly Val Met Leu Thr His Arg Ser Leu Val Thr Asn Leu Val Gln Ala
225                 230                 235                 240

His Arg Leu Ile Pro Leu Arg Pro Gly Asp Arg Val Leu Ala Val Leu
                245                 250                 255

Pro Phe Phe His Ile Tyr Gly Leu Val Gly Leu Met Ser Ala Pro Leu
            260                 265                 270

Arg Asn Gly Ala Thr Val Val Leu Pro Arg Phe Asp Leu Glu Gly
        275                 280                 285

Phe Leu Ala Ala Val Glu Lys His Arg Val Thr Thr Leu Tyr Val Ala
    290                 295                 300

Pro Pro Ile Val Leu Ala Leu Ala Lys His Pro Ala Val Ala Arg Tyr
305                 310                 315                 320

Asp Leu Ser Ser Val Arg His Val Phe Ser Ala Ala Ala Pro Leu Asp
                325                 330                 335

Ala Glu Ile Ala Ala Ala Cys Ala Ala Arg Val Gly Val Pro Leu Val
            340                 345                 350

Arg Gln Ala Tyr Gly Met Thr Glu Leu Ser Pro Gly Cys Tyr Ala Val
        355                 360                 365

Pro Leu Asp Glu Pro Ala Pro Pro Gly Thr Val Gly Leu Leu Phe
    370                 375                 380

```
Pro Ser Thr Glu Met Arg Leu Leu Arg Leu Asp Asp Pro Gly Arg Cys
385                 390                 395                 400

Val Gly Pro Gly Glu Asp Gly Glu Ile Ala Ile Arg Gly Pro Gln Val
            405                 410                 415

Met Lys Gly Tyr Leu Gly Arg Pro Glu Ala Thr Ala Glu Met Ile Asp
            420                 425                 430

Ala Asp Gly Trp Leu Arg Thr Gly Asp Val Gly Arg Val Asp Ala Asp
            435                 440                 445

Gly Trp Leu His Val Val Asp Arg Val Lys Glu Leu Ile Lys Tyr Lys
            450                 455                 460

Gly Phe Gln Val Ala Pro Ala Glu Leu Glu Ala Leu Leu Leu Thr His
465                 470                 475                 480

Gly Gly Ile Ala Asp Ala Ala Val Ile Gly Val Tyr Asp Glu Asp Glu
            485                 490                 495

Gly Thr Glu Ile Pro His Ala Phe Val Val Arg Arg Pro Gly Gly Ala
            500                 505                 510

Gly Asp Ser Leu Thr Ala Ala Asp Val Ala Ala His Val Ala Ala Arg
            515                 520                 525

Val Ser Pro Tyr Lys Lys Val Arg Arg Val Ser Phe Val Ser Gly Val
            530                 535                 540

Pro Arg Ala Ala Ser Gly Lys Ile Leu Arg Arg Glu Leu Arg Ala Ala
545                 550                 555                 560

Arg Arg Ser Pro Arg Gly Thr Asp Pro Gly Asp Glu Asp Arg Glu Gly
            565                 570                 575

Ala Thr Pro

<210> SEQ ID NO 50
<211> LENGTH: 1740
<212> TYPE: DNA
<213> ORGANISM: artificial
<220> FEATURE:
<223> OTHER INFORMATION: coding sequence for SEQ ID NO: 49

<400> SEQUENCE: 50
atgtccgctt ctactccatc tccaggtcca tctggtaccc catccggtac tccaccatcc     60
ggtccatctg gtactccatc cccaggtcca gctggtgccg gtaccgctcc agtattcaga    120
tctagatacc agacatcga accagtttct gaaccattgc acgaagctgt tttgggtaga    180
gccgccggtt acggttccga accagccttg gtcgacggtt tgaccggtgc cgtcgtatct    240
tacgctagat ggacagaga tcacagaaga atcgccgccg ccttggccgc cgctggtgtc    300
agaaagggtg acgtcgtcgc cttgcactct ccaaactcta ccggttaccc agccgtcttg    360
tacggtgcct tgagagccgg tgccaccgtt accactgctc acccattggc tactgctgaa    420
gaattggcca gacaattgag agactctgcc gccagatgga tcgttaccgc cgccccatgt    480
ttggaaaccg ccagaagagc cgccgaattg accccaggta tcggtgaaat cttcgtattc    540
gacagagccg aaggtcacac cggtgttgcc gctatgttgg actccaccgc tccagaacca    600
gccgtcccag tcgacccaga ccaagacgtc gctttgttgc catactcctc tggtaccacc    660
ggtaccccaa agggtgttat gttgactcac agatccttgg tcaccaactt ggtccaagcc    720
cacagattga tcccattgag gccaggtgac agagtcttgg ccgttttgcc attcttccac    780
atctacggtt tggtcggttt gatgtctgcc ccattgagaa acggtgctac cgtcgtcgtc    840
ttgccaagat tcgacttgga aggtttcttg gctgccgtcg aaaagcacag agtcaccact    900
```

```
ttgtacgttg ccccaccaat cgttttggct tggccaagc acccagctgt tgccagatac      960
gacttgtcct ctgtcagaca cgtattctct gccgccgccc cattggacgc tgaaatcgct     1020
gctgcctgtg ccgccagagt cggtgttcca ttggtcagac aagcttacgg tatgaccgaa     1080
ttgtctccag gttgttacgc cgtcccattg gacgaaccag ccccaccacc aggtactgtc     1140
ggtttgttgt tcccatccac cgaaatgaga ttgttgagat tggacgaccc aggtagatgt     1200
gtcggtccag gtgaggacgg tgaaatcgcc atcagaggtc acaagtcat gaagggttac      1260 ttgggtagac cagaagccac cgccgaaatg atcgacgctg atggttggtt gagaaccggt     1320
gacgtcggta gagtcgacgc tgacggttgg ttgcacgtcg ttgacagagt taaggaattg     1380
atcaagtaca agggtttcca agtcgctcca gccgaattgg aagctttgtt gttgacccac     1440
ggtggtatcg ctgacgccgc cgttatcggt gtttacgacg aggacgaagg tactgaaatc     1500
ccacacgctt tcgttgtcag aaggccaggt ggtgctggtg actccttgac cgccgccgac     1560
gtcgccgccc acgtcgccgc tagagtctcc ccatacaaga aggtcagaag agtctctttc     1620
gtatccggtg ttccaagagc cgcttctggt aagatcttga aagagaatt gagagccgct      1680 agaagatccc caagaggtac tgacccaggt gacgaggaca gagaaggtgc cactccataa     1740
```

<210> SEQ ID NO 51
<211> LENGTH: 400
<212> TYPE: PRT
<213> ORGANISM: Hordeum vulgare

<400> SEQUENCE: 51

```
Met Ser Ala Ala Val Arg Leu Lys Glu Val Arg Met Ala Gln Arg Ala
1               5                   10                  15

Glu Gly Leu Ala Thr Val Leu Ala Ile Gly Thr Ala Val Pro Ala Asn
                20                  25                  30

Cys Val Tyr Gln Ala Thr Tyr Pro Asp Tyr Tyr Phe Arg Val Thr Lys
            35                  40                  45

Ser Glu His Leu Ala Asp Leu Lys Glu Lys Phe Gln Arg Met Cys Asp
        50                  55                  60

Lys Ser Met Ile Arg Lys Arg His Met His Leu Thr Glu Glu Ile Leu
65                  70                  75                  80

Ile Lys Asn Pro Lys Ile Cys Ala His Met Glu Thr Ser Leu Asp Ala
                85                  90                  95

Arg His Ala Ile Ala Leu Val Glu Val Pro Lys Leu Gly Gln Gly Ala
            100                 105                 110

Ala Glu Lys Ala Ile Lys Glu Trp Gly Gln Pro Leu Ser Lys Ile Thr
        115                 120                 125

His Leu Val Phe Cys Thr Thr Ser Gly Val Asp Met Pro Gly Ala Asp
    130                 135                 140

Tyr Gln Leu Thr Lys Leu Leu Gly Leu Ser Pro Thr Val Lys Arg Leu
145                 150                 155                 160

Met Met Tyr Gln Gln Gly Cys Phe Gly Gly Ala Thr Val Leu Arg Leu
                165                 170                 175

Ala Lys Asp Ile Ala Glu Asn Asn Arg Gly Ala Arg Val Leu Val Val
            180                 185                 190

Cys Ser Glu Ile Thr Ala Met Ala Phe Arg Gly Pro Cys Lys Ser His
        195                 200                 205

Leu Asp Ser Leu Val Gly His Ala Leu Phe Gly Asp Gly Ala Ala Ala
    210                 215                 220

Ala Ile Ile Gly Ala Asp Pro Asp Gln Leu Asp Glu Gln Pro Val Phe
```

```
Gln Leu Val Ser Ala Ser Gln Thr Ile Leu Pro Glu Ser Glu Gly Ala
            245                 250                 255

Ile Asp Gly His Leu Thr Glu Ala Gly Leu Thr Ile His Leu Leu Lys
            260                 265                 270

Asp Val Pro Gly Leu Ile Ser Glu Asn Ile Glu Gln Ala Leu Glu Asp
            275                 280                 285

Ala Phe Glu Pro Leu Gly Ile His Asn Trp Asn Ser Ile Phe Trp Ile
290                 295                 300

Ala His Pro Gly Gly Pro Ala Ile Leu Asp Arg Val Glu Asp Arg Val
305                 310                 315                 320

Gly Leu Asp Lys Lys Arg Met Arg Ala Ser Arg Glu Val Leu Ser Glu
            325                 330                 335

Tyr Gly Asn Met Ser Ser Ala Ser Val Leu Phe Val Leu Asp Val Met
            340                 345                 350

Arg Lys Ser Ser Ala Lys Asp Gly Leu Ala Thr Thr Gly Glu Gly Lys
            355                 360                 365

Asp Trp Gly Val Leu Phe Gly Phe Gly Pro Gly Leu Thr Val Glu Thr
            370                 375                 380

Leu Val Leu His Ser Val Pro Val Pro Val Pro Thr Ala Ala Ser Ala
385                 390                 395                 400

<210> SEQ ID NO 52
<211> LENGTH: 1203
<212> TYPE: DNA
<213> ORGANISM: artificial
<220> FEATURE:
<223> OTHER INFORMATION: coding sequence for SEQ ID NO: 51

<400> SEQUENCE: 52
atgtccgctg ctgttagatt gaaggaagtt agaatggctc aaagagctga aggtttggct      60
actgttttgg ccattggtac cgccgttcca gccaactgtg tttaccaagc tacctaccca     120
gactactact tcagagtcac taagtctgaa cacttggctg acttgaagga aagttccaa      180 agaatgtgtg acaagtccat gatcagaaag agacacatgc acttgaccga gaaatcttg     240 attaagaacc caaagatctg tgctcacatg gaaacctctt ggacgctag acacgccatt     300 gctttggtcg aagtcccaaa gttgggtcaa ggtgctgctg aaaaggctat caaggaatgg     360
ggtcaaccat tgtccaagat cacccacttg gtttttctgta ctacctctgg tgtcgacatg     420
ccaggtgccg actaccaatt gaccaagttg ttgggttttgt ccccaactgt taagagattg     480
atgatgtacc aacaaggttg tttcggtggt gccactgttt tgagattggc caaggacatc     540
gctgaaaaca acagaggtgc tagagttttg gttgtctgtt ctgaaatcac cgccatggcc     600
ttcagaggtc catgtaagtc ccacttggac tctttggtcg gtcacgcttt gttcggtgat     660
ggtgctgctg ctgccatcat cggtgctgac ccagaccaat ggacgaaca accagttttc     720 caattggttt ctgcttctca aaccatcttg ccagaatctg aaggtgccat cgacggtcac     780
ttgactgaag ctggtttgac catccacttg ttgaaggacg ttccaggttt gatctctgaa     840
aacatcgaac aagctttgga agatgctttc gaaccattgg gtatccacaa ctggaactcc     900
atcttctgga ttgctcaccc aggtggtcca gccatcttgg acagagtcga agatagagtt     960
ggtttggaca agaagagaat gagagcttct agaagtttt tgtctgaata cggtaacatg    1020
tcctctgctt ctgttttgtt cgtcttggac gttatgagaa agtcatccgc aaggatggt    1080 ttggccacta ctggtgaagg taaggactgg ggtgtcttgt tcggtttcgg tccaggtttg    1140
```

```
accgtcgaaa ctttggtctt gcactctgtc ccagtcccag tcccaaccgc cgcttctgct    1200
taa                                                                  1203
```

<210> SEQ ID NO 53
<211> LENGTH: 392
<212> TYPE: PRT
<213> ORGANISM: Citrus sinensis

<400> SEQUENCE: 53

Met Ser Ala Thr Val Gln Glu Ile Arg Asn Ala Gln Arg Ala Asp Gly
1               5                   10                  15

Pro Ala Thr Val Leu Ala Ile Gly Thr Ala Thr Pro Ala His Ser Val
                20                  25                  30

Asn Gln Ala Asp Tyr Pro Asp Tyr Tyr Phe Arg Ile Thr Lys Ser Glu
            35                  40                  45

His Met Thr Glu Leu Lys Glu Lys Phe Lys Arg Met Cys Asp Lys Ser
        50                  55                  60

Met Ile Lys Lys Arg Tyr Met Tyr Leu Thr Glu Glu Ile Leu Lys Glu
65                  70                  75                  80

Asn Pro Asn Met Cys Ala Tyr Met Ala Pro Ser Leu Asp Ala Arg Gln
                85                  90                  95

Asp Ile Val Val Val Glu Val Pro Lys Leu Gly Lys Glu Ala Ala Thr
            100                 105                 110

Lys Ala Ile Lys Glu Trp Gly Gln Pro Lys Ser Lys Ile Thr His Leu
        115                 120                 125

Ile Phe Cys Thr Thr Ser Gly Val Asp Met Pro Gly Ala Asp Tyr Gln
130                 135                 140

Leu Thr Lys Leu Ile Gly Leu Arg Pro Ser Val Lys Arg Phe Met Met
145                 150                 155                 160

Tyr Gln Gln Gly Cys Phe Ala Gly Gly Thr Val Leu Arg Leu Ala Lys
                165                 170                 175

Asp Leu Ala Glu Asn Asn Lys Gly Ala Arg Val Leu Val Val Cys Ser
            180                 185                 190

Glu Ile Thr Ala Val Thr Phe Arg Gly Pro Ala Asp Thr His Leu Asp
        195                 200                 205

Ser Leu Val Gly Gln Ala Leu Phe Gly Asp Gly Ala Ala Ala Val Ile
210                 215                 220

Val Gly Ala Asp Pro Asp Thr Ser Val Glu Arg Pro Leu Tyr Gln Leu
225                 230                 235                 240

Val Ser Thr Ser Gln Thr Ile Leu Pro Asp Ser Asp Gly Ala Ile Asp
                245                 250                 255

Gly His Leu Arg Glu Val Gly Leu Thr Phe His Leu Leu Lys Asp Val
            260                 265                 270

Pro Gly Leu Ile Ser Lys Asn Ile Glu Lys Ser Leu Ser Glu Ala Phe
        275                 280                 285

Ala Pro Leu Gly Ile Ser Asp Trp Asn Ser Ile Phe Trp Ile Ala His
290                 295                 300

Pro Gly Gly Pro Ala Ile Leu Asp Gln Val Glu Ser Lys Leu Gly Leu
305                 310                 315                 320

Lys Gly Glu Lys Leu Lys Ala Thr Arg Gln Val Leu Ser Glu Tyr Gly
                325                 330                 335

Asn Met Ser Ser Ala Cys Val Leu Phe Ile Leu Asp Glu Met Arg Lys
            340                 345                 350

Lys Ser Val Glu Glu Ala Lys Ala Thr Thr Gly Glu Gly Leu Asp Trp
             355                 360                 365

Gly Val Leu Phe Gly Phe Gly Pro Gly Leu Thr Val Glu Thr Val Val
         370                 375                 380

Leu His Ser Val Pro Ile Lys Ala
385                 390

<210> SEQ ID NO 54
<211> LENGTH: 1179
<212> TYPE: DNA
<213> ORGANISM: artificial
<220> FEATURE:
<223> OTHER INFORMATION: coding sequence for SEQ ID NO: 53

<400> SEQUENCE: 54
atgtccgcta ccgttcaaga atcagaaac gctcaaagag ccgacggtcc agccaccgtc      60
ttggccatcg gtactgccac tccagcccac tctgtcaacc aagctgatta cccagactac     120
tacttcagaa tcactaagtc tgaacacatg actgaattga aggaaaagtt caagagaatg     180
tgtgacaagt ctatgattaa gaagagatac atgtacttga ctgaagaaat tttgaaggaa     240
aacccaaaca tgtgtgctta catggctcca tctttggacg ctagacaaga cattgttgtt     300
gtcgaagttc aaagttggg taaggaagct gctactaagg ccatcaagga tggggtcaa     360
ccaaagtcta agatcaccca cttgatcttc tgtaccacct ccggtgtcga catgccaggt     420
gccgactacc aattgaccaa gttgatcggt ttaagaccat ccgtcaagag attcatgatg     480
taccaacaag ttgtttcgc cggtggtact gttttgagat ggctaagga cttggctgaa     540
aacaacaagg gtgctagagt tttggttgtc tgttctgaaa tcactgctgt cactttcaga     600
ggtccagccg atactcactt ggattctttg gttggtcaag ctttgttcgg tgatggtgct     660
gctgctgtta tcgttggtgc cgatccagac acttctgtcg aaagaccatt gtaccaattg     720
gtttctactt ctcaaactat cttgccagac tctgacggtg ctattgacgg tcacttgaga     780
gaagtcggtt tgactttcca cttgttgaag gacgtcccag gttgatctc taagaacatc     840
gaaaagtctt tgtctgaagc tttcgcccca ttgggtatct ctgactggaa ctctatcttc     900
tggatcgctc acccaggtgg tccagctatt ttggaccaag ttgaatctaa gttgggtttg     960
aagggtgaaa agttgaaggc cactagacaa gttttgtctg aatacggtaa catgtcatct    1020
gcttgtgtct tgttcatctt ggacgaaatg agaaagaagt ctgttgaaga agctaaggcc    1080
accaccggtg aaggtttgga ttggggtgtt ttgttcggtt tcggtccagg tttgaccgtc    1140
gaaaccgttg ttttgcactc tgtcccaatc aaggcttaa                           1179

<210> SEQ ID NO 55
<211> LENGTH: 391
<212> TYPE: PRT
<213> ORGANISM: Citrus sinensis

<400> SEQUENCE: 55

Met Ser Leu Thr Val Asp Glu Val Arg Lys Ala Gln Arg Ala Glu Gly
1               5                   10                  15

Pro Ala Thr Ile Met Ala Ile Gly Thr Ala Thr Pro Pro Asn Cys Val
            20                  25                  30

Asp Gln Ser Thr Tyr Pro Asp Tyr Tyr Phe Arg Ile Thr Asn Ser Glu
        35                  40                  45

His Met Thr Asp Leu Lys Glu Lys Phe Lys Arg Met Cys Asp Lys Ser
    50                  55                  60

```
Met Ile Lys Lys Arg Tyr Met Tyr Leu Thr Glu Ile Leu Lys Glu
 65                  70                  75                  80

Asn Pro Asn Val Cys Ala Tyr Met Ala Pro Ser Leu Asp Thr Arg Gln
                 85                  90                  95

Asp Met Val Val Glu Val Pro Arg Leu Gly Lys Glu Ala Ala Thr
                100                 105                 110

Lys Ala Ile Lys Glu Trp Gly Gln Pro Lys Ser Lys Ile Thr His Leu
            115                 120                 125

Val Phe Cys Thr Thr Ser Gly Val Asp Met Pro Gly Ala Asp Tyr Arg
    130                 135                 140

Leu Thr Lys Leu Leu Gly Leu Arg Pro Ser Val Lys Arg Leu Met Met
145                 150                 155                 160

Tyr Gln Gln Gly Cys Phe Ala Gly Gly Thr Val Leu Arg Leu Ala Lys
                165                 170                 175

Asp Leu Ala Glu Asn Asn Lys Gly Ala Arg Val Leu Val Cys Ser
            180                 185                 190

Glu Ile Thr Ala Val Thr Phe Arg Gly Pro Ser Asp Thr His Leu Asp
            195                 200                 205

Ser Leu Val Gly Gln Ala Leu Phe Gly Asp Gly Ala Ala Ile Ile
    210                 215                 220

Ile Gly Ala Asp Pro Ile Pro Glu Ile Glu Lys Pro Met Phe Glu Leu
225                 230                 235                 240

Val Ser Thr Ala Gln Thr Ile Leu Pro Asp Ser Asp Gly Ser Ile Asp
                245                 250                 255

Gly His Leu Arg Glu Val Gly Leu Thr Phe His Leu Leu Lys Asp Val
            260                 265                 270

Pro Gly Leu Ile Ser Lys Asn Ile Gln Lys Ser Leu Thr Glu Ala Phe
            275                 280                 285

Lys Pro Leu Gly Ile Ser Asp Trp Asn Ser Ile Phe Trp Ile Ala His
    290                 295                 300

Pro Gly Gly Pro Thr Ile Leu Asp Gln Val Glu Lys Leu Gly Leu
305                 310                 315                 320

Lys Pro Glu Lys Leu Arg Ala Thr Arg His Val Leu Ser Glu Tyr Gly
                325                 330                 335

Asn Met Ser Ser Ala Cys Val Leu Phe Ile Leu Asp Glu Met Arg Lys
            340                 345                 350

Lys Ser Ala Glu Asp Gly Leu Glu Thr Ala Gly Glu Gly Leu Glu Trp
    355                 360                 365

Gly Val Leu Phe Gly Phe Gly Pro Gly Leu Thr Val Glu Thr Val Val
    370                 375                 380

Leu His Ser Val Ala Ala Ala
385                 390
```

<210> SEQ ID NO 56
<211> LENGTH: 1176
<212> TYPE: DNA
<213> ORGANISM: artificial
<220> FEATURE:
<223> OTHER INFORMATION: coding sequence for SEQ ID NO: 55

<400> SEQUENCE: 56
atgtccttga ccgtcgatga agttagaaag gctcaaagag ccgaaggtcc agccactatc    60
atggccattg gtactgctac cccaccaaac tgtgttgatc aatctactta cccagattac   120
tacttcagaa tcactaactc tgaacacatg actgatttga ggaaaagtt caagagaatg   180

-continued

```
tgtgacaagt ccatgatcaa gaagagatac atgtacttga ctgaagaaat cttgaaggaa      240
aacccaaacg tttgtgctta catggctcca tctttggata ctagacaaga tatggttgtt      300
gttgaagttc aagattggg  taaggaagct gccaccaagg ccattaagga atggggtcaa      360
ccaaagtcca agatcaccca cttggtattc tgtaccactt ctggtgttga catgccaggt      420
gccgattaca gattgactaa gttgttgggt ttaagaccat ccgtcaagag attgatgatg      480
taccaacaag gttgtttcgc cggtggtact gttttgagat ggccaaggac ttggccgaa       540
aacaacaagg gtgctagagt cttggttgtt tgttccgaaa tcaccgctgt tactttcaga      600
ggtccatctg acacccactt ggattctttg gttggtcaag ccttgttcgg tgatggtgct      660
gctgctatta tcattggtgc cgacccaatc ccagaaatcg aaaagccaat gttcgaattg      720
gtatctactg cccaaactat cttgccagat tctgatggtt ctatcgacgg tcacttgaga      780
gaagttggtt tgaccttcca cttgttgaag gatgttccag gtttgatttc taagaacatc      840
caaaagtctt tgaccgaagc tttcaagcca ttgggtatct ctgactggaa ctctattttc      900
tggatcgctc acccaggtgg tccaactatt ttggaccaag tcgaagaaaa gttgggtttg      960
aagccagaaa agttgagagc cactagacac gttttgtctg aatacggtaa catgtcatct     1020
gcttgtgttt tgttcatttt ggacgaaatg agaaagaagt ctgctgaaga tggtttggaa     1080
accgctggtg aaggtttgga atggggtgtc ttgttcggtt tcggtccagg tttgactgtt     1140
gaaaccgttg tcttgcactc tgttgccgct gcttaa                               1176
```

<210> SEQ ID NO 57
<211> LENGTH: 352
<212> TYPE: PRT
<213> ORGANISM: Streptomyces clavuligerus

<400> SEQUENCE: 57

```
Met Ser Ala Val Leu Cys Lys Pro Ala Ile Ala Val Pro Asp His Ile
1               5                   10                  15

Ile Thr Asn Glu Glu Thr Leu Glu Leu Ala Arg Arg Leu His Ser Asp
            20                  25                  30

His Pro Gln Leu Ala Leu Ala Cys Arg Leu Ile Glu His Thr Gly Val
        35                  40                  45

Arg Lys Arg His Leu Ile Gln Pro Ile Asp Glu Val Leu Lys His Pro
    50                  55                  60

Gly Leu Asp Ala Arg Ser Ala Thr Tyr Glu Thr Ser Lys Ala Arg
65                  70                  75                  80

Val Pro Ser Val Val Arg Arg Ala Leu Asp Gln Ala Glu Leu Glu Pro
                85                  90                  95

Asp Gln Ile Asp Leu Ile Ile Tyr Val Ser Cys Thr Gly Phe Met Met
            100                 105                 110

Pro Ser Leu Ala Ser Trp Leu Val Asn Thr Met Gly Phe Arg Ala Asp
        115                 120                 125

Thr Arg Gln Leu Pro Ile Ala Gln Leu Gly Cys Ala Ala Gly Gly Ala
    130                 135                 140

Ala Val Asn Arg Ala His Asp Phe Cys Thr Ala Tyr Pro Gly Thr Asn
145                 150                 155                 160

Val Leu Ile Val Ala Cys Glu Phe Cys Ser Leu Cys Tyr Gln Pro Thr
                165                 170                 175

Asp Leu Gly Ile Gly Ser Leu Leu Ser Asn Gly Leu Phe Gly Asp Gly
            180                 185                 190

Ile Ala Ala Ala Val Val Arg Gly Glu Glu Gly Thr Gly Met Arg Leu
```

```
            195                 200                 205
Glu Arg Asn Gly Thr Tyr Leu Ile Pro His Thr Glu Glu Trp Ile Ser
    210                 215                 220

Tyr Ala Val Arg Ser Thr Gly Phe His Phe Gln Leu Asp Lys Arg Val
225                 230                 235                 240

Pro Gly Thr Met Glu Pro Leu Ser Pro Ala Leu Arg Ala Leu Ala Glu
                245                 250                 255

Gln His Gln Trp Asn Ala Gly Lys Leu Asp Phe Tyr Ile Ile His Ala
            260                 265                 270

Gly Gly Pro Arg Ile Leu Asp Asp Leu Ser Arg Phe Leu Asp Val Pro
        275                 280                 285

Pro Gly Ala Phe Arg His Ser Arg Ala Thr Leu Thr Glu Tyr Gly Asn
    290                 295                 300

Ile Ala Ser Ala Val Val Leu Asp Ala Leu Gly Arg Leu Phe Asp Glu
305                 310                 315                 320

Gln Ser Ala Leu Asp Gly His His Gly Met Leu Ala Gly Phe Gly Pro
                325                 330                 335

Gly Ile Ile Ala Glu Met Ser Leu Gly Thr Trp Val Ser Pro Glu Ser
            340                 345                 350

<210> SEQ ID NO 58
<211> LENGTH: 1059
<212> TYPE: DNA
<213> ORGANISM: artificial
<220> FEATURE:
<223> OTHER INFORMATION: coding sequence for SEQ ID NO: 57

<400> SEQUENCE: 58
atgtccgctg ttttgtgtaa gccagccatc gccgttccag accacatcat caccaacgaa      60
gaaaccttgg aattggctag aagattgcac tctgaccacc acaattggc tttggcttgt      120 agattgatcg aacacactgg tgttagaaag agacacttga tccaaccaat cgacgaagtt      180
ttgaagcacc aggtttgga cgctagatct gccacctacg aaaccgaatc caaggctaga      240
gttccatctg tgttagaag agctttggac caagctgaat ggaaccaga tcaaatcgac      300 ttgatcatct acgtatcctg taccggtttc atgatgcca ccttggcctc ctggttggtc      360
aacaccatgg gtttcagagc tgacaccaga caattgccaa tcgcccaatt gggttgtgct      420
gctggtggtg ctgccgtcaa cagagcccac gacttctgta ccgcctaccc aggtaccaac      480
gtcttgatcg ttgcctgtga attctgttct ttgtgttacc aaccaaccga tttgggtatc      540
ggttctttgt tgtccaacgg tttgttcggt gacggtatcg ccgccgctgt tgtcagaggt      600
gaagaaggta ccggtatgag attggaaaga acggtacct acttgatccc acacaccgaa      660
gaatggatct cctacgctgt tagatccacc ggtttccact ccaattgga caagagagtc      720 ccaggtacca tggaaccatt gtctccagct tgagagcct ggccgaaca caccaatgg      780 aacgccggta agttggactt ctacatcatc acgctggtg gtccaagaat cttggacgat      840
ttgtctagat tcttggacgt tccaccaggt gccttcagac actctagagc cactttgacc      900
gaatacggta acatcgcctc tgccgtcgtt ttggacgcct tgggtagatt gttcgacgaa      960
caatccgcct tggacggtca ccacggtatg ttggctggtt tcggtccagg tatcatcgcc     1020
gaaatgtcct tgggtacctg ggtttctcca gaatcctaa                            1059

<210> SEQ ID NO 59
<211> LENGTH: 401
<212> TYPE: PRT
```

-continued

<213> ORGANISM: Streptomyces clavuligerus

<400> SEQUENCE: 59

```
Met Ser Ser Thr Gly Ser Ser Ala His Tyr Cys Pro Phe Asp Tyr Ala
1               5                   10                  15

Glu Ala Leu Glu Phe Asp Pro Thr Leu Arg Arg Phe Met Arg Glu Glu
            20                  25                  30

Pro Val Ala Arg Ile Arg Leu Pro His Gly Ala Gly Glu Ala Trp Leu
        35                  40                  45

Val Thr Gly Tyr Asp Asp Val Arg Thr Val Thr Asp Arg Arg Phe
    50                  55                  60

Ser Arg His Ala Val Val Gly Arg Asp Phe Pro Arg Met Thr Pro Glu
65                  70                  75                  80

Pro Ile Val Gln Asp Glu Ala Ile Asn Val Met Asp Pro Pro Ala Ser
                85                  90                  95

Ser Arg Leu Arg Ser Leu Val Ser Lys Gly Phe Ala Pro Glu Gln Ile
            100                 105                 110

Glu Arg Met Arg Pro Tyr Ile Gln Arg Ala Val Asp Asp Leu Leu Asp
        115                 120                 125

Arg Met Ala Glu Asp Ser Ser Ala Asp Leu Met Arg His Leu Ala Gly
130                 135                 140

Pro Leu Pro Leu Ile Thr Ile Cys Glu Val Leu Glu Ile Pro Pro Ala
145                 150                 155                 160

Asp Gln Glu Thr Leu Arg Gly His Ala Arg Thr Met Met Asn Ile Ser
                165                 170                 175

Val Asp Asn Lys Ala Ala Ala Val Arg Ala Lys Ala Asp Leu Arg Ala
            180                 185                 190

Tyr Phe Ala Asp Leu Thr Ala Arg Arg Ala Asp Pro Gly Glu Asp
        195                 200                 205

Leu Ile Ser Val Leu Ala Thr Ala Arg Asp Gly Asp Glu Leu Leu Asp
210                 215                 220

Asp Gln Glu Leu Thr Val Met Ala Met Val Leu Leu Ile Thr Gly Gln
225                 230                 235                 240

Asp Thr Thr Thr Tyr Glu Leu Gly Asn Leu Ser Tyr Thr Leu Leu Thr
                245                 250                 255

Arg Pro Asp Val Arg Asp Leu Leu Arg Asp Arg Pro Glu Arg Leu Ala
            260                 265                 270

Gln Thr Ile Asn Glu Leu Leu Arg Phe Ile Pro Phe Arg Lys Gly Val
        275                 280                 285

Gly Ile Pro Arg Val Ala Thr Glu Asp Val Glu Leu Ser Gly Val Thr
290                 295                 300

Ile Pro Ala Gly Asp Ile Val His Val Ser Tyr Leu Thr Ala Asn Arg
305                 310                 315                 320

Asp Gly Arg Lys Phe Arg Pro Asp Glu Leu Asp Phe Asp Arg Thr
                325                 330                 335

Ala Pro Ser His Met Thr Phe Gly Trp Gly Ala His His Cys Leu Gly
            340                 345                 350

Ala Pro Leu Ala Gln Ala Glu Met Glu Thr Ala Phe Arg Thr Leu Leu
        355                 360                 365

Glu Arg Phe Pro Gly Ile Ala Leu Ala Lys Pro Ala Glu Asp Val Glu
370                 375                 380

Trp Asn Thr Thr Ser Ile Trp Arg Tyr Pro Leu Ala Leu Pro Val Thr
385                 390                 395                 400
```

Trp

<210> SEQ ID NO 60
<211> LENGTH: 1206
<212> TYPE: DNA
<213> ORGANISM: artificial
<220> FEATURE:
<223> OTHER INFORMATION: coding sequence for SEQ ID NO: 59

<400> SEQUENCE: 60

```
atgtcctcca ccggttcctc tgctcactac tgtccattcg actacgccga agccttggaa    60
ttcgacccaa ctttgagaag attcatgaga gaagaaccag tcgctagaat cagattgcca   120
cacggtgctg gtgaagcttg gttggtcacc ggttacgacg atgttagaac cgttaccacc   180
gacagaagat tctctagaca cgccgttgtc ggtagagact cccaagaat gactccagaa    240
ccaatcgtcc aagacgaagc catcaacgtc atggacccac cagcttcttc tagattgaga   300
tctttggttt ccaagggttt cgccccagaa caaatcgaaa gaatgaggcc atacatccaa   360
agagccgttg acgacttgtt ggacagaatg gctgaggact cctccgccga cttgatgaga   420
cacttggctg gtccattgcc attgatcacc atctgtgaag tcttggaaat cccaccagcc   480
gaccaagaaa ccttgagagg tcacgccaga actatgatga acatctctgt tgacaacaag   540
gccgccgccg ttagagccaa ggccgatttg agagcctact cgctgactt gactgccaga    600
agaagagctg acccaggtga ggacttgatc tctgttttgg ccactgccag ggacggtgac   660
gaattgttgg acgaccaaga attgaccgtc atggctatgg tcttgttgat caccggtcaa   720
gacaccacca cctacgaatt gggtaacttg tcctacacct tgttgaccag accagacgtc   780
agagatttgt tgagagacag accagaaaga ttggctcaaa ctatcaacga attgttgaga   840
ttcatcccat tcagaaaggg tgtcggtatc ccaagagttg ccaccgagga cgttgaattg   900
tctggtgtta ctatcccagc cggtgacatc gtccacgtat cctacttgac cgccaacaga   960
gatggtagaa agttcgacag accagacgaa ttggacttcg acagaaccgc ccatcccac   1020
atgaccttcg gttggggtgc tcaccactgt ttgggtgccc cattggctca gccgaaatg   1080
gaaaccgcct tcagaacttt gttggaaaga ttcccaggta tcgctttggc taagccagcc   1140
gaggacgttg aatggaacac cacctctatc tggagatacc cattggcttt gccagtcacc   1200
tggtaa                                                              1206
```

<210> SEQ ID NO 61
<211> LENGTH: 246
<212> TYPE: PRT
<213> ORGANISM: Arabidopsis thaliana

<400> SEQUENCE: 61

```
Met Ser Ser Ser Asn Ala Cys Ala Ser Pro Ser Phe Pro Ala Val
1               5                   10                  15

Thr Lys Leu His Val Asp Ser Val Thr Phe Val Pro Ser Val Lys Ser
                20                  25                  30

Pro Ala Ser Ser Asn Pro Leu Phe Leu Gly Gly Ala Gly Val Arg Gly
            35                  40                  45

Leu Asp Ile Gln Gly Lys Phe Val Ile Phe Thr Val Ile Gly Val Tyr
        50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                85                  90                  95
```

```
Thr Gly Ala Phe Glu Lys Phe Ile Lys Val Thr Met Lys Leu Pro Leu
            100                 105                 110

Thr Gly Gln Gln Tyr Ser Glu Lys Val Thr Glu Asn Cys Val Ala Ile
            115                 120                 125

Trp Lys Gln Leu Gly Leu Tyr Thr Asp Cys Glu Ala Lys Ala Val Glu
130                 135                 140

Lys Phe Leu Glu Ile Phe Lys Glu Gly Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys
            180                 185                 190

Leu Leu Ala Glu Ala Val Leu Glu Ser Ile Ile Gly Lys Asn Gly Val
            195                 200                 205

Ser Pro Gly Thr Arg Leu Ser Val Ala Glu Arg Leu Ser Gln Leu Met
        210                 215                 220

Met Lys Asn Lys Asp Glu Lys Glu Val Ser Asp His Ser Val Glu Glu
225                 230                 235                 240

Lys Leu Ala Lys Glu Asn
                245

<210> SEQ ID NO 62
<211> LENGTH: 741
<212> TYPE: DNA
<213> ORGANISM: artificial
<220> FEATURE:
<223> OTHER INFORMATION: coding sequence for SEQ ID NO: 61

<400> SEQUENCE: 62
atgtcctcta gcaatgcgtg tgcctccccg tccccgttcc cggctgttac gaagctgcat      60
gtcgattcag ttacctttgt cccgtccgtg aagtccccgg cgagcagcaa cccgctgttt     120
ctgggcggtg caggtgtccg tggtctggat attcagggca aatttgtgat tttcaccgtg     180
atcggcgttt atctggaagg caatgcggtc ccgtcactgt cggtgaaatg gaagggtaaa     240
accacggaag aactgaccga atctattccg ttttccgcg aaatcgttac gggcgcgttc     300
gaaaagttca tcaaggtcac catgaaactg ccgctgacgg gtcagcaata ttcagaaaag     360
gttaccgaaa actgcgtcgc catctggaaa caactgggcc tgtacacgga ctgtgaagcg     420
aaggccgtcg aaaagtttct ggaaatttc aagaagaaa cctttccgcc gggcagttcc     480
atcctgttcg cactgagccc gaccggttct ctgacggttg ctttcagtaa agatgactcc     540
atcccggaaa ccggcattgc agtgatcgaa aacaagctgc tggcagaagc tgttctggaa     600
agcattatcg gcaaaaatgg tgtgtcaccg ggtacgcgtc tgtcggttgc ggaacgcctg     660
agccagctga tgatgaaaaa taagatgaa aaggaagtgt cggaccacag cgttgaagaa     720
aaactggcaa aggaaaacta a                                                741

<210> SEQ ID NO 63
<211> LENGTH: 719
<212> TYPE: PRT
<213> ORGANISM: Citrus sinensis

<400> SEQUENCE: 63

Met Ser Glu Ile Gly Ala Thr Thr Glu Asn Gly His Gln Asn Gly Gly
1               5                   10                  15

Leu Glu Gly Leu Cys Lys Asn Asn Asn Tyr Asn Tyr Ser Ser Gly Asp
```

```
            20                  25                  30
Ala Leu Asn Trp Gly Val Met Ala Glu Thr Leu Lys Gly Ser His Leu
         35                  40                  45
Glu Glu Val Lys Arg Met Val Ala Glu Tyr Arg Lys Pro Val Val Asn
         50                  55                  60
Leu Gly Gly Glu Thr Leu Thr Val Ala Gln Val Ala Ala Ile Ala Thr
65                  70                  75                  80
Ser Ser Thr Asn Val Glu Leu Ser Glu Ser Ala Arg Glu Gly Val Lys
                 85                  90                  95
Ala Ser Ser Asp Trp Val Met Glu Ser Met Asn Lys Gly Thr Asp Ser
                100                 105                 110
Tyr Gly Val Thr Thr Gly Phe Gly Ala Thr Ser His Arg Arg Thr Lys
                115                 120                 125
Asn Gly Gly Ala Leu Gln Lys Glu Leu Ile Arg Phe Leu Asn Ala Gly
                130                 135                 140
Ile Phe Gly Asn Gly Thr Glu Ser Ser His Thr Leu Pro His Ser Ala
145                 150                 155                 160
Thr Arg Ala Ala Met Leu Val Arg Val Asn Thr Leu Leu Gln Gly Tyr
                165                 170                 175
Ser Gly Ile Arg Phe Glu Ile Leu Glu Ala Ile Thr Lys Leu Leu Asn
                180                 185                 190
His Asn Ile Thr Pro Cys Leu Pro Leu Arg Gly Thr Ile Thr Ala Ser
                195                 200                 205
Gly Asp Leu Val Pro Leu Ser Tyr Ile Ala Gly Leu Leu Thr Gly Arg
                210                 215                 220
Pro Asn Ser Lys Ala Thr Gly Pro Asn Gly Glu Ile Ile Asp Ala Gln
225                 230                 235                 240
Glu Ala Ser Lys Gln Ala Gly Phe Gly Phe Phe Glu Leu Gln Pro Lys
                245                 250                 255
Glu Gly Leu Ala Leu Val Asn Gly Thr Ala Val Gly Ser Gly Leu Ala
                260                 265                 270
Ser Met Val Leu Phe Glu Ala Asn Asn Leu Ala Leu Leu Ser Glu Ile
                275                 280                 285
Leu Ser Ala Ile Phe Ala Glu Val Met Gln Gly Lys Pro Glu Phe Thr
                290                 295                 300
Asp His Leu Thr His Lys Leu Lys His His Pro Gly Gln Ile Glu Ala
305                 310                 315                 320
Ala Ala Ile Met Glu His Ile Leu Asp Gly Ser Ser Tyr Val Asn Val
                325                 330                 335
Ala Lys Lys Leu His Glu Ile Asp Pro Leu Gln Lys Pro Lys Gln Asp
                340                 345                 350
Arg Tyr Ala Leu Arg Thr Ser Pro Gln Trp Leu Gly Pro Gln Ile Glu
                355                 360                 365
Val Ile Arg Phe Ala Thr Lys Ser Ile Glu Arg Glu Ile Asn Ser Val
                370                 375                 380
Asn Asp Asn Pro Leu Ile Asp Val Ser Arg Asn Lys Ala Leu His Gly
385                 390                 395                 400
Gly Asn Phe Gln Gly Thr Pro Ile Gly Val Ser Met Asp Asn Thr Arg
                405                 410                 415
Leu Ala Ile Ala Ala Ile Gly Lys Leu Met Phe Ala Gln Phe Ser Glu
                420                 425                 430
Leu Val Asn Asp Phe Tyr Asn Asn Gly Leu Pro Ser Asn Leu Ser Gly
                435                 440                 445
```

Gly Arg Asn Pro Ser Leu Asp Tyr Gly Phe Lys Gly Ala Glu Ile Ala
    450                 455                 460

Met Ala Ser Tyr Cys Ser Glu Leu Gln Phe Leu Ala Asn Pro Val Thr
465                 470                 475                 480

Asn His Val Gln Ser Ala Glu Gln His Asn Gln Asp Val Asn Ser Leu
                485                 490                 495

Gly Leu Ile Ser Ser Arg Lys Thr Ala Glu Ala Val Asp Ile Leu Lys
            500                 505                 510

Leu Met Ser Ser Thr Phe Leu Val Ala Leu Cys Gln Ala Ile Asp Leu
        515                 520                 525

Arg His Leu Glu Glu Asn Leu Lys His Thr Val Lys Asn Thr Val Ser
530                 535                 540

Gln Val Ala Lys Lys Val Leu Thr Val Gly Ala Ser Gly Glu Leu His
545                 550                 555                 560

Pro Ser Arg Phe Cys Glu Lys Asp Leu Leu Lys Ala Ala Asp Arg Glu
                565                 570                 575

His Val Phe Ala Tyr Ile Asp Asp Pro Cys Ser Ala Thr Tyr Pro Leu
            580                 585                 590

Met Gln Lys Leu Arg Gln Val Leu Val Glu His Ala Leu Asn Asn Gly
        595                 600                 605

Glu Asn Glu Lys Thr Ala Asn Ser Ser Ile Phe Gln Lys Ile Ala Ala
610                 615                 620

Phe Glu Glu Glu Leu Lys Thr Val Leu Pro Lys Val Glu Asn Ala
625                 630                 635                 640

Arg Gln Thr Val Glu Asn Gly Ser Pro Thr Ile Pro Asn Arg Ile Lys
                645                 650                 655

Glu Cys Arg Ser Tyr Pro Leu Tyr Arg Phe Val Arg Glu Gly Leu Gly
            660                 665                 670

Ser Asn Phe Leu Thr Gly Glu Lys Val Thr Ser Pro Gly Glu Glu Phe
        675                 680                 685

Asp Lys Val Phe Thr Ala Met Cys Gln Gly Lys Ile Ile Asp Pro Met
690                 695                 700

Leu Glu Cys Leu Arg Glu Trp Asn Gly Ala Pro Leu Pro Ile Cys
705                 710                 715

<210> SEQ ID NO 64
<211> LENGTH: 2160
<212> TYPE: DNA
<213> ORGANISM: artificial
<220> FEATURE:
<223> OTHER INFORMATION: coding sequence for SEQ ID NO: 63

<400> SEQUENCE: 64
atgtccgaaa tcggtgccac tactgaaaac ggtcaccaaa cggtggcct cgaaggcttg         60 tgtaagaaca taactacaa ctactcttct ggtgatgctt tgaactgggg tgttatggct        120
gaaactttga agggttctca cttggaagaa gttaagagaa tggttgctga atacagaaag        180
ccagttgtca acttgggtgg tgaaactttg accgttgctc aagttgctgc cattgccact        240
tcctctacta cgttgaatt gtctgaatct gccagagaag gtgtcaaggc ctcttctgat        300
tgggttatgg aatctatgaa caagggtacc gactcttacg tgttactac tggcttcggt        360 gccacttcgc acagaagaac caagaacggt ggtgctttgc aaaaggaatt gattagattc        420
ttgaacgctg gtatcttcgg taacggtact gaatcttctc acactttgcc acactctgct        480
actagagctg ccatgttggt tcgtgttaac acattgttgc aaggttactc cggtatcaga        540

```
ttcgaaatct tggaagctat cactaagttg ttgaaccaca acatcactcc atgtttgcca    600
ttgagaggta ctatcactgc ttctggtgat ttggttccat tgtcctacat agccggcttg    660
ttgaccggtc gtccaaactc taaggccacc ggtccaaacg gtgaaatcat tgatgcccaa    720
gaagcctcta agcaagctgg tttcggtttc ttcgaattgc aaccaaagga gggcttggct    780
ctcgtcaacg gtactgctgt tggttctggt ttggcttcta tggttttgtt cgaagctaac    840
aatctcgcgt tgttgtcgga aattttgtct gctattttcg ctgaagtcat gcaaggtaag    900
ccagaattca ccgatcactt gactcacaag ttgaagcacc acccaggtca aattgaagct    960
gctgctatca tggaacacat cttggatggt tcttcttacg ttaacgttgc taagaagttg    1020
cacgaaattg atccattgca aaagccaaag caagatagat acgccttgag aacttctcca    1080
caatggttgg gtccacaaat cgaagttatt agattcgcta ccaagtctat gaaagagaa    1140 atcaactctg ttaacgacaa cccattgatc gacgtttcta gaaacaaggc cttgcacggt    1200
ggtaacttcc aaggtacccc aattggtgtc tctatggaca caccagatt ggctattgct    1260 gctatcggta agttgatgtt cgcccaattc tctgaattgg tcaacgattt ctacaacaac    1320
ggtttgccat ctaacttgtc tggtggtaga acccatctt tggattacgg tttcaagggt    1380
gctgaaattg ctatggcttc ctactgttct gaattgcaat tcttggccaa cccagttact    1440
aaccacgtcc aatctgctga caacacaac caagatgtta actccttggg tttgatctct    1500
tccagaaaga ctgctgaagc tgtcgacatc ttgaagttga tgtcatccac tttcttggtt    1560
gctttgtgtc aagctattga tttgagacac ttggaagaaa acttgaagca cactgtcaag    1620
aacactgtct ctcaagttgc taagaaggtc ttgaccgtcg gtgcttctgg tgaattgcac    1680
ccatctagat tctgtgaaaa ggatttgttg aaggctgctg atagaaaca cgttttcgct    1740 tacattgatg acccatgttc tgctacctac ccattgatgc aaaagttgag acaagttttg    1800
gttgaacacg ctttgaacaa cggtgaaaac gaaaagactg ccaactcttc tatcttccaa    1860
aagattgctg ccttcgaaga agaattaaag accgttttgc caaggaagt tgaaaacgcc    1920 agacaaactg ttgaaaacgg ttctccaact attccaaaca gaatcaagga atgtagatct    1980
tacccattgt acagattcgt tagagaaggt ttgggttcta acttcttgac tggtgaaaag    2040
gttacttctc caggtgaaga attcgacaag gttttcactg ctatgtgtca aggtaagatc    2100
attgatccaa tgttggaatg tttgagagaa tggaacggtg ccccattgcc aatttgttaa    2160
```

<210> SEQ ID NO 65
<211> LENGTH: 715
<212> TYPE: PRT
<213> ORGANISM: Citrus sinensis

<400> SEQUENCE: 65

Met Ser Glu Ala Ser His Glu Asn Gln Ser Gly Gly Asn Ile Pro Ser
1               5                   10                  15

Gly Lys Leu Cys Thr Asn Ile Asp Pro Leu Asn Trp Val Ser Ala Ser
            20                  25                  30

Glu Ser Leu Lys Gly Ser His Leu Asp Glu Val Lys Arg Met Val Ser
        35                  40                  45

Glu Tyr Arg Lys Gln Val Val Arg Leu Gly Gly Glu Thr Leu Thr Ile
    50                  55                  60

Ala Gln Val Ala Ala Val Ala Ser Arg Asp Gly Gly Val Thr Val Glu
65                  70                  75                  80

Leu Asn Glu Glu Ala Arg Ala Gly Val Lys Ala Ser Ser Asp Trp Val

```
                85                  90                  95
Met Glu Ser Met Asn Lys Gly Thr Asp Ser Tyr Gly Ile Thr Thr Gly
                100                 105                 110

Phe Gly Ala Thr Ser His Arg Arg Thr Lys Gln Gly Ala Ala Leu Gln
                115                 120                 125

Lys Glu Leu Ile Arg Phe Leu Asn Ala Gly Ile Phe Gly Lys Gly Thr
130                 135                 140

Glu Ser Cys Gln Met Leu Pro His Thr Ala Thr Arg Ala Ala Met Leu
145                 150                 155                 160

Val Arg Ile Asn Thr Leu Leu Gln Gly Tyr Ser Gly Ile Arg Phe Glu
                165                 170                 175

Ile Leu Glu Ala Ile Thr Lys Phe Leu Asn Arg Asn Ile Thr Pro Cys
                180                 185                 190

Leu Pro Leu Arg Ala Ser Ile Thr Ala Ser Gly Asp Leu Ile Pro Phe
                195                 200                 205

Ser Tyr Ile Ala Gly Leu Leu Thr Gly Arg Leu Asn Ser Val Ala Val
                210                 215                 220

Gly Pro Asn Gly Glu Ser Leu Asn Ala Ala Glu Ala Phe Ser Gln Ala
225                 230                 235                 240

Gly Ile Asp Gly Gly Phe Phe Glu Leu Gln Pro Lys Glu Gly Leu Ala
                245                 250                 255

Leu Val Asn Gly Thr Gly Val Gly Ala Gly Leu Ala Ser Ile Val Leu
                260                 265                 270

Phe Glu Ala Asn Ile Leu Thr Val Leu Ser Glu Val Leu Ser Ala Ile
                275                 280                 285

Phe Ala Glu Ala Met Leu Gly Lys Pro Glu Phe Thr Asp His Leu Thr
                290                 295                 300

His Lys Leu Lys His His Pro Gly Gln Ile Glu Ala Ala Ala Ile Met
305                 310                 315                 320

Glu His Ile Leu Asp Gly Ser Ser Tyr Val Lys Ala Ala Gln Lys Leu
                325                 330                 335

His Glu Ile Asp Pro Leu Gln Lys Pro Lys Gln Asp Arg Tyr Ala Leu
                340                 345                 350

Arg Thr Ser Pro Gln Trp Leu Gly Pro Gln Ala Glu Val Ile Arg Ala
                355                 360                 365

Ser Thr Lys Ser Ile Glu Arg Glu Ile Asn Ser Val Asn Asp Asn Pro
                370                 375                 380

Leu Ile Asp Val Ser Arg Asn Lys Ala Leu His Gly Gly Asn Phe Gln
385                 390                 395                 400

Gly Thr Pro Ile Gly Val Ser Met Asp Asn Ser Arg Leu Ala Ile Ala
                405                 410                 415

Ser Ile Gly Lys Leu Met Phe Ala Gln Phe Ser Glu Leu Val Asn Asp
                420                 425                 430

Phe Tyr Ser Asn Gly Leu Pro Ser Asn Leu Ser Gly Gly Arg Asn Pro
                435                 440                 445

Ser Leu Asp Tyr Gly Phe Lys Gly Ala Glu Ile Ala Met Ala Ala Tyr
                450                 455                 460

Cys Ser Glu Leu Gln Phe Leu Ala Asn Pro Val Thr Asn His Val Gln
465                 470                 475                 480

Ser Ala Glu Gln His Asn Gln Asp Val Asn Ser Leu Gly Leu Ile Ser
                485                 490                 495

Ala Arg Lys Thr Ala Glu Ala Val Asp Ile Leu Lys Leu Met Ser Ser
                500                 505                 510
```

Thr Tyr Leu Ile Ala Leu Cys Gln Ala Ile Asp Leu Arg His Leu Glu
        515                 520                 525

Glu Asn Leu Lys Ser Thr Val Lys Asn Thr Ile Ser Gln Val Val Lys
    530                 535                 540

Lys Val Leu Thr Met Gly Val Asn Gly Glu Leu His Pro Ser Arg Phe
545                 550                 555                 560

Cys Glu Lys Asp Leu Leu Lys Val Val Asp Arg Glu Tyr Val Phe Ser
                565                 570                 575

Tyr Ala Asp Asp Pro Cys Ser Ala Thr Tyr Pro Leu Met Gln Lys Leu
            580                 585                 590

Arg Gln Val Leu Val Asp His Ala Leu Thr Asn Asn Glu Asp Leu Lys
        595                 600                 605

Asn Ala Asn Ala Ser Ile Phe Leu Lys Ile Gly Ala Phe Glu Glu Glu
    610                 615                 620

Leu Lys Thr Leu Leu Pro Lys Glu Val Glu Ser Ala Arg Ser Ala Phe
625                 630                 635                 640

Glu Ser Gly Asn Leu Glu Ile Pro Asn Arg Ile Lys Glu Cys Arg Ser
                645                 650                 655

Tyr Pro Leu Tyr Arg Phe Val Arg Glu Glu Leu Gly Ala Arg Tyr Leu
            660                 665                 670

Thr Gly Glu Lys Ala Ile Ser Pro Gly Glu Glu Cys Asp Lys Val Phe
        675                 680                 685

Thr Ala Ile Cys Gln Gly Lys Ile Ile Asp Pro Leu Leu Glu Cys Leu
    690                 695                 700

Lys Glu Trp Asp Gly Ser Pro Leu Pro Ile Cys
705                 710                 715

<210> SEQ ID NO 66
<211> LENGTH: 2148
<212> TYPE: DNA
<213> ORGANISM: artificial
<220> FEATURE:
<223> OTHER INFORMATION: coding sequence for SEQ ID NO: 65

<400> SEQUENCE: 66
atgtccgaag cttctcacga aaaccaatct ggtggtaaca ttccatctgg taagttgtgt      60
actaacattg atccattgaa ctgggttttct gcttctgaat cttttgaaggg ttctcacttg    120 gatgaagtta agagaatggt ttctgaatac agaaagcaag ttgttagatt gggtggtgaa     180
accttgacta tcgctcaagt tgctgctgtt gcttctagag atggtggtgt cactgttgaa     240
ttgaacgaag aagccagagc tggtgtcaag gcttcttctg attgggttat ggaatctatg     300
aacaagggta ctgattctta cggcatcact actggcttcg gtgctacttc gcacagaaga     360
accaagcaag gtgctgcctt gcaaaaggaa ttgattagat tcttgaacgc tggtatcttc     420
ggtaagggta ctgaatcctg tcaaatgttg ccacacactg ctactagagc tgctatgctc    480
gttcgtatca acacattgtt gcaaggttac tctggtatta gattcgaaat tttggaagct    540
atcactaagt tcttgaacag aaacattact ccatgtttgc cattgagagc ctccatcact    600
gcgtcgggtg atctcatccc attctcgtac atcgccggtt tgttgaccgg tagattgaac    660
tctgttgctg ttggtccaaa cggtgaatct ttgaacgctg ctgaagcttt ctctcaagct    720
ggtattgatg gtggtttctt cgaattgcaa ccaaaggagg gcttggcgtt ggttaacggt    780
actggtgttg gtgctggttt tggcttctat tgttttgttcg aagctaacat tttgactgtt    840
ttgtccgaag ttttgtctgc tatttttcgct gaagctatgt tgggtaagcc agaattcact    900

-continued

```
gatcacttga ctcacaagtt gaagcaccac ccaggtcaaa ttgaagctgc tgctatcatg      960
gaacacatct tggatggttc ttcttacgtt aaggctgctc aaaagttgca cgaaattgac     1020
ccattgcaaa agccaaagca agatagatac gctttgagaa cttctccaca atggttgggt     1080
ccacaagctg aagttattag agcttctact aagtctattg aaagagaaat taactctgtt     1140
aacgataacc cattgattga tgtttctaga acaaggcttt gcacggtgg taacttccaa      1200
ggtaccccaa ttggtgtctc tatggataac tctagattgg ctattgcttc tattggtaag     1260
ttgatgttcg ctcaattctc tgaattggtt aacgatttct actctaacgg tttgccatct     1320
aacttgtctg gtggtagaaa cccatctttg gattacggtt tcaagggtgc cgaaatcgct     1380
atggctgctt actgttccga attgcaattc ttggccaacc cagttactaa ccacgtccaa     1440
tctgctgaac aacacaacca agatgttaac tctttgggtt tgatctctgc cagaaagact     1500
gctgaagctg ttgatatctt gaagttgatg tcctctactt acttgattgc tttgtgtcaa     1560
gctatcgact tgagacactt ggaagaaaac ttgaagtcta ctgttaagaa cactatctct     1620
caagttgtta agaaggtctt gactatgggt gtcaacggtg aattgcaccc atctagattc     1680
tgtgaaaagg atttgttgaa ggttgttgat agagaatacg ttttctctta cgctgatgat     1740
ccatgttctg ctacttaccc attgatgcaa aagttgagac aagtcttggt tgatcacgct     1800
ttgactaaca acgaagattt gaagaacgct aacgcttcta tcttcttgaa aataggtgcg     1860
ttcgaagaag aactcaagac cttgttgcca aaggaagttg aatctgctag atctgctttc     1920
gaatctggta acttggaaat cccaaacaga attaaggaat gtagatccta cccattgtac     1980
agattcgtta gagaagaatt gggtgctaga tacttgactg gtgaaaaggc tatctctcca     2040
ggtgaagaat gtgataaggt tttcactgct atttgtcaag gtaagatcat tgatccattg     2100
ttggaatgtt tgaaggaatg ggatggttct ccattgccaa tttgttaa                  2148
```

<210> SEQ ID NO 67
<211> LENGTH: 537
<212> TYPE: PRT
<213> ORGANISM: Citrus sinensis

<400> SEQUENCE: 67

```
Met Ser Ala Asn Leu Val Thr Ile Ser Phe Phe Ser Ile Leu Leu Thr
1               5                   10                  15

Ile Ser Leu Leu Ser Phe Asn Lys Ser Leu Asn Leu Ile Ser Ile Thr
            20                  25                  30

Leu Pro Leu Val Pro Leu Ile Ala Tyr Val Leu Lys Ser Phe Leu Lys
        35                  40                  45

Ser Ser Lys Ala Phe Tyr Pro Pro Thr Pro Ile Ser Ile Pro Ile Phe
    50                  55                  60

Gly Asn Trp Leu Gln Val Gly Asn Asp Leu Asn His Arg Leu Leu Ala
65                  70                  75                  80

Ser Met Ala Gln Ile Tyr Gly Pro Val Phe Arg Leu Lys Leu Gly Ser
                85                  90                  95

Lys Asn Leu Ile Val Val Ser Glu Pro Asp Leu Ala Thr Gln Val Leu
            100                 105                 110

His Thr Gln Gly Val Glu Phe Gly Ser Arg Pro Arg Asn Val Val Phe
        115                 120                 125

Asp Ile Phe Thr Gly Asn Gly Gln Asp Met Val Phe Thr Val Tyr Gly
    130                 135                 140

Glu His Trp Arg Lys Met Arg Arg Ile Met Thr Leu Pro Phe Phe Thr
```

```
            145                 150                 155                 160
Asn Lys Val Val His Asn Tyr Ser Asp Met Trp Glu Gln Glu Met Asp
                    165                 170                 175
Leu Val Val His Asp Leu Lys Asn Asp Tyr Glu Ser Val Ser Thr Lys
                    180                 185                 190
Gly Ile Val Ile Arg Lys Arg Leu Gln Leu Met Leu Tyr Asn Ile Met
                    195                 200                 205
Tyr Arg Met Met Phe Asp Ala Lys Phe Glu Ser Gln Glu Asp Pro Leu
    210                 215                 220
Phe Ile Glu Ala Thr Arg Phe Asn Ser Glu Arg Ser Arg Leu Ala Gln
225                 230                 235                 240
Ser Phe Glu Tyr Asn Tyr Gly Asp Phe Ile Pro Leu Leu Arg Pro Phe
                    245                 250                 255
Leu Arg Gly Tyr Leu Asn Lys Cys Arg Asp Leu Gln Cys Arg Arg Leu
                    260                 265                 270
Ala Phe Phe Asn Asn Asn Phe Val Glu Lys Arg Arg Lys Ile Met Ala
                    275                 280                 285
Ala Asn Gly Glu Lys His Lys Ile Ser Cys Ala Ile Asp His Ile Ile
    290                 295                 300
Asp Ala Gln Met Lys Gly Glu Ile Thr Glu Glu Asn Val Ile Tyr Ile
305                 310                 315                 320
Val Glu Asn Ile Asn Val Ala Ala Ile Glu Thr Thr Leu Trp Ser Met
                    325                 330                 335
Glu Trp Ala Ile Ala Glu Leu Val Asn His Pro Glu Val Gln Gln Lys
                    340                 345                 350
Ile Arg Arg Glu Ile Ser Thr Val Leu Lys Gly Asn Pro Val Thr Glu
                    355                 360                 365
Ser Asn Leu His Glu Leu Pro Tyr Leu Gln Ala Ala Val Lys Glu Val
    370                 375                 380
Leu Arg Leu His Thr Pro Ile Pro Leu Leu Val Pro His Met Asn Leu
385                 390                 395                 400
Glu Glu Ala Lys Leu Gly Gly Phe Thr Ile Pro Lys Glu Ser Lys Ile
                    405                 410                 415
Val Val Asn Ala Trp Trp Leu Ala Asn Asn Pro Lys Trp Trp Glu Lys
                    420                 425                 430
Pro Glu Glu Phe Arg Pro Glu Arg Phe Leu Glu Glu Cys Asn Ile
                    435                 440                 445
Asp Ala Val Ala Gly Gly Lys Val Asp Phe Arg Tyr Leu Pro Phe
    450                 455                 460
Gly Val Gly Arg Arg Ser Cys Pro Gly Ile Ile Leu Ala Leu Pro Ile
465                 470                 475                 480
Leu Gly Leu Val Ile Ala Lys Leu Val Thr Ser Phe Glu Met Lys Ala
                    485                 490                 495
Pro Gln Gly Ile Asp Lys Ile Asp Val Ser Glu Lys Gly Gly Gln Phe
                    500                 505                 510
Ser Leu His Ile Ala Asn His Ser Thr Val Val Phe Asp Pro Ile Met
                    515                 520                 525
Glu Ser Leu Ser Gln Pro Met Pro Gln
    530                 535
```

<210> SEQ ID NO 68
<211> LENGTH: 1614
<212> TYPE: DNA
<213> ORGANISM: artificial
<220> FEATURE:
<223> OTHER INFORMATION: coding sequence for SEQ ID NO: 67

<400> SEQUENCE: 68

```
atgtccgcta acttggttac tatttctttc ttctctatct tgttgactat ctctttgttg      60
tctttcaaca agtctttgaa cttgatctct atcactttgc cattggttcc attgattgct     120
tacgttttga agtccttctt gaagtcatct aaggccttct acccaccaac tccaatctct     180
atcccaatct tcggtaactg gttgcaagtt ggtaacgact tgaaccacag attgttggct     240
tctatggctc aaatttacgg tccagttttc agattgaagt tgggttctaa gaacttgatc     300
gttgtttctg aaccagacct cgctactcaa gtgctacaca ctcaaggtgt tgaattcggt     360
tccagaccaa gaaacgttgt tttcgatatt ttcactggta acggtcaaga catggtattt     420
actgtctacg gcgaacactg gagaaagatg agaagaatta tgactttgcc attcttcacc     480
aacaaggttg ttcacaacta ctctgacatg tgggaacaag aaatggactt ggttgttcac     540
gacttgaaga acgattacga gtctgtaagc actaagggta ttgttattag aaagagattg     600
caattgatgt tgtacaacat tatgtacaga atgatgttcg atgctaagtt cgaatctcaa     660
gaagatccat tgttcattga agctactaga ttcaactctg aaagatctag attggcgcag     720
agcttcgaat acaactacgg tgatttcatt ccattgttaa gaccattctt gagaggttac     780
ttgaacaagt gtagagactt gcaatgtaga agattggctt tcttcaacaa caacttcgtt     840
gaaaagagaa gaaagatcat ggctgccaac ggtgaaaagc acaagatctc ttgtgccatt     900
gatcacatca ttgatgctca aatgaagggt gaaatcactg aagaaaacgt tatttacatt     960
gttgaaaaca tcaacgttgc tgctatcgaa actactttgt ggtccatgga atgggctatc    1020
gctgaattgg tcaaccaccc agaagttcaa caaaagatca aagagaaat ctctactgtc     1080
ttgaagggta acccagtcac tgaatctaac ttgcacgaat gccatactt gcaagccgct     1140
gttaaggaag ttttgagatt gcacactcca attccattgt tggttccaca catgaacttg    1200
gaagaagcta agttgggtgg tttcactatt ccaaaggaat ccaagattgt tgttaacgct    1260
tggtggttgg ctaacaaccc aaagtggtgg gaaaagccag aagaattcag accagaaaga    1320
ttcttggaag aagaatgtaa cattgatgct gttgctggtg gtggtaaggt tgacttcaga    1380
tacttgccat cggtgttgg tagaagatct tgtccaggta taatattggc tctcccaatc    1440
ttgggcttgg ttattgctaa gttggttact tcttccgaaa tgaaggctcc acaaggtatc    1500
gataagattg acgtttctga aaagggtggt caattctctt tgcacattgc taaccactct    1560
actgttgtct tgatccaat catggaatct ttgtcccaac caatgccaca ataa           1614
```

<210> SEQ ID NO 69
<211> LENGTH: 520
<212> TYPE: PRT
<213> ORGANISM: Citrus sinensis

<400> SEQUENCE: 69

```
Met Ser Asp Leu Asn Gly Trp Cys Asn Ser Gly Asn Gln Asn Met Cys
1               5                   10                  15

Cys Cys Gln Ser Tyr Val Lys Arg Gly Tyr Asp Arg Val Leu Ser Phe
            20                  25                  30

Asn Gly Leu Ile Thr Val Ser Lys Leu Arg Gly Lys Arg Phe Lys Leu
        35                  40                  45

Pro Pro Gly Pro Leu Pro Val Pro Val Phe Gly Asn Trp Leu Gln Val
    50                  55                  60
```

Gly Asp Asp Leu Asn His Arg Asn Leu Ser Asp Leu Ala Lys Lys Tyr
65                  70                  75                  80

Gly Asp Val Leu Leu Arg Met Gly Gln Arg Asn Leu Val Val Val
            85                  90                  95

Ser Ser Pro Asp His Ala Lys Glu Val Leu His Thr Gln Gly Val Glu
            100                 105                 110

Phe Gly Ser Arg Thr Arg Asn Val Val Phe Asp Ile Phe Thr Gly Lys
            115                 120                 125

Gly Gln Asp Met Val Phe Thr Val Tyr Gly Glu His Trp Arg Lys Met
130                 135                 140

Arg Arg Ile Met Thr Val Pro Phe Phe Thr Asn Lys Val Val Gln Gln
145                 150                 155                 160

Gln Arg Phe Asn Trp Glu Asp Glu Ala Ala Arg Val Val Glu Asp Val
            165                 170                 175

Lys Lys Asp Pro Glu Ala Ala Thr Asn Gly Ile Val Leu Arg Arg Arg
            180                 185                 190

Leu Gln Leu Met Met Tyr Asn Asn Met Tyr Arg Ile Met Phe Asp Arg
        195                 200                 205

Arg Phe Glu Ser Gln Asp Asp Pro Leu Phe Asn Arg Leu Lys Ala Leu
        210                 215                 220

Asn Gly Glu Arg Ser Arg Leu Ala Gln Ser Phe Glu Tyr Asn Tyr Gly
225                 230                 235                 240

Asp Phe Ile Pro Ile Leu Arg Pro Phe Leu Arg Gly Tyr Leu Lys Ile
                245                 250                 255

Cys Lys Glu Val Lys Glu Arg Arg Leu Gln Leu Phe Lys Asp Tyr Phe
                260                 265                 270

Val Glu Glu Arg Lys Lys Leu Ala Ser Thr Lys Ser Met Ser Asn Glu
            275                 280                 285

Ser Leu Lys Cys Ala Ile Asp His Ile Leu Asp Ala Gln Thr Lys Gly
        290                 295                 300

Glu Ile Asn Glu Asp Asn Val Leu Tyr Ile Val Glu Asn Ile Asn Val
305                 310                 315                 320

Ala Ala Ile Glu Thr Thr Leu Trp Ser Ile Glu Trp Gly Ile Ala Glu
                325                 330                 335

Leu Val Asn His Pro Glu Ile Gln Lys Lys Leu Arg Asn Glu Leu Asp
            340                 345                 350

Thr Val Leu Gly Pro Gly His Gln Ile Thr Glu Pro Asp Thr His Lys
        355                 360                 365

Leu Pro Tyr Leu Gln Ala Val Ile Lys Glu Thr Leu Arg Leu Arg Met
        370                 375                 380

Ala Ile Pro Leu Leu Val Pro His Met Asn Leu His Asp Ala Lys Leu
385                 390                 395                 400

Gly Gly Tyr Asp Val Pro Ala Glu Ser Lys Ile Leu Val Asn Ala Trp
            405                 410                 415

Trp Leu Ala Asn Asn Pro Ala Gln Trp Lys Lys Pro Glu Glu Phe Arg
            420                 425                 430

Pro Glu Arg Phe Leu Glu Glu Ser Lys Val Glu Ala Asn Gly Asn
        435                 440                 445

Asp Phe Arg Tyr Leu Pro Phe Gly Val Gly Arg Arg Ser Cys Pro Gly
        450                 455                 460

Ile Ile Leu Ala Leu Pro Ile Leu Gly Ile Thr Ile Gly Arg Leu Val
465                 470                 475                 480

Gln Asn Phe Glu Leu Leu Pro Pro Pro Gly Gln Ser Lys Ile Asp Thr 485                 490                 495
Ala Glu Lys Gly Gly Gln Phe Ser Leu His Ile Leu Lys His Ser Thr
            500                 505                 510

Ile Val Ala Lys Pro Arg Ser Phe
            515                 520

<210> SEQ ID NO 70
<211> LENGTH: 1563
<212> TYPE: DNA
<213> ORGANISM: artificial
<220> FEATURE:
<223> OTHER INFORMATION: coding sequence for SEQ ID NO: 69

<400> SEQUENCE: 70

| | | |
|---|---|---|
| atgtccgact tgaacggttg gtgtaactct ggtaaccaaa acatgtgttg ttgtcaatct | 60 |
| tacgttaaga gaggttacga tagagttttg tctttcaacg gtttgattac cgtttctaag | 120 |
| ttgagaggta agagattcaa gttgccacca ggtccattgc cagtcccagt tttcggtaac | 180 |
| tggttgcaag tcggtgatga cttgaaccac agaaacttgt ccgacttggc caagaagtac | 240 |
| ggtgatgtct tgttgttgag aatgggtcaa agaaacttgg tcgtcgtttc ttctccagac | 300 |
| cacgccaagg aagtcttgca cactcaaggt gttgaattcg ttctagaac tcgtaatgtc | 360 |
| gtgttcgaca tcttcactgg taagggtcaa gatatggttt tcactgtcta cggcgaacac | 420 |
| tggagaaaga tgaagaat catgaccgtc ccattcttca ctaacaaggt tgttcaacaa | 480 |
| caaagattca actgggaaga tgaagccgct agagtcgttg aagatgttaa gaaggaccca | 540 |
| gaagctgcta ccaacggtat cgtcttgaga gaaagattgc aattgatgat gtacaacaac | 600 |
| atgtacagaa ttatgttcga tagaagattc gaatctcaag atgatccatt gttcaacaga | 660 |
| ttgaaggctt tgaacggtga agatctagat tggcgcaga gcttcgaata caactacggt | 720 |
| gatttcattc aatttttaag accattcttg agaggttact tgaagatttg taggaagtt | 780 |
| aaggaaagaa gattgcaatt gttcaaggac tacttcgttg aagaaagaaa gaagttggct | 840 |
| tctactaagt ctatgtctaa cgaatctttg aagtgtgcta tcgatcacat tttggacgct | 900 |
| caaactaagg gtgaaatcaa cgaagataac gttttgtaca tcgttgaaaa catcaacgtt | 960 |
| gccgctatcg aaactacttt tgtggtctat cgaatggggta ttgctgaatt ggttaaccac | 1020 |
| ccagaaatcc aaaagaagtt gagaaacgaa ttggacaccg ttttgggtcc aggtcaccaa | 1080 |
| atcactgaac cagacaccca aagttgcca tacttgcaag ccgttatcaa ggaaactttg | 1140 |
| agattgagaa tggctattcc attgttggtt ccacacatga acttgcacga cgccaagttg | 1200 |
| ggtggttacg acgtcccagc tgaatctaag atcttggtta acgcttggtg gttggccaac | 1260 |
| aacccagccc aatggaagaa gccagaagaa ttcagaccag aaagattctt ggaagaagaa | 1320 |
| tccaaggttg aagctaacgg taacgacttc agatacttgc cattcggtgt tggtagaaga | 1380 |
| tcttgtccag gtataatatt ggctctccca atttttgggca tcactattgg tagattggtt | 1440 |
| caaaacttcg aattgttgcc accaccaggt caatctaaga ttgacactgc tgaaaagggt | 1500 |
| ggtcaattct cttttgcacat tttgaagcac tctaccattg ttgccaagcc aagatctttc | 1560 |
| taa | 1563 |

<210> SEQ ID NO 71
<211> LENGTH: 513
<212> TYPE: PRT
<213> ORGANISM: Saccharothrix espanaensis

<400> SEQUENCE: 71

```
Met Ser Thr Ile Thr Ser Pro Ala Pro Ala Gly Arg Leu Asn Asn Val
1               5                   10                  15

Arg Pro Met Thr Gly Glu Glu Tyr Leu Glu Ser Leu Arg Asp Gly Arg
                20                  25                  30

Glu Val Tyr Ile Tyr Gly Glu Arg Val Asp Asp Val Thr Thr His Leu
            35                  40                  45

Ala Phe Arg Asn Ser Val Arg Ser Ile Ala Arg Leu Tyr Asp Val Leu
        50                  55                  60

His Asp Pro Ala Ser Glu Gly Val Leu Arg Val Pro Thr Asp Thr Gly
65                  70                  75                  80

Asn Gly Gly Phe Thr His Pro Phe Phe Lys Thr Ala Arg Ser Ser Glu
                    85                  90                  95

Asp Leu Val Ala Ala Arg Glu Ala Ile Val Gly Trp Gln Arg Leu Val
                100                 105                 110

Tyr Gly Trp Met Gly Arg Thr Pro Asp Tyr Lys Ala Ala Phe Phe Gly
            115                 120                 125

Thr Leu Asp Ala Asn Ala Glu Phe Tyr Gly Pro Phe Glu Ala Asn Ala
        130                 135                 140

Arg Arg Trp Tyr Arg Asp Ala Gln Glu Arg Val Leu Tyr Phe Asn His
145                 150                 155                 160

Ala Ile Val His Pro Pro Val Asp Arg Asp Arg Pro Ala Asp Arg Thr
                165                 170                 175

Ala Asp Ile Cys Val His Val Glu Glu Thr Asp Ser Gly Leu Ile
        180                 185                 190

Val Ser Gly Ala Lys Val Val Ala Thr Gly Ser Ala Met Thr Asn Ala
    195                 200                 205

Asn Leu Ile Ala His Tyr Gly Leu Pro Val Arg Asp Lys Lys Phe Gly
    210                 215                 220

Leu Val Phe Thr Val Pro Met Asn Ser Pro Gly Leu Lys Leu Ile Cys
225                 230                 235                 240

Arg Thr Ser Tyr Glu Leu Met Val Ala Thr Gln Gly Ser Pro Phe Asp
                245                 250                 255

Tyr Pro Leu Ser Ser Arg Leu Asp Glu Asn Asp Ser Ile Met Ile Phe
            260                 265                 270

Asp Arg Val Leu Val Pro Trp Glu Asn Val Phe Met Tyr Asp Ala Gly
        275                 280                 285

Ala Ala Asn Ser Phe Ala Thr Gly Ser Gly Phe Leu Glu Arg Phe Thr
        290                 295                 300

Phe His Gly Cys Thr Arg Leu Ala Val Lys Leu Asp Phe Ile Ala Gly
305                 310                 315                 320

Cys Val Met Lys Ala Val Glu Val Thr Gly Thr Thr His Phe Arg Gly
                325                 330                 335

Val Gln Ala Gln Val Gly Glu Val Leu Asn Trp Arg Asp Val Phe Trp
            340                 345                 350

Gly Leu Ser Asp Ala Met Ala Lys Ser Pro Asn Ser Trp Val Gly Gly
        355                 360                 365

Ser Val Gln Pro Asn Leu Asn Tyr Gly Leu Ala Tyr Arg Thr Phe Met
    370                 375                 380

Gly Val Gly Tyr Pro Arg Ile Lys Glu Ile Ile Gln Gln Thr Leu Gly
385                 390                 395                 400

Ser Gly Leu Ile Tyr Leu Asn Ser Ala Ala Asp Trp Lys Asn Pro
                405                 410                 415
```

```
Asp Val Arg Pro Tyr Leu Asp Arg Tyr Leu Arg Gly Ser Arg Gly Ile
            420                 425                 430

Gln Ala Ile Asp Arg Val Lys Leu Leu Lys Leu Leu Trp Asp Ala Val
        435                 440                 445

Gly Thr Glu Phe Ala Gly Arg His Glu Leu Tyr Glu Arg Asn Tyr Gly
    450                 455                 460

Gly Asp His Glu Gly Ile Arg Val Gln Thr Leu Gln Ala Tyr Gln Ala
465                 470                 475                 480

Asn Gly Gln Ala Ala Leu Lys Gly Phe Ala Glu Gln Cys Met Ser
                485                 490                 495

Glu Tyr Asp Leu Asp Gly Trp Thr Arg Pro Asp Leu Ile Asn Pro Gly
            500                 505                 510

Thr
```

<210> SEQ ID NO 72
<211> LENGTH: 1542
<212> TYPE: DNA
<213> ORGANISM: artificial
<220> FEATURE:
<223> OTHER INFORMATION: coding sequence for SEQ ID NO: 71

<400> SEQUENCE: 72

```
atgtccacca tcacttctcc agctccagct ggtagattga caacgtcag accaatgact      60
ggtgaagaat acttggaatc tttgagagat ggtagaaag tctacatcta cggtgaaaga    120
gtcgacgacg tcaccactca cttggccttc agaaactctg ttagatccat cgctagattg    180
tacgacgttt tgcacgaccc agcttcggag ggtgtactaa gagttccaac cgacactggt    240
aatggtggct tcactcatcc attcttcaag accgcccgtt cttctgaaga tttggtcgcc    300
gctagagaag ccatcgtcgg ttggcaaaga ttggtttacg gttggatggg tagaaccccca   360
gattacaagg ctgcgttctt cggtactctc gacgccaacg ccgaattcta cggtccattc    420
gaagccaacg ccagaagatg gtacagagat gcccaagaaa gagttttgta cttcaaccac    480
gctatcgttc acccaccagt cgacagagac agaccagccg acagaaccgc cgacatctgt    540
gttcacgttg aagaagaaac cgactctggt ttgatcgttt ccggtgccaa ggttgtcgct    600
accggttccg ctatgaccaa cgctaacttg atcgctcact acggtttgcc agttagagac    660
aagaagttcg gtttggtttt cactgtccca atgaactctc aggtttgaa gttgatctgt    720
agaacctcct acgaattgat ggtcgctact caaggttctc cattcgacta cccattatct    780
tctagattgg acgaaaacga ctctatcatg atcttcgaca gagttttggt tccatgggaa    840
aacgtttca tgtacgacgc tggtgctgcc aactccttcg ccaccggttc tggtttcttg    900
gaaagattca ccttccacgg ttgtaccaga ttggctgtca agttggactt catcgccggt    960
tgtgtcatga aggctgttga agtcaccggt accactcact tcagaggtgt tcaagctcaa   1020
gtcggtgaag ttttgaactg gagagatgtt ttctggggtt tgtccgacgc tatggccaag   1080
tctccaaaact cttgggtcgg tggttctgtt caaccaaact tgaactacgg tttggcttac   1140
agaaccttca tgggtgttgg ttacccaaga atcaaggaaa tcatccaaca aaccttgggt   1200
tctggtttga tctacttgaa ctcctctgcc gccgactgga agaacccaga cgtcagacca   1260
tacttggaca gatacttgag aggttctaga ggtatccaag ctatcgacag agtcaagttg   1320
ttgaagttgt tgtgggacgc tgtcggtacc gaattcgccg gtagacacga attgtacgaa   1380
agaaactacg gtggtgacca cgaaggtatc agagttcaaa ccttgcaagc ttaccaagct   1440
aacggtcagg cggccgctct caagggtttc gcggaacaat gtatgtccga atacgacttg   1500
```
gacggttgga ctagaccaga cttgatcaac ccaggtacct aa 1542

<210> SEQ ID NO 73
<211> LENGTH: 498
<212> TYPE: PRT
<213> ORGANISM: Beta vulgaris

<400> SEQUENCE: 73

```
Met Ser Asp His Ala Thr Leu Ala Met Ile Leu Ala Ile Leu Phe Ile
1               5                   10                  15

Ser Phe His Phe Ile Lys Leu Leu Phe Ser Gln Gln Thr Thr Lys Leu
            20                  25                  30

Leu Pro Pro Gly Pro Lys Pro Leu Pro Ile Ile Gly Asn Ile Leu Glu
        35                  40                  45

Val Gly Lys Lys Pro His Arg Ser Phe Ala Asn Leu Ala Lys Ile His
50                  55                  60

Gly Pro Leu Ile Ser Leu Arg Leu Gly Ser Val Thr Thr Ile Val Val
65                  70                  75                  80

Ser Ser Ala Asp Val Ala Lys Glu Met Phe Leu Lys Lys Asp His Pro
                85                  90                  95

Leu Ser Asn Arg Thr Ile Pro Asn Ser Val Thr Ala Gly Asp His His
            100                 105                 110

Lys Leu Thr Met Ser Trp Leu Pro Val Ser Pro Lys Trp Arg Asn Phe
        115                 120                 125

Arg Lys Ile Thr Ala Val His Leu Leu Ser Pro Gln Arg Leu Asp Ala
    130                 135                 140

Cys Gln Thr Phe Arg His Ala Lys Val Gln Gln Leu Tyr Glu Tyr Val
145                 150                 155                 160

Gln Glu Cys Ala Gln Lys Gly Gln Ala Val Asp Ile Gly Lys Ala Ala
                165                 170                 175

Phe Thr Thr Ser Leu Asn Leu Leu Ser Lys Leu Phe Phe Ser Val Glu
            180                 185                 190

Leu Ala His His Lys Ser His Thr Ser Gln Glu Phe Lys Glu Leu Ile
        195                 200                 205

Trp Asn Ile Met Glu Asp Ile Gly Lys Pro Asn Tyr Ala Asp Tyr Phe
    210                 215                 220

Pro Ile Leu Gly Cys Val Asp Pro Ser Gly Ile Arg Arg Arg Leu Ala
225                 230                 235                 240

Cys Ser Phe Asp Lys Leu Ile Ala Val Phe Gln Gly Ile Ile Cys Glu
                245                 250                 255

Arg Leu Ala Pro Asp Ser Ser Thr Thr Thr Thr Thr Thr Asp Asp
            260                 265                 270

Val Leu Asp Val Leu Leu Gln Leu Phe Lys Gln Asn Glu Leu Thr Met
        275                 280                 285

Gly Glu Ile Asn His Leu Leu Val Asp Ile Phe Asp Ala Gly Thr Asp
    290                 295                 300

Thr Thr Ser Ser Thr Leu Glu Trp Val Met Thr Glu Leu Ile Arg Asn
305                 310                 315                 320

Pro Glu Met Met Glu Lys Ala Gln Glu Glu Ile Lys Gln Val Leu Gly
                325                 330                 335

Lys Asp Lys Gln Ile Gln Glu Ser Asp Ile Ile Asn Leu Pro Tyr Leu
            340                 345                 350

Gln Ala Ile Ile Lys Glu Thr Leu Arg Leu His Pro Pro Thr Val Phe
        355                 360                 365
```

```
Leu Leu Pro Arg Lys Ala Asp Thr Asp Val Glu Leu Tyr Gly Tyr Ile
    370                 375                 380
Val Pro Lys Asp Ala Gln Ile Leu Val Asn Leu Trp Ala Ile Gly Arg
385                 390                 395                 400
Asp Pro Asn Ala Trp Gln Asn Ala Asp Ile Phe Ser Pro Glu Arg Phe
                405                 410                 415
Ile Gly Cys Glu Ile Asp Val Lys Gly Arg Asp Phe Gly Leu Leu Pro
            420                 425                 430
Phe Gly Ala Gly Arg Arg Ile Cys Pro Gly Met Asn Leu Ala Ile Arg
        435                 440                 445
Met Leu Thr Leu Met Leu Ala Thr Leu Leu Gln Phe Phe Asn Trp Lys
    450                 455                 460
Leu Glu Gly Asp Ile Ser Pro Lys Asp Leu Asp Met Asp Glu Lys Phe
465                 470                 475                 480
Gly Ile Ala Leu Gln Lys Thr Lys Pro Leu Lys Leu Ile Pro Ile Pro
                485                 490                 495
Arg Tyr

<210> SEQ ID NO 74
<211> LENGTH: 1497
<212> TYPE: DNA
<213> ORGANISM: artificial
<220> FEATURE:
<223> OTHER INFORMATION: coding sequence for SEQ ID NO: 73

<400> SEQUENCE: 74
atgtccgatc acgctacttt ggcgatgata ttggccatcc tattcatttc tttccacttc      60
atcaagttgt tgttctctca acaaactacc aagttgttgc caccaggtcc aaagccattg     120
ccaatcattg gtaacatctt ggaagttggt aagaagccac acagatcttt cgctaacttg     180
gctaagattc acgtccatt gatctctttg agattgggtt ctgttactac tattgttgtt      240
tcttctgctg atgttgctaa ggaaatgttc ttgaagaagg accacccatt gtctaacaga     300
actattccaa actctgtcac tgccggtgac caccacaagt tgaccatgtc ttggttgcca     360
gtttctccaa agtggagaaa cttcagaaag attactgccg tccacttgtt gtctccacaa     420
agattggatg cttgtcaaac cttcagacac gccaaggttc aacaattgta cgaatacgtt     480
caagaatgtg ctcaaaaggg tcaagctgtt gatattggta aggctgcttt cactacctcc     540
ttgaacttgt tgtctaagtt gttcttctct gttgaattgg cccaccacaa gtctcacact     600
tctcaagaat caaggaatt gatctggaac attatggaag atattggtaa gccaaactac     660
gctgattact cccaatttt gggttgtgtt gatccatctg gtattagaag aagattggct     720
tgttctttcg acaagttgat tgctgttttc caaggtatca tctgtgaaag attggctcca     780
gattcttcta ctacaaccac tactaccact gatgatgttt tggacgtttt gttgcaattg     840
ttcaagcaaa acgaattgac tatgggtgaa attaaccact tgttggtcga cattttcgat     900
gctggtactg acactacttc ttctactttg aatgggtca tgactgaatt gattagaaac      960
ccagaaatga tggaaaaggc tcaagaagaa attaagcaag ttttgggtaa ggataagcaa    1020
attcaagaat ctgacattat taacttgcca tacttgcaag ccattatcaa ggaaactttg    1080
agattgcacc caccaactgt tttcttgttg ccaagaaagg ccgacactga tgttgaattg    1140
tacggttaca ttgttccaaa ggatgctcaa atcttggtta acttgtgggc tattggtaga    1200
gatccaaacg cttggcaaaa cgctgatatt ttctctccag aaagattcat cggttgtgaa    1260
```

-continued

```
attgatgtca agggtagaga tttcggtttg ttgccattcg gtgccggtag aagaatctgt    1320
ccaggtatga acttggccat tagaatgttg actttgatgt tggctacttt gttgcaattc    1380
ttcaactgga agttggaagg tgacatctct ccaaaggact tggacatgga tgaaaagttc    1440
ggtattgctt tgcaaaagac taagccattg aagttgattc caatcccaag atactaa      1497

<210> SEQ ID NO 75
<211> LENGTH: 413
<212> TYPE: PRT
<213> ORGANISM: Rhodopseudomonas palustris

<400> SEQUENCE: 75

Met Ser Thr Thr Ala Pro Ser Leu Val Pro Val Thr Thr Pro Ser Gln
1               5                   10                  15

His Gly Ala Gly Val Pro His Leu Gly Ile Asp Pro Phe Ala Leu Asp
                20                  25                  30

Tyr Phe Ala Asp Pro Tyr Pro Glu Gln Glu Thr Leu Arg Glu Ala Gly
            35                  40                  45

Pro Val Val Tyr Leu Asp Lys Trp Asn Val Tyr Gly Val Ala Arg Tyr
        50                  55                  60

Ala Glu Val Tyr Ala Val Leu Asn Asp Pro Leu Thr Phe Cys Ser Ser
65                  70                  75                  80

Arg Gly Val Gly Leu Ser Asp Phe Lys Lys Glu Lys Pro Trp Arg Pro
                85                  90                  95

Pro Ser Leu Ile Leu Glu Ala Asp Pro Ala His Thr Arg Thr Arg
            100                 105                 110

Ala Val Leu Ser Lys Val Leu Ser Pro Ala Thr Met Lys Arg Leu Arg
        115                 120                 125

Asp Gly Phe Ala Ala Ala Asp Ala Lys Ile Asp Glu Leu Leu Ala
    130                 135                 140

Arg Gly Gly Asn Ile Asp Ala Ile Ala Asp Leu Ala Glu Ala Tyr Pro
145                 150                 155                 160

Leu Ser Val Phe Pro Asp Ala Met Gly Leu Lys Gln Glu Gly Arg Glu
                165                 170                 175

Asn Leu Leu Pro Tyr Ala Gly Leu Val Leu Asn Ala Phe Gly Pro Pro
            180                 185                 190

Asn Glu Leu Arg Gln Ser Ala Ile Glu Arg Ser Ala Pro His Gln Ala
        195                 200                 205

Tyr Val Ala Glu Gln Cys Gln Arg Pro Asn Leu Ala Pro Gly Gly Phe
    210                 215                 220

Gly Ala Cys Ile His Ala Phe Ser Asp Thr Gly Ile Thr Pro Glu
225                 230                 235                 240

Glu Ala Pro Leu Leu Val Arg Ser Leu Leu Ser Ala Gly Leu Asp Thr
                245                 250                 255

Thr Val Asn Gly Ile Ala Ala Val Tyr Cys Leu Ala Arg Phe Pro
            260                 265                 270

Asp Glu Phe Ala Arg Leu Arg Ala Asp Pro Ser Leu Ala Arg Asn Ala
        275                 280                 285

Phe Glu Glu Ala Val Arg Phe Glu Ser Pro Val Gln Thr Phe Phe Arg
    290                 295                 300

Thr Thr Thr Arg Asp Val Glu Leu Ala Gly Ala Thr Ile Gly Glu Gly
305                 310                 315                 320

Glu Lys Val Leu Met Phe Leu Gly Ser Ala Asn Arg Asp Pro Arg Arg
                325                 330                 335
```

Trp Asp Asp Pro Asp Arg Tyr Asp Ile Thr Arg Lys Thr Ser Gly His
            340                 345                 350

Val Gly Phe Gly Ser Gly Val His Met Cys Val Gly Gln Leu Val Ala
        355                 360                 365

Arg Leu Glu Gly Glu Val Val Leu Ala Ala Leu Ala Arg Lys Val Ala
    370                 375                 380

Ala Ile Glu Ile Ala Gly Pro Leu Lys Arg Arg Phe Asn Asn Thr Leu
385                 390                 395                 400

Arg Gly Leu Glu Ser Leu Pro Ile Gln Leu Thr Pro Ala
                405                 410

<210> SEQ ID NO 76
<211> LENGTH: 1242
<212> TYPE: DNA
<213> ORGANISM: artificial
<220> FEATURE:
<223> OTHER INFORMATION: coding sequence for SEQ ID NO: 75

<400> SEQUENCE: 76

| | | |
|---|---|---|
| atgtccacca ctgctccatc tttggttcca gttaccactc catcccaaca cggtgctggt | 60 |
| gttccacact tgggtatcga tccattcgct ttggactact tcgccgatcc atacccagaa | 120 |
| caagaaactt tgagagaagc tggtccagtt gtctacttgg acaagtggaa cgtctacggt | 180 |
| gtcgccagat acgctgaagt atacgccgta ctcaacgatc cattgacctt ctgttcctct | 240 |
| agaggtgttg gtttgtctga tttcaagaag gaaaagccat ggaggccacc atctttgatc | 300 |
| ttggaagccg acccaccagc tcacaccaga accagagctg ttttgtctaa ggttttgtct | 360 |
| ccagctacta tgaagagatt gagagatggt ttcgctgctg ctgctgacgc caagatcgat | 420 |
| gaattgttgg ccagaggtgg taacatcgat gctatcgccg acttggccga gcctacccca | 480 |
| ttgtctgttt tcccagatgc gatgggtttg aagcaagaag gcagagaaaa cttgttgcca | 540 |
| tacgcgggct tggttttgaa cgcattcggt ccaccaaacg aattgagaca atctgctatc | 600 |
| gaaagatctg ctccacacca gcctacgtt gccgaacaat gtcaaagacc aaacttggct | 660 |
| ccaggtggtt tcggtgcctg tatccacgcc ttctctgaca ccggtgaaat cactccagaa | 720 |
| gaagccccat tgttggttag atctttgttg tctgctggtt tggacactac cgtcaacggt | 780 |
| attgctgctg ctgtttactg tttggctaga ttcccagacg aattcgctag attgagagcc | 840 |
| gatccatctt tggccagaaa cgccttcgaa gaagctgtta gattcgaatc tccagttcaa | 900 |
| accttcttca gaaccaccac tagagatgtc gaattggctg gtgccactat cggtgaaggt | 960 |
| gaaaaggttt tgatgttctt gggttccgcc aacagagatc caagaagatg ggacgatcca | 1020 |
| gacagatacg acatcaccag aaagacctct gggcatgtcg gcttcggttc tggtgttcac | 1080 |
| atgtgtgtcg gtcaattggt cgccagattg gaaggtgaag ttgttttggc cgctttggct | 1140 |
| agaaaggttg ctgctatcga aatcgccggt ccattgaaga aagattcaa caacactttg | 1200 |
| agaggtttgg aatctttgcc aatccaattg actccagctt aa | 1242 |

<210> SEQ ID NO 77
<211> LENGTH: 718
<212> TYPE: PRT
<213> ORGANISM: Arabidopsis thaliana

<400> SEQUENCE: 77

Met Ser Asp Gln Ile Glu Ala Met Leu Cys Gly Gly Gly Glu Lys Thr
1               5                   10                  15

Lys Val Ala Val Thr Thr Lys Thr Leu Ala Asp Pro Leu Asn Trp Gly

```
                20              25              30
Leu Ala Ala Asp Gln Met Lys Gly Ser His Leu Asp Glu Val Lys Lys
            35              40              45
Met Val Glu Glu Tyr Arg Arg Pro Val Val Asn Leu Gly Gly Glu Thr
            50              55              60
Leu Thr Ile Gly Gln Val Ala Ala Ile Ser Thr Val Gly Gly Ser Val
65              70              75              80
Lys Val Glu Leu Ala Glu Thr Ser Arg Ala Gly Val Lys Ala Ser Ser
            85              90              95
Asp Trp Val Met Glu Ser Met Asn Lys Gly Thr Asp Ser Tyr Gly Val
            100             105             110
Thr Thr Gly Phe Gly Ala Thr Ser His Arg Arg Thr Lys Asn Gly Thr
            115             120             125
Ala Leu Gln Thr Glu Leu Ile Arg Phe Leu Asn Ala Gly Ile Phe Gly
            130             135             140
Asn Thr Lys Glu Thr Cys His Thr Leu Pro Gln Ser Ala Thr Arg Ala
145             150             155             160
Ala Met Leu Val Arg Val Asn Thr Leu Leu Gln Gly Tyr Ser Gly Ile
            165             170             175
Arg Phe Glu Ile Leu Glu Ala Ile Thr Ser Leu Leu Asn His Asn Ile
            180             185             190
Ser Pro Ser Leu Pro Leu Arg Gly Thr Ile Thr Ala Ser Gly Asp Leu
            195             200             205
Val Pro Leu Ser Tyr Ile Ala Gly Leu Leu Thr Gly Arg Pro Asn Ser
            210             215             220
Lys Ala Thr Gly Pro Asp Gly Glu Ser Leu Thr Ala Lys Glu Ala Phe
225             230             235             240
Glu Lys Ala Gly Ile Ser Thr Gly Phe Phe Asp Leu Gln Pro Lys Glu
            245             250             255
Gly Leu Ala Leu Val Asn Gly Thr Ala Val Gly Ser Gly Met Ala Ser
            260             265             270
Met Val Leu Phe Glu Ala Asn Val Gln Ala Val Leu Ala Glu Val Leu
            275             280             285
Ser Ala Ile Phe Ala Glu Val Met Ser Gly Lys Pro Glu Phe Thr Asp
            290             295             300
His Leu Thr His Arg Leu Lys His His Pro Gly Gln Ile Glu Ala Ala
305             310             315             320
Ala Ile Met Glu His Ile Leu Asp Gly Ser Ser Tyr Met Lys Leu Ala
            325             330             335
Gln Lys Val His Glu Met Asp Pro Leu Gln Lys Pro Lys Gln Asp Arg
            340             345             350
Tyr Ala Leu Arg Thr Ser Pro Gln Trp Leu Gly Pro Gln Ile Glu Val
            355             360             365
Ile Arg Gln Ala Thr Lys Ser Ile Glu Arg Glu Ile Asn Ser Val Asn
            370             375             380
Asp Asn Pro Leu Ile Asp Val Ser Arg Asn Lys Ala Ile His Gly Gly
385             390             395             400
Asn Phe Gln Gly Thr Pro Ile Gly Val Ser Met Asp Asn Thr Arg Leu
            405             410             415
Ala Ile Ala Ala Ile Gly Lys Leu Met Phe Ala Gln Phe Ser Glu Leu
            420             425             430
Val Asn Asp Phe Tyr Asn Asn Gly Leu Pro Ser Asn Leu Thr Ala Ser
            435             440             445
```

```
Ser Asn Pro Ser Leu Asp Tyr Gly Phe Lys Gly Ala Glu Ile Ala Met
    450                 455                 460

Ala Ser Tyr Cys Ser Glu Leu Gln Tyr Leu Ala Asn Pro Val Thr Ser
465                 470                 475                 480

His Val Gln Ser Ala Glu Gln His Asn Gln Asp Val Asn Ser Leu Gly
                485                 490                 495

Leu Ile Ser Ser Arg Lys Thr Ser Glu Ala Val Asp Ile Leu Lys Leu
                500                 505                 510

Met Ser Thr Thr Phe Leu Val Gly Ile Cys Gln Ala Val Asp Leu Arg
                515                 520                 525

His Leu Glu Glu Asn Leu Arg Gln Thr Val Lys Asn Thr Val Ser Gln
            530                 535                 540

Val Ala Lys Lys Val Leu Thr Thr Gly Ile Asn Gly Glu Leu His Pro
545                 550                 555                 560

Ser Arg Phe Cys Glu Lys Asp Leu Leu Lys Val Val Asp Arg Glu Gln
                565                 570                 575

Val Phe Thr Tyr Val Asp Asp Pro Cys Ser Ala Thr Tyr Pro Leu Met
                580                 585                 590

Gln Arg Leu Arg Gln Val Ile Val Asp His Ala Leu Ser Asn Gly Glu
            595                 600                 605

Thr Glu Lys Asn Ala Val Thr Ser Ile Phe Gln Lys Ile Gly Ala Phe
            610                 615                 620

Glu Glu Glu Leu Lys Ala Val Leu Pro Lys Glu Val Glu Ala Ala Arg
625                 630                 635                 640

Ala Ala Tyr Gly Asn Gly Thr Ala Pro Ile Pro Asn Arg Ile Lys Glu
                645                 650                 655

Cys Arg Ser Tyr Pro Leu Tyr Arg Phe Val Arg Glu Glu Leu Gly Thr
                660                 665                 670

Lys Leu Leu Thr Gly Glu Lys Val Val Ser Pro Gly Glu Glu Phe Asp
            675                 680                 685

Lys Val Phe Thr Ala Met Cys Glu Gly Lys Leu Ile Asp Pro Leu Met
690                 695                 700

Asp Cys Leu Lys Glu Trp Asn Gly Ala Pro Ile Pro Ile Cys
705                 710                 715
```

<210> SEQ ID NO 78
<211> LENGTH: 2157
<212> TYPE: DNA
<213> ORGANISM: artificial
<220> FEATURE:
<223> OTHER INFORMATION: coding sequence for SEQ ID NO: 77

<400> SEQUENCE: 78

```
atgtccgatc aaatcgaagc tatgttgtgt ggtggtggtg aaaaaacaaa agttgctgtt      60
actactaaga ccttggccga tccattgaat tggggtttgg ctgctgatca aatgaagggt     120
tctcatttgg atgaagtcaa gagatggtc gaagaataca aaggccagt tgttaatttg      180 ggtggtgaaa ctttgactat tggtcaagtt gctgctattt ctactgttgg tggttctgtt     240
aaggttgaat ggctgaaaac ttctagagct ggtgttaagg cttcttctga ttgggttatg     300
gaatctatga acaagggtac tgattcttac ggtgttacta caggttttgg tgctacttct     360
catagaagaa ctaagaatgg tactgccttg caaaccgaat tgatcagatt tttgaacgcc     420
ggtatttccg gtaacaccaa agaaacttgt catacccttgc cacaatctgc tactagagct     480
gctatgttgg ttagagttaa cactttgttg caaggttact ccggtatcag attcgaaatt     540
```

-continued

```
ttggaagcta tcacctcctt gttgaaccat aacatttctc catctttgcc attgagaggt    600
actattactg cttctggtga tttggttcca ttgtcttata ttgctggttt gttgactggt    660
agaccaaact ctaaagctac tggtccagat ggtgaatcat tgactgctaa agaagctttt    720
gaaaaggctg gtatctctac tggttttttc gacttgcaac ctaaagaagg tttggctttg    780
gttaatggta cagctgttgg ttctggtatg gcttctatgg ttttgtttga agctaacgtt    840
caagctgttt tggccgaagt tttgtctgct atttttgctg aagttatgtc cggtaagcca    900
gaattcactg atcatttgac ccatagattg aaacatcacc caggtcaaat tgaagctgct    960
gcaattatgg aacatatctt ggatggttcc tcttacatga agttggctca aaaagttcac   1020
gaaatggacc cattgcaaaa gccaaaacaa gatagatacg ctttgagaac ttctccacaa   1080
tggttgggtc cacaaataga agttattaga caagccacca gtccatcga aagagaaatc   1140
aattctgtta acgacaaccc attgatcgac gtcagtagaa acaaagctat tcatggtggt   1200
aacttccaag gtactccaat tggtgtttct atggacaaca ctagattggc tattgctgcc   1260
attggtaaat tgatgttcgc tcaattctcc gaattggtca cgattttta caacaacggt   1320
ttgccttcta acttgaccgc ttcttctaat ccatcattgg attacggttt taagggtgct   1380
gaaattgcta tggcttcata ctgttctgaa ttgcaatact tggctaaccc agttacctct   1440
catgttcaat ctgctgaaca cacaatcaa gacgttaact ccttgggttt gatctcttct   1500
agaaagactt ctgaagccgt tgacatcttg aagttgatgt ctactacatt cttggtcggt   1560
atttgccaag ctgttgattt gagacatttg aagaaaact tgagacaaac cgtcaagaac   1620
accgtttcac aagttgctaa gaaagtttg accaccggta ttaacggtga attgcatcca   1680
tctagattct gcgaaaagga tttgttgaag gtcgttgata gagaacaagt tttcacctac   1740
gttgatgatc catgttctgc tacttatcca ttgatgcaaa gattgagaca gtcatcgtt   1800
gatcatgctt tgtctaatgg tgaaaccgaa agaacgctg ttacctccat ttttccaaaag   1860
attggtgctt tcgaagaaga attgaaggcc gttttgccaa agaagttga agcagctaga   1920
gcagcttacg gtaacggtac tgctccaatt ccaaatagaa tcaaagaatg cagatcctac   1980
ccattataca gattcgttag agaagaatta ggtactaagt tgttgaccgg tgaaaaggtt   2040
gtttctccag gtgaagaatt cgataaggtt ttcactgcta tgtgcgaagg taaattgatc   2100
gatccattga tggactgctt gaagaatgg aatggtgctc ctattcctat ctgctaa       2157
```

<210> SEQ ID NO 79
<211> LENGTH: 506
<212> TYPE: PRT
<213> ORGANISM: Arabidopsis thaliana

<400> SEQUENCE: 79

```
Met Ser Asp Leu Leu Leu Glu Lys Ser Leu Ile Ala Val Phe Val
1               5                   10                  15

Ala Val Ile Leu Ala Thr Val Ile Ser Lys Leu Arg Gly Lys Lys Leu
            20                  25                  30

Lys Leu Pro Pro Gly Pro Ile Pro Ile Pro Ile Phe Gly Asn Trp Leu
        35                  40                  45

Gln Val Gly Asp Asp Leu Asn His Arg Asn Leu Val Asp Tyr Ala Lys
    50                  55                  60

Lys Phe Gly Asp Leu Phe Leu Leu Arg Met Gly Gln Arg Asn Leu Val
65                  70                  75                  80

Val Val Ser Ser Pro Asp Leu Thr Lys Glu Val Leu Leu Thr Gln Gly
```

```
                85                  90                  95
Val Glu Phe Gly Ser Arg Thr Arg Asn Val Val Phe Asp Ile Phe Thr
            100                 105                 110
Gly Lys Gly Gln Asp Met Val Phe Thr Val Tyr Gly Glu His Trp Arg
            115                 120                 125
Lys Met Arg Arg Ile Met Thr Val Pro Phe Phe Thr Asn Lys Val Val
            130                 135                 140
Gln Gln Asn Arg Glu Gly Trp Glu Phe Glu Ala Ala Ser Val Val Glu
145                 150                 155                 160
Asp Val Lys Lys Asn Pro Asp Ser Ala Thr Lys Gly Ile Val Leu Arg
                165                 170                 175
Lys Arg Leu Gln Leu Met Met Tyr Asn Asn Met Phe Arg Ile Met Phe
            180                 185                 190
Asp Arg Arg Phe Glu Ser Glu Asp Asp Pro Leu Phe Leu Arg Leu Lys
            195                 200                 205
Ala Leu Asn Gly Glu Arg Ser Arg Leu Ala Gln Ser Phe Glu Tyr Asn
            210                 215                 220
Tyr Gly Asp Phe Ile Pro Ile Leu Arg Pro Phe Leu Arg Gly Tyr Leu
225                 230                 235                 240
Lys Ile Cys Gln Asp Val Lys Asp Arg Ile Ala Leu Phe Lys Lys
                245                 250                 255
Tyr Phe Val Asp Glu Arg Lys Gln Ile Ala Ser Ser Lys Pro Thr Gly
            260                 265                 270
Ser Glu Gly Leu Lys Cys Ala Ile Asp His Ile Leu Glu Ala Glu Gln
            275                 280                 285
Lys Gly Glu Ile Asn Glu Asp Asn Val Leu Tyr Ile Val Glu Asn Ile
            290                 295                 300
Asn Val Ala Ala Ile Glu Thr Thr Leu Trp Ser Ile Glu Trp Gly Ile
305                 310                 315                 320
Ala Glu Leu Val Asn His Pro Glu Ile Gln Ser Lys Leu Arg Asn Glu
                325                 330                 335
Leu Asp Thr Val Leu Gly Pro Gly Val Gln Val Thr Glu Pro Asp Leu
            340                 345                 350
His Lys Leu Pro Tyr Leu Gln Ala Val Val Lys Glu Thr Leu Arg Leu
            355                 360                 365
Arg Met Ala Ile Pro Leu Leu Val Pro His Met Asn Leu His Asp Ala
            370                 375                 380
Lys Leu Ala Gly Tyr Asp Ile Pro Ala Glu Ser Lys Ile Leu Val Asn
385                 390                 395                 400
Ala Trp Trp Leu Ala Asn Asn Pro Asn Ser Trp Lys Lys Pro Glu Glu
                405                 410                 415
Phe Arg Pro Glu Arg Phe Phe Glu Glu Ser His Val Glu Ala Asn
            420                 425                 430
Gly Asn Asp Phe Arg Tyr Val Pro Phe Gly Val Gly Arg Arg Ser Cys
            435                 440                 445
Pro Gly Ile Ile Leu Ala Leu Pro Ile Leu Gly Ile Thr Ile Gly Arg
450                 455                 460
Met Val Gln Asn Phe Glu Leu Leu Pro Pro Gly Gln Ser Lys Val
465                 470                 475                 480
Asp Thr Ser Glu Lys Gly Gly Gln Phe Ser Leu His Ile Leu Asn His
                485                 490                 495
Ser Ile Ile Val Met Lys Pro Arg Asn Cys
                500                 505
```

<210> SEQ ID NO 80
<211> LENGTH: 1521
<212> TYPE: DNA
<213> ORGANISM: artificial
<220> FEATURE:
<223> OTHER INFORMATION: coding sequence for SEQ ID NO: 79

<400> SEQUENCE: 80

```
atgtccgact tgttgttgtt ggaaaagtcc ttgattgctg ttttcgttgc tgttattttg      60
gccaccgtta tctctaaatt gagaggtaag aaattgaagt tgccaccagg tccaattcca     120
atcccaattt ttggtaattg gttgcaagtt ggtgatgact tgaaccacag aaacttggtt     180
gattacgcta aaaagttcgg tgatttgttc ttgttgagaa tgggtcaaag aaatttggtc     240
gttgtttcct caccagactt gaccaaagaa gttttgttga ctcaaggtgt cgaattcggt     300
tccagaacta gaaatgttgt tttcgatatc ttcaccggta agggtcaaga tatggttttt     360
actgtttacg gtgaacattg gagaaagatg agaagaatta tgaccgttcc attcttcacc     420
aacaaggttg tccaacaaaa cagagaaggt tgggaatttg aagctgcttc tgttgttgaa     480
gatgtcaaga gaatccagat tctgctact aagggtatcg ttttgagaaa agattgcaa      540
ttgatgatgt acaacaacat gttcagaatc atgttcgaca aagatttgaa tccgaagat     600
gaccctttgt ttttgagatt gaaggctttg aacggtgaaa gatctagatt ggctcaatcc     660
ttcgaataca actacggtga tttcatccca atcttaagac cattcttgag aggttacttg     720
aagatctgcc aagatgttaa ggatagaaga tcgccttgt tcaaaaagta cttcgttgac     780
gaaagaaagc aaatcgcttc ttctaaacct actggttctg aaggtttgaa gtgcgccatt     840
gatcatattt tggaagctga acaaaagggt gaaatcaacg aagataacgt cttgtacatc     900
gtcgaaaaca ttaacgttgc tgctattgaa actaccttgt ggtctattga tgggggtatt     960
gctgaattgg ttaatcaccc agaaatccaa tccaagttga aaacgaatt ggatactgtt    1020
ttgggtccag tgttcaagt tactgaacct gacttgcata agttgccata cttgcaagct    1080
gttgtaaaag aaaaccttga gattaagaat gccatcccct tgttggttcc acatatgaac    1140
ttgcatgatg ctaaattggc cggttatgat attccagccg aatccaagat tttggttaat    1200
gcttggtggt tggctaacaa tccaaattct tggaaaaagc cagaagaatt cagaccagaa    1260
agattttcg aagaagaaag tcacgttgaa gccaacggta tgattttag atacgttcca    1320
tttggtgttg gtagaagatc ttgtccaggt attatcttgg ctttgccaat tttgggtatt    1380
accatcggta aatggtcca aaacttcgaa ttattgccac acctggtca atctaaggtt    1440
gatacttctg aaaagggtgg tcaattctcc ttgcatattt tgaaccactc catcatcgtt    1500
atgaagccaa gaaactgtta a                                             1521
```

<210> SEQ ID NO 81
<211> LENGTH: 384
<212> TYPE: PRT
<213> ORGANISM: Saccharomyces cerevisiae

<400> SEQUENCE: 81

```
Met Ser Lys Ser Lys Thr Phe Leu Phe Thr Ser Glu Ser Val Gly Glu
1               5                   10                  15

Gly His Pro Asp Lys Ile Cys Asp Gln Val Ser Asp Ala Ile Leu Asp
            20                  25                  30

Ala Cys Leu Glu Gln Asp Pro Phe Ser Lys Val Ala Cys Glu Thr Ala
        35                  40                  45
```

Ala Lys Thr Gly Met Ile Met Val Phe Gly Glu Ile Thr Thr Lys Ala
 50                  55                  60

Arg Leu Asp Tyr Gln Gln Ile Val Arg Asp Thr Ile Lys Lys Ile Gly
 65                  70                  75                  80

Tyr Asp Asp Ser Ala Lys Gly Phe Asp Tyr Lys Thr Cys Asn Val Leu
                 85                  90                  95

Val Ala Ile Glu Gln Gln Ser Pro Asp Ile Ala Gln Gly Leu His Tyr
            100                 105                 110

Glu Lys Ser Leu Glu Asp Leu Gly Ala Gly Asp Gln Gly Ile Met Phe
        115                 120                 125

Gly Tyr Ala Thr Asp Glu Thr Pro Glu Gly Leu Pro Leu Thr Ile Leu
130                 135                 140

Leu Ala His Lys Leu Asn Met Ala Met Ala Asp Ala Arg Arg Asp Gly
145                 150                 155                 160

Ser Leu Pro Trp Leu Arg Pro Asp Thr Lys Thr Gln Val Thr Val Glu
                165                 170                 175

Tyr Glu Asp Asp Asn Gly Arg Trp Val Pro Lys Arg Ile Asp Thr Val
            180                 185                 190

Val Ile Ser Ala Gln His Ala Asp Glu Ile Ser Thr Ala Asp Leu Arg
        195                 200                 205

Thr Gln Leu Gln Lys Asp Ile Val Glu Lys Val Ile Pro Lys Asp Met
210                 215                 220

Leu Asp Glu Asn Thr Lys Tyr Phe Ile Gln Pro Ser Gly Arg Phe Val
225                 230                 235                 240

Ile Gly Gly Pro Gln Gly Asp Ala Gly Leu Thr Gly Arg Lys Ile Ile
                245                 250                 255

Val Asp Ala Tyr Gly Gly Ala Ser Ser Val Gly Gly Gly Ala Phe Ser
            260                 265                 270

Gly Lys Asp Tyr Ser Lys Val Asp Arg Ser Ala Ala Tyr Ala Ala Arg
        275                 280                 285

Trp Val Ala Lys Ser Leu Val Ala Ala Gly Leu Cys Lys Arg Val Gln
290                 295                 300

Val Gln Phe Ser Tyr Ala Ile Gly Ile Ala Glu Pro Leu Ser Leu His
305                 310                 315                 320

Val Asp Thr Tyr Gly Thr Ala Thr Lys Ser Asp Asp Glu Ile Ile Glu
                325                 330                 335

Ile Ile Lys Lys Asn Phe Asp Leu Arg Pro Gly Val Leu Val Lys Glu
            340                 345                 350

Leu Asp Leu Ala Arg Pro Ile Tyr Leu Pro Thr Ala Ser Tyr Gly His
        355                 360                 365

Phe Thr Asn Gln Glu Tyr Ser Trp Glu Lys Pro Lys Lys Leu Glu Phe
370                 375                 380

<210> SEQ ID NO 82
<211> LENGTH: 1155
<212> TYPE: DNA
<213> ORGANISM: artificial
<220> FEATURE:
<223> OTHER INFORMATION: coding sequence for SEQ ID NO: 81

<400> SEQUENCE: 82
atgtccaaga gcaaaacttt cttatttacc tctgaatccg tcggtgaagg tcacccagac        60
aagatttgtg accaagtttc tgatgctatt ttggacgctt gtttagaaca agatccattc       120
tccaaggttg cctgtgaaac agctgccaaa actggtatga ttatggtttt cggtgaaatt       180

```
accaccaaag ctagacttga ctaccaacaa atagtaagag ataccatcaa gaagattggt    240
tatgacgatt ctgccaaggg tttcgactac aagacatgta atgttttagt agctatcgaa    300
caacaatctc cagatatcgc tcaaggtctg cactatgaaa agagcttaga agatttaggt    360
gctggtgacc aaggtataat gtttggttac gctacagacg aaactccaga agggttacca    420
ttgaccattc ttttggctca caaattgaac atggctatgg cagatgctag aagagatggt    480
tctctcccat ggttgaggcc agacacaaag actcaagtca ctgtcgaata cgaggacgac    540
aatggtagat gggttccaaa gaggatagat accgttgtta tttctgctca acatgctgat    600
gaaatttcca ccgctgactt gagaactcaa cttcaaaaag atattgttga aaaggtcata    660
ccaaaggata tgttagacga aaataccaaa tatttcatcc aaccatccgg tagattcgtc    720
atcggtggtc ctcaaggtga cgctggtttg accggtagaa agattattgt cgacgcttac    780
ggtggtgcct catccgtcgg tggtggtgcc ttctccggta aggactattc caaggtcgat    840
cgttccgctg cttacgctgc tagatgggtt gccaagtctc tagttgccgc tggtttgtgt    900
aagagagtcc aagtccaatt ttcatatgct attggtattg ctgaaccatt gtctttacat    960
gtggacacct atggtacagc tacaaaatca gatgacgaaa tcattgaaat tattaagaag   1020
aacttcgact tgaggccagg tgtgttagta aaggaattag atttggctag accaatttac   1080
ttaccaaccg cttcttatgg tcacttcact aatcaagagt actcatggga aaaaccaaag   1140
aaattggaat tttaa                                                   1155
```

<210> SEQ ID NO 83
<211> LENGTH: 521
<212> TYPE: PRT
<213> ORGANISM: Escherichia coli

<400> SEQUENCE: 83

```
Met Ser Lys Pro Glu Asp Phe Arg Ala Ser Thr Gln Arg Pro Phe Thr
1               5                   10                  15

Gly Glu Glu Tyr Leu Lys Ser Leu Gln Asp Gly Arg Glu Ile Tyr Ile
            20                  25                  30

Tyr Gly Glu Arg Val Lys Asp Val Thr Thr His Pro Ala Phe Arg Asn
        35                  40                  45

Ala Ala Ala Ser Val Ala Gln Leu Tyr Asp Ala Leu His Lys Pro Glu
    50                  55                  60

Met Gln Asp Ser Leu Cys Trp Asn Thr Asp Thr Gly Ser Gly Gly Tyr
65                  70                  75                  80

Thr His Lys Phe Phe Arg Val Ala Lys Ser Ala Asp Asp Leu Arg Gln
                85                  90                  95

Gln Arg Asp Ala Ile Ala Glu Trp Ser Arg Leu Ser Tyr Gly Trp Met
            100                 105                 110

Gly Arg Thr Pro Asp Tyr Lys Ala Ala Phe Gly Cys Ala Leu Gly Ala
        115                 120                 125

Asn Pro Gly Phe Tyr Gly Gln Phe Glu Gln Asn Ala Arg Asn Trp Tyr
    130                 135                 140

Thr Arg Ile Gln Glu Thr Gly Leu Tyr Phe Asn His Ala Ile Val Asn
145                 150                 155                 160

Pro Pro Ile Asp Arg His Leu Pro Thr Asp Lys Val Lys Asp Val Tyr
                165                 170                 175

Ile Lys Leu Glu Lys Glu Thr Asp Ala Gly Ile Ile Val Ser Gly Ala
            180                 185                 190
```

Lys Val Val Ala Thr Asn Ser Ala Leu Thr His Tyr Asn Met Ile Gly
            195                 200                 205

Phe Gly Ser Ala Gln Val Met Gly Glu Asn Pro Asp Phe Ala Leu Met
        210                 215                 220

Phe Val Ala Pro Met Asp Ala Asp Gly Val Lys Leu Ile Ser Arg Ala
225                 230                 235                 240

Ser Tyr Glu Met Val Ala Gly Ala Thr Gly Ser Pro Tyr Asp Tyr Pro
                245                 250                 255

Leu Ser Ser Arg Phe Asp Glu Asn Asp Ala Ile Leu Val Met Asp Asn
            260                 265                 270

Val Leu Ile Pro Trp Glu Asn Val Leu Ile Tyr Arg Asp Phe Asp Arg
        275                 280                 285

Cys Arg Arg Trp Thr Met Glu Gly Gly Phe Ala Arg Met Tyr Pro Leu
    290                 295                 300

Gln Ala Cys Val Arg Leu Ala Val Lys Leu Asp Phe Ile Thr Ala Leu
305                 310                 315                 320

Leu Lys Lys Ser Leu Glu Cys Thr Gly Thr Leu Glu Phe Arg Gly Val
                325                 330                 335

Gln Ala Asp Leu Gly Glu Val Val Ala Trp Arg Asn Thr Phe Trp Ala
            340                 345                 350

Leu Ser Asp Ser Met Cys Ser Glu Ala Thr Pro Trp Val Asn Gly Ala
        355                 360                 365

Tyr Leu Pro Asp His Ala Ala Leu Gln Thr Tyr Arg Val Leu Ala Pro
    370                 375                 380

Met Ala Tyr Ala Lys Ile Lys Asn Ile Ile Glu Arg Asn Val Thr Ser
385                 390                 395                 400

Gly Leu Ile Tyr Leu Pro Ser Ser Ala Arg Asp Leu Asn Asn Pro Gln
                405                 410                 415

Ile Asp Gln Tyr Leu Ala Lys Tyr Val Arg Gly Ser Asn Gly Met Asp
            420                 425                 430

His Val Gln Arg Ile Lys Ile Leu Lys Leu Met Trp Asp Ala Ile Gly
        435                 440                 445

Ser Glu Phe Gly Gly Arg His Glu Leu Tyr Glu Ile Asn Tyr Ser Gly
    450                 455                 460

Ser Gln Asp Glu Ile Arg Leu Gln Cys Leu Arg Gln Ala Gln Asn Ser
465                 470                 475                 480

Gly Asn Met Asp Lys Met Met Ala Met Val Asp Arg Cys Leu Ser Glu
                485                 490                 495

Tyr Asp Gln Asp Gly Trp Thr Val Pro His Leu His Asn Asn Asp Asp
            500                 505                 510

Ile Asn Met Leu Asp Lys Leu Leu Lys
        515                 520

<210> SEQ ID NO 84
<211> LENGTH: 1566
<212> TYPE: DNA
<213> ORGANISM: artificial
<220> FEATURE:
<223> OTHER INFORMATION: coding sequence for SEQ ID NO: 83

<400> SEQUENCE: 84
atgtccaaac cagaagattt ccgcgccagt acccaacgtc ctttcaccgg ggaagagtat       60
ctgaaaagcc tgcaggatgg tcgcgagatc tatatctatg cgagcgagt gaaagacgtc      120 accactcatc cggcatttcg taatgcggca gcgtctgttg cccagctgta cgacgcactg      180

```
cacaaaccgg agatgcagga ctctctgtgt tggaacaccg acaccggcag cggcggctat    240
acccataaat tcttccgcgt ggcgaaaagt gccgacgacc tgcgccagca acgcgacgcc    300
atcgctgagt ggtcacgcct gagctatggc tggatgggcc gtaccccaga ctacaaagcc    360
gctttcggtt gcgcactggg cgcgaatccg ggcttttacg gtcagttcga gcagaacgcc    420
cgtaactggt acacccgtat tcaggaaact ggcctctact ttaaccacgc gattgttaac    480
ccaccgatcg atcgtcattt gccgaccgat aaagtgaaag acgtttacat caagctggaa    540
aaagagactg acgccgggat tatcgtcagc ggtgcgaaag tggttgccac caactcggcg    600
ctgactcact acaacatgat tggcttcggc tcggcacaag tgatgggcga aaacccggac    660
ttcgcactga tgttcgttgc gccaatggat gccgatggcg tgaaattaat ctcccgcgcc    720
tcttatgaga tggtcgcggg tgctaccggc tcgccatacg actacccgct ctccagccgc    780
ttcgatgaga acgatgcgat tctggtgatg gataacgtgc tgattccatg gaaaacgtg     840 ctgatctacc gcgattttga tcgctgccgt cgctggacga tggaaggcgg ttttgcccgt    900
atgtatccgc tgcaagcctg tgtgcgcctg gcagtgaaat tagacttcat tacggcactg    960
ctgaaaaaat cactcgaatg taccggcacc ctggagttcc gtggtgtgca ggccgatctc    1020
ggtgaagtgg tagcgtggcg caacaccttc tgggcattga gtgactcgat gtgttcagaa    1080
gcaacgccgt gggtcaacgg ggcttattta ccggatcatg ccgcactgca acctatcgc    1140 gtactggcac caatggccta cgcgaagatc aaaaacatta tcgaacgcaa cgttaccagt    1200
ggcctgatct atctcccttc cagtgcccgt gacctgaata tccgcagat cgaccagtat    1260 ctggcgaagt atgtgcgcgg ttcgaacggt atggatcacg tccagcgcat caagatcctc    1320
aaactgatgt gggatgctat tggcagcgaa tttggtggtc gtcacgaact gtatgaaatc    1380
aactactccg gtagccagga tgagattcgc ctgcagtgtc tgcgccaggc acaaaactcc    1440
ggcaatatgg acaagatgat ggcgatggtt gatcgctgcc tgtcggaata cgaccaggac    1500
ggctggactg tgccgcacct gcacaacaac gacgatatca acatgctgga taagctgctg    1560
aaataa                                                              1566
```

<210> SEQ ID NO 85
<211> LENGTH: 171
<212> TYPE: PRT
<213> ORGANISM: Escherichia coli

<400> SEQUENCE: 85

```
Met Ser Gln Leu Asp Glu Gln Arg Leu Arg Phe Arg Asp Ala Met Ala
1               5                   10                  15

Ser Leu Ser Ala Ala Val Asn Ile Ile Thr Thr Glu Gly Asp Ala Gly
            20                  25                  30

Gln Cys Gly Ile Thr Ala Thr Ala Val Cys Ser Val Thr Asp Thr Pro
        35                  40                  45

Pro Ser Leu Met Val Cys Ile Asn Ala Asn Ser Ala Met Asn Pro Val
    50                  55                  60

Phe Gln Gly Asn Gly Lys Leu Cys Val Asn Val Leu Asn His Glu Gln
65                  70                  75                  80

Glu Leu Met Ala Arg His Phe Ala Gly Met Thr Gly Met Ala Met Glu
                85                  90                  95

Glu Arg Phe Ser Leu Ser Cys Trp Gln Lys Gly Pro Leu Ala Gln Pro
            100                 105                 110

Val Leu Lys Gly Ser Leu Ala Ser Leu Glu Gly Glu Ile Arg Asp Val
        115                 120                 125
```

Gln Ala Ile Gly Thr His Leu Val Tyr Leu Val Glu Ile Lys Asn Ile
        130                 135                 140

Ile Leu Ser Ala Glu Gly His Gly Leu Ile Tyr Phe Lys Arg Arg Phe
145                 150                 155                 160

His Pro Val Met Leu Glu Met Glu Ala Ala Ile
                165                 170

<210> SEQ ID NO 86
<211> LENGTH: 516
<212> TYPE: DNA
<213> ORGANISM: artificial
<220> FEATURE:
<223> OTHER INFORMATION: coding sequence for SEQ ID NO: 85

<400> SEQUENCE: 86
atgtcccaat tagatgaaca acgcctgcgc tttcgtgacg cgatggccag cctgtcggca      60
gcggtaaata ttatcaccac cgagggcgac gccggacaat gcggattac ggcaacggcc      120 gtctgctcgg tcacggatac accaccgtcg ctgatggtgt gcattaacgc caacagtgcg     180
atgaacccgg ttttcaggg caacggcaag ttgtgcgtca acgtcctcaa ccatgagcag      240
gaactgatgg cacgccactt cgcgggcatg acaggcatgg cgatggaaga gcgttttagc     300
ctctcatgct ggcaaaaagg tccgctggcg cagccggtgc taaaaggttc gctggccagt     360
cttgaaggtg agatccgcga tgtgcaggca attggcacac atctggtgta tctggtggag     420
attaaaaaca tcatcctcag tgcagaaggt catggactta tctactttaa acgccgtttc     480
catccggtga tgctggaaat ggaagctgcg atttaa                               516

<210> SEQ ID NO 87
<211> LENGTH: 233
<212> TYPE: PRT
<213> ORGANISM: Arabidopsis thaliana

<400> SEQUENCE: 87

Met Ser Ala Lys Asp Glu Ala Lys Gly Leu Leu Lys Ser Glu Glu Leu
1               5                   10                  15

Tyr Lys Tyr Ile Leu Glu Thr Ser Val Tyr Pro Arg Glu Pro Glu Val
                20                  25                  30

Leu Arg Glu Leu Arg Asn Ile Thr His Asn His Pro Gln Ala Gly Met
            35                  40                  45

Ala Thr Ala Pro Asp Ala Gly Gln Leu Met Gly Met Leu Leu Asn Leu
        50                  55                  60

Val Asn Ala Arg Lys Thr Ile Glu Val Gly Val Phe Thr Gly Tyr Ser
65                  70                  75                  80

Leu Leu Leu Thr Ala Leu Thr Leu Pro Glu Asp Gly Lys Val Ile Ala
                85                  90                  95

Ile Asp Met Asn Arg Asp Ser Tyr Glu Ile Gly Leu Pro Val Ile Lys
                100                 105                 110

Lys Ala Gly Val Glu His Lys Ile Asp Phe Lys Glu Ser Glu Ala Leu
            115                 120                 125

Pro Ala Leu Asp Glu Leu Leu Asn Asn Lys Val Asn Glu Gly Gly Phe
        130                 135                 140

Asp Phe Ala Phe Val Asp Ala Asp Lys Leu Asn Tyr Trp Asn Tyr His
145                 150                 155                 160

Glu Arg Leu Ile Arg Leu Ile Lys Val Gly Gly Ile Ile Val Tyr Asp
                165                 170                 175

```
Asn Thr Leu Trp Gly Gly Ser Val Ala Glu Pro Asp Ser Ser Thr Pro
                180                 185                 190

Glu Trp Arg Ile Glu Val Lys Lys Ala Thr Leu Glu Leu Asn Lys Lys
            195                 200                 205

Leu Ser Ala Asp Gln Arg Val Gln Ile Ser Gln Ala Ala Leu Gly Asp
        210                 215                 220

Gly Ile Thr Ile Cys Arg Arg Leu Tyr
225                 230
```

<210> SEQ ID NO 88
<211> LENGTH: 702
<212> TYPE: DNA
<213> ORGANISM: artificial
<220> FEATURE:
<223> OTHER INFORMATION: coding sequence for SEQ ID NO: 87

<400> SEQUENCE: 88

```
atgtccgcta aggatgaagc caagggtttg ttgaagtctg aagaattgta caagtacatc     60
ttggaaactt ctgtttaccc aagagaacca gaagttttga gagaattgag aaacattact    120
cacaaccacc acaagctgg tatggctact gctccagacg ctggtcaatt gatgggtatg    180
ttgttgaact tggttaacgc tagaaagact atcgaagttg tgttttcac tggttactct    240
ttgttgttga ctgctttgac tttgccagaa gatggtaagg ttatcgccat tgacatgaac    300
agagactctt acgaaatcgg tttgccagtt atcaagaagg ctggtgttga acacaagatt    360
gatttcaagg aatctgaagc tttgccagcc ttggacgaat tgttgaacaa caaggttaac    420
gaaggtggtt tcgacttcgc tttcgttgat gctgacaagt tgaactactg gaactaccac    480
gaaagattga ttagattgat caaggttggt ggtatcatcg tttacgataa cactttgtgg    540
ggtggttctg ttgctgaacc agactcttcc actccagaat ggagaatcga agtcaagaag    600
gctaccttgg aattgaacaa gaagttgtct gctgatcaaa gagttcaaat ctctcaagct    660
gctttgggtg atggtatcac tatttgtaga agattgtact aa                      702
```

<210> SEQ ID NO 89
<211> LENGTH: 222
<212> TYPE: PRT
<213> ORGANISM: Homo sapiens

<400> SEQUENCE: 89

```
Met Ser Gly Asp Thr Lys Glu Gln Arg Ile Leu Asn His Val Leu Gln
1               5                   10                  15

His Ala Glu Pro Gly Asn Ala Gln Ser Val Leu Glu Ala Ile Asp Thr
            20                  25                  30

Tyr Cys Glu Gln Lys Glu Trp Ala Met Asn Val Gly Asp Lys Lys Gly
        35                  40                  45

Lys Ile Val Asp Ala Val Ile Gln Glu His Gln Pro Ser Val Leu Leu
    50                  55                  60

Glu Leu Gly Ala Tyr Cys Gly Tyr Ser Ala Val Arg Met Ala Arg Leu
65                  70                  75                  80

Leu Ser Pro Gly Ala Arg Leu Ile Thr Ile Glu Ile Asn Pro Asp Cys
                85                  90                  95

Ala Ala Ile Thr Gln Arg Met Val Asp Phe Ala Gly Val Lys Asp Lys
            100                 105                 110

Val Thr Leu Val Val Gly Ala Ser Gln Asp Ile Ile Pro Gln Leu Lys
        115                 120                 125

Lys Lys Tyr Asp Val Asp Thr Leu Asp Met Val Phe Leu Asp His Trp
```

```
                130                 135                 140
Lys Asp Arg Tyr Leu Pro Asp Thr Leu Leu Glu Glu Cys Gly Leu
145                 150                 155                 160

Leu Arg Lys Gly Thr Val Leu Leu Ala Asp Asn Val Ile Cys Pro Gly
                165                 170                 175

Ala Pro Asp Phe Leu Ala His Val Arg Gly Ser Ser Cys Phe Glu Cys
            180                 185                 190

Thr His Tyr Gln Ser Phe Leu Glu Tyr Arg Glu Val Val Asp Gly Leu
                195                 200                 205

Glu Lys Ala Ile Tyr Lys Gly Pro Gly Ser Glu Ala Gly Pro
210                 215                 220

<210> SEQ ID NO 90
<211> LENGTH: 669
<212> TYPE: DNA
<213> ORGANISM: artificial
<220> FEATURE:
<223> OTHER INFORMATION: coding sequence for SEQ ID NO: 89

<400> SEQUENCE: 90
atgtccggtg acaccaagga acaaagaatc ttgaaccacg ttttgcaaca cgctgaacca     60
ggtaacgctc aatctgtttt ggaagccatt gacacctact gtgaacaaaa ggaatgggcc    120
atgaacgttg gtgacaagaa gggtaagatc gttgacgccg ttattcaaga acaccaacca    180
tccgttttgt tggaattggg tgcctactgt ggttactctg ctgttagaat ggccagattg    240
ttgtctccag gtgctagatt gatcaccatc gaaatcaacc cagactgtgc cgccatcacc    300
caaagaatgg ttgatttcgc tggtgttaag acaaggtca ccttggttgt tggtgcttcc    360
caagacatca tcccacaatt gaagaagaag tacgatgttg acactttgga catggttttc    420
ttggaccact ggaaggacag atacttgcca gacactttgt tgttggaaga atgtggtttg    480
ttgagaaagg gtactgtttt gttggctgac aacgttatct gtccaggtgc tccagacttc    540
ttggctcacg ttagaggttc ttcttgtttc gaatgtactc actaccaatc tttcttggaa    600
tacagagaag ttgttgacgg tttggaaaag gccatctaca agggtccagg ttctgaagct    660
ggtccataa                                                            669

<210> SEQ ID NO 91
<211> LENGTH: 354
<212> TYPE: PRT
<213> ORGANISM: Citrus clementina

<400> SEQUENCE: 91

Met Ser Gly Ser Ile Val Asp Gly Glu Arg Asp Gln Ser Phe Ala Tyr
1                 5                   10                  15

Ala Asn Gln Leu Ala Met Gly Thr Val Leu Pro Met Ala Met Gln Ala
                20                  25                  30

Val Tyr Glu Leu Gly Ile Phe Gln Ile Ile Asp Lys Ala Gly Pro Gly
            35                  40                  45

Ala Lys Leu Ser Ala Ser Asp Ile Ala Ala Gln Leu Pro Thr Lys Asn
        50                  55                  60

Lys Asp Ala Pro Thr Met Leu Asp Arg Ile Leu Arg Leu Leu Ala Ser
65                  70                  75                  80

Tyr Ser Val Val Glu Cys Ser Leu Asp Gly Ser Gly Ala Arg Arg Arg
                85                  90                  95

Tyr Ser Leu Asn Ser Val Ser Lys Tyr Val Pro Asn Lys Asp Gly
                100                 105                 110
```

```
Val Ser Leu Gly Pro Ala Leu Gln Met Ile Gln Asp Lys Val Phe Leu
        115                 120                 125
Glu Ser Trp Ser His Leu Lys Asp Ala Ile Leu Glu Gly Gly Ile Pro
130                 135                 140
Phe Asn Arg Ala His Gly Met His Ala Phe Glu Tyr Gly Arg Val Asp
145                 150                 155                 160
Pro Arg Phe Asn Lys His Phe Asn Thr Ala Met Tyr Asn His Thr Ser
                165                 170                 175
Leu Ile Met Ser Asn Ile Leu Glu Ser Tyr Lys Gly Phe Ala Asn Ile
            180                 185                 190
Lys Gln Leu Val Asp Val Gly Gly Asn Leu Gly Val Thr Leu Gln Ala
        195                 200                 205
Ile Thr Ser Lys Tyr Pro Tyr Ile Lys Gly Ile Asn Phe Asp Gln Pro
    210                 215                 220
His Val Ile Glu His Ala Pro Leu His Pro His Ile Glu His Val Ala
225                 230                 235                 240
Gly Asp Met Phe Gln Ser Val Pro Lys Gly Asp Ala Ile Phe Leu Lys
                245                 250                 255
Trp Ile Leu His Asp Trp Asp Asp Glu His Cys Leu Lys Leu Leu Lys
            260                 265                 270
Asn Cys Tyr Lys Ser Val Pro Glu Asp Gly Lys Val Ile Val Val Glu
        275                 280                 285
Leu Met Leu Pro Glu Val Pro Asn Thr Ser Ile Glu Ser Lys Ser Asn
290                 295                 300
Ser His Ile Asp Val Leu Met Met Thr Gln Asn Pro Gly Gly Lys Glu
305                 310                 315                 320
Arg Thr Lys His Glu Phe Met Thr Leu Ala Thr Gly Ala Gly Phe Ser
                325                 330                 335
Gly Ile Arg Phe Asp Leu Val Thr Gly Asn Phe Trp Val Met Glu Phe
            340                 345                 350
Tyr Lys

<210> SEQ ID NO 92
<211> LENGTH: 1065
<212> TYPE: DNA
<213> ORGANISM: Artificial Sequence
<220> FEATURE:
<223> OTHER INFORMATION: coding sequence for SEQ ID NO: 91

<400> SEQUENCE: 92
atgtccggtt ctatcgttga tggtgaaaga gatcaatctt tcgcttacgc taaccaattg      60
gctatgggta ctgttttgcc aatggccatg caagctgttt acgaattggg tattttccaa     120
atcatcgaca aggctggtcc aggtgctaag ttgtctgctt ctgatattgc tgcccaattg     180
ccaaccaaga caaggacgc tccaactatg ctcgacagaa tactaagatt gttggcttct     240
tactctgttg ttgaatgttc tttggatggt tctggtgcca aagaagata ctctttgaac     300 tctgtctcca gtactacgt tccaaacaag gatggtgtct ctttgggtcc agctttgcaa     360
atgattcaag acaaggtttt cttggaatct tggtcccact tgaaggatgc tattttggaa     420
ggtggtattc cattcaacag agcccacggt atgcacgctt tcgaatacgg tagagttgac     480
ccaagattca acaagcactt caacactgct atgtacaacc acacctcttt gattatgtct     540 aacatttttgg aatcttacaa gggtttcgcc aacatcaagc aattggtcga tgttggtggt     600
aacttgggcg taactctcca agccatcact tccaagtacc catacattaa gggtatcaac     660
```

```
ttcgaccaac cacacgttat tgaacacgcc ccattgcacc cacacattga acacgttgct    720
ggtgatatgt tccaatctgt tccaaagggt gacgccattt tcttgaagtg gatcttgcac    780
gattgggacg atgaacactg tttgaagttg ttgaagaact gttacaagtc tgttccagaa    840
gatggtaagg ttatcgttgt tgaattgatg ttgccagaag ttccaaacac ttctattgaa    900
tctaagtcta actcccacat tgacgttttg atgatgactc aaaacccagg tggtaaggaa    960
agaactaagc acgaattcat gaccttggct actggtgctg gtttctctgg tatcagattc   1020
gatttggtta ctggtaactt ctgggttatg gaattctaca agtaa                   1065
```

<210> SEQ ID NO 93
<211> LENGTH: 250
<212> TYPE: PRT
<213> ORGANISM: Citrus sinensis

<400> SEQUENCE: 93

```
Met Ser Ala Ala Asn Arg Glu Asp Gln Glu Glu Asn Lys Asp Arg Tyr
1               5                   10                  15

Phe Lys Ala Val His Gly Asn Lys Thr Leu Leu Gln Ser Glu Lys Leu
            20                  25                  30

Tyr Glu Tyr Ile Leu Glu Thr Ser Val Tyr Pro Arg Glu Pro Gln Cys
        35                  40                  45

Leu Lys Glu Ile Arg Glu Leu Thr Tyr Lys His Pro Leu Ser Pro Met
    50                  55                  60

Met Thr Ser Pro Asp Glu Ala Gln Phe Phe Ser Met Leu Leu Lys Leu
65                  70                  75                  80

Ile Asn Ala Lys Asn Thr Met Glu Ile Gly Val Phe Thr Gly Tyr Ser
                85                  90                  95

Leu Leu Ala Thr Ala Leu Ala Ile Pro Asp Asp Gly Lys Ile Leu Ala
            100                 105                 110

Leu Asp Ile Thr Lys Glu His Tyr Glu Lys Gly Leu Pro Ile Ile Gln
        115                 120                 125

Lys Ala Gly Val Ala His Lys Ile Asp Phe Arg Glu Gly Pro Ala Leu
    130                 135                 140

Pro Leu Leu Asp Gln Leu Ile Gln His Glu Lys Tyr His Gly Thr Phe
145                 150                 155                 160

Asp Phe Val Phe Val Asp Ala Asp Lys Asp Asn Tyr Val Asn Tyr His
                165                 170                 175

Lys Arg Leu Ile Glu Leu Val Lys Val Gly Val Ile Gly Tyr Asp
            180                 185                 190

Asn Thr Leu Trp Gly Gly Ser Val Val Ala Pro Pro Asp Ala Asp Leu
        195                 200                 205

Asp Glu His Ile Leu Tyr Leu Arg Asp Phe Val Gln Glu Leu Asn Lys
    210                 215                 220

Ala Leu Ala Val Asp Pro Arg Ile Glu Ile Cys Gln Leu Ser Ile Ala
225                 230                 235                 240

Asp Gly Val Thr Leu Cys Arg Arg Ile Gly
                245                 250
```

<210> SEQ ID NO 94
<211> LENGTH: 753
<212> TYPE: DNA
<213> ORGANISM: Artificial Sequence
<220> FEATURE:
<223> OTHER INFORMATION: coding sequence for SEQ ID NO: 93

<400> SEQUENCE: 94

```
atgtccgctg ctaacagaga agatcaagaa gaaaacaagg atagatactt caaggctgtt    60
cacggtaaca agaccttgtt gcaatctgaa aagttgtacg aatacatctt ggaaacctct   120
gtttacccaa gagaaccaca atgtttgaag gaaatcagag aattgactta caagcaccca   180
ttgtctccaa tgatgacttc tccagatgaa gctcaattct tctctatgtt gttgaagttg   240
atcaacgcca agaacaccat ggagataggt gtattcaccg ttactctttt gttggccact   300
gccttggcca ttccagacga tggtaagatt ttggccttgg acatcaccaa ggaacactac   360
gaaaagggtt tgccaatcat tcaaaaggct ggtgttgctc acaagattga cttcagagaa   420
ggtccagctt tgccattatt ggatcaatta atccaacacg aaaagtacca tggcacattc   480
gacttcgtct tgttgatgc tgacaaggat aactacgtta actaccacaa gagattgatt   540
gaattggtta aggttggtgg tgttattggt tacgacaaca ccttgtgggg tggttctgtt   600
gttgctccac cagatgccga cttggatgaa cacatcttgt acttgagaga tttcgttcaa   660
gaattgaaca aggccttggc cgttgatcca agaatagaaa tttgtcaatt gtccattgct   720
gatggtgtta ctttgtgtag aagaattggt taa                                753
```

<210> SEQ ID NO 95
<211> LENGTH: 514
<212> TYPE: PRT
<213> ORGANISM: Arabidopsis thaliana

<400> SEQUENCE: 95

```
Met Ser Ala Thr Leu Phe Leu Thr Ile Leu Ala Thr Val Leu Phe
1               5                   10                  15

Leu Ile Leu Arg Ile Phe Ser His Arg Arg Asn Arg Ser His Asn Asn
            20                  25                  30

Arg Leu Pro Pro Gly Pro Asn Pro Trp Pro Ile Ile Gly Asn Leu Pro
        35                  40                  45

His Met Gly Thr Lys Pro His Arg Thr Leu Ser Ala Met Val Thr Thr
    50                  55                  60

Tyr Gly Pro Ile Leu His Leu Arg Leu Gly Phe Val Asp Val Val
65                  70                  75                  80

Ala Ala Ser Lys Ser Val Ala Glu Gln Phe Leu Lys Ile His Asp Ala
                85                  90                  95

Asn Phe Ala Ser Arg Pro Pro Asn Ser Gly Ala Lys His Met Ala Tyr
            100                 105                 110

Asn Tyr Gln Asp Leu Val Phe Ala Pro Tyr Gly His Arg Trp Arg Leu
        115                 120                 125

Leu Arg Lys Ile Ser Ser Val His Leu Phe Ser Ala Lys Ala Leu Glu
    130                 135                 140

Asp Phe Lys His Val Arg Gln Glu Glu Val Gly Thr Leu Thr Arg Glu
145                 150                 155                 160

Leu Val Arg Val Gly Thr Lys Pro Val Asn Leu Gly Gln Leu Val Asn
                165                 170                 175

Met Cys Val Val Asn Ala Leu Gly Arg Glu Met Ile Gly Arg Arg Leu
            180                 185                 190

Phe Gly Ala Asp Ala Asp His Lys Ala Asp Glu Phe Arg Ser Met Val
        195                 200                 205

Thr Glu Met Met Ala Leu Ala Gly Val Phe Asn Ile Gly Asp Phe Val
    210                 215                 220

Pro Ser Leu Asp Trp Leu Asp Leu Gln Gly Val Ala Gly Lys Met Lys
```

```
                225                 230                 235                 240
Arg Leu His Lys Arg Phe Asp Ala Phe Leu Ser Ser Ile Leu Lys Glu
                245                 250                 255

His Glu Met Asn Gly Gln Asp Gln Lys His Thr Asp Met Leu Ser Thr
                260                 265                 270

Leu Ile Ser Leu Lys Gly Thr Asp Leu Asp Gly Asp Gly Gly Ser Leu
                275                 280                 285

Thr Asp Thr Glu Ile Lys Ala Leu Leu Leu Asn Met Phe Thr Ala Gly
                290                 295                 300

Thr Asp Thr Ser Ala Ser Thr Val Asp Trp Ala Ile Ala Glu Leu Ile
305                 310                 315                 320

Arg His Pro Asp Ile Met Val Lys Ala Gln Glu Glu Leu Asp Ile Val
                325                 330                 335

Val Gly Arg Asp Arg Pro Val Asn Glu Ser Asp Ile Ala Gln Leu Pro
                340                 345                 350

Tyr Leu Gln Ala Val Ile Lys Glu Asn Phe Arg Leu His Pro Pro Thr
                355                 360                 365

Pro Leu Ser Leu Pro His Ile Ala Ser Glu Ser Cys Glu Ile Asn Gly
                370                 375                 380

Tyr His Ile Pro Lys Gly Ser Thr Leu Leu Thr Asn Ile Trp Ala Ile
385                 390                 395                 400

Ala Arg Asp Pro Asp Gln Trp Ser Asp Pro Leu Ala Phe Lys Pro Glu
                405                 410                 415

Arg Phe Leu Pro Gly Gly Glu Lys Ser Gly Val Asp Val Lys Gly Ser
                420                 425                 430

Asp Phe Glu Leu Ile Pro Phe Gly Ala Gly Arg Arg Ile Cys Ala Gly
                435                 440                 445

Leu Ser Leu Gly Leu Arg Thr Ile Gln Phe Leu Thr Ala Thr Leu Val
                450                 455                 460

Gln Gly Phe Asp Trp Glu Leu Ala Gly Gly Val Thr Pro Glu Lys Leu
465                 470                 475                 480

Asn Met Glu Glu Ser Tyr Gly Leu Thr Leu Gln Arg Ala Val Pro Leu
                485                 490                 495

Val Val His Pro Lys Pro Arg Leu Ala Pro Asn Val Tyr Gly Leu Gly
                500                 505                 510

Ser Gly

<210> SEQ ID NO 96
<211> LENGTH: 1545
<212> TYPE: DNA
<213> ORGANISM: Artificial Sequence
<220> FEATURE:
<223> OTHER INFORMATION: coding sequence for SEQ ID NO: 95

<400> SEQUENCE: 96
atgtccgcta ctttgttctt gactatcttg ttggctactg ttttgttctt gatcttgaga      60
atcttctctc acagaagaaa cagatctcac aacaacagat tgccaccagg tccaaaccca     120
tggccaatca tcggtaactt gccacacatg ggtactaagc cacacagaac tttgtctgct     180
atggttacta cttacggtcc aatcttgcac ttgagattgg gtttcgttga cgttgttgtt     240
gctgcttcta gtctgttgc tgaacaattc ttgaagatcc acgacgctaa cttcgcttct     300
agaccaccaa actctggtgc taagcacatg gcttacaact accaagactt ggttttcgct     360
ccatacggtc acagatggag attgttgaga aagatctctt ctgttcactt gttctctgct     420
```

```
aaggctttgg aagatttcaa gcacgttaga caagaagaag ttggtacttt gactagagaa    480
ttggttagag ttggtactaa gccagttaac ttgggtcaat tggttaacat gtgtgttgtt    540
aacgctttgg gtagagaaat gatcggtaga agattgttcg gtgctgacgc tgaccacaag    600
gctgacgaat tcagatctat ggttactgaa atgatggctt tggctggtgt tttcaacatc    660
ggtgacttcg ttccatcttt ggactggttg gacttgcaag gtgttgctgg taagatgaag    720
agattgcaca agagattcga cgcttcttg tcatctatct tgaaggaaca cgaaatgaac    780
ggtcaagacc aaaagcacac tgacatgttg tctactttga tctcttgaa gggtactgac    840
ttggacggtg acggtggttc tttgactgac actgaaatca aggctttgtt gttgaacatg    900
ttcactgctg gtactgacac ttctgcttct actgttgact gggctatcgc tgaattgatc    960
agacacccag acatcatggt taaggctcaa gaagaattgg acatcgttgt tggtagagac    1020
agaccagtta acgaatctga catcgctcaa ttgccatact gcaagctgt tatcaaggaa    1080
aacttcagat gcacccacc aactccattg tctttgccac acatcgcttc tgaatcttgt    1140
gaaatcaacg gttaccacat cccaaagggt tctactttgt tgactaacat ctgggctatc    1200
gctagggacc cagaccaatg gtctgaccca ttggctttca agccagaaag attcttgcca    1260
ggtggtgaaa agtctggtgt tgacgttaag ggttctgact tcgaattgat cccattcggt    1320
gctggtagaa gaatctgtgc tggtttgtct ttgggtttga gaactatcca attcttgact    1380
gctactttgg ttcaaggttt cgactgggaa ttggctggtg tgttactcc agaaaagttg    1440
aacatggaag aatcttacgg tttgactttg caaagagctg ttccattggt gttcaccca    1500
aagccaagat ggctccaaa cgtttacggt ttgggttctg gttaa                    1545
```

<210> SEQ ID NO 97
<211> LENGTH: 571
<212> TYPE: PRT
<213> ORGANISM: Arabidopsis thaliana

<400> SEQUENCE: 97

```
Met Ser Val Leu Gln Gln Thr His Phe Leu Thr Lys Lys Ile Asp
1               5                   10                  15

Gln Glu Asp Glu Glu Glu Pro Ser His Asp Phe Ile Phe Arg Ser
            20                  25                  30

Lys Leu Pro Asp Ile Phe Ile Pro Asn His Leu Pro Leu Thr Asp Tyr
            35                  40                  45

Val Phe Gln Arg Phe Ser Gly Asp Gly Asp Ser Ser Thr Thr
            50                  55                  60

Cys Ile Ile Asp Gly Ala Thr Gly Arg Ile Leu Thr Tyr Ala Asp Val
65                  70                  75                  80

Gln Ile Asn Met Arg Arg Ile Ala Thr Gly Ile His Arg Leu Gly Ile
                85                  90                  95

Arg His Gly Asp Val Val Met Leu Leu Leu Pro Asn Ser Pro Glu Phe
                100                 105                 110

Ala Leu Ser Phe Leu Ala Val Ala Tyr Leu Gly Ala Val Ser Thr Thr
                115                 120                 125

Ala Asn Pro Phe Tyr Thr Gln Pro Glu Ile Ala Lys Gln Ala Lys Ala
                130                 135                 140

Ser Ala Ala Lys Met Ile Ile Thr Lys Lys Cys Leu Val Asp Lys Leu
145                 150                 155                 160

Thr Asn Leu Lys Asn Asp Gly Val Leu Ile Val Cys Leu Asp Asp
                165                 170                 175
```

Gly Asp Asn Gly Val Val Ser Ser Asp Asp Gly Cys Val Ser Phe
            180                 185                 190

Thr Glu Leu Thr Gln Ala Asp Glu Thr Glu Leu Leu Lys Pro Lys Ile
            195                 200                 205

Ser Pro Glu Asp Thr Val Ala Met Pro Tyr Ser Ser Gly Thr Thr Gly
210                 215                 220

Leu Pro Lys Gly Val Met Ile Thr His Lys Gly Leu Val Thr Ser Ile
225                 230                 235                 240

Ala Gln Lys Val Asp Gly Glu Asn Pro Asn Leu Asn Phe Thr Ala Asn
            245                 250                 255

Asp Val Ile Leu Cys Phe Leu Pro Met Phe His Ile Tyr Ala Leu Asp
            260                 265                 270

Ala Leu Met Leu Ser Ala Met Arg Thr Gly Ala Ala Leu Leu Ile Val
            275                 280                 285

Pro Arg Phe Glu Leu Asn Leu Val Met Glu Leu Ile Gln Arg Tyr Lys
            290                 295                 300

Val Thr Val Val Pro Val Ala Pro Pro Val Val Leu Ala Phe Ile Lys
305                 310                 315                 320

Ser Pro Glu Thr Glu Arg Tyr Asp Leu Ser Ser Val Arg Ile Met Leu
            325                 330                 335

Ser Gly Ala Ala Thr Leu Lys Lys Glu Leu Glu Asp Ala Val Arg Leu
            340                 345                 350

Lys Phe Pro Asn Ala Ile Phe Gly Gln Gly Tyr Gly Met Thr Glu Ser
            355                 360                 365

Gly Thr Val Ala Lys Ser Leu Ala Phe Ala Lys Asn Pro Phe Lys Thr
370                 375                 380

Lys Ser Gly Ala Cys Gly Thr Val Ile Arg Asn Ala Glu Met Lys Val
385                 390                 395                 400

Val Asp Thr Glu Thr Gly Ile Ser Leu Pro Arg Asn Lys Ser Gly Glu
            405                 410                 415

Ile Cys Val Arg Gly His Gln Leu Met Lys Gly Tyr Leu Asn Asp Pro
            420                 425                 430

Glu Ala Thr Ala Arg Thr Ile Asp Lys Asp Gly Trp Leu His Thr Gly
            435                 440                 445

Asp Ile Gly Phe Val Asp Asp Asp Glu Ile Phe Ile Val Asp Arg
450                 455                 460

Leu Lys Glu Leu Ile Lys Phe Lys Gly Tyr Gln Val Ala Pro Ala Glu
465                 470                 475                 480

Leu Glu Ala Leu Leu Ile Ser His Pro Ser Ile Asp Asp Ala Ala Val
            485                 490                 495

Val Ala Met Lys Asp Glu Val Ala Asp Glu Val Pro Val Ala Phe Val
            500                 505                 510

Ala Arg Ser Gln Gly Ser Gln Leu Thr Glu Asp Asp Val Lys Ser Tyr
            515                 520                 525

Val Asn Lys Gln Val Val His Tyr Lys Arg Ile Lys Met Val Phe Phe
            530                 535                 540

Ile Glu Val Ile Pro Lys Ala Val Ser Gly Lys Ile Leu Arg Lys Asp
545                 550                 555                 560

Leu Arg Ala Lys Leu Glu Thr Met Cys Ser Lys
            565                 570

<210> SEQ ID NO 98
<211> LENGTH: 1716
<212> TYPE: DNA

<213> ORGANISM: Artificial Sequence
<220> FEATURE:
<223> OTHER INFORMATION: coding sequence for SEQ ID NO: 97

<400> SEQUENCE: 98

```
atgtccgttt tgcaacaaca aactcacttc ttgactaaga agatcgatca agaagatgaa      60
gaagaagaac catctcacga tttcattttc agatctaagt tgccagatat cttcatccca     120
aaccacttgc cattgaccga ttacgtattc caaagattct ccggtgatgg tgacggtgat     180
tcctctacta cctgtatcat cgacggtgcc actggccgta tcctcaccta cgccgatgtt     240
caaatcaaca tgagaagaat cgctaccggt atccacagat gggtatcag acacggtgac      300
gtcgttatgt tgttgttgcc aaactctcca gaattcgctt tgtctttctt ggccgttgct     360
tacttgggtg ccgtttccac taccgctaac ccattctaca ctcaaccaga atcgctaag      420
caagctaagg cctccgccgc taagatgatc atcactaaga aatgcctggt cgataagttg     480
actaacttga agaacgacgg tgttttgatc gtttgtttgg acgatgacgg tgacaatggc     540
gttgtgagct cttctgatga tggttgtgtt tctttcactg aattgactca agctgacgaa     600
actgaattgt tgaagccaaa gatctctcca gaagatactg ttgctatgcc atactcttcc     660
ggcactactg gtttaccaaa gggtgttatg attactcaca agggtttggt tacttctatc     720
gctcaaaagg tcgacggtga aaacccaaac ttgaacttca ctgccaacga cgtcatcttg     780
tgtttcttgc aatgttcca catttacgct ttggacgctt tgatgttgtc tgctatgaga      840
accggtgctg ctttgttgat cgttccaaga ttcgaattga acttggttat ggaattgatt     900
caaagataca aggtcactgt tgttccagtt gctccaccag ttgttttggc tttcattaag     960
tccccagaaa ctgaaagata cgacttatct tctgttagaa ttatgttgtc tggtgctgct    1020
actttgaaga aggaattgga agatgccgtt agattgaagt tcccaaacgc cattttcggt    1080
caaggttacg gtatgaccga tccggtact gttgctaagt cgctcgcgtt cgctaagaac     1140
ccattcaaga ccaagtccgg tgcttgtggt actgttatca gaaacgccga atgaaggtt    1200
gtcgataccg aaaccggtat ctccttgcca agaaacaagt ctggtgaaat ctgtgtcaga    1260
ggtcaccaat tgatgaaggg ttacttgaac gatccagaag ctactgctag aaccatcgac    1320
aaggacggtt ggttgcacac tggtgatatt ggtttcgttg atgatgatga tgaaatcttc    1380
attgttgata gattgaagga attgatcaag ttcaagggtt accaagttgc tccagctgaa    1440
ttggaagctt tgttgatttc tcacccatct atcgatgatg ccgctgttgt tgctatgaag    1500
gatgaagttg ctgatgaagt tccagttgct tcgttgcta gatctcaagg ttctcaattg    1560
actgaagatg atgtcaagtc ttacgttaac aagcaagttg ttcactacaa gagaattaag    1620
atggttttct tcatcgaagt tatcccaaag gctgtttctg gtaagatttt gagaaaggat    1680
ttgagagcta agttggaaac catgtgttct aagtaa                              1716
```

<210> SEQ ID NO 99
<211> LENGTH: 561
<212> TYPE: PRT
<213> ORGANISM: Citrus clementina

<400> SEQUENCE: 99

```
Met Ser Ile Ser Ile Ala Thr Lys Lys Pro Glu Leu Ser Leu Asp Ile
1               5                   10                  15

Ser Ser Pro Ala Pro Pro Ala Pro Ser Asn Glu Lys Ile Ala Thr His
            20                  25                  30

Ile Phe Lys Ser Lys Leu Pro Asp Ile Pro Ile Ser Asn His Leu Pro
```

```
              35                  40                  45
Leu His Thr Tyr Cys Phe Gln Asp Arg Leu Ser Asp Asp Pro Cys Leu
 50                  55                  60

Ile Val Gly Leu Thr Gly Lys Thr Tyr Ser Tyr Ala Glu Thr His Leu
 65                  70                  75                  80

Ile Cys Arg Lys Thr Ala Ala Gly Leu Ser Asn Leu Gly Ile Lys Lys
                 85                  90                  95

Gly Asp Val Ile Met Ile Leu Leu Gln Asn Cys Ala Glu Phe Val Phe
                100                 105                 110

Ser Phe Met Gly Ala Ser Met Ile Gly Ala Val Thr Thr Ala Asn
            115                 120                 125

Pro Phe Tyr Thr Ser Ala Glu Ile Leu Lys Gln Phe Arg Thr Ser Gly
        130                 135                 140

Ala Lys Leu Ile Ile Thr Met Ser Gln Tyr Val Asp Arg Leu Pro Lys
145                 150                 155                 160

Thr Asp Lys Asp Phe Thr Val Ile Thr Ile Asp Ala Pro Pro Glu Asn
                165                 170                 175

Cys Leu His Phe Thr Val Leu Ser Glu Ala Asp Glu Asp Gln Ile Pro
            180                 185                 190

Glu Val Ala Ile Glu Pro Asp Asp Pro Val Ala Leu Pro Phe Ser Ser
        195                 200                 205

Gly Thr Thr Gly Leu Pro Lys Gly Val Val Leu Thr His Lys Ser Leu
210                 215                 220

Ile Thr Ser Val Ala Gln Gln Val Asp Gly Glu Asn Pro Asn Leu Tyr
225                 230                 235                 240

Leu Thr Asn Gly Asp Val Val Leu Cys Val Leu Pro Leu Phe His Ile
                245                 250                 255

Tyr Ser Leu Asn Ser Val Leu Leu Cys Ser Leu Arg Ala Gly Ala Gly
            260                 265                 270

Val Leu Leu Met Gln Lys Phe Glu Ile Gly Ala Leu Leu Glu Leu Ile
        275                 280                 285

Gln Arg His Arg Val Ser Val Ala Ala Val Val Pro Pro Leu Val Leu
290                 295                 300

Ala Leu Ala Lys Asn Pro Met Val Ala Asp Tyr Asp Leu Ser Ser Ile
305                 310                 315                 320

Arg Val Val Leu Ser Gly Ala Ala Pro Leu Gly Lys Glu Leu Glu Asp
                325                 330                 335

Ala Leu Arg Ser Arg Val Pro Gln Ala Ile Leu Gly Gln Gly Tyr Gly
            340                 345                 350

Met Thr Glu Ala Gly Pro Val Leu Ser Met Cys Leu Gly Phe Ala Lys
        355                 360                 365

Gln Pro Phe Pro Thr Lys Ser Gly Ser Cys Gly Thr Val Val Arg Asn
370                 375                 380

Ala Glu Leu Lys Val Ile Asp Pro Glu Ile Gly Ala Ser Leu Pro His
385                 390                 395                 400

Asn Gln Pro Gly Glu Ile Cys Ile Arg Gly Pro Gln Ile Met Lys Gly
                405                 410                 415

Tyr Leu Asn Asp Pro Glu Ala Thr Ala Ala Thr Ile Asp Val Glu Gly
            420                 425                 430

Trp Leu His Thr Gly Asp Ile Gly Tyr Val Asp Asp Asp Glu Val
        435                 440                 445

Phe Ile Val Asp Arg Val Lys Glu Ile Ile Lys Phe Lys Gly Phe Gln
450                 455                 460
```

Val Pro Pro Ala Glu Ile Glu Ala Leu Leu Leu Ser His Pro Ser Ile
465                 470                 475                 480

Gly Asp Ala Ala Val Val Pro Gln Lys Asp Glu Val Ala Gly Glu Val
            485                 490                 495

Pro Val Ala Phe Val Val Arg Ser Asn Gly Phe Glu Leu Thr Glu Glu
            500                 505                 510

Ala Ile Lys Glu Tyr Ile Ala Lys Gln Val Val Phe Tyr Lys Arg Leu
            515                 520                 525

His Lys Ile Tyr Phe Val His Ala Ile Pro Lys Ser Pro Ser Gly Lys
            530                 535                 540

Ile Leu Arg Lys Asp Leu Arg Ala Lys Leu Ala Ser Ser Met Pro Leu
545                 550                 555                 560

Asn

<210> SEQ ID NO 100
<211> LENGTH: 1686
<212> TYPE: DNA
<213> ORGANISM: Artificial Sequence
<220> FEATURE:
<223> OTHER INFORMATION: coding sequence for SEQ ID NO: 99

<400> SEQUENCE: 100

| | | | | | |
|---|---|---|---|---|---|
| atgtccatct | ctatcgccac | taagaagcca | gaattgtctt | tggatatctc | ttctccagct | 60 |
| ccaccagctc | catccaacga | aaagatcgcc | acccacattt | tcaagtctaa | gttgccagat | 120 |
| atcccaatct | ccaaccactt | gccattgcac | acttactgtt | tccaagatag | attgtctgac | 180 |
| gacccatgtt | tgatcgttgg | tttgactggt | aagacttact | cttacgccga | aactcacttg | 240 |
| atctgtagaa | agaccgctgc | cggtttgtct | aacttgggta | tcaagaaggg | tgacgttatc | 300 |
| atgatcttgt | tgcaaaactg | tccgaattc | gtttctctt | tcatgggtgc | ttccatgatc | 360 |
| ggtgctgtca | ctactactgc | caacccattc | tacacttctg | ctgaaatctt | gaagcaattc | 420 |
| agaacctctg | gtgccaagtt | gattatcact | atgtctcaat | acgtcgacag | attgccaaag | 480 |
| actgacaagg | atttcactgt | tatcactatc | gatgccccac | agaaaactg | tttgcacttc | 540 |
| actgttttgt | ctgaagctga | tgaagatcaa | atcccagaag | ttgccatcga | accagacgat | 600 |
| ccagttgctt | tgccattctc | ttctggtacc | actggtttgc | caagggtgt | tgttttgact | 660 |
| cataagagct | tgatcacctc | tgttgctcaa | caagttgacg | tgaaaaccc | aaacttgtac | 720 |
| ttgactaacg | tgacgttgt | tttgtgtgtt | ttgccattgt | tccacattta | ctcttttgaac | 780 |
| tctgttttgt | tgtgttcttt | gagagctggt | gctggtgttt | tgttgatgca | aaagttcgaa | 840 |
| atcggtgctt | tgttggaatt | gatccaaaga | cacagagttt | ctgttgctgc | tgttgttcca | 900 |
| ccattggttt | tggctttggc | caagaaccca | atggttgctg | attacgactt | gtcatctatc | 960 |
| agagttgttt | tgtccggtgc | tgctccattg | ggtaaggaat | tggaagatgc | tttgagatct | 1020 |
| agagtcccac | aagctatctt | gggtcaaggt | tacggtatga | ctgaagctgg | tccagttttg | 1080 |
| tctatgtgtt | tgggttttcgc | taagcaacca | ttcccaacta | agtctggttc | ttgtggtacc | 1140 |
| gttgttagaa | acgctgaatt | gaaggttatt | gacccagaaa | ttggtgcctc | cttgccacac | 1200 |
| aaccaaccag | gtgaaatttg | tatcagaggt | ccacaaatta | tgaagggtta | cttgaacgat | 1260 |
| ccagaagcta | ctgctgctac | tatcgacgtt | gaaggttggt | tgcacactgg | tgacatcggt | 1320 |
| tacgttgatg | atgatgatga | agtttttcatc | gtcgatagag | tcaaggaaat | catcaagttc | 1380 |
| aagggtttcc | aagttccacc | agctgaaatt | gaagccttgt | tgttgtctca | cccatctatt | 1440 |

-continued

```
ggtgatgctg ctgttgttcc acaaaaggat gaagttgcgg gtgaagttcc agttgcgttc     1500
gttgttcgtt cgaacggctt cgaattgacc gaggaagcca ttaaggaata catcgctaag     1560
caagttgttt tctacaagag attgcacaag atttacttcg ttcacgctat tccaaagtct     1620
ccatccggta agattttgag aaaggatttg agagccaagt tggcctcttc tatgccattg     1680
aactaa                                                                1686
```

<210> SEQ ID NO 101
<211> LENGTH: 365
<212> TYPE: PRT
<213> ORGANISM: Angelica archangelica

<400> SEQUENCE: 101

```
Met Ser Ala Pro Thr Thr Ile Thr Ala Leu Ala Gln Glu Lys Thr Leu
1               5                   10                  15

Asn Leu Ala Phe Val Arg Asp Glu Asp Glu Arg Pro Lys Val Ala Tyr
            20                  25                  30

Asn Gln Phe Ser Asn Glu Ile Pro Ile Ile Ser Leu Ala Gly Met Asp
        35                  40                  45

Asp Asp Thr Gly Arg Arg Pro Gln Ile Cys Arg Lys Ile Val Glu Ala
    50                  55                  60

Phe Glu Asp Trp Gly Ile Phe Gln Val Val Asp His Gly Ile Asp Gly
65                  70                  75                  80

Thr Leu Ile Ser Glu Met Thr Arg Leu Ser Arg Glu Phe Phe Ala Leu
                85                  90                  95

Pro Ala Glu Glu Lys Leu Arg Tyr Asp Thr Thr Gly Gly Lys Arg Gly
            100                 105                 110

Gly Phe Thr Ile Ser Thr His Leu Gln Gly Asp Asp Val Lys Asp Trp
        115                 120                 125

Arg Glu Phe Val Thr Tyr Phe Ser Tyr Pro Ile Asp Asp Arg Asp Tyr
    130                 135                 140

Ser Arg Trp Pro Asp Lys Pro Gln Gly Trp Arg Ser Thr Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Glu Lys Glu Ala Leu Thr Lys Ala Cys Val
            180                 185                 190

Asn Met Glu Gln Lys Val Leu Ile Asn Tyr Tyr Pro Thr Cys Pro Glu
        195                 200                 205

Pro Asp Leu Thr Leu Gly Val Arg Arg His Thr Asp Pro Gly Thr Ile
    210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly Tyr Leu Ser Asn Gly Arg Phe Lys
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Arg Ile Arg Glu Gly Glu Lys Ala Val Leu Asp Glu Ala Ile Thr Tyr
305                 310                 315                 320

Ala Glu Met Tyr Lys Lys Asn Met Thr Lys His Ile Glu Val Ala Thr
```

Leu Lys Lys Leu Ala Lys Glu Lys Arg Leu Gln Glu Glu Lys Ala Lys
                340                 345                 350

Leu Glu Thr Glu Ser Lys Ser Ala Asp Gly Ile Ser Ala
            355                 360                 365

<210> SEQ ID NO 102
<211> LENGTH: 1098
<212> TYPE: DNA
<213> ORGANISM: Artificial Sequence
<220> FEATURE:
<223> OTHER INFORMATION: coding sequence for SEQ ID NO:101

<400> SEQUENCE: 102

| | | | | | |
|---|---|---|---|---|---|
| atgtccgctc | caactactat | cactgctttg | gctcaagaaa | agactttgaa | cttggctttc | 60 |
| gttagagatg | aagatgaaag | accaaaggtt | gcttacaacc | aattctctaa | cgaaatccca | 120 |
| atcatctctt | tggctggtat | ggacgacgac | actggtagga | ggccacaaat | ctgtagaaag | 180 |
| atcgttgaag | ctttcgaaga | ttggggtatc | ttccaagttg | ttgaccacgg | tatcgacggt | 240 |
| actttgatct | ctgaaatgac | tagattgtct | agagaattct | tcgctttgcc | agctgaagaa | 300 |
| aagttgagat | acgacactac | tggtggtaag | agaggtggtt | tcactatctc | tactcacttg | 360 |
| caaggtgacg | acgttaagga | ctggagagaa | ttcgttactt | acttctctta | cccaatcgac | 420 |
| gacagagact | actctagatg | gccagacaag | ccacaaggtt | ggagatctac | tactgaagtt | 480 |
| tactctgaaa | agttgatggt | tttgggtgct | aagttgttgg | aagttttgtc | tgaagctatg | 540 |
| ggtttggaaa | aggaagcttt | gactaaggct | tgtgttaaca | tggaacaaaa | ggttttgatc | 600 |
| aactactacc | caacttgtcc | agaaccagac | ttgactttgg | gtgttaggag | acacactgac | 660 |
| ccaggtacta | tcactatctt | gttgcaagac | atggttggtg | gtttgcaagc | tactagagat | 720 |
| ggtggtaaga | cttggatcac | tgttcaacca | gttgaaggtg | ctttcgttgt | taacttgggt | 780 |
| gaccacggtc | actacttgtc | taacggtaga | ttcaagaacg | ctgaccacca | agctgttgtt | 840 |
| aactctactt | cttctagatt | gtctatcgct | actttccaaa | acccagctca | aaacgctatc | 900 |
| gtttacccat | tgagaatcag | agaaggtgaa | aaggctgttt | tggacgaagc | tatcacttac | 960 |
| gctgaaatgt | acaagaagaa | catgactaag | cacatcgaag | ttgctacttt | gaagaagttg | 1020 |
| gctaaggaaa | agagattgca | agaagaaaag | gctaagttgg | aaactgaatc | taagtctgct | 1080 |
| gacggtatct | ctgcttaa | | | | | 1098 |

<210> SEQ ID NO 103
<211> LENGTH: 514
<212> TYPE: PRT
<213> ORGANISM: Cynara cardunculus var. scolymus

<400> SEQUENCE: 103

Met Ser Gln Val His Glu Thr Leu Thr Pro Ala Val Ile Ala Ala Val
1               5                   10                  15

Val Leu Ser Ser Val Phe Leu Tyr Leu Leu Phe Lys Lys Lys Gln Asn
                20                  25                  30

His Arg Leu Pro Pro Ser Pro Pro Ser Leu Pro Ile Ile Gly His Leu
            35                  40                  45

His His Leu Gly Pro Leu Ile His Gln Ser Phe His His Leu Ser Thr
        50                  55                  60

Arg Tyr Gly Pro Leu Ile His Leu Arg Leu Gly Ser Val Pro Cys Ile
65                  70                  75                  80

-continued

```
Val Ala Ser Thr Pro Asp Leu Ala Arg Asp Phe Leu Lys Thr Asn Glu
             85                  90                  95
Leu Ala Phe Ser Ser Arg Lys His Ser Leu Ala Ile Asp His Ile Thr
            100                 105                 110
Tyr Gly Val Ala Phe Ala Phe Ala Pro Tyr Gly Pro Tyr Trp Lys Phe
            115                 120                 125
Ile Lys Lys Met Ser Thr Val Glu Leu Leu Gly Asn Gln Asn Leu Gly
            130                 135                 140
His Phe Leu Pro Ile Arg Thr His Glu Ile Gln Glu Leu Leu Gln Thr
145                 150                 155                 160
Leu Thr Glu Lys Ala Lys Arg Arg Glu Ser Val Asn Leu Thr Glu Glu
            165                 170                 175
Leu Leu Lys Leu Thr Asn Asn Val Ile Cys Gln Met Met Met Ser Ile
            180                 185                 190
Arg Cys Ser Gly Thr Asn Ser Glu Ala Asp Glu Ala Lys Asn Leu Val
            195                 200                 205
Arg Glu Val Thr Gln Ile Phe Gly Glu Phe Asn Val Ser Asp Phe Ile
            210                 215                 220
Trp Phe Cys Lys Asn Ile Asp Leu Gln Gly Phe Lys Lys Arg Tyr Thr
225                 230                 235                 240
Asp Thr His Lys Arg Tyr Asp Ala Leu Leu Glu Lys Ile Ile Phe Glu
            245                 250                 255
Arg Glu Glu Lys Arg Arg Lys Glu Gly Lys Arg Glu Asp Gly Lys Gly
            260                 265                 270
Lys Asp Phe Leu Asp Met Leu Leu Asp Val Leu Glu Asp Ala Lys Ala
            275                 280                 285
Glu Ile Lys Ile Thr Arg Asp His Ile Lys Ala Leu Ile Leu Asp Phe
            290                 295                 300
Phe Thr Ala Ala Thr Asp Thr Thr Ala Ile Ala Leu Glu Trp Met Leu
305                 310                 315                 320
Val Glu Leu Ile Ser Asn Pro Lys Val Leu Glu Ile Ala Arg Glu Glu
            325                 330                 335
Ile Asp Gln Val Val Gly Asn Glu Arg Leu Val Gln Glu Ser Asp Ala
            340                 345                 350
Pro Asn Leu Pro Tyr Ile Gln Ala Ile Ile Lys Glu Ala Leu Arg Leu
            355                 360                 365
His Pro Pro Ile Pro Met Leu Ile Arg Lys Ser Ile Glu Asp Val Ser
            370                 375                 380
Val Gln Gly Tyr Asp Ile Pro Ala Gly Thr Met Leu Phe Val Asn Ile
385                 390                 395                 400
Trp Ser Ile Gly Arg Asn Pro Lys Tyr Trp Glu Ser Pro Leu Glu Phe
            405                 410                 415
Lys Pro His Arg Phe Leu Glu Asp Pro Val Lys Lys Ser Leu Asp
            420                 425                 430
Ile Lys Gly Gln Ser Phe Gln Leu Leu Pro Phe Gly Thr Gly Arg Arg
            435                 440                 445
Gly Cys Pro Gly Ile Asn Leu Ala Met Arg Glu Leu Pro Val Val Ile
            450                 455                 460
Ala Gly Leu Ile Gln Cys Phe Glu Trp Asn Val Asn Gly Lys Gln Val
465                 470                 475                 480
Leu Asp Met Asp Glu Arg Ala Gly Leu Thr Ala Pro Arg Ala Ala Asp
            485                 490                 495
Phe Val Cys Val Pro Ser Val Arg Glu Asn Ser Pro Met Met Phe Thr
```

Ser Thr

<210> SEQ ID NO 104
<211> LENGTH: 1545
<212> TYPE: DNA
<213> ORGANISM: Artificial Sequence
<220> FEATURE:
<223> OTHER INFORMATION: coding sequence for SEQ ID NO:103

<400> SEQUENCE: 104

```
atgtcccaag ttcacgaaac tttgactcca gctgttatcg ctgctgttgt tttgtcatct      60
gttttcttgt acttgttgtt caagaagaag caaaaccaca gattgccacc atctccacca     120
tctttgccaa tcatcggtca cttgcaccac ttgggtccat tgatcccacca atctttccac     180
cacttgtcta ctagatacgg tccattgatc cacttgagat tgggttctgt tccatgtatc     240
gttgcttcta ctccagactt ggctagagac ttcttgaaaa ctaacgaatt ggctttctct     300
tctagaaagc actctttggc tatcgaccac atcacttacg tgttgctttt cgctttcgct     360
ccatacggtc catactggaa gttcatcaag aagatgtcta ctgttgaatt gttgggtaac     420
caaaacttgg gtcacttctt gccaatcaga actcacgaaa tccaagaatt gttgcaaact     480
ttgactgaaa aggctaagag aagagaatct gttaacttga ctgaagaatt gttgaagttg     540
actaacaacg ttatctgtca aatgatgatg tctatcagat gttctggtac taactctgaa     600
gctgacgaag ctaagaactt ggttagagaa gttactcaaa tcttcggtga attcaacgtt     660
tctgacttca tctggttctg taagaacatc gacttgcaag gtttcaagaa gagatacact     720
gacactcaca agagatacga cgctttgttg aaaagatca tcttcgaaag agaagaaaag     780
agaagaaagg aaggtaagag agaagatggt aagggtaagg acttcttgga catgttgttg     840
gacgttttgg aagatgctaa ggctgaaatc aagatcacta gagatcacat caaggctttg     900
atcttggact cttcactgc tgctactgac actactgcta tcgctttgga atggatgttg     960
gttgaattga tctctaaccc aaaggttttg gaaatcgcta gagaagaaat cgaccaagtt    1020
gttggtaacg aaagattggt tcaagaatct gacgctccaa acttgccata catccaagct    1080
atcatcaagg aagctttgag attgcaccca ccaatcccaa tgttgatcag aaagtctatc    1140
gaagatgttt ctgttcaagg ttacgacatc ccagctggta ctatgttgtt cgttaacatc    1200
tggtctatcg gtagaaaccc aaagtactgg aatctccat tggaattcaa gccacacaga    1260
ttcttggaag atgacccagt taagaagtct ttggacatca gggtcaatc tttccaattg    1320
ttgccattcg gtactggtag aagaggttgt ccaggtatca acttggctat gagagaattg    1380
ccagttgtta tcgctggttt gatccaatgt ttcgaatgga acgttaacgg taagcaagtt    1440
ttggacatgg acgaaagagc tggtttgact gctccaagag ctgctgactt cgtttgtgtt    1500
ccatctgtta gagaaaactc tccaatgatg ttcacttcta cttaa                    1545
```

<210> SEQ ID NO 105
<211> LENGTH: 507
<212> TYPE: PRT
<213> ORGANISM: Perilla frutescens var. crispa

<400> SEQUENCE: 105

```
Met Ser Ala Leu Tyr Ala Ala Leu Phe Leu Leu Ser Ala Ala Val Val
1               5                  10                  15

Arg Ser Val Leu Asp Arg Lys Arg Gly Arg Pro Pro Tyr Pro Pro Gly
            20                  25                  30
```

Pro Phe Pro Leu Pro Ile Ile Gly His Leu His Leu Leu Gly Pro Arg
                35                  40                  45

Leu His Gln Thr Phe His Asp Leu Ser Gln Arg Tyr Gly Pro Leu Met
 50                  55                  60

Gln Leu Arg Leu Gly Ser Ile Arg Cys Val Ile Ala Ala Ser Pro Glu
 65                  70                  75                  80

Leu Ala Lys Glu Cys Leu Lys Thr His Glu Leu Val Phe Ser Ser Arg
                 85                  90                  95

Lys His Ser Thr Ala Ile Asp Ile Val Thr Tyr Asp Ser Ser Phe Ala
                100                 105                 110

Phe Ser Pro Tyr Gly Pro Tyr Trp Lys Phe Ile Lys Lys Leu Cys Thr
                115                 120                 125

Tyr Glu Leu Leu Gly Ala Arg Asn Leu Ala His Phe Gln Pro Ile Arg
                130                 135                 140

Thr Leu Glu Val Lys Ser Phe Leu Gln Ile Leu Met Arg Lys Gly Glu
145                 150                 155                 160

Ser Gly Glu Ser Phe Asn Val Thr Glu Glu Leu Val Lys Leu Thr Ser
                165                 170                 175

Asn Val Ile Ser His Met Met Leu Ser Ile Arg Cys Ser Glu Thr Glu
                180                 185                 190

Ser Glu Ala Glu Ala Arg Thr Val Ile Arg Glu Val Thr Gln Ile
                195                 200                 205

Phe Gly Glu Phe Asp Val Ser Asp Ile Ile Trp Leu Cys Lys Asn Phe
                210                 215                 220

Asp Phe Gln Gly Ile Arg Lys Arg Ser Glu Asp Ile Gln Arg Arg Tyr
225                 230                 235                 240

Asp Ala Leu Leu Glu Lys Ile Ile Thr Asp Arg Glu Lys Gln Arg Arg
                245                 250                 255

Thr His Gly Gly Gly Gly Gly Gly Glu Ala Lys Asp Phe Leu Asp
                260                 265                 270

Met Phe Leu Asp Ile Met Glu Ser Gly Lys Ala Glu Val Lys Phe Thr
                275                 280                 285

Arg Glu His Leu Lys Ala Leu Ile Leu Asp Phe Phe Thr Ala Gly Thr
                290                 295                 300

Asp Thr Thr Ala Ile Val Cys Glu Trp Ala Ile Ala Glu Val Ile Asn
305                 310                 315                 320

Asn Pro Asn Val Leu Lys Lys Ala Gln Glu Glu Ile Ala Asn Ile Val
                325                 330                 335

Gly Phe Asp Arg Ile Leu Gln Glu Ser Asp Ala Pro Asn Leu Pro Tyr
                340                 345                 350

Leu Gln Ala Leu Ile Lys Glu Thr Phe Arg Leu His Pro Pro Ile Pro
                355                 360                 365

Met Leu Ala Arg Lys Ser Ile Ser Asp Cys Val Ile Asp Gly Tyr Met
                370                 375                 380

Ile Pro Ala Asn Thr Leu Leu Phe Val Asn Leu Trp Ser Met Gly Arg
385                 390                 395                 400

Asn Pro Lys Ile Trp Asp Tyr Pro Thr Ala Phe Gln Pro Glu Arg Phe
                405                 410                 415

Leu Glu Lys Glu Lys Ala Ala Ile Asp Val Lys Gly Gln His Phe Glu
                420                 425                 430

Leu Leu Pro Phe Gly Thr Gly Arg Arg Gly Cys Pro Gly Met Leu Leu
                435                 440                 445

```
Ala Ile Gln Glu Val Val Ile Ile Gly Thr Met Ile Gln Cys Phe
    450                 455                 460

Asp Trp Lys Leu Pro Asp Gly Ser Gly His Val Asp Met Ala Glu Arg
465                 470                 475                 480

Pro Gly Leu Thr Ala Pro Arg Glu Thr Asp Leu Phe Cys Arg Val Val
                485                 490                 495

Pro Arg Val Asp Pro Leu Val Val Ser Thr Gln
            500                 505
```

```
<210> SEQ ID NO 106
<211> LENGTH: 1524
<212> TYPE: DNA
<213> ORGANISM: Artificial Sequence
<220> FEATURE:
<223> OTHER INFORMATION: coding sequence for SEQ ID NO:105

<400> SEQUENCE: 106
```

| | | | | |
|---|---|---|---|---|
| atgtccgctt | tgtacgctgc | tttgttcttg | ttgtctgctg | ctgttgttag atctgttttg | 60 |
| gacagaaaga | gaggtagacc | accatacccc | ccaggtccat | tcccattgcc aatcatcggt | 120 |
| cacttgcact | tgtttgggtcc | aagattgcac | caaactttcc | acgacttgtc tcaaagatac | 180 |
| ggtccattga | tgcaattgag | attgggttct | atcagatgtg | ttatcgctgc ttctccagaa | 240 |
| ttggctaagg | aatgtttgaa | aactcacgaa | ttggttttct | cttctagaaa gcactctact | 300 |
| gctatcgaca | tcgttactta | cgactcttct | ttcgctttct | ctccatacgg tccatactgg | 360 |
| aagttcatca | agaagttgtg | tacttacgaa | ttgttgggtg | ctagaaactt ggctcacttc | 420 |
| caaccaatca | gaactttgga | agttaagtct | ttcttgcaaa | tcttgatgag aaagggtgaa | 480 |
| tctggtgaat | cttccaacgt | tactgaagaa | ttggttaagt | tgacttctaa cgttatctct | 540 |
| cacatgatgt | tgtctatcag | atgttctgaa | actgaatctg | aagctgaagc tgctagaact | 600 |
| gttatcagag | aagttactca | aatcttcggt | gaattcgacg | tttctgacat catctggttg | 660 |
| tgtaagaact | tcgacttcca | aggtatcaga | aagagatctg | aagatatcca aagaagatac | 720 |
| gacgctttgt | tggaaaagat | catcactgac | agagaaaagc | aaagaagaac tcacggtggt | 780 |
| ggtggtggtg | gtggtgaagc | taaggacttc | ttggacatgt | tcttggacat catggaatct | 840 |
| ggtaaggctg | aagttaagtt | cactagagaa | cacttgaagg | cttttgatctt ggacttcttc | 900 |
| actgctggta | ctgacactac | tgctatcgtt | tgtgaatggg | ctatcgctga agttatcaac | 960 |
| aacccaaacg | ttttgaagaa | ggctcaagaa | gaaatcgcta | acatcgttgg tttcgacaga | 1020 |
| atcttgcaag | aatctgacgc | tccaaacttg | ccatacttgc | aagctttgat caaggaaact | 1080 |
| ttcagattgc | acccaccaat | cccaatgttg | gctagaaagt | ctatctctga ctgtgttatc | 1140 |
| gacggttaca | tgatcccagc | taacactttg | ttgttcgtta | acttgtggtc tatgggtaga | 1200 |
| aacccaaaga | tctgggacta | cccaactgct | ttccaaccag | aaagattctt ggaaaaggaa | 1260 |
| aaggctgcta | tcgacgttaa | gggtcaacac | ttcgaattgt | tgccattcgg tactggtaga | 1320 |
| agaggttgtc | caggtatgtt | gttggctatc | caagaagttt | tatcatcat cggtactatg | 1380 |
| atccaatgtt | tcgactggaa | gttgccagac | ggttctggtc | acgttgacat ggctgaaaga | 1440 |
| ccaggtttga | ctgctccaag | agaaactgac | ttgttctgta | gagttgttcc aagagttgac | 1500 |
| ccattggttg | tttctactca | ataa | | | 1524 |

```
<210> SEQ ID NO 107
<211> LENGTH: 515
<212> TYPE: PRT
<213> ORGANISM: Dahlia pinnata
```

<400> SEQUENCE: 107

```
Met Ser Asn Thr Leu Leu Val Leu Gln Met Val Ile Pro Ala Ile Ile
1               5                   10                  15

Ala Phe Val Ile Phe His Leu Leu Phe Phe Lys Ser Lys Pro Asn Arg
            20                  25                  30

Arg Leu Pro Pro Ser Pro Ser Leu Pro Ile Ile Gly His Leu His
        35                  40                  45

His Leu Gly Pro Leu Ile His Gln Ser Phe Asn Arg Leu Ser Ala Arg
    50                  55                  60

Tyr Gly Pro Leu Ile His Leu Arg Leu Gly Ser Val Ser Cys Val Val
65                  70                  75                  80

Ala Asp Ala Pro Asp Leu Ala Gln Glu Leu Leu Gln Lys Asn Asp Leu
                85                  90                  95

Ala Phe Ala Asn Arg Lys His Thr Leu Ala Ile Asp His Val Thr Tyr
            100                 105                 110

Gly Val Ala Phe Ala Phe Ala Pro Tyr Gly Pro Tyr Trp Arg Phe Ile
            115                 120                 125

Lys Lys Met Ser Thr Val Glu Leu Leu Gly Ile Gln Asn Leu Gly His
        130                 135                 140

Phe Leu Pro Ile Arg Thr Gln Glu Ile His Gly Leu Leu Leu Thr Leu
145                 150                 155                 160

Thr Glu Lys Ser Lys Gln Asn Glu Ser Val Asn Met Thr Asn Glu Leu
                165                 170                 175

Leu Lys Leu Ser Asn Asn Ile Ile Cys Gln Met Met Met Gly Ile Arg
            180                 185                 190

Cys Ser Gly Asn Lys Thr Glu Ala Glu Glu Ala Lys Asn Leu Val Arg
        195                 200                 205

Glu Val Thr Thr Ile Phe Gly Glu Phe Asn Val Ser Asp Phe Ile Trp
210                 215                 220

Phe Cys Lys Lys Leu Asp Leu Gln Gly Phe Lys Lys Arg Tyr Glu Asp
225                 230                 235                 240

Ile Arg Thr Arg Tyr Asp Ala Leu Leu Glu Arg Ile Ile Phe Ala Arg
            245                 250                 255

Glu Glu Met Arg Lys Glu Gly Lys Gly Met Glu Asp Gly Lys Gly Lys
            260                 265                 270

Asp Phe Leu Asp Met Leu Leu Asp Val Leu Glu Asp Lys Ala Glu
        275                 280                 285

Ile Lys Ile Thr Arg Asn His Ile Lys Ala Leu Ile Leu Asp Phe Val
    290                 295                 300

Thr Ala Gly Thr Asp Thr Thr Ala Val Ile Ile Glu Trp Thr Leu Val
305                 310                 315                 320

Glu Leu Ile Lys Asn Pro Met Val Met Glu Lys Ala Lys Gln Glu Leu
                325                 330                 335

Asp Glu Val Val Gly Asn Thr Arg Leu Val Glu Glu Ser Asp Ala Pro
            340                 345                 350

Lys Leu Pro Tyr Ile Gln Ala Ile Ile Lys Glu Ala Phe Arg Leu His
        355                 360                 365

Pro Pro Ile Pro Met Ile Ile Arg Lys Ser Asn Glu Asn Val Ser Val
            370                 375                 380

Lys Ser Gly Tyr Glu Ile Pro Ala Gly Ser Ile Leu Phe Val Asn Asn
385                 390                 395                 400

Trp Ser Ile Gly Arg Asn Pro Lys Tyr Trp Glu Ser Pro Leu Glu Phe
```

```
            405                 410                 415
Lys Pro Asp Arg Phe Leu Lys Glu Gly Val Leu Lys Pro Ser Leu Asp
        420                 425                 430

Ile Arg Gly Gln Asn Phe Gln Ile Leu Pro Phe Gly Thr Gly Arg Arg
            435                 440                 445

Ser Cys Pro Gly Ile Asn Met Ala Met Arg Gln Leu Pro Val Val Val
    450                 455                 460

Ala Ile Leu Ile Gln Cys Phe Glu Trp Thr Val Asn Asp Lys Gln Val
465                 470                 475                 480

Leu Asn Met Asp Glu Arg Gly Gly Leu Thr Thr Pro Arg Ala Thr Asp
            485                 490                 495

Leu Val Cys Phe Pro Leu Leu Arg Lys Asn Ser Pro His Ser Met Phe
        500                 505                 510

Thr Ser Val
        515

<210> SEQ ID NO 108
<211> LENGTH: 1548
<212> TYPE: DNA
<213> ORGANISM: Artificial Sequence
<220> FEATURE:
<223> OTHER INFORMATION: coding sequence for SEQ ID NO:107

<400> SEQUENCE: 108
atgtccaaca ctttgttggt tttgcaaatg gttatcccag ctatcatcgc tttcgttatc      60
ttccacttgt tgttcttcaa gtctaagcca aacagaagat gccaccatc tccaccatct     120 ttgccaatca tcggtcactt gcaccacttg gtccattga tccaccaatc tttcaacaga     180
ttgtctgcta gatacggtcc attgatccac ttgagattgg gttctgtttc ttgtgttgtt     240
gctgacgctc cagacttggc tcaagaattg ttgcaaaaga cgacttggc tttcgctaac     300 agaaagcaca ctttggctat cgaccacgtt acttacggtg ttgctttcgc tttcgctcca     360
tacggtccat actggagatt catcaagaag atgtctactg ttgaattgtt gggtatccaa     420
aacttgggtc acttcttgcc aatcagaact caagaaatcc acggtttgtt gttgactttg     480
actgaaaagt ctaagcaaaa cgaatctgtt aacatgacta cgaattgtt gaagttgtct     540 aacaacatca tctgtcaaat gatgatgggt atcagatgtt ctggtaacaa gactgaagct     600
gaagaagcta agaacttggt tagagaagtt actactatct tcggtgaatt caacgtttct     660
gacttcatct ggttctgtaa gaagttggac ttgcaaggtt tcaagaagag atacgaagat     720
atcagaacta gatacgacgc tttgttggaa agaatcatct tcgctagaga gaaaatgaga     780
aaggaaggta agggtatgga agatggtaag ggtaaggact tcttggacat gttgttggac     840
gttttggaag atgacaaggc tgaaatcaag atcactagaa accacatcaa ggctttgatc     900
ttggacttcg ttactgctgg tactgacact actgctgtta tcatcgaatg gactttggtt     960
gaattgatca gaacccaat ggttatggaa aaggctaagc aagaattgga cgaagttgtt    1020
ggtaacacta gattggttga agaatctgac gctccaaagt tgccatacat ccaagctatc    1080
atcaaggaag ctttcagatt gcacccacca atcccaatga tcatcagaaa gtctaacgaa    1140
aacgtttctg ttaagtctgg ttacgaaatc ccagctggtt ctatcttgtt cgttaacaac    1200
tggtctatcg gtagaaaccc aaagtactgg gaatctccat ggaattcaa gccagacaga    1260 ttcttgaagg aaggtgtttt gaagccatct ttggacatca gaggtcaaaa cttccaaatc    1320
ttgccattcg gtactggtag aagatcttgt ccaggtatca acatggctat gagacaattg    1380
```

-continued

```
ccagttgttg ttgctatctt gatccaatgt ttcgaatgga ctgttaacga caagcaagtt    1440
ttgaacatgg acgaaagagg tggtttgact actccaagag ctactgactt ggtttgtttc    1500
ccattgttga gaaagaactc tccacactct atgttcactt ctgtttaa                 1548
```

<210> SEQ ID NO 109
<211> LENGTH: 515
<212> TYPE: PRT
<213> ORGANISM: Callistephus chinensis

<400> SEQUENCE: 109

```
Met Ser Asn Ile Phe Glu Val Phe Gln Ser Val Ser Pro Ala Ile Ile
1               5                   10                  15

Ala Ile Phe Phe Ile Ser Ser Leu Phe Ile Tyr Leu Val Leu Ile Arg
            20                  25                  30

Asn Gln Lys Ser Leu Ser Leu Pro Pro Ser Pro Pro Ala Leu Pro Ile
        35                  40                  45

Ile Gly His Leu His His Leu Gly Pro Leu Ile His His Ser Phe His
    50                  55                  60

Asp Leu Ser Thr Arg Tyr Gly Pro Leu Ile His Leu Arg Leu Gly Ser
65                  70                  75                  80

Val Pro Cys Val Val Ala Ser Thr Pro Asp Leu Ala Arg Asp Phe Leu
                85                  90                  95

Lys Thr Asn Glu Leu Ala Phe Ser Arg Lys His Ser Leu Ala Ile
            100                 105                 110

Asp His Val Thr Tyr Gly Val Ser Phe Ala Phe Ala Pro Tyr Gly Pro
        115                 120                 125

Tyr Trp Lys Phe Ile Lys Lys Thr Ser Ile Val Glu Leu Leu Gly Asn
    130                 135                 140

Gln Asn Leu Ser Asn Phe Leu Pro Ile Arg Thr Gln Glu Val His Glu
145                 150                 155                 160

Leu Leu Gln Thr Leu Met Val Lys Ser Lys Asn Glu Ser Val Asn
                165                 170                 175

Leu Ser Glu Glu Leu Leu Lys Leu Thr Asn Asn Val Ile Cys Gln Met
            180                 185                 190

Met Met Ser Ile Arg Cys Ser Gly Thr Asn Asn Glu Ala Asp Glu Ala
        195                 200                 205

Lys Asn Leu Val Arg Glu Val Thr Lys Ile Phe Gly Glu Phe Asn Ile
    210                 215                 220

Ser Asp Phe Ile Cys Leu Phe Lys Asn Ile Asp Leu Gln Gly Phe Lys
225                 230                 235                 240

Lys Arg Tyr Val Asp Thr His Thr Arg Tyr Asn Ala Leu Leu Glu Lys
                245                 250                 255

Met Ile Phe Glu Arg Glu Glu Lys Arg Gln Lys Lys Ser Glu Asp
            260                 265                 270

Gly Lys Gly Lys Asp Phe Leu Asp Ile Leu Leu Asp Val Leu Glu Asp
        275                 280                 285

Glu Asn Ala Glu Ile Lys Ile Thr Arg Asp His Ile Lys Ala Leu Ile
    290                 295                 300

Leu Asp Phe Phe Thr Ala Ala Thr Asp Thr Thr Ala Ile Ser Ile Glu
305                 310                 315                 320

Trp Thr Leu Val Glu Leu Thr Asn Asn Pro Lys Val Leu Glu Asn Ala
                325                 330                 335

Arg Lys Glu Ile Ala Glu Val Val Gly Asp Glu Arg Leu Val Gln Glu
            340                 345                 350
```

Ser Asp Ile Pro Asn Leu Pro Tyr Ile Gln Ala Ile Ile Lys Glu Thr
        355                 360                 365

Leu Arg Met His Pro Pro Ile Pro Met Val Ile Arg Lys Ser Ile Asp
    370                 375                 380

Asn Val Thr Val Gln Gly Tyr Asp Ile Arg Ala Gly Thr Met Leu Phe
385                 390                 395                 400

Val Asn Ile Trp Ser Ile Gly Arg Asn Pro Leu Tyr Trp Glu Ser Pro
                405                 410                 415

Leu Glu Phe Lys Pro His Arg Phe Leu Asp Gly His Ala Arg Asn Leu
            420                 425                 430

Asp Val Lys Gly Gln Cys Phe Gln Leu Leu Pro Phe Gly Thr Gly Arg
            435                 440                 445

Arg Gly Cys Pro Gly Ile Ser Leu Ala Met Arg Glu Leu Pro Val Val
        450                 455                 460

Ile Ala Gly Leu Ile Gln Cys Phe Glu Trp Asn Ala Asn Asp Lys Glu
465                 470                 475                 480

Val Leu Ser Met Asp Glu Arg Ala Gly Leu Thr Ala Pro Arg Ala Val
                485                 490                 495

Asp Leu Glu Phe Val Pro Leu Met Arg Gln Asn Cys Pro Asn Ile Phe
            500                 505                 510

Val Ser Ala
        515

<210> SEQ ID NO 110
<211> LENGTH: 1548
<212> TYPE: DNA
<213> ORGANISM: artificial
<220> FEATURE:
<223> OTHER INFORMATION: coding sequence for SEQ D NO 109

<400> SEQUENCE: 110

```
atgtccaaca tcttcgaagt tttccaatct gtttctccag ctatcatcgc tatcttcttc      60
atctcttctt tgttcatcta cttggttttg atcagaaacc aaaagtcttt gtctttgcca     120
ccatctccac cagcttttgcc aatcatcggt cacttgcacc acttgggtcc attgatccac     180
cactctttcc acgacttgtc tactagatac ggtccattga tccacttgag attgggttct     240
gttccatgtg ttgttgcttc tactccagac ttggctagag acttcttgaa actaacgaa     300
ttggctttct cttctagaaa gcactctttg gctatcgacc acgttactta cggtgtttct     360
ttcgcttttcg ctccatacgg tccatactgg aagttcatca gaaaacttc tatcgttgaa     420
ttgttgggta accaaaactt gtctaacttc ttgccaatca gaactcaaga gttcacgaa     480
ttgttgcaaa ctttgatggt taagtctaag aagaacgaat ctgttaactt gtctgaagaa     540
ttgttgaagt tgactaacaa cgttatctgt caaatgatga tgtctatcag atgttctggt     600
actaacaacg aagctgacga agctaagaac ttggttagag aagttactaa gatcttcggt     660
gaattcaaca tctctgactt catctgtttg ttcaagaaca tcgacttgca aggtttcaag     720
aagagatacg ttgacactca cactagatac aacgctttgt ggaaaagat gatcttcgaa     780
agagaagaaa agagaaagca aagaagtct gaagatggta agggtaagga cttcttggac     840
atcttgttgg acgttttgga agatgaaaac gctgaaatca gatcactag agatcacatc     900
aaggctttga tcttggactt cttcactgct gctactgaca ctactgctat ctctatcgaa     960
tggacttttgg ttgaattgac taacaaccca aaggttttgg aaaacgctag aaaggaaatc    1020
gctgaagttg ttggtgacga agattggtt caagaatctg acatcccaaa cttgccatac    1080
```

-continued

```
atccaagcta tcatcaagga aactttgaga atgcacccac caatcccaat ggttatcaga      1140
aagtctatcg acaacgttac tgttcaaggt tacgacatca gagctggtac tatgttgttc      1200
gttaacatct ggtctatcgg tagaaaccca ttgtactggg aatctccatt ggaattcaag      1260
ccacacagat tcttggacgg tcacgctaga aacttggacg ttaagggtca atgtttccaa      1320
ttgttgccat tcggtactgg tagaagaggt tgtccaggta tctctttggc tatgagagaa      1380
ttgccagttg ttatcgctgg tttgatccaa tgtttcgaat ggaacgctaa cgacaaggaa      1440
gttttgtcta tggacgaaag agctggtttg actgctccaa gagctgttga cttggaattc      1500
gttccattga tgagacaaaa ctgtccaaac atcttcgttt ctgcttaa                   1548
```

<210> SEQ ID NO 111
<211> LENGTH: 356
<212> TYPE: PRT
<213> ORGANISM: Apium graveolens

<400> SEQUENCE: 111

```
Met Ser Ala Pro Ser Thr Ile Thr Ala Leu Ser Gln Glu Lys Thr Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Val Pro Ile Ile Ser Leu Ala Gly Leu Asp
        35                  40                  45

Asp Asp Ser Asn Gly Arg Arg Ala Glu Ile Cys Arg Lys Ile Val Glu
    50                  55                  60

Ala Phe Glu Glu Trp Gly Ile Phe Gln Val Val Asp His Gly Ile Asp
65                  70                  75                  80

Ser Gly Leu Ile Ser Glu Met Ser Arg Leu Ser Arg Glu Phe Phe Ala
                85                  90                  95

Leu Pro Ala Glu Glu Lys Leu Val Tyr Asp Thr Thr Gly Glu Lys Lys
            100                 105                 110

Gly Gly Phe Thr Ile Ser Thr His Leu Gln Gly Asp Asp Val Arg Asp
        115                 120                 125

Trp Arg Glu Phe Val Thr Tyr Phe Ser Tyr Pro Ile Ser Ala Arg Asp
    130                 135                 140

Tyr Ser Arg Trp Pro Lys Lys Pro Glu Gly Trp Arg Ser Thr Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Glu Lys Glu Ala Leu Thr Lys Ala Cys
            180                 185                 190

Val Glu Met Glu Gln Lys Val Leu Ile Asn Tyr Tyr Pro Thr Cys Pro
        195                 200                 205

Glu Pro Asp Leu Thr Leu Gly Val Arg Arg His Thr Asp Pro Gly Thr
    210                 215                 220

Ile Thr Ile Leu Leu Gln Asp Met Val Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
            260                 265                 270

Arg Asn Ala Asp His Gln Ala Val Val Asn Ser Thr Ser Thr Arg Leu
        275                 280                 285
```

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Asn Met Thr Lys His Ile Ala Val Ala
                325                 330                 335

Thr Gln Lys Lys Leu Ala Lys Glu Lys Arg Leu Gln Asp Glu Lys Ala
            340                 345                 350

Lys Met Lys Ile
        355

<210> SEQ ID NO 112
<211> LENGTH: 1071
<212> TYPE: DNA
<213> ORGANISM: artificial
<220> FEATURE:
<223> OTHER INFORMATION: coding sequence for SEQ ID NO: 111

<400> SEQUENCE: 112

```
atgtccgctc catctactat cactgctttg tctcaagaaa agactttgaa cttggacttc      60
gttagagatg aagatgaaag accaaaggtt gcttacaacc aattctctaa cgaagttcca     120
atcatctctt tggctggttt ggacgacgac tctaacggta gaagagctga atctgtaga     180
aagatcgttg aagctttcga gaatggggt atcttccaag ttgttgacca cggtatcgac     240
tctggtttga tctctgaaat gtctagattg tctagagaat tcttcgcttt gccagctgaa     300
gaaaagttgg tttacgacac tactggtgaa aagaagggtg gtttcactat ctctactcac     360
ttgcaaggtg acgacgttag agactggaga gaattcgtta cttacttctc ttacccaatc     420
tctgctagag actactctag atggccaaag aagccagaag gttggagatc tactactgaa     480
gtttactctg aaaagttgat ggttttgggt gctaagttgt tggaagtttt gtctgaagct     540
atgggtttgg aaaaggaagc tttgactaag gcttgtgttg aaatggaaca aaaggttttg     600
atcaactact acccaacttg tccagaacca gacttgactt tgggtgttag agacacact      660
gacccaggta ctatcactat cttgttgcaa gacatggttg gtggtttgca agctactaga     720
gatggtggta agacttggat cactgttcaa ccagttgaag gtgctttcgt tgttaacttg     780
ggtgaccacg tcactacttt gtctaacggt agattcagaa acgctgacca ccaagctgtt     840
gttaactcta cttctactag attgtctatc gctactttcc aaaacccagc tcaaaacgct     900
atcgtttacc cattgaagat cagagaaggt gaaaaggcta tcttggacga agctatcact     960
tacgctgaaa tgtacaagaa gaacatgact aagcacatcg ctgttgctac tcaaaagaag    1020
ttggctaagg aaaagagatt gcaagacgaa aaggctaaga tgaagatcta a              1071
```

<210> SEQ ID NO 113
<211> LENGTH: 521
<212> TYPE: PRT
<213> ORGANISM: Medicago truncatula

<400> SEQUENCE: 113

Met Ser Glu Pro Leu Leu Leu Ala Phe Thr Leu Phe Leu Ser Leu
1               5                   10                  15

Ile Cys Tyr Ile Ile Phe Gln Pro Ile Leu Asn Arg His Lys Asn Leu
                20                  25                  30

Pro Pro Ser Pro Leu Phe Lys Leu Pro Ile Ile Gly His Met His Met
            35                  40                  45

Leu Gly Pro Leu Leu His His Ser Phe Asp Arg Leu Ser Gln Lys Tyr

```
            50                  55                  60
Gly Pro Ile Phe Ser Leu Asn Phe Gly Ser Val Leu Cys Val Val Ala
 65                  70                  75                  80

Ser Thr Pro His Tyr Ala Lys Gln Ile Leu Gln Ile Asn Glu His Ala
                     85                  90                  95

Phe Asn Cys Arg Asn Glu Ser Thr Ala Ile Lys Arg Leu Thr Tyr Glu
                100                 105                 110

Ala Ser Leu Ala Phe Ala Pro Tyr Gly Glu Tyr Trp Arg Phe Ile Lys
                115                 120                 125

Lys Leu Ser Met Asn Glu Leu Leu Gly Ser Arg Ser Ile Ser Ser Phe
                130                 135                 140

Gln His Leu Arg Leu Gln Glu Thr His Asn Leu Leu Lys Leu Phe Ala
145                 150                 155                 160

Asp Lys Ala Lys Asn Tyr Glu Ala Val Asn Val Thr Gln Glu Leu Leu
                165                 170                 175

Lys Leu Ser Asn Asn Val Ile Ser Lys Met Met Leu Gly Glu Ala Glu
                180                 185                 190

Glu Ala Arg Asp Val Val Arg Asp Val Thr Glu Ile Phe Gly Glu Phe
                195                 200                 205

Asn Val Ser Asp Phe Ile Trp Leu Phe Lys Lys Leu Asp Leu Gln Gly
                210                 215                 220

Phe Gly Lys Arg Ile Glu Asp Leu Phe Met Arg Phe Asp Thr Leu Val
225                 230                 235                 240

Glu Arg Ile Ile Ser Lys Arg Glu Leu Arg Lys Asn Lys Gly Arg
                245                 250                 255

Lys Glu Asn Lys Gly Glu Gln Gly Ala Glu Phe Arg Asp Phe Leu Asp
                260                 265                 270

Ile Leu Leu Asp Cys Ala Glu Asp Gln Asn Ser Glu Ile Lys Val Gln
                275                 280                 285

Arg Val His Ile Lys Ala Leu Ile Met Asp Phe Phe Thr Ala Gly Thr
                290                 295                 300

Asp Thr Thr Ser Ile Ser Thr Glu Trp Ala Leu Val Glu Leu Met Asn
305                 310                 315                 320

Asn Pro Ser Leu Leu Gln Lys Ala Arg Glu Glu Ile Asp Asn Val Val
                325                 330                 335

Gly Lys Asn Arg Leu Val Asp Glu Ser Asp Gly Pro Asn Leu Pro Tyr
                340                 345                 350

Ile Gln Ala Ile Ile Lys Glu Thr Phe Arg Leu His Pro Pro Val Pro
                355                 360                 365

Met Val Thr Arg Arg Cys Val Thr Gln Cys Lys Ile Glu Asn Tyr Val
                370                 375                 380

Ile Pro Glu Asn Ser Leu Ile Phe Val Asn Asn Trp Ala Met Gly Arg
385                 390                 395                 400

Asn Ser Ala Tyr Trp Asp Lys Pro Leu Glu Phe Asn Pro Glu Arg Phe
                405                 410                 415

Leu Lys Asn Ser Thr Asn Ser Asn Gly Val Ile Asp Val Arg Gly Gln
                420                 425                 430

Asn Phe Gln Ile Leu Pro Phe Gly Ser Gly Arg Arg Met Cys Pro Gly
                435                 440                 445

Val Thr Leu Ala Met Gln Glu Val Pro Ala Leu Leu Gly Ala Ile Ile
                450                 455                 460

Gln Cys Phe Asp Phe Asn Phe Val Gly Pro Lys Gly Glu Ile Leu Lys
465                 470                 475                 480
```

Gly Gly Asp Ile Val Ile Asp Val Asn Glu Arg Pro Gly Leu Thr Ala
            485                 490                 495

Pro Arg Val His Asp Leu Val Cys Val Pro Val Glu Arg Phe Ala Cys
        500                 505                 510

Gly Gly Pro Leu Gln Ser Leu Gly Cys
        515                 520

<210> SEQ ID NO 114
<211> LENGTH: 1566
<212> TYPE: DNA
<213> ORGANISM: artificial
<220> FEATURE:
<223> OTHER INFORMATION: coding sequence for SEQ ID NO: 113

<400> SEQUENCE: 114

| | | |
|---|---|---|
| atgtccgaac cattgttgtt ggctttcact ttgttcttgt catctttgat ctgttacatc | 60 |
| atcttccaac caatcttgaa cagacacaag aacttgccac catctccatt gttcaagttg | 120 |
| ccaatcatcg gtcacatgca catgtttggg ccattgttgc accactcttt cgacagattg | 180 |
| tctcaaaagt acggtccaat cttctctttg aacttcggtt ctgttttgtg tgttgttgct | 240 |
| tctactccac actacgctaa gcaaatcttg caaatcaacg aacacgcttt caactgtaga | 300 |
| aacgaatcta ctgctatcaa gagattgact tacgaagctt ctttggcttt cgctccatac | 360 |
| ggtgaatact ggagattcat caagaagttg tctatgaacg aattgttggg ttctagatct | 420 |
| atctcttctt ccaacactt gagattgcaa gaaactcaca acttgttgaa gttgttcgct | 480 |
| gacaaggcta gaactacga gctgttaac gttactcaag aattgttgaa gttgtctaac | 540 |
| aacgttatct ctaagatgat gttgggtgaa gctgaagaag ctagagatgt tgttagagat | 600 |
| gttactgaaa tcttcggtga attcaacgtt tctgacttca tctggttgtt caagaagttg | 660 |
| gacttgcaag gtttcggtaa agaatcgaa gatttgttca tgagattcga cactttggtt | 720 |
| gaaagaatca tctctaagag agaagaattg agaaagaaca agggtagaaa ggaaaacaag | 780 |
| ggtgaacaag gtgctgaatt cagagacttc ttggacatct tgttggactg tgctgaagat | 840 |
| caaaactctg aaatcaaggt tcaaagagtt cacatcaagg cttttgatcat ggacttcttc | 900 |
| actgctggta ctgacactac ttctatctct actgaatggg ctttggttga attgatgaac | 960 |
| aacccatctt tgttgcaaaa ggctagagaa gaaatcgaca cgttgttgg taagaacaga | 1020 |
| ttggttgacg aatctgacgg tccaaacttg ccatacatcc aagctatcat caaggaaact | 1080 |
| ttcagattgc acccaccagt tccaatggtt actagaagat gtgttactca atgtaagatc | 1140 |
| gaaaactacg ttatcccaga aaactctttg atcttcgtta caactgggc tatgggtaga | 1200 |
| aactctgctt actgggacaa gccattggaa ttcaacccag aaagattctt gaagaactct | 1260 |
| actaactcta acggtgttat cgacgttaga ggtcaaaact ccaaatctt gccattcggt | 1320 |
| tctggtagaa gaatgtgtcc aggtgttact ttggctatgc aagaagttcc agctttgttg | 1380 |
| ggtgctatca tccaatgttt cgacttcaac ttcgttggtc aaagggtga atcttgaag | 1440 |
| ggtggtgaca tcgttatcga cgttaacgaa agaccaggtt tgactgctcc aagagttcac | 1500 |
| gacttggttt gtgttccagt tgaaagattc gcttgtggtg gtccattgca atctttgggt | 1560 |
| tgttaa | 1566 |

<210> SEQ ID NO 115
<211> LENGTH: 366
<212> TYPE: PRT
<213> ORGANISM: Cuminum cyminum

<400> SEQUENCE: 115

Met Ser Ala Pro Thr Thr Ile Thr Ala Leu Ala Gln Glu Lys Thr Leu
1               5                   10                  15

Asn Ser Asp Phe Val Arg Asp Glu Asp Glu Arg Pro Lys Val Ala Tyr
            20                  25                  30

Asn Gln Phe Ser Thr Glu Ile Pro Ile Ile Ser Leu Ala Gly Ile Asp
        35                  40                  45

Asp Asp Ser Lys Gly Arg Arg Pro Glu Val Cys Arg Lys Ile Val Glu
    50                  55                  60

Ala Phe Glu Asp Trp Gly Ile Phe Gln Val Val Asp His Gly Val Asp
65                  70                  75                  80

Ser Ala Leu Ile Ser Glu Met Ser Arg Leu Ser Arg Glu Phe Phe Ala
                85                  90                  95

Leu Pro Ala Glu Glu Lys Leu Arg Tyr Asp Thr Thr Gly Gly Lys Arg
            100                 105                 110

Gly Gly Phe Thr Ile Ser Thr His Gln Gln Gly Asp Asp Val Arg Asp
        115                 120                 125

Trp Arg Glu Phe Val Thr Tyr Phe Ser Tyr Pro Val Asp Ala Arg Asp
    130                 135                 140

Tyr Ser Arg Trp Pro Glu Lys Pro Glu Gly Trp Arg Ser Val Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Asp Lys Gly Ala Leu Thr Lys Ala Cys
            180                 185                 190

Val Asn Met Glu Gln Lys Val Leu Ile Asn Tyr Tyr Pro Thr Cys Pro
        195                 200                 205

Glu Pro Asp Leu Thr Leu Gly Val Arg Arg His Thr Asp Pro Gly Thr
    210                 215                 220

Ile Thr Ile Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Val Phe
                245                 250                 255

Val Val Asn Leu Gly Asp His Gly His Tyr Leu Ser Asn Gly Arg Phe
            260                 265                 270

Lys Asn Ala Asp His Gln Ala Val Val Asn Ser Thr Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Pro Ile Leu Glu Glu Ala Ile Thr
305                 310                 315                 320

Tyr Ala Glu Met Tyr Lys Lys Asn Met Thr Lys His Ile Glu Val Ala
                325                 330                 335

Thr Gln Lys Lys Leu Ala Lys Glu Lys Arg Leu Gln Glu Glu Lys Ala
            340                 345                 350

Lys Leu Glu Thr Lys Thr Lys Ser Ala Asp Gly Ile Leu Ala
        355                 360                 365

<210> SEQ ID NO 116
<211> LENGTH: 1101
<212> TYPE: DNA
<213> ORGANISM: artificial
<220> FEATURE:
<223> OTHER INFORMATION: coding sequence for SEQ ID NO: 115

<400> SEQUENCE: 116

```
atgtccgctc caactactat cactgctttg gctcaagaaa agactttgaa ctctgacttc      60
gttagagatg aagatgaaag accaaaggtt gcttacaacc aattctctac tgaaatccca     120
atcatctctt tggctggtat cgacgacgac tctaagggta ggaggccaga agtttgtaga     180
aagatcgttg aagctttcga agattggggt atcttccaag ttgttgacca cggtgttgac     240
tctgctttga tctctgaaat gtctagattg tctagagaat tcttcgcttt gccagctgaa     300
gaaaagttga gatacgacac tactggtggt aagagaggtg gtttcactat ctctactcac     360
caacaaggtg acgacgttag agactggaga gaattcgtta cttacttctc ttacccagtt     420
gacgctagag actactctag atggccagaa aagccagaag gttggagatc tgttactgaa     480
gtttactctg aaaagttgat ggttttgggt gctaagttgt ggaagtttt gtctgaagct     540
atgggtttgg acaagggtgc tttgactaag gcttgtgtta acatggaaca aaaggttttg     600
atcaactact acccaacttg tccagaacca gacttgactt gggtgttag agacacact      660
gacccaggta ctatcactat cttgttgcaa gacatggttg gtggtttgca agctactagg     720
gacggtggta agacttggat cactgttcaa ccagttgaag tgttttcgt tgttaacttg     780
ggtgaccacg gtcactactt gtctaacggt agattcaaga acgctgacca ccaagctgtt     840
gttaactcta cttcttctag attgtctatc gctactttcc aaaacccagc tcaaaacgct     900
atcgtttacc cattgaagat cagagaaggt gaaaagccaa tcttggaaga agctatcact     960
tacgctgaaa tgtacaagaa gaacatgact aagcacatcg aagttgctac tcaaaagaag    1020
ttggctaagg aaaagagatt gcaagaagaa aaggctaagt tggaaactaa gactaagtct    1080
gctgacggta tcttggctta a                                              1101
```

<210> SEQ ID NO 117
<211> LENGTH: 356
<212> TYPE: PRT
<213> ORGANISM: Aethusa cynapium

<400> SEQUENCE: 117

```
Met Ser Ala Pro Thr Thr Ile Thr Ala Leu Ser Gln Glu Lys Ser Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Ile Pro Ile Ile Ser Leu Ala Gly Met Asp
        35                  40                  45

Asp Asp Ser Asn Gly Arg Arg Pro Glu Ile Cys Arg Lys Ile Val Glu
    50                  55                  60

Ala Phe Glu Asp Trp Gly Ile Phe Gln Val Val Asp His Gly Ile Asp
65                  70                  75                  80

Lys Gly Leu Ile Ser Gln Met Ser Arg Leu Ser Arg Glu Phe Phe Ala
                85                  90                  95

Leu Pro Ala Glu Glu Lys Leu Arg Tyr Asp Thr Thr Gly Gly Lys Arg
            100                 105                 110

Gly Gly Phe Thr Ile Ser Thr His Leu Gln Gly Asp Asp Val Lys Asp
        115                 120                 125

Trp Arg Glu Phe Val Thr Tyr Phe Ser Tyr Pro Ile Glu Asp Arg Asp
    130                 135                 140

Tyr Ser Arg Trp Pro Glu Lys Pro Glu Gly Trp Arg Ser Thr Thr Glu
145                 150                 155                 160
```

```
Val Tyr Ser Glu Lys Leu Met Val Leu Gly Ala Lys Leu Leu Glu Val
            165                 170                 175
Leu Ser Glu Ala Met Gly Leu Gly Lys Glu Ala Leu Thr Lys Ala Cys
        180                 185                 190
Val Asn Met Glu Gln Lys Val Leu Ile Asn Tyr Tyr Pro Thr Cys Pro
        195                 200                 205
Glu Pro Asp Leu Thr Leu Gly Val Arg Arg His Thr Asp Pro Gly Thr
        210                 215                 220
Ile Thr Ile Leu Leu Gln Asp Met Val Gly Leu Gln Ala Thr Arg
225                 230                 235                 240
Asp Gly Gly Lys Thr Trp Ile Thr Val Gln Pro Val Glu Gly Ala Phe
                245                 250                 255
Val Val Asn Leu Gly Asp His Gly His Tyr Leu Ser Asn Gly Arg Phe
            260                 265                 270
Lys Asn Ala Asp His Gln Ala Val Val Asn Ser Thr Ser Ser Arg Leu
        275                 280                 285
Ser Ile Ala Thr Phe Gln Asn Pro Ala Gln Asn Ala Ile Val Tyr Pro
        290                 295                 300
Leu Lys Ile Arg Glu Gly Glu Lys Ala Ile Leu Asp Glu Ala Ile Thr
305                 310                 315                 320
Tyr Ala Glu Met Tyr Lys Lys Asn Met Thr Lys His Ile Glu Val Ala
                325                 330                 335
Ala Leu Lys Lys Leu Ala Lys Glu Lys Arg Leu Gln Asp Glu Lys Ala
            340                 345                 350
Lys Leu Glu Met
        355

<210> SEQ ID NO 118
<211> LENGTH: 1071
<212> TYPE: DNA
<213> ORGANISM: artificial
<220> FEATURE:
<223> OTHER INFORMATION: coding sequence for SEQ ID NO: 117

<400> SEQUENCE: 118
atgtccgctc caactactat cactgctttg tctcaagaaa agtctttgaa cttggacttc      60
gttagagatg aagatgaaag accaaaggtt gcttacaacc aattctctaa cgaaatccca     120
atcatctctt tggctggtat ggacgacgac tctaacggta ggaggccaga aatctgtaga     180
aagatcgttg aagctttcga gattggggt atcttccaag ttgttgacca cggtatcgac     240
aagggtttga tctctcaaat gtctagattg tctagagaat tcttcgcttt gccagctgaa     300
gaaaagttga gatacgacac tactggtggt aagagaggtg gtttcactat ctctactcac     360
ttgcaaggtg acgacgttaa ggactggaga gaattcgtta cttacttctc ttacccaatc     420
gaagatagag actactctag atggccagaa aagccagaag ttggagatc tactactgaa     480 gtttactctg aaaagttgat ggttttgggt gctaagttgt tggaagtttt gtctgaagct     540
atgggtttgg aaaaggaagc tttgactaag gcttgtgtta acatggaaca aaaggttttg     600
atcaactact acccaacttg tccagaacca gacttgactt tgggtgttag agagacacact     660 gacccaggta ctatcactat cttgttgcaa gacatggttg tggtttgca agctactagg     720 gacggtggta agacttggat cactgttcaa ccagttgaag gtgctttcgt tgttaacttg     780
ggtgaccacg gtcactactt gtctaacggt agattcaaga acgctgacca ccaagctgtt     840
gttaactcta cttcttctag attgtctatc gctactttcc aaaacccagc tcaaaacgct     900
```

```
atcgtttacc cattgaagat cagagaaggt gaaaaggcta tcttggacga agctatcact    960
tacgctgaaa tgtacaagaa gaacatgact aagcacatcg aagttgctgc tttgaagaag   1020
ttggctaagg aaaagagatt gcaagacgaa aaggctaagt tggaaatgta a            1071
```

<210> SEQ ID NO 119
<211> LENGTH: 366
<212> TYPE: PRT
<213> ORGANISM: Conium maculatum

<400> SEQUENCE: 119

```
Met Ser Ala Pro Thr Thr Ile Thr Ala Leu Ala Gln Glu L

```
Asn Met Glu Lys Lys Ser Lys Ser Ala His Gly Ile Ser Ala
        355                 360                 365

<210> SEQ ID NO 120
<211> LENGTH: 1101
<212> TYPE: DNA
<213> ORGANISM: artificial
<220> FEATURE:
<223> OTHER INFORMATION: coding sequence for SEQ ID NO: 119

<400> SEQUENCE: 120
atgtccgctc caactactat cactgctttg gctcaagaaa agactttgaa cttggctttc     60
gttagagatg aagatgaaag accaaaggtt gcttacaacg aattctctaa cgaaatccca    120
atcatctctt ggctggtttt ggaaaacgac tctgacggta aaggccagaa aatctgtaga    180
aagatcgttg aagctttcga aaactggggt atcttccaag ttgttgacca cggtatcgac    240
tctgctttga tctctgaaat gtctagattg tctagagaat tcttcgcttt gccagctgaa    300
gaaaagttga gatacgacac tactggtggt aagagaggtg gtttcactat ctctactcac    360
ttgcaaggtg acgacgttag agactggaga gaattcgtta cttacttctc ttacccaatc    420
gacgctagag actactctag atggccagac aagccagaag gttggagatc tatcactgaa    480
gtttactctg aaagattgat ggttttgggt gctaagttgt tggaagtttt gtctgaagct    540
atgggttttgg aaaaggaagc tttgactaag gcttgtgtta acatggaaca aaaggttttg    600
atcaactact acccaacttg tccagaacca gacttgactt gggtgttag aaggcacact    660
gacccaggta ctatcactgt tttgttgcaa gacatggttg gtggtttgca agctactaga    720
gatggtggta agacttggat cactgttcaa ccagttgaag gtgctttcgt tgttaacttg    780
ggtgaccacg tcactactt gtctaacggt agattcaaga acgctgacca ccaagctgtt    840
gttaactctt cttcttctag attgtctatc gctactttcc aaaacccagc tcaaaacgct    900
atcgtttacc cattgaagat cagagaaggt gaaaaggcta tcttggacga agctatcact    960
tacgctgaaa tgtacaagaa gaacatgact aagcacatcg aagttgctac tttgaagaag   1020
ttggctaagg aaaagagatt gcaagacgaa aaggctaaca tggaaaagaa gtctaagtct   1080
gctcacggta tctctgctta a                                              1101

<210> SEQ ID NO 121
<211> LENGTH: 535
<212> TYPE: PRT
<213> ORGANISM: Camellia sinensis

<400> SEQUENCE: 121

Met Ser Phe Asp Leu Ile Ser Ile Ala Thr Leu Phe Phe Val Ile Ile
1               5                   10                  15

Ser Thr Thr Ile Leu Leu Ser Ile Asn His Phe Lys Lys Pro Pro
            20                  25                  30

His Leu Arg Arg Arg Leu Ser Leu Pro Pro Thr Pro Phe Ala Leu Pro
        35                  40                  45

Ile Ile Gly His Leu His Leu Leu Gly Pro Ile Ile His Arg Ser Phe
    50                  55                  60

His Asp Leu Ser Ser Arg Tyr Gly Pro Leu Phe His Leu Arg Leu Gly
65                  70                  75                  80

Ser Val Pro Cys Phe Val Val Ser Thr Pro Glu Leu Ala Lys Glu Phe
                85                  90                  95

Leu Leu Thr His Glu Leu Lys Phe Ser Ser Arg Arg Asp Ser Ile Ala
```

-continued

```
                100                 105                 110
Ile Gln Arg Leu Thr Tyr Asp Ser Ala Phe Ala Phe Ala Pro Tyr Gly
            115                 120                 125
Pro Tyr Trp Lys Phe Leu Lys Lys Leu Cys Thr Cys Asp Leu Leu Gly
            130                 135                 140
Ala Arg Ser Ile Asn His Phe Leu Pro Thr Arg Thr Arg Glu Leu His
145                 150                 155                 160
Cys Phe Val Arg Leu Leu Ile Asp Lys Ala Val Ala Cys Glu Pro Val
            165                 170                 175
Asn Ile Thr Lys Glu Leu Ser Thr Leu Ala Asn Asn Ile Ile Ser Gln
            180                 185                 190
Met Met Ile Gly Val Arg Cys Ser Gly Thr Thr Gly Glu Ala Glu Glu
            195                 200                 205
Ala Thr Thr Leu Ala Arg Glu Val Thr Lys Ile Phe Gly Glu Phe Asn
            210                 215                 220
Val Ser Asp Phe Met Trp Val Ile Arg Asn Phe Asp Leu Gln Gly Phe
225                 230                 235                 240
Arg Lys Arg Val Glu Asp Ile Tyr Thr Arg Tyr Asp Ala Leu Leu Glu
            245                 250                 255
Arg Ile Ile Thr Asn Arg Glu Glu Val Arg Glu Lys Asn Val Gln Glu
            260                 265                 270
Arg Lys Leu Gly Val Gly Glu Gly His His Val Lys Asp Phe Leu Asp
            275                 280                 285
Leu Leu Leu Asp Val Leu Glu Glu Asp His Ser Glu Ile Asn Phe Ser
            290                 295                 300
Arg Asp Asn Ile Lys Gly Leu Ile Leu Asp Phe Phe Thr Ala Gly Thr
305                 310                 315                 320
Asp Thr Ser Ser Ile Ala Ile Glu Trp Ala Leu Ala Glu Leu Ile Asn
                325                 330                 335
Asn Pro Arg Val Leu Gln Lys Ala Gln Glu Glu Ile Asp Asn Val Val
            340                 345                 350
Gly Lys His Arg Leu Val Ser Glu Ser Asp Gly Pro Asn Leu Pro Tyr
            355                 360                 365
Ile Gln Ala Ile Ile Arg Glu Ala Leu Arg Leu His Pro Pro Val Pro
370                 375                 380
Leu Ile Thr Arg Lys Ser Ile Glu Asp Cys Met Ile Gln Gly Tyr Asn
385                 390                 395                 400
Ile Pro Ala Asn Ser Met Leu Phe Val Asn Val Trp Ser Leu Ala Arg
                405                 410                 415
Asn Pro Lys Tyr Trp Asp Ser Pro Leu Asp Phe Leu Pro Glu Arg Phe
            420                 425                 430
Leu Arg Pro Glu Lys Gly Gly Pro Val Gly Pro Thr Asp Val Lys Gly
            435                 440                 445
Gln His Phe Gln Leu Leu Pro Phe Gly Thr Gly Arg Arg Gly Cys Pro
            450                 455                 460
Gly Thr Ser Leu Ala Met Gln Glu Leu Pro Ala Met Leu Ala Ala Met
465                 470                 475                 480
Ile Gln Cys Phe Glu Trp Lys Val Asn Gln Ser Gly Asp Val Met
            485                 490                 495
Asn Gly Asp Gly Ala Leu Asp Met Thr Glu Gln Pro Gly Met Thr Ala
            500                 505                 510
Pro Arg Ala His Asp Leu Val Cys Met Pro Ile Pro Arg Ile Asp Gln
            515                 520                 525
```

Leu Tyr Ala Leu Leu Asp Pro
        530                 535

<210> SEQ ID NO 122
<211> LENGTH: 1608
<212> TYPE: DNA
<213> ORGANISM: artificial
<220> FEATURE:
<223> OTHER INFORMATION: coding sequence for SEQ ID NO:121

<400> SEQUENCE: 122

```
atgtccttcg acttgatctc tatcgctact ttgttcttcg ttatcatctc tactactatc      60
ttgttgttgt ctatcaacca cttcaagaag ccaccacact tgagaagaag attgtctttg     120
ccaccaactc cattcgcttt gccaatcatc ggtcacttgc acttgttggg tccaatcatc     180
cacagatctt ccacgactt gtcatctaga tacggtccat tgttccactt gagattgggt      240
tctgttccat gtttcgttgt ttctactcca gaattggcta aggaattctt gttgactcac     300
gaattgaagt tctcttctag aagagactct atcgctatcc aaagattgac ttacgactct     360
gctttcgctt tcgctccata cggtccatac tggaagttct tgaagaagtt gtgtacttgt     420
gacttgttgg gtgctagatc tatcaaccac ttcttgccaa ctagaactag agaattgcac     480
tgtttcgtta gattgttgat cgacaaggct gttgcttgtg aaccagttaa catcactaag     540
gaattgtcta ctttggctaa caacatcatc tctcaaatga tgatcggtgt tagatgttct     600
ggtactactg gtgaagctga agaagctact actttggcta gagaagttac taagatcttc     660
ggtgaattca cgtttctga cttcatgtgg gttatcagaa cttcgactt gcaaggtttc      720
agaaagagag ttgaagatat ctacactaga tacgacgctt tgttggaaag aatcatcact     780
aacagagaag aagttagaga aaagaacgtt caagaaagaa agtgggtgt tggtgaaggt      840
caccacgtta aggacttctt ggacttgttg ttggacgttt tggaagaaga tcactctgaa     900
atcaacttct ctagagacaa catcaagggt ttgatcttgg acttcttcac tgctggtact     960
gacacttctt ctatcgctat cgaatgggct ttggctgaat tgatcaacaa cccaagagtt    1020
ttgcaaaagg ctcaagaaga atcgacaac gttgttggta agcacagatt ggtttctgaa     1080
tctgacggtc aaacttgcc atacatccaa gctatcatca gagaagcttt gagattgcac     1140
ccaccagttc cattgatcac tagaaagtct atcgaagatt gtatgatcca aggttacaac    1200
atcccagcta actctatgtt gttcgttaac gtttggtctt tggctagaaa cccaaagtac    1260
tgggactctc cattggactt cttgccagaa agattcttga ggccagaaaa gggtggtcca    1320
gttggtccaa ctgacgttaa gggtcaacac ttccaattgt tgccattcgg tactggtaga    1380
agaggttgtc caggtacttc tttggctatg caagaattgc cagctatgtt ggctgctatg    1440
atccaatgtt tcgaatggaa ggttgttaac caatctggtg acgttatgaa cggtgacggt    1500
gctttggaca tgactgaaca accaggtatg actgctccaa gagctcacga cttggtttgt    1560
atgccaatcc aagaatcga ccaattgtac gctttgttgg acccataa                  1608
```

<210> SEQ ID NO 123
<211> LENGTH: 517
<212> TYPE: PRT
<213> ORGANISM: Saussurea medusa

<400> SEQUENCE: 123

Met Ser Gln Val Leu Gln Thr Leu Thr Pro Ala Val Ile Ala Ala Val
1               5                   10                  15

```
Leu Leu Ser Ser Leu Phe Leu Tyr Leu Ile Lys Lys Asn Gln Asn
            20                  25                  30

His Arg Leu Pro Pro Ser Pro Pro Ser Leu Pro Ile Ile Gly His Leu
        35                  40                  45

His His Leu Gly Pro Leu Ile His Gln Ser Phe His His Leu Ser Thr
    50                  55                  60

Lys Tyr Gly Pro Leu Ile His Leu Arg Leu Gly Ser Val Thr Cys Val
65                  70                  75                  80

Val Ala Ser Thr Pro Asp Leu Ala Arg Asp Phe Leu Lys Thr Asn Glu
                85                  90                  95

Leu Ala Phe Ser Ser Arg Lys His Ser Leu Ala Ile Asp His Ile Thr
            100                 105                 110

Tyr Gly Val Ala Phe Ala Phe Ala Pro Tyr Gly Pro Tyr Trp Lys Phe
        115                 120                 125

Ile Lys Lys Met Ser Thr Val Glu Leu Leu Gly Asn Gln Asn Leu Gly
    130                 135                 140

His Phe Leu Pro Ile Arg Thr Gln Glu Ile His Glu Leu Leu His Thr
145                 150                 155                 160

Leu Met Asn Lys Ala Lys Lys Arg Glu Ser Val Asn Leu Thr Glu Glu
                165                 170                 175

Leu Leu Lys Leu Thr Asn Asn Val Ile Cys Gln Met Met Met Ser Ile
            180                 185                 190

Arg Cys Ser Gly Thr Asn Ser Glu Ala Asp Glu Ala Lys Asn Leu Val
        195                 200                 205

Arg Glu Val Thr Gln Ile Phe Gly Glu Phe Asn Val Ser Asp Phe Ile
210                 215                 220

Trp Phe Cys Lys Asn Ile Asp Leu Gln Gly Phe Lys Lys Arg Tyr Glu
225                 230                 235                 240

Asp Thr His Arg Arg Tyr Asp Val Leu Leu Glu Lys Ile Ile Leu Glu
                245                 250                 255

Arg Glu Glu Glu Arg Arg Lys Glu Gly Lys Arg Glu Asp Gly Asn Lys
            260                 265                 270

Gly Lys Asp Phe Leu Asp Met Leu Leu Asp Val Leu Glu Asp Gly Lys
        275                 280                 285

Ala Glu Ile Gln Ile Thr Arg Asp His Ile Lys Ala Leu Ile Leu Asp
290                 295                 300

Phe Phe Thr Ala Ala Thr Asp Thr Thr Ala Ile Ala Leu Glu Trp Met
305                 310                 315                 320

Leu Val Glu Leu Ile Arg Asn Pro Lys Val Leu Glu Ile Ala Arg Glu
                325                 330                 335

Glu Ile Asp His Ile Ile Gly Asn Glu Arg Leu Val Gln Glu Ser Asp
            340                 345                 350

Ile Pro Asn Leu Pro Tyr Ile Gln Ala Ile Ile Lys Glu Thr Leu Arg
        355                 360                 365

Leu His Pro Pro Ile Pro Met Leu Ile Arg Lys Ser Ile Glu Asn Val
370                 375                 380

Ser Val Gln Gly Tyr Asp Ile Pro Ala Gly Thr Met Leu Phe Val Asn
385                 390                 395                 400

Ile Trp Ser Ile Gly Arg Asn Pro Lys Tyr Trp Glu Ser Pro Leu Glu
                405                 410                 415

Phe Lys Pro His Arg Phe Leu Glu Glu Asp Asn Ala Leu Lys Ser Ser
            420                 425                 430

Phe Asp Ile Lys Gly Gln Asn Phe Gln Leu Leu Pro Phe Gly Thr Gly
```

```
            435                 440                 445
Arg Arg Gly Cys Pro Gly Ile Asn Leu Ala Met Lys Glu Leu Pro Val
    450                 455                 460

Val Ile Ala Gly Leu Ile Gln Cys Phe Glu Trp Asn Ile Asn Glu Lys
465                 470                 475                 480

Gln Val Leu Asp Met Asp Glu Arg Ala Gly Leu Thr Ala Pro Arg Ala
                485                 490                 495

Ala Asp Phe Val Cys Val Pro Ser Ile Arg Glu Asp Ser Pro Lys Ser
            500                 505                 510

Phe Ile Thr Ser Thr
        515

<210> SEQ ID NO 124
<211> LENGTH: 1554
<212> TYPE: DNA
<213> ORGANISM: artificial
<220> FEATURE:
<223> OTHER INFORMATION: coding sequence for SEQ ID NO:123

<400> SEQUENCE: 124
atgtcccaag ttttgcaaac tttgactcca gctgttatcg ctgctgtttt gttgtcatct     60
ttgttcttgt acttgttgat caagaagaac caaaaccaca gattgccacc atctccacca    120
tctttgccaa tcatcggtca cttgcaccac ttggtccat tgatccacca atctttccac     180
cacttgtcta ctaagtacgg tccattgatc cacttgagat tgggttctgt tacttgtgtt    240
gttgcttcta ctccagactt ggctagagac ttcttgaaaa ctaacgaatt ggctttctct    300
tctagaaagc actctttggc tatcgaccac atcacttacg tgttgctttt cgctttcgct    360
ccatacggtc catactggaa gttcatcaag aagatgtcta ctgttgaatt gttgggtaac    420
caaaacttgg gtcacttctt gccaatcaga actcaagaaa tccacgaatt gttgcacact    480
ttgatgaaca aggctaagaa gagagaatct gttaacttga ctgaagaatt gttgaagttg    540
actaacaacg ttatctgtca aatgatgatg tctatcagat gttctggtac taactctgaa    600
gctgacgaag ctaagaactt ggttagagaa gttactcaaa tcttcggtga attcaacgtt    660
tctgacttca tctggttctg taagaacatc gacttgcaag gtttcaagaa gagatacgaa    720
gatactcaca agagatacga cgttttgttg gaaagatca tcttggaaag agaagaagaa    780
agaagaaagg aagtaagag agaagatggt aacaaggta aggacttctt ggacatgttg    840
ttggacgttt tggaagatgg taaggctgaa atccaaatca ctagagatca catcaaggct    900
ttgatcttgg acttcttcac tgctgctact gacactactg ctatcgcttt ggaatggatg    960
ttggttgaat tgatcagaaa cccaaaggtt ttggaaatcg ctagagaaga aatcgaccac   1020
atcatcggta cgaaagatt ggttcaagaa tctgacatcc aaacttgcc atacatccaa    1080 gctatcatca aggaaacttt gagattgcac ccaccaatcc aatgttgat cagaaagtct   1140 atcgaaaacg tttctgttca aggttacgac atcccagctg gtactatgtt gttcgttaac   1200
atctggtcta tcggtagaaa cccaaagtac tgggaatctc cattggaatt caagccacac   1260
agattcttgg aagaagataa cgctttgaag tcatctttcg acatcaaggg tcaaaacttc   1320
caattgttgc cattcggtac tggtagaaga ggttgtccag gtatcaactt ggctatgaag   1380
gaattgccag ttgttatcgc tggtttgatc caatgtttcg aatggaacat caacgaaaag   1440
caagttttgg acatggacga aagagctggt ttgactgctc aagagctgc tgacttcgtt    1500 tgtgttccat ctatcagaga agattctcca aagtctttca tcacttctac ttaa         1554
```

<210> SEQ ID NO 125
<211> LENGTH: 510
<212> TYPE: PRT
<213> ORGANISM: Plectranthus barbatus

<400> SEQUENCE: 125

| | | | | | | | | | | | | | | | |
|---|---|---|---|---|---|---|---|---|---|---|---|---|---|---|---|
| Met | Ser | Asp | His | Val | Glu | Ala | Ala | Leu | Phe | Ala | Ala | Ile | Phe | Leu | Leu |
| 1 | | | | 5 | | | | | 10 | | | | | 15 | |
| Ser | Ala | Ala | Leu | Leu | Asn | His | Leu | Leu | Thr | Gly | Lys | Arg | Arg | Gln | Asn |
| | | | 20 | | | | | 25 | | | | | 30 | | |
| Ala | Tyr | Pro | Pro | Gly | Pro | Phe | Pro | Leu | Pro | Ile | Ile | Gly | His | Leu | His |
| | | | | 35 | | | | | 40 | | | | | 45 | |
| Leu | Leu | Gly | Pro | Arg | Leu | His | His | Thr | Phe | His | Asp | Leu | Thr | Gln | Arg |
| | 50 | | | | | 55 | | | | | 60 | | | | |
| Tyr | Gly | Pro | Leu | Met | Gln | Val | Arg | Leu | Gly | Ser | Ile | Arg | Cys | Val | Ile |
| 65 | | | | | 70 | | | | | 75 | | | | | 80 |
| Ala | Ala | Thr | Pro | Glu | Leu | Ala | Lys | Glu | Phe | Leu | Lys | Thr | Ser | Glu | Leu |
| | | | | 85 | | | | | 90 | | | | | 95 | |
| Val | Phe | Ser | Ala | Arg | Lys | His | Ser | Thr | Ala | Ile | Asp | Ile | Val | Thr | Tyr |
| | | | 100 | | | | | 105 | | | | | 110 | | |
| Glu | Ser | Ser | Phe | Ala | Phe | Ser | Pro | Tyr | Gly | Pro | Tyr | Trp | Lys | Tyr | Ile |
| | | | | 115 | | | | | 120 | | | | | 125 | |
| Lys | Lys | Leu | Cys | Thr | Tyr | Glu | Leu | Leu | Gly | Ala | Arg | Asn | Leu | Asn | His |
| | | | 130 | | | | | 135 | | | | | 140 | | |
| Phe | Leu | Pro | Ile | Arg | Thr | Ile | Glu | Val | Lys | Thr | Phe | Leu | Glu | Ala | Leu |
| 145 | | | | | 150 | | | | | 155 | | | | | 160 |
| Met | Gln | Lys | Gly | Lys | Thr | Gly | Glu | Arg | Leu | Asn | Val | Thr | Glu | Glu | Leu |
| | | | | 165 | | | | | 170 | | | | | 175 | |
| Val | Lys | Leu | Thr | Ser | Asn | Val | Ile | Ser | Gln | Met | Met | Leu | Ser | Ile | Arg |
| | | | 180 | | | | | 185 | | | | | 190 | | |
| Cys | Ser | Gly | Thr | Glu | Gly | Glu | Thr | Glu | Ala | Val | Arg | Thr | Val | Ile | Arg |
| | | | | 195 | | | | | 200 | | | | | 205 | |
| Glu | Val | Thr | Gln | Ile | Phe | Gly | Glu | Phe | Asp | Val | Ala | Asp | Ile | Ile | Trp |
| | 210 | | | | | 215 | | | | | 220 | | | | |
| Phe | Cys | Lys | Asn | Phe | Asp | Phe | Gln | Gly | Ile | Arg | Lys | Arg | Ser | Glu | Asp |
| 225 | | | | | 230 | | | | | 235 | | | | | 240 |
| Ile | Gln | Arg | Arg | Tyr | Asp | Ala | Leu | Leu | Glu | Lys | Ile | Ile | Thr | Asp | Arg |
| | | | | 245 | | | | | 250 | | | | | 255 | |
| Glu | Lys | Gln | Arg | Arg | Thr | Gln | His | Gly | Gly | Glu | Ala | Lys | Asp | Phe | Leu |
| | | | 260 | | | | | 265 | | | | | 270 | | |
| Asp | Met | Phe | Leu | Asp | Ile | Met | Lys | Ser | Gly | Lys | Ala | Glu | Val | Asn | Phe |
| | | 275 | | | | | 280 | | | | | 285 | | | |
| Thr | Arg | Asp | His | Leu | Lys | Ala | Leu | Ile | Leu | Asp | Phe | Phe | Thr | Ala | Gly |
| | 290 | | | | | 295 | | | | | 300 | | | | |
| Thr | Asp | Thr | Thr | Ala | Ile | Val | Val | Gly | Trp | Ala | Ile | Ala | Glu | Leu | Ile |
| 305 | | | | | 310 | | | | | 315 | | | | | 320 |
| Asn | Asn | Pro | Asn | Val | Leu | Lys | Lys | Ala | Gln | Ala | Glu | Ile | Asp | Lys | Val |
| | | | | 325 | | | | | 330 | | | | | 335 | |
| Val | Gly | Leu | His | Arg | Ile | Leu | Gln | Glu | Ser | Asp | Gly | Pro | Asn | Leu | Pro |
| | | | 340 | | | | | 345 | | | | | 350 | | |
| Tyr | Leu | Asn | Ala | Val | Ile | Lys | Glu | Thr | Phe | Arg | Leu | His | Pro | Pro | Ile |
| | | 355 | | | | | 360 | | | | | 365 | | | |
| Pro | Met | Leu | Ser | Arg | Lys | Ser | Ile | Ser | Asp | Cys | Val | Ile | Asp | Gly | Tyr |
| | 370 | | | | | 375 | | | | | 380 | | | | |

Thr Ile Pro Ala Asn Thr Leu Leu Phe Val Asn Ile Trp Ser Met Gly
385                 390                 395                 400

Arg Asn Pro Lys Ile Trp Asp Asn Pro Met Ala Phe Arg Pro Glu Arg
            405                 410                 415

Phe Leu Glu Lys Glu Lys Thr Gly Ile Asp Ile Lys Gly Gln His Phe
        420                 425                 430

Glu Leu Leu Pro Phe Gly Thr Gly Arg Arg Gly Cys Pro Gly Met Leu
    435                 440                 445

Leu Ala Ile Arg Glu Val Val Val Ile Ile Gly Thr Val Ile Gln Cys
450                 455                 460

Phe Asp Trp Lys Leu Pro Val Asp Asp Val Ser Gly Leu Val Asp Met
465                 470                 475                 480

Thr Glu Arg Pro Gly Leu Thr Ala Pro Arg Ala Asp Asp Leu Ile Cys
            485                 490                 495

Arg Val Val Pro Arg Val Asp Pro Leu Val Val Ser Gly His
            500                 505                 510

<210> SEQ ID NO 126
<211> LENGTH: 1533
<212> TYPE: DNA
<213> ORGANISM: artificial
<220> FEATURE:
<223> OTHER INFORMATION: coding sequence for SEQ ID NO: 125

<400> SEQUENCE: 126

```
atgtccgacc acgttgaagc tgctttgttc gctgctatct tcttgttgtc tgctgctttg      60
ttgaaccact tgttgactgg taagagaagg caaaacgctt acccaccagg tccattccca     120
ttgccaatca tcggtcactt gcacttgttg ggtccaagat tgcaccacac tttccacgac     180
ttgactcaaa gatacggtcc attgatgcaa gttagattgg ttctatcag atgtgttatc      240
gctgctactc cagaattggc taaggaattc ttgaaaactt ctgaattggt tttctctgct     300
agaaagcact ctactgctat cgacatcgtt acttacgaat cttctttcgc tttctctcca     360
tacggtccat actggaagta catcaagaag ttgtgtactt acgaattgtt gggtgctaga     420
aacttgaacc acttcttgcc aatcagaact atcgaagtta gactttctt ggaagctttg      480
atgcaaaagg gtaagactgg tgaaagattg aacgttactg aagaattggt taagttgact     540
tctaacgtta tctctcaaat gatgttgtct atcagatgtt ctggtactga aggtgaaact     600
gaagctgtta gaactgttat cagagaagtt actcaaatct cggtgaatt cgacgttgct     660
gacatcatct ggtctgtaa gaacttcgac ttccaaggta tcagaaagag atctgaagat     720
atccaaagaa gatacgacgc tttgttggaa aagatcatca ctgacagaga aaagcaaaga     780
agaactcaac acggtggtga agctaaggac ttccttggaca tgttcttgga catcatgaag     840
tctggtaagg ctgaagttaa cttcactaga gatcacttga aggctttgat cttggacttc     900
ttcactgctg gtactgacac tactgctatc gttgttggtt gggctatcgc tgaattgatc     960
aacaacccaa acgttttgaa gaaggctcaa gctgaaatcg acaaggttgt tggtttgcac    1020
agaatcttgc aagaatctga cggtccaaac ttgccatact tgaacgctgt tatcaaggaa    1080
actttcagat tgcacccacc aatcccaatg ttgtctagaa agtctatctc tgactgtgtt    1140
atcgacggtt acactatccc agctaacact ttgttgttcg ttaacatctg gtctatgggt    1200
agaaacccaa agatctggga caacccaatg gctttcagac cagaaagatt cttggaaaag    1260
gaaaagactg gtatcgacat caagggtcaa cacttcgaat tgttgccatt cggtactggt    1320
```

-continued

```
agaagaggtt gtccaggtat gttgttggct atcagagaag ttgttgttat catcggtact    1380
gttatccaat gtttcgactg gaagttgcca gttgacgacg tttctggttt ggttgacatg    1440
actgaaagac caggtttgac tgctccaaga gctgacgact tgatctgtag agttgttcca    1500
agagttgacc cattggttgt ttctggtcac taa                                 1533
```

```
<210> SEQ ID NO 127
<211> LENGTH: 506
<212> TYPE: PRT
<213> ORGANISM: Scutellaria baicalensis

<400> SEQUENCE: 127

Met Ser Glu Val Thr Leu Asn Val Ala Leu Leu Leu Ser Ala Ala
1               5                   10                  15

Val Cys Leu Met Val Phe Thr Gly Lys Arg Arg Arg Leu Pro Asn
                20                  25                  30

Pro Gly Pro Phe Pro Leu Pro Ile Gly Asn Leu Asn Leu Val
                35                  40                  45

Ser Pro Arg Leu His His Thr Phe His Met Leu Ala Gln Arg Tyr Gly
        50                  55                  60

Pro Ile Met Lys Phe Arg Leu Gly Ser Ile Pro Cys Leu Val Val Ser
65                  70                  75                  80

Thr Pro Glu Leu Ala Lys Asp Ile Leu Lys Thr His Glu Leu Ile Phe
                85                  90                  95

Ser Ser Arg Val Lys Ser Thr Ala Ile Asp Ile Val Thr Tyr Gly Val
                100                 105                 110

Ser Phe Ala Phe Ser Pro Tyr Gly Pro Tyr Trp Lys Tyr Ile Lys Lys
            115                 120                 125

Leu Cys Thr Tyr Glu Leu Leu Gly Ser Arg Met Leu Asn His Phe Glu
    130                 135                 140

Pro Leu Arg Ala Leu Glu Val Arg Glu Phe Leu Lys Asp Val Met Ala
145                 150                 155                 160

Met Gly Lys Ala Gly Lys Ser Phe Asn Val Thr Glu Glu Leu Met Lys
                165                 170                 175

Leu Thr Ser Asn Val Met Ser Asn Met Met Leu Ser Ile Arg Ala Ala
            180                 185                 190

Glu Ser Glu Glu Gln Ala Glu Val Ala Arg Thr Leu Ile Arg Glu Val
        195                 200                 205

Ser Gln Leu Phe Gly Glu Phe Asp Phe Gly Asp Met Leu Trp Phe Cys
    210                 215                 220

Lys Ser Phe Asp Phe Gln Gly Ile Lys Lys Arg Ser Lys Asp Ile Lys
225                 230                 235                 240

Val Arg Tyr Asp Ala Leu Leu Glu Lys Ile Leu Thr Asp Arg Glu Asn
                245                 250                 255

Val Arg Arg Gln Asn Gly Val Val Glu Pro Lys Asp Met Leu Asp Met
            260                 265                 270

Phe Leu Asp Ile Met Glu Gly Gly Lys Thr Asp Val Glu Phe Thr Arg
        275                 280                 285

Glu His Leu Lys Ala Val Ile Leu Asp Phe Leu Thr Ala Gly Thr Asp
    290                 295                 300

Thr Thr Ala Ile Thr Val Glu Trp Val Leu Ala Glu Leu Met Asn Ser
305                 310                 315                 320

Pro Lys Ala Met Lys Lys Ala Gln Asp Glu Met Asp Arg Val Val Gly
                325                 330                 335
```

```
Arg Glu Arg Met Met Ala Glu Ser Asp Ala Pro Asn Leu Pro Tyr Phe
                340                 345                 350
Leu Ala Ile Ile Lys Glu Thr Phe Arg Leu His Pro Pro Ile Pro Leu
            355                 360                 365
Ile Ile Arg Arg Ser Ile Glu Asp Cys Val Ile Asp Gly Tyr His Ile
        370                 375                 380
Pro Ala Asp Thr Leu Ala Phe Ile Asn Val Trp Ser Met Gly Arg Asn
385                 390                 395                 400
Glu Lys Tyr Trp Asp Ser Pro Leu Ser Phe Arg Pro Glu Arg Phe Leu
                405                 410                 415
Glu Gly Asp Asn Ala Ala Ile Asp Ile Lys Gly Met His Phe Glu Leu
            420                 425                 430
Leu Pro Phe Gly Ser Gly Arg Arg Gly Cys Pro Gly Met Leu Ser Ala
        435                 440                 445
Ile Gln Glu Val Leu Ile Ile Ala Gly Thr Val Ile Gln Cys Phe Asp
    450                 455                 460
Trp Glu Gln Ala Asp Gly Ser Gly Arg Val Asp Met Ser Glu Arg Pro
465                 470                 475                 480
Gly Leu Thr Thr Pro Arg Glu Ile Asp Leu Val Cys Arg Val Val Pro
                485                 490                 495
Arg Val Asp Glu Arg Val Ile Ser Gly His
            500                 505

<210> SEQ ID NO 128
<211> LENGTH: 1521
<212> TYPE: DNA
<213> ORGANISM: artificial
<220> FEATURE:
<223> OTHER INFORMATION: coding sequence for SEQ ID NO:127

<400> SEQUENCE: 128
atgtccgaag ttactttgaa cgttgctttg ttgttgttgt ctgctgctgt ttgtttgatg      60
gttttcactg gtaagagaag aagaagattg ccaaacccac caggtccatt cccattgcca     120
ttgatcggta acttgaactt ggtttctcca agattgcacc acactttcca catgttggct     180
caaagatacg gtccaatcat gaagttcaga ttgggttcta tcccatgttt ggttgttttct    240
actccagaat ggctaaggca tcttgaaact cacgaattg atcttctc ttctagagtt        300
aagtctactg ctatcgacat cgttacttac ggtgtttctt tcgctttctc tccatacggt     360
ccatactgga gtacatcaa gaagttgtgt acttacgaat tgttgggttc tagaatgttg      420
aaccacttcg aaccattgag agctttggaa gttagaatt cttgaagga cgttatggct      480
atgggtaagg ctggtaagtc tttcaacgtt actgaagaat tgatgaagtt gacttctaac     540
gttatgtcta acatgatgtt gtctatcaga gctgctgaat ctgaagaaca agctgaagtt     600
gctagaactt tgatcagaga agtttctcaa ttgttcggtg aattcgactt cggtgacatg     660
ttgtggttct gtaagtcttt cgacttccaa ggtatcaaga agatctaa ggacatcaag       720
gttagatacg acgctttgtt ggaaaagatc ttgactgaca gagaaaacgt taggagacaa     780
aacggtgttg ttgaaccaaa ggacatgttg gacatgttct ggacatcat ggaaggtggt     840
aagactgact tgaattcac tagaacac ttgaaggctg ttatcttgga cttcttgact       900
gctggtactg acactactgc tatcactgtt gaatgggttt tggctgaatt gatgaactct     960
ccaaaggcta tgaagaaggc tcaagacgaa atggacagag ttgttggtag agaaagaatg    1020
atggctgaat ctgacgctcc aaacttgcca tacttcttgg ctatcatcaa ggaaactttc    1080
```

```
agattgcacc caccaatccc attgatcatc agaagatcta tcgaagattg tgttatcgac   1140
ggttaccaca tcccagctga cactttggct ttcatcaacg tttggtctat gggtagaaac   1200
gaaaagtact gggactctcc attgtctttc agaccagaaa gattcttgga aggtgacaac   1260
gctgctatcg acatcaaggg tatgcacttc gaattgttgc cattcggttc tggtagaaga   1320
ggttgtccag gtatgttgtc tgctatccaa gaagttttga tcatcgctgg tactgttatc   1380
caatgtttcg actgggaaca agctgacggt tctggtagag ttgacatgtc tgaaagacca   1440
ggtttgacta ctccaagaga aatcgacttg gtttgtagag ttgttccaag agttgacgaa   1500
agagttatct ctggtcacta a                                             1521
```

<210> SEQ ID NO 129
<211> LENGTH: 510
<212> TYPE: PRT
<213> ORGANISM: Dorcoceras hygrometricum

<400> SEQUENCE: 129

```
Met Ser Asp Leu Val Gln Ile Thr Leu Ser Ala Ala Leu Leu Leu
1               5                   10                  15

Ser Ala Ala Phe Leu His Thr Ile Phe Ala Thr Lys Arg Arg Leu
            20                  25                  30

Ser Pro Pro Gly Pro Leu Ala Leu Pro Ile Ile Gly His Leu His
        35                  40                  45

Leu Leu Gly Pro Arg Leu His Gln Thr Phe His Asp Leu Ser Leu Arg
50                  55                  60

His Gly Pro Ile Phe Asn Leu Arg Leu Gly Ser Val Ala Cys Ala Val
65                  70                  75                  80

Val Ser Thr Pro Glu Leu Ala Lys Glu Cys Leu Lys Thr His Glu Leu
                85                  90                  95

Val Phe Ser Ser Arg Lys His Ser Thr Ala Ile Asp Ile Val Thr Tyr
            100                 105                 110

Asp Ser Ser Phe Ala Phe Ser Pro Tyr Gly Pro Tyr Trp Lys Tyr Ile
        115                 120                 125

Lys Lys Leu Cys Thr Tyr Glu Leu Leu Gly Ala Arg Asn Leu Leu His
    130                 135                 140

Phe Gln Pro Ile Arg Thr Leu Glu Val Asn Ser Phe Val Gly Thr Leu
145                 150                 155                 160

Met Asn Lys Ala Glu Ser Gly Glu Ser Phe Asn Val Thr Glu Glu Leu
                165                 170                 175

Val Lys Leu Thr Ser Asn Val Ile Ser His Met Met Leu Gly Ile Arg
            180                 185                 190

Cys Ser Gly Thr Glu Gly Glu Ala Glu Ala Ala Arg Thr Val Ile Arg
        195                 200                 205

Glu Val Thr Gln Ile Phe Gly Glu Phe Asp Val Ala Asp Ile Ile Trp
    210                 215                 220

Phe Cys Lys Asn Phe Asp Phe Gln Gly Ile Arg Lys Arg Ser Glu Asp
225                 230                 235                 240

Ile Gln Arg Arg Tyr Asp Ala Leu Leu Glu Lys Ile Ile Thr Asp Arg
                245                 250                 255

Glu Glu Leu Arg Arg Ser His Gly Gly Ala Ala Gly Glu Ala Arg Asp
            260                 265                 270

Phe Leu Asp Met Phe Leu Asp Ile Met Glu Gly Gly Lys Ser Glu Val
        275                 280                 285

Thr Phe Thr Arg Glu His Leu Lys Ala Leu Ile Leu Asp Phe Phe Thr
```

```
                    290                 295                 300
Ala Gly Thr Asp Thr Thr Ala Ile Val Thr Glu Trp Ala Ile Ser Glu
305                 310                 315                 320

Leu Ile Asn Asn Pro Lys Val Leu Glu Lys Ala Gln Gln Glu Ile Asp
                325                 330                 335

Lys Val Ile Gly Ser Gly Arg Leu Val Gln Glu Ser Asp Ala Pro Asn
            340                 345                 350

Leu Pro Tyr Leu Met Ala Val Ile Lys Glu Thr Phe Arg Leu His Pro
        355                 360                 365

Pro Ile Pro Met Leu Ser Arg Lys Ser Ile Ser Asp Cys Val Ile Asp
    370                 375                 380

Gly Tyr Asp Val Pro Ala Lys Ser Leu Leu Phe Val Asn Ile Trp Ser
385                 390                 395                 400

Met Gly Arg Asn Pro Lys Ile Trp Glu Ser Pro Leu Glu Phe Arg Pro
                405                 410                 415

Glu Arg Phe Leu Glu Arg Glu Lys Ser Ser Ile Asp Ile Lys Gly Gln
            420                 425                 430

His Phe Glu Leu Leu Pro Phe Gly Thr Gly Arg Arg Gly Cys Pro Gly
        435                 440                 445

Met Leu Leu Gly Ile Gln Glu Val Val Ile Ile Gly Thr Met Val
    450                 455                 460

Gln Cys Phe Asp Trp Lys Leu Ser Asp Gly Ser Gly Gln Val Asp Met
465                 470                 475                 480

Thr Glu Arg Pro Gly Leu Thr Ala Pro Arg Ala His Asp Leu Phe Cys
                485                 490                 495

Arg Val Val Pro Arg Ile Asn Pro Val Val Val Ser Gly Asn
            500                 505                 510

<210> SEQ ID NO 130
<211> LENGTH: 1533
<212> TYPE: DNA
<213> ORGANISM: artificial
<220> FEATURE:
<223> OTHER INFORMATION: coding sequence for SEQ ID NO: 129

<400> SEQUENCE: 130
atgtccgact tggttcaaat cactttgtct gctgctttgt tgttgttgtc tgctgctttc      60
ttgcacacta tcttcgctac taagagaaga agattgtctc caccaccagg tccattggct     120
ttgccaatca tcggtcactt gcacttgttg ggtccaagat gcaccaaac tttccacgac      180 ttgtctttga cacacggtcc aatcttcaac ttgagattgg ttctgttgc ttgtgctgtt      240 gtttctactc cagaattggc taaggaatgt ttgaaaactc acgaattggt tttctcttct     300
agaaagcact ctactgctat cgacatcgtt acttacgact cttctttcgc tttctctcca     360
tacggtccat actggaagta catcaagaag ttgtgtactt acgaattgtt gggtgctaga     420
aacttgttgc acttccaacc aatcagaact ttggaagtta actctttcgt tggtactttg     480
atgaacaagg ctgaatctgg tgaatctttc aacgttactg aagaattggt taagttgact     540
tctaacgtta tctctcacat gatgttgggt atcagatgtt ctggtactga aggtgaagct     600
gaagctgcta gaactgttat cagagaagtt actcaaatct cgggtgaatt cgacgttgct     660
gacatcatct ggttctgtaa gaacttcgac ttccaaggta tcagaaagag atctgaagat     720
atccaaagaa gatacgacgc tttgttggaa aagatcatca ctgacagaga agaattgaga     780
agatctcacg gtggtgctgc tggtgaagct agagacttct ggacatgtt cttggacatc     840
```

```
atggaaggtg gtaagtctga agttactttc actagagaac acttgaaggc tttgatcttg    900
gacttcttca ctgctggtac tgacactact gctatcgtta ctgaatgggc tatctctgaa    960
ttgatcaaca acccaaaggt tttggaaaag gctcaacaag aaatcgacaa ggttatcggt   1020
tctggtagat tggttcaaga atctgacgct ccaaacttgc catacttgat ggctgttatc   1080
aaggaaactt tcagattgca cccaccaatc ccaatgttgt ctagaaagtc tatctctgac   1140
tgtgttatcg acggttacga cgttccagct aagtctttgt tgttcgttaa catctggtct   1200
atgggtagaa acccaaagat ctgggaatct ccattggaat tcagaccaga aagattcttg   1260
gaaagagaaa agtcatctat cgacatcaag ggtcaacact tcgaattgtt gccattcggt   1320
actggtagaa gaggttgtcc aggtatgttg ttgggtatcc aagaagttgt tatcatcatc   1380
ggtactatgg ttcaatgttt cgactggaag ttgtctgacg ttctggtca agttgacatg   1440
actgaaagac caggtttgac tgctccaaga gctcacgact tgttctgtag agttgttcca   1500
agaatcaacc cagttgttgt ttctggtaac taa                                1533
```

<210> SEQ ID NO 131
<211> LENGTH: 507
<212> TYPE: PRT
<213> ORGANISM: Antirrhinum majus

<400> SEQUENCE: 131

```
Met Ser Ser Thr Leu Val Tyr Ser Thr Leu Phe Ile Leu Ser Thr Leu
1               5                   10                  15

Leu Leu Thr Leu Leu Thr Arg Thr Arg Arg Lys Thr Arg Pro Pro Gly
            20                  25                  30

Pro Leu Ala Leu Pro Leu Ile Gly His Leu His Leu Leu Gly Pro Lys
        35                  40                  45

Leu His His Thr Phe His Gln Phe Ser Gln Arg Tyr Gly Pro Leu Ile
    50                  55                  60

Gln Leu Tyr Leu Gly Ser Val Pro Cys Val Val Ala Ser Thr Pro Glu
65                  70                  75                  80

Leu Ala Arg Glu Phe Leu Lys Thr His Glu Leu Asp Phe Ser Ser Arg
                85                  90                  95

Lys His Ser Thr Ala Ile Asp Ile Val Thr Tyr Asp Ser Ser Phe Ala
            100                 105                 110

Phe Ala Pro Tyr Gly Pro Tyr Trp Lys Phe Ile Lys Lys Leu Cys Thr
        115                 120                 125

Tyr Glu Leu Leu Gly Ala Arg Asn Leu Ser His Phe Gln Pro Ile Arg
    130                 135                 140

Ala Leu Glu Val Asn Ser Phe Leu Arg Ile Leu Tyr Glu Lys Thr Glu
145                 150                 155                 160

Gln Lys Gln Ser Val Asn Val Thr Glu Glu Leu Val Lys Leu Thr Ser
                165                 170                 175

Asn Val Ile Ser Asn Met Met Leu Gly Ile Arg Cys Ser Gly Thr Glu
            180                 185                 190

Gly Glu Ala Glu Val Ala Arg Thr Val Ile Arg Glu Val Thr Gln Ile
        195                 200                 205

Phe Gly Glu Phe Asp Val Ser Glu Ile Val Trp Phe Cys Lys Asn Leu
    210                 215                 220

Asp Leu Gln Gly Ile Arg Lys Arg Ser Glu Ile Arg Arg Arg Tyr
225                 230                 235                 240

Asp Ala Leu Leu Glu Lys Ile Ile Ser Asp Arg Glu Arg Leu Arg Leu
                245                 250                 255
```

Arg Gly Gly Gly Gly Gly Gly Glu Val Lys Asp Phe Leu Asp
            260                 265                 270

Met Leu Leu Asp Val Met Glu Ser Glu Lys Ser Glu Val Glu Phe Thr
        275                 280                 285

Arg Glu His Leu Lys Ala Leu Ile Leu Asp Phe Phe Thr Ala Gly Thr
        290                 295                 300

Asp Thr Thr Ala Ile Thr Thr Glu Trp Ala Ile Ala Glu Leu Ile Ser
305                 310                 315                 320

Asn Pro Asn Val Leu Lys Lys Ala Gln Glu Glu Met Asp Lys Val Ile
                325                 330                 335

Gly Ser Gln Arg Leu Leu Gln Glu Ser Asp Ala Pro Asn Leu Pro Tyr
            340                 345                 350

Leu Asn Ala Ile Ile Lys Glu Thr Phe Arg Leu His Pro Pro Ile Pro
        355                 360                 365

Met Leu Thr Arg Lys Ser Ile Ser Asp Val Val Asn Gly Tyr Thr
        370                 375                 380

Ile Pro Ala Lys Thr Leu Leu Phe Val Asn Leu Trp Ser Met Gly Arg
385                 390                 395                 400

Asn Pro Asn Tyr Trp Glu Asn Pro Met Glu Phe Arg Pro Glu Arg Phe
                405                 410                 415

Leu Glu Lys Gly Thr Gly Ser Ile Asp Val Lys Gly Gln His Phe Glu
            420                 425                 430

Leu Leu Pro Phe Gly Thr Gly Arg Arg Gly Cys Pro Gly Met Leu Leu
        435                 440                 445

Gly Met Gln Glu Leu Phe Ser Ile Ile Gly Ala Met Val Gln Cys Phe
    450                 455                 460

Asp Trp Lys Leu Pro Asp Gly Val Lys Ser Val Asp Met Thr Glu Arg
465                 470                 475                 480

Pro Gly Leu Thr Ala Pro Arg Ala Asn Asp Leu Val Cys Gln Leu Val
                485                 490                 495

Pro Arg Ile Asp Pro Val Val Val Ser Gly Pro
            500                 505

<210> SEQ ID NO 132
<211> LENGTH: 1524
<212> TYPE: DNA
<213> ORGANISM: artificial
<220> FEATURE:
<223> OTHER INFORMATION: coding sequence for SEQ ID NO: 131

<400> SEQUENCE: 132
atgtcctcta ctttggttta ctctactttg ttcatcttgt ctactttgtt gttgactttg      60
ttgactagaa ctagaagaaa gactagacca ccaggtccat ggctttgcc attgatcggt     120
cacttgcact tgttgggtcc aaagttgcac cacactttcc accaattctc tcaaagatac     180
ggtccattga tccaattgta cttgggttct gttccatgtg ttgttgcttc tactccagaa     240
ttggctagag aattcttgaa aactcacgaa ttggacttct cttctagaaa gcactctact     300
gctatcgaca tcgttactta cgactcttct ttcgctttcg ctccatacgg tccatactgg     360
aagttcatca gaagttgtg tacttacgaa ttgttgggtg ctagaaactt gtctcacttc     420
caaccaatca gagctttgga agttaactct ttcttgagaa tcttgtacga aaagactgaa     480
caaaagcaat ctgttaacgt tactgaagaa ttggttaagt tgacttctaa cgttatctct     540
aacatgatgt tgggtatcag atgttctggt actgaaggtg aagctgaagt tgctagaact     600

```
gttatcagag aagttactca aatcttcggt gaattcgacg tttctgaaat cgtttggttc    660
tgtaagaact tggacttgca aggtatcaga aagagatctg aagatatcag aagaagatac    720
gacgctttgt tggaaaagat catctctgac agagaaagat tgagattgag aggtggtggt    780
ggtggtggtg gtggtgaagt taaggacttc ttggacatgt tgttggacgt tatggaatct    840
gaaaagtctg aagttgaatt cactagagaa cacttgaagg ctttgatctt ggacttcttc    900
actgctggta ctgacactac tgctatcact actgaatggg ctatcgctga attgatctct    960
aacccaaacg ttttgaagaa ggctcaagaa gaaatggaca aggttatcgg ttctcaaaga   1020
ttgttgcaag aatctgacgc tccaaacttg ccatacttga acgctatcat caaggaaact   1080
ttcagattgc acccaccaat cccaatgttg actagaaagt ctatctctga cgttgttgtt   1140
aacggttaca ctatcccagc taagactttg ttgttcgtta acttgtggtc tatgggtaga   1200
aacccaaact actgggaaaa cccaatggaa ttcagaccag aaagattctt ggaaaagggt   1260
actggttcta tcgacgttaa gggtcaacac ttcgaattgt tgccattcgg tactggtaga   1320
agaggttgtc caggtatgtt gttgggtatg caagaattgt tctctatcat cggtgctatg   1380
gttcaatgtt tcgactggaa gttgccagac ggtgttaagt ctgttgacat gactgaaaga   1440
ccaggtttga ctgctccaag agctaacgac ttggtttgtc aattggttcc aagaatcgac   1500
ccagttgttg tttctggtcc ataa                                          1524
```

<210> SEQ ID NO 133
<211> LENGTH: 511
<212> TYPE: PRT
<213> ORGANISM: Erythranthe lewisii

<400> SEQUENCE: 133

```
Met Ser Asn Gln Thr Met Asp Leu Pro Glu Ile Cys Leu Tyr Ala Val
1               5                   10                  15

Ile Leu Phe Val Ser Thr Leu Leu Ile Leu Gly Ile Tyr Lys Arg Lys
            20                  25                  30

Arg Ser His Ile Pro Ser Pro Pro Gly Pro Phe Ala Leu Pro Val Ile
        35                  40                  45

Gly His Leu His Leu Leu Gly Pro Arg Ile His Thr Phe His Asp
    50                  55                  60

Leu Ser Gln Arg Tyr Gly Pro Leu Phe Gln Leu Ser Leu Gly Ser Val
65                  70                  75                  80

Arg Cys Val Val Val Ser Thr Pro Glu Leu Ala Arg Glu Phe Leu Lys
                85                  90                  95

Thr His Glu Leu Val Phe Ser Ser Arg Lys His Thr Thr Ala Ile Asp
            100                 105                 110

Ile Val Thr Tyr Glu Ser Ser Phe Ala Phe Ser Pro Tyr Gly Pro Tyr
        115                 120                 125

Trp Lys Tyr Ile Lys Lys Leu Cys Thr Tyr Glu Leu Leu Gly Ala Arg
    130                 135                 140

Asn Leu Ala Asn Phe Glu Pro Val Arg Asn Val Glu Ile Lys Asp Phe
145                 150                 155                 160

Leu Lys Val Met Ser Asn Lys Ala Asn Thr Gly Glu Ile Val Asn Val
                165                 170                 175

Thr Glu Glu Leu Val Lys Leu Thr Ser Asn Val Ile Ser His Met Met
            180                 185                 190

Leu Gly Ile Arg Cys Ser Gly Thr Glu Gly Glu Ala Glu Ala Ala Arg
        195                 200                 205
```

Asn Val Ile Arg Asp Val Thr Gln Ile Phe Gly Glu Phe Asp Val Ser
210             215             220

Asp Ile Ile Trp Phe Cys Lys Asn Phe Asp Leu Gln Gly Ile Arg Arg
225             230             235             240

Arg Ser Glu Asp Ile Gln Lys Arg Tyr Asp Gly Leu Leu Glu Lys Ile
            245             250             255

Ile Thr Asp Arg Glu Lys Thr Arg Gly Gly Gly Gly Gly Val Lys
            260             265             270

Asp Phe Leu Asp Met Leu Leu Asp Val Met Asp Ser Lys Asn Ser Asp
            275             280             285

Val Lys Phe Thr Arg Glu His Leu Lys Ala Leu Ile Leu Asp Phe Phe
290             295             300

Thr Ala Gly Thr Asp Thr Thr Ala Ile Ala Val Glu Trp Ser Ile Ala
305             310             315             320

Glu Leu Leu Arg Asn Pro Lys Val Ile Lys Lys Ala Gln Gln Glu Ile
            325             330             335

Asp Asn Val Val Gly Ser Gln Arg Leu Leu Gln Glu Ser Asp Ala Pro
            340             345             350

Lys Leu Pro Tyr Ile Met Ala Ile Ile Lys Glu Thr Phe Arg Leu His
            355             360             365

Pro Pro Ile Pro Met Ile Ser Arg Lys Ser Val Ser Asp Cys Ala Ile
370             375             380

Asn Gly Cys Met Ile Arg Ala Asn Thr Leu Leu Phe Val Asn Ile Trp
385             390             395             400

Ser Ile Gly Arg Asn Pro Met Tyr Trp Glu Arg Pro Met Glu Phe Arg
            405             410             415

Pro Glu Arg Phe Leu Asp Pro Gly Cys Gly Ser Ile Asp Val Lys Gly
            420             425             430

Gln Asn Phe Glu Leu Met Pro Phe Gly Thr Gly Arg Arg Gly Cys Pro
            435             440             445

Gly Met Leu Leu Ala Met Gln Glu Leu Val Ala Ile Ile Gly Ala Met
450             455             460

Val Gln Cys Phe Glu Trp Gln Leu Pro Asp Asp Ser Gln Asp Val Asp
465             470             475             480

Met Thr Glu Arg Pro Gly Leu Thr Ala Pro Arg Ala Asn Asp Leu Phe
            485             490             495

Cys Arg Val Val Pro Arg Val Asp Val Ala Val Val Ser Gly Asn
            500             505             510

<210> SEQ ID NO 134
<211> LENGTH: 1536
<212> TYPE: DNA
<213> ORGANISM: artificial
<220> FEATURE:
<223> OTHER INFORMATION: coding sequence for SEQ ID NO: 133

<400> SEQUENCE: 134
atgtccaacc aaactatgga cttgccagaa atctgtttgt acgctgttat cttgttcgtt      60
tctactttgt tgatcttggg tatctacaag agaaagagat ctcacatccc atctccacca     120
ggtccattcg ctttgccagt tatcggtcac ttgcacttgt gggtccaag aatccaccac      180 actttccacg acttgtctca agatacggt ccattgttcc aattgtcttt gggttctgtt      240
agatgtgttg ttgtttctac tccagaattg gctagaaat tcttgaaaac tcacgaattg      300
gttttctctt ctagaaagca cactactgct atcgacatcg ttacttacga atcttctttc     360

```
gctttctctc catacggtcc atactggaag tacatcaaga agttgtgtac ttacgaattg      420
ttgggtgcta gaaacttggc taacttcgaa ccagttagaa acgttgaaat caaggacttc      480
ttgaaggtta tgtctaacaa ggctaacact ggtgaaatcg ttaacgttac tgaagaattg      540
gttaagttga cttctaacgt tatctctcac atgatgttgg gtatcagatg ttctggtact      600
gaaggtgaag ctgaagctgc tagaaacgtt atcagagatg ttactcaaat cttcggtgaa      660
ttcgacgttt ctgacatcat ctggttctgt aagaacttcg acttgcaagg tatcagaaga      720
agatctgaag atatccaaaa gagatacgac ggtttgttgg aaaagatcat cactgacaga      780
gaaaagacta gaggtggtgg tggtggtggt gttaaggact tcttggacat gttgttggac      840
gttatggact ctaagaactc tgacgttaag ttcactagag aacacttgaa ggctttgatc      900
ttggacttct tcactgctgg tactgacact actgctatcg ctgttgaatg gtctatcgct      960
gaattgttga gaaacccaaa ggttatcaag aaggctcaac aagaaatcga caacgttgtt     1020
ggttctcaaa gattgttgca agaatctgac gctccaaagt tgccatacat catggctatc     1080
atcaaggaaa ctttcagatt gcacccacca atcccaatga tctctagaaa gtctgtttct     1140
gactgtgcta tcaacggttg tatgatcaga gctaacactt tgttgttcgt taacatctgg     1200
tctatcggta gaaacccaat gtactgggaa agaccaatgg aattcagacc agaaagattc     1260
ttggacccag gttgtggttc tatcgacgtt aagggtcaaa acttcgaatt gatgccattc     1320
ggtactggta gaagaggttg tccaggtatg ttgttggcta tgcaagaatt ggttgctatc     1380
atcggtgcta tggttcaatg tttcgaatgg caattgccag acgactctca agacgttgac     1440
atgactgaaa gaccaggttt gactgctcca agagctaacg acttgttctg tagagttgtt     1500
ccaagagttg acgttgctgt tgtttctggt aactaa                               1536
```

METHOD FOR BIOSYNTHESISING DIOSMETIN AND/OR HESPERETIN IN A MICROORGANISM

CROSS-REFERENCE TO RELATED APPLICATION

This application is the U.S. national stage application of International Patent Application No. PCT/EP2020/053493, filed Feb. 11, 2020.

The Sequence Listing for this application is labeled "Seq-List.txt" which was created on Aug. 5, 2021 and is 417 KB. The entire content of the sequence listing is incorporated herein by reference in its entirety.

FIELD OF THE INVENTION

The present invention relates to a method for producing diosmetin and hesperetin.

TECHNOLOGICAL BACKGROUND

Diosmetin and hesperetin are, respectively, an O-methylated flavone and an O-methylated flavanone. These compounds are of interest per se, but also as biosynthetic intermediates for the production of other molecules of interest.

Thus, there is an unsatisfied need for a process for the biosynthesis of diosmetin and hesperetin.

SUMMARY OF THE INVENTION

The inventors have developed a biosynthesis of diosmetin and hesperetin in a microorganism.

The present invention thus relates to the use of a recombinant microorganism comprising a heterologous nucleic acid sequence coding for an O-methyltransferase (OMT) which is capable of methylating eriodictyol and/or luteolin in position 4' for the production of diosmetin and/or hesperetin.

The invention also relates to a recombinant microorganism comprising a heterologous nucleic acid sequence coding for an O-methyltransferase (OMT) which is capable of methylating eriodictyol and/or luteolin in position 4', the microorganism being a yeast.

In one embodiment, the O-methyltransferase (OMT) is an O-methyltransferase (OMT) from *Homo sapiens*.

In another embodiment, the O-methyltransferase (OMT) is selected from an enzyme comprising a sequence SEQ ID NO: 89 and polypeptides comprising a sequence having at least 60, 70, 80, 85, 90 or 95% identity with this sequence and having O-methyltransferase activity.

In another embodiment, the O-methyltransferase (OMT) is an O-methyltransferase (OMT) from *Arabidopsis thaliana*.

In another embodiment, the O-methyltransferase (OMT) is selected from an enzyme is selected from the enzyme comprising a sequence SEQ ID NO: 87 and polypeptides comprising a sequence having at least 60, 70, 80, 85, 90 or 95% identity with this sequence and having O-methyltransferase activity.

In a preferred embodiment, the O-methyltransferase (OMT) is an O-methyltransferase (OMT) from *Citrus*, in particular *Citrus clementina* or *Citrus sinensis*. In particular, the O-methyltransferase (OMT) may be selected from an enzyme comprising a sequence chosen from SEQ ID NOs 91 and 93 and polypeptides comprising a sequence having at least 60, 70, 80, 85, 90 or 95% identity with one of these sequences and having O-methyltransferase activity. Preferably, the O-methyltransferase (OMT) is selected from an enzyme comprising a sequence chosen from SEQ ID NO: 91 and polypeptides comprising a sequence having at least 60, 70, 80, 85, 90 or 95% identity with this sequence and having O-methyltransferase activity. According to another preferred alternative, the O-methyltransferase (OMT) is selected from an enzyme comprising a sequence chosen from SEQ ID NO: 93 and polypeptides comprising a sequence having at least 60, 70, 80, 85, 90 or 95% identity with this sequence and having O-methyltransferase activity.

Preferably, the microorganism also comprises a heterologous or endogenous nucleic acid sequence coding for an S-adenosylmethionine synthetase (SAMT).

Preferably, the microorganism also comprises an endogenous or heterologous nucleic acid sequence coding for a flavone synthase (FNS), in particular a flavone synthase which is capable of producing luteolin from eriodictyol, preferably from *Arabidopsis thaliana*, *Petroselinum crispum*, *Zea mays*, *Lonicera japonica*, *Lonicera macranthoides*, *Callistephus chinensis*, *Apium graveolens*, *Medicago truncatula*, *Cuminum cyminum*, *Aethusa cynapium*, *Angelica archangelica*, *Conium maculatum*, *Camellia sinensis*, *Cynara cardunculus* var *scolymus*, *Saussurea medusa*, *Plectranthus barbatus*, *Scutellaria baicalensis*, *Dorcoceras hygrometricum*, *Antirrhinum majus*, *Perilla frutescens* var *crispa*, *Dahlia pinnata* or *Erythranthe lewisii*. The flavone synthase (FNS) may be selected from enzymes comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity. According to a preferred embodiment, the flavone synthase (FNS) is selected from enzymes comprising a sequence chosen from SEQ ID NOs: 37, 33 and 35, preferably SEQ ID NO: 37 and polypeptides comprising a sequence having at least 60, 70, 80, 85, 90 or 95% sequence identity with one of these sequences, preferably with SEQ ID NO: 37 and having flavone synthase activity.

Preferably, the microorganism also comprises:
- a heterologous nucleic acid sequence coding for a tyrosine ammonia lyase (TAL); and/or a heterologous nucleic acid sequence coding for a phenylalanine ammonia lyase (PAL) and a heterologous nucleic acid sequence coding for a cinnamate 4-hydroxylase (C4H);
- a heterologous nucleic acid sequence coding for a 4-coumaroyl-CoA ligase (4CL);
- a heterologous nucleic acid sequence coding for a chalcone synthase (CHS);
- a heterologous nucleic acid sequence coding for a chalcone isomerase (CHI);
- a heterologous nucleic acid sequence coding for a flavonoid 3'-monooxygenase (F3'H); and
- optionally, a heterologous nucleic acid sequence coding for a 4-methoxybenzoate O-demethylase which is capable of converting tyrosine into L-DOPA and also p-coumaric acid into caffeic acid; or a heterologous nucleic acid sequence coding for a p-coumarate 3-hydroxylase which is capable of converting p-coumaric acid into caffeic acid.

In particular, the microorganism may comprise:
a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) from *Arabidopsis thaliana, Citrus clementina, Petroselinum crispum* or *Streptomyces clavuligerus*; a 4CL comprising a sequence chosen from SEQ ID NOs: 97, 99, 43, 45, 47 and 49 and polypeptides comprising a sequence having at least 60, 70, 80, 85, 90 or 95% sequence identity with one of these sequences and having 4-coumarate-CoA ligase activity; in particular a 4CL comprising a sequence selected from SEQ ID NOs: 97, 99 and 45 and polypeptides comprising a sequence having at least 60, 70, 80, 85, 90 or 95% sequence identity with this sequence and having 4-coumarate-CoA ligase activity, and preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity, preferably a CHI comprising a sequence chosen from SEQ ID NO: 61 and polypeptides comprising a sequence having at least 60, 70, 80, 85, 90 or 95% sequence identity with this sequence and having chalcone isomerase activity; and a heterologous nucleic acid sequence coding for a flavonoid 3'-monooxygenase (F3'H) from *Callistephus chinensis, Perilla frutescens* var. *crispa, Petunia* x *hybrida, Gerbera hybrida, Citrus sinensis, Arabidopsis thaliana, Pilosella officinarum, Osteospermum* hybrid cultivar, *Phanerochaete chrysosporium, Citrus clementina* or *Streptomyces avermitilis*, preferably an enzyme comprising a sequence chosen from SEQ ID NOs: 7, 1, 3, 5, 9, 11, 13, 15, 17, 19, 21 and 95 and polypeptides comprising a sequence having at least 60, 70, 80, 85, 90 or 95% sequence identity with one of these sequences and having flavonoid 3'-monooxygenase activity, preferably selected from enzymes having the SEQ ID NOs: 7, 11, 17 and 95 and polypeptides having at least 60, 70, 80, 85, 90 or 95% identity with one of these sequences and having flavonoid 3'-monooxygenase activity.

Preferably, the microorganism also comprises a heterologous or endogenous nucleic acid sequence coding for a cytochrome P450 reductase (CPR), in particular a CPR having a sequence chosen from SEQ ID NOs: 25, 23, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with one of these sequences and having cytochrome P450 reductase activity.

In a preferred embodiment, the microorganism is a yeast of the genus *Saccharomyces*, in particular *Saccharomyces cerevisiae*.

The present invention relates to the use of a microorganism as defined in the present patent application for producing diosmetin and/or hesperetin.

The invention also relates to a method for producing diosmetin and/or hesperetin comprising the cultivation of a microorganism as defined in the present patent application, and optionally the harvesting of the diosmetin and/or hesperetin.

Preferably, during the use of the microorganism according to the invention for producing diosmetin and/or hesperetin or in the method according to the invention, no naringenin, apigenin, eriodictyol and/or luteolin is supplied to the medium.

DETAILED DESCRIPTION OF THE INVENTION

The inventors thus explored several biosynthetic pathways and succeeded in developing the biosynthesis of hesperetin and/or diosmetin in a microorganism. Specifically, hesperetin and/or diosmetin may be obtained from eriodictyol and/or luteolin by methylation in position 4'.

Eriodictyol and luteolin bear at least two hydroxyls that are capable of being methylated, in positions 5, 7, 3' and 4'. Thus, in a preferred embodiment, the yeast comprises a heterologous or endogenous nucleic acid coding for a cytochrome P450 reductase, an NADPH-cytochrome P450 reductase. This enzyme belongs to the class EC 1.6.2.4. It is thus necessary to identify methylases that are capable of specifically methylating the hydroxyl group in position 4', notably relative to those in positions 5, 7 and 3'.

Methylases are very numerous in nature and represent a large family of enzymes whose substrates are difficult to define. Many methylases having flavones and flavanones as substrate introduce the methyl group into position 7. Others result in the production of mixtures of compounds containing multiple methylations in positions 7, 3' and 4'. Notably, the specificity of the position of methylation of aromatic catechols is very often in the meta position (position 3' or 5') and rarely in the para position, position 4' (Pandey et al., 2016, Biotechnol. Adv., 34, 634-662).

The only enzyme that appears to show specificity for position 4' is an enzyme from *Glycine max*, SOMT-2, which is capable in *E. coli* of methylating several flavonoids including apigenin and naringenin specifically in position 4' (Kim et al., 2005, Journal of Biotechnology 119: 155-162). However, its capacity for accepting eriodictyol and/or luteolin is unknown. Moreover, the inventors observed that this enzyme does not function in a yeast.

It was thus necessary to identify methylases that are capable of introducing a methyl group in position 4' of eriodictyol and/or luteolin, and the inventors succeeded in identifying such O-methyltransferases (OMT).

Definition

The term "microorganism" refers to a unicellular organism. Preferably, the microorganism is a bacterium or a yeast.

The term "recombinant microorganism" refers to a microorganism which is not found in nature and which contains a genome modified following insertion, modification or deletion of one or more heterologous genetic elements.

The term "recombinant nucleic acid" refers to a nucleic acid which has been modified and does not exist in a natural microorganism. For example, this term may denote a coding sequence or gene which is operatively linked to a promoter which is not the natural promoter. This may also denote a coding sequence in which the introns have been deleted for genes comprising exons and introns.

The term "heterologous" means that the gene has been introduced by genetic engineering into the cell. It may be present therein in episomal or chromosomal form. The origin of the gene may be different from the cell into which it is introduced. However, the gene may also originate from the same species as the cell into which it is introduced, but it is considered as heterologous on account of its unnatural environment. For example, the gene or the nucleic acid sequence is heterologous since it is under the control of a promoter other than its natural promoter, it is introduced into a position different from that in which it is naturally located. The host cell may contain a copy of the endogenous gene prior to the introduction of the heterologous gene or it may not contain an endogenous copy. Moreover, the nucleic acid sequence may be heterologous in the sense that the coding sequence has been optimized for expression in the host microorganism. Preferably, in the present document, a heterologous nucleic acid sequence codes for a protein which is heterologous to the host cell, i.e. which is not naturally present in the yeast.

As used herein, the term "native" or "endogenous", relative to the host microorganism, refers to a genetic element or to a protein that is naturally present in said microorganism. The term "gene" denotes any nucleic acid coding for a protein. The term "gene" covers DNA, such as cDNA or gDNA, and also RNA. The gene may first be prepared via recombinant, enzymatic and/or chemical techniques, and subsequently replicated in a host cell or a system in vitro. The gene typically comprises an open reading frame coding for a desired protein. The gene may contain additional sequences such as a transcription terminator or a signal peptide.

As a result of degeneracy of the genetic code, several nucleic acids may code for a particular polypeptide. Thus, the codons in the coding sequence for a given polypeptide may be modified such that optimum expression in a particular microorganism is obtained, for example by using suitable codon translation tables for this microorganism. The nucleic acids may also be optimized according to a preferable GC content for the particular yeast and/or to reduce the number of repeat sequences. In certain embodiments, the heterologous nucleic acids were codon-optimized for expression in the microorganism concerned. Codon optimization may be performed via routine processes known in the art (see, for example, Welch, M., et al. (2011), Methods in Enzymology 498: 43-66).

The term "operatively linked" denotes a configuration in which a control sequence is placed in a suitable position relative to a coding sequence, such that the control sequence controls the expression of the coding sequence.

The term "control sequences" denotes the nucleic acid sequences required for the expression of a gene. The control sequences may be native or heterologous. Control sequences that are well known and currently used by those skilled in the art will be preferred. Such control sequences comprise, but without being limited thereto, a leader, a polyadenylation sequence, a propeptide sequence, a promoter, a signal peptide sequence and a transcription terminator. Preferably, the control sequences comprise a promoter and a transcription terminator.

The term "expression cassette" denotes a nucleic acid construct comprising a coding region, i.e. a gene, and a regulating region, i.e. a region comprising one or more control sequences, which are operatively linked. Preferably, the control sequences are suitable for use in the host microorganism.

As used herein, the term "expression vector" denotes a DNA or RNA molecule which comprises an expression cassette. Preferably, the expression vector is a linear or circular double-stranded DNA molecule. The vector may also comprise an origin of replication, a selection marker, etc.

For the purposes of the present invention, the term "percentage of identity" between two nucleic acid sequences or amino acid sequences is intended to denote a percentage of nucleotides or of amino acid residues that are identical between the two sequences to be compared, obtained after the best alignment, this percentage being purely statistical and the differences between the two sequences being distributed randomly and over their entire length. The best alignment or optimum alignment is the alignment for which the percentage of identity between the two sequences to be compared, as calculated below, is the highest. Sequence comparisons between two nucleic acid or amino acid sequences are conventionally performed by comparing these sequences after they have been optimally aligned, said comparison being performed by segment or by comparison window to identify and compare the local regions with sequence similarity. The alignment for the purposes of determining the percentage of amino acid sequence identity may be performed in various ways that are well known in the field, for example by using computer software available on the Internet, such as blast.ncbi.nlm.Nih.gov or Worldwide Website ebi.ac.uk/Tools/emboss/. A person skilled in the art can determine the appropriate parameters for measuring the alignment, including any algorithm necessary to obtain a maximum alignment over the entire length of the sequences compared. For the purposes of the present invention, the values of the percentage of amino acid sequence identity refer to values generated using the EMBOSS Needle pair sequence alignment program which creates an optimum global alignment of two sequences by means of the Needleman-Wunsch algorithm, in which all the search parameters are defined by default Notation matrix=BLOSUM62, Open gap=10, Extended gap=0.5, end gap penalty=false, open end gap=10 and extended end gap=0.5. In certain embodiments, all the percentages of identity mentioned in the present patent application may be set at least 60%, at least 70%, at least 80%, at least 85%, preferably at least 90% identity, more preferably at least 95% identity. In particular, the embodiments in which all the percentages of sequence identity of the enzymes are at least 80% or at least 85%, preferably at least 90% or at least 95% sequence identity are considered as described.

In one embodiment, the polypeptides may contain 1, 2, 3, 4, 5, 6, 7, 8, 9 or 10 additions, substitutions or deletions relative to the sequences described in the SEQ ID NOs. In particular, these additions, substitutions or deletions are introduced at the N-terminal end, the C-terminal end or at both ends.

The polypeptides may optionally be in the form of a fusion protein.

The terms "overexpression" and "increased expression" as used herein are used interchangeably and mean that the expression of a gene or of an enzyme is increased relative to an unmodified microorganism, for example a wild-type microorganism or a microorganism not comprising the genetic modifications described herein. The term "wild-type" refers to an unmodified microorganism existing in nature. The increased expression of an enzyme is usually obtained by increasing the expression of the gene coding for said enzyme. In embodiments in which the gene or the enzyme is not naturally present in the microorganism of the invention, i.e. a heterologous gene or enzyme, the terms "overexpression" and "expression" may be used interchangeably. To increase the expression of a gene, a person skilled in the art can use any known technique such as increasing the number of copies of the gene in the microorganism, by using a promoter inducing a high level of expression of the gene, i.e. a strong promoter, by using elements which stabilize the corresponding messenger RNA or sequences which sequester the ribosomal binding site (RBS) and the sequences surrounding same. In particular, overexpression may be obtained by increasing the number of copies of the gene in the microorganism. One or more copies of the gene may be introduced into the genome via recombination processes, known to those skilled in the art, including the replacement of the genes or multi-copy integration (see, for example, the international patent application WO 2015/092013). Preferably, an expression cassette comprising the gene, preferably placed under the control of a strong promoter, is integrated into the genome. As a variant, the gene may be carried by an expression vector, preferably a plasmid, comprising an expression cassette with the gene of interest preferably placed under the control of a strong promoter. The expression vector may be present in the microorganism in one or more copies, depending on the nature of the origin of replication. Overexpression of the gene may also be obtained by using a promoter which induces a high level of expression of the gene. For example, the promoter of an endogenous gene may be replaced with a stronger promoter, i.e. a promoter which induces a higher level of expression. The endogenous gene under the control of a promoter which is not the natural promoter is termed a heterologous nucleic acid. The promoters that are suitable for use in the present invention are known to those skilled in the art and may be constitutive or inducible, and may be endogenous or heterologous.

The term "comprising" also means "consisting of" or "consisting essentially of". The term "consisting essentially of" means that the sequence may contain 1, 2, 3, 4, 5, 6, 7, 8, 9 or 10 additions, substitutions or deletions relative to the sequences described in the SEQ ID NOs.

Microorganisms

The microorganism according to the present invention may be a eukaryotic or prokaryotic microorganism.

In a first embodiment, the microorganism is a eukaryote. Preferably, it is a yeast of the Saccharomycetales, Sporidiobolales and Schizosaccharomycetales orders. The yeast may be selected, for example, from *Pichia, Kluyveromyces, Saccharomyces, Schizosaccharomyces, Candida, Lipomyces, Rhodotorula, Rhodosporidium, Yarrowia,* or *Debaryomyces*. In one embodiment, the yeast is chosen from *Pichia pastoris, Kluyveromyces lactis, Kluyveromyces marxianus, Saccharomyces cerevisiae, Saccharomyces carlsbergensis, Saccharomyces diastaticus, Saccharomyces douglasii, Saccharomyces kluyveri, Saccharomyces norbensis, Saccharomyces oviformis, Schizosaccharomyces pombe, Candida albicans, Candida tropicalis, Rhodotorula glutinis, Rhodosporidium toruloides, Yarrowia lipolytica, Debaryomyces hansenii* and *Lipomyces starkeyi*. In a preferred embodiment, the microorganism is a *Saccharomyces* yeast, preferably a *Saccharomyces cerevisiae* yeast. Alternatively, the microorganism may be a fungus, preferably a filamentous fungus. Preferably, it is chosen from *Aspergillus, Trichoderma, Neurospora, Podospora, Endothia, Mucor, Cochiobolus* or *Pyricularia*. Preferentially, the fungus is chosen from *Aspergillus nidulans, Aspergillus niger, Aspergillus awomari, Aspergillus oryzae, Aspergillus terreus, Neurospora crassa, Trichoderma reesei* and *Trichoderma viride*.

In a second embodiment, the microorganism is a prokaryote. Preferably, it is a bacterium, notably chosen from the phylum Acidobacteria, Actinobacteria, Aquificae, Bacterioidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae or Verrucomicrobia. Preferably, the bacterium belongs to the genus *Acaryochloris, Acetobacter, Actinobacillus, Agrobacterium, Alicyclobacillus, Anabaena, Anacystis, Anaerobiospirillum, Aquifex, Arthrobacter, Arthrospira, Azobacter, Bacillus, Brevibacterium, Burkholderia, Chlorobium, Chromatium, Chlorobaculum, Clostridium, Corynebacterium, Cupriavidus, Cyanothece, Enterobacter, Deinococcus, Erwinia, Escherichia, Geobacter, Gloeobacter, Gluconobacter, Hydrogenobacter, Klebsiella, Lactobacillus, Lactococcus, Mannheimia, Mesorhizobium, Methylobacterium, Microbacterium, Microcystis, Nitrobacter, Nitrosomonas, Nitrospina, Nitrospira, Nostoc, Phormidium, Prochlorococcus, Pseudomonas, Ralstonia, Rhizobium, Rhodobacter, Rhodococcus, Rhodopseudomonas, Rhodospirillum, Salmonella, Scenedesmun, Serratia, Shigella, Staphylococcus, Streptomyces, Synechoccus, Synechocystis, Thermosynechococcus, Trichodesmium* or *Zymomonas*. More preferably, the bacterium is chosen from the species *Agrobacterium tumefaciens, Anaerobiospirillum succiniciproducens, Actinobacillus succinogenes, Aquifex aeolicus, Aquifex pyrophilus, Bacillus subtilis, Bacillus amyloliquefacines, Brevibacterium ammoniagenes, Brevibacterium immariophilum, Clostridium pasteurianum, Clostridium ljungdahlii, Clostridium acetobutylicum, Clostridium beigerinckii, Corynebacterium glutamicum, Cupriavidus necator, Cupriavidus metallidurans, Enterobacter sakazakii, Escherichia coli, Gluconobacter oxydans, Hydrogenobacter thermophilus, Klebsiella oxytoca, Lactococcus lactis, Lactobacillus plantarum, Mannheimia succiniciproducens, Mesorhizobium loti, Pseudomonas aeruginosa, Pseudomonas mevalonii, Pseudomonas pudica, Pseudomonas putida, Pseudomonas fluorescens, Rhizobium etli, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus, Streptomyces coelicolor, Zymomonas mobilis, Acaryochloris marina, Anabaena variabilis, Arthrospira platensis, Arthrospira maxima, Chlorobium tepidum, Chlorobaculum sp., Cyanothece sp., Gloeobacter violaceus, Microcystis aeruginosa, Nostoc punctiforme, Prochlorococcus marinus, Synechoccus elongatus, Synechocystis sp., Thermosynechococcus elongatus, Trichodesmium erythraeum* and *Rhodopseudomonas palustris*. In a preferred embodiment, the microorganism is an *Escherichia coli* bacterium, for example *E. coli* BL21, *E. coli* BL21 (DE3), *E. coli* MG1655 or *E. coli* W31 10 and derivatives thereof. In an alternative embodiment, the microorganism is a bacterium of the *Streptomyces* genus, in particular *Streptomyces venezuelae*.

The microorganisms may have been modified to increase the production of tyrosine and/or phenylalanine, preferably tyrosine. Notably, the genes responsible for the feedback inhibition of the production of tyrosine and/or phenylalanine, preferably of tyrosine, may be inactivated. Alternatively or cumulatively, the pathway for the biosynthesis of tyrosine and/or phenylalanine, preferably of tyrosine, may be optimized, notably by redirecting the flow of carbon from other metabolic pathways toward that of tyrosine and/or phenylalanine, preferably of tyrosine. These modifications and these genes are well known to those skilled in the art (see U.S. Pat. No. 8,809,028; Pandey et al., 2016, Biotechnol. Adv., 34, 634-662).

Thus, in one embodiment, the microorganism produces large amounts of tyrosine and/or of phenylalanine, in particular from a simple carbon source such as glucose.

Modifications Enabling the Production of Hesperetin and/or Diosmetin

The recombinant microorganism according to the present invention was modified to produce hesperetin and/or diosmetin. Notably, to enable the microorganism to synthesize hesperetin and/or diosmetin from eriodictyol and/or luteolin, respectively, the microorganism was modified to introduce an enzyme that is capable of methylating the hydroxyl in position 4' of eriodictyol and/or luteolin, preferably of specifically methylating the hydroxyl in position 4' of eriodictyol and/or luteolin.

In a first embodiment, the recombinant microorganism is capable of producing eriodictyol and/or luteolin: in particular, it has been modified for this purpose. In an alternative embodiment, eriodictyol and/or luteolin may be provided to the microorganism, for example by adding these compounds to the culture medium.

In a particular embodiment, the microorganism produces hesperetin. Diosmetin may then be prepared from hesperetin by chemical conversion, notably by oxidation, or biochemical conversion.

In a preferred embodiment, the microorganism produces hesperetin and diosmetin.

Thus, the recombinant microorganism comprises an O-methyltransferase (OMT) which is capable of methylating eriodictyol and/or luteolin in position 4', preferably which is capable of specifically methylating the hydroxyl in position 4' of eriodictyol and/or luteolin so as to minimize the possibility of double methylation of the two hydroxyls or methylation of the other hydroxyl.

OMT: O-Methyltransferase

O-Methyltransferases (OMT) are a very large family of enzymes having targets that are difficult to define. The inventors had to identify and select O-methyltransferases that are capable of methylating eriodictyol and/or luteolin in position 4' (para position).

Preferably, the enzyme was selected so as to have a preference for methylation in position 4' of eriodictyol and/or luteolin. In a preferred embodiment, the enzyme is specific for position 4' of eriodictyol and/or luteolin. The term "specific" means that the methyl group introduced by the enzyme onto eriodictyol and/or luteolin is found in position 4' in 60% of the cases, the remainder being introduced into position 3', preferably in 70% of the cases, and even more preferably in 80% of the cases.

The term "4'-O-methyltransferase activity" means the transformation of a 4'-hydroxyflavonoid into a 4'-methoxyflavonoid by a 4'-O-methyltransferase enzyme. To determine whether there is 4'-O-methyltransferase activity, an enzymatic test may be performed, which consists of the in vitro incubation of a mixture composed of the 4'-O-methyltransferase enzyme, a 4'-hydroxyflavonoid and S-adenosyl-L-methionine, under optimum conditions (pH, temperature, ions, etc.). After a certain incubation time, the appearance of the 4'-methoxyflavonoid is observed in UPLC-MS in comparison with the expected standard.

In the present case, the 4'-hydroxyflavonoid is eriodictyol or luteolin, which will be transformed, respectively, into their 4'-methoxyflavonoid form, i.e. into hesperetin or diosmetin.

The microorganism may thus comprise a heterologous nucleic acid sequence coding for an O-methyltransferase which is capable of methylating eriodictyol and/or luteolin in position 4'.

This enzyme is present only in higher eukaryotes, in particular in plants.

In one embodiment, the O-methyltransferase (OMT) is an enzyme from *Arabidopsis thaliana*. In another embodiment, the O-methyltransferase (OMT) originates from a higher eukaryote, preferably from a mammal. In particular, the O-methyltransferase (OMT) is of human origin (*Homo sapiens*).

In a particular embodiment, the OMT is selected from enzymes comprising a sequence chosen from SEQ ID NOs: 87 and 89 and polypeptides comprising a sequence having at least 60, 70, 80, 85, 90 or 95% identity with one of these sequences and having O-methyltransferase activity, notably with eriodictyol and/or luteolin as substrate and with methylation in position 4'.

In one embodiment, the OMT is selected from the enzyme comprising a sequence chosen from SEQ ID NO: 89 and polypeptides comprising a sequence having at least 60, 70, 80, 85, 90 or 95% identity with this sequence and having O-methyltransferase activity.

In another embodiment, the OMT is selected from the enzyme comprising a sequence chosen from SEQ ID NO: 87 and polypeptides comprising a sequence having at least 60, 70, 80, 85, 90 or 95% identity with this sequence and having O-methyltransferase activity. Thus, the OMT may be from *Arabidopsis thaliana*. The nucleic acid sequences coding for this enzyme and protein sequences are described in NCBI under the reference numbers NM_118755.4 and NP_567739.1, respectively. The protein is also described in UniProtKB/Swiss Prot under the reference number Q9C5D7, and more particularly in SEQ ID NO: 87.

Alternatively, the OMT is from *Homo sapiens*. The nucleic acid sequences coding for this enzyme and protein sequences are described in NCBI under the reference numbers NM_007310.2 and NP_009294.1, respectively. The protein is also described in UniProtKB/Swiss Prot under the reference number P21964, and more particularly in SEQ ID NO: 89.

The OMT from *Homo sapiens* has the advantage of accepting eriodictyol and luteolin as substrate for the methylation, whereas the OMT from *Arabidopsis thaliana* has a strong preference for eriodictyol. Conversely, if the synthesis of hesperetin is to be favored relative to that of diosmetin, the OMT from *Arabidopsis thaliana* might have an advantage.

In a preferred embodiment, the OMT is an OMT from *Citrus*, in particular *Citrus clementina* or *Citrus sinensis*. In a particularly preferred embodiment, the OMT is selected from an enzyme comprising a sequence chosen from SEQ ID NOs 91 and 93 and polypeptides comprising a sequence having at least 60, 70, 80, 85, 90 or 95% identity with one of these sequences and having O-methyltransferase activity.

Preferably, the OMT is selected from an enzyme comprising a sequence chosen from SEQ ID NO: 91 and polypeptides comprising a sequence having at least 60, 70, 80, 85, 90 or 95% identity with this sequence and having O-methyltransferase activity.

Alternatively, the OMT is selected from an enzyme comprising a sequence chosen from SEQ ID NO: 93 and polypeptides comprising a sequence having at least 60, 70, 80, 85, 90 or 95% identity with this sequence and having O-methyltransferase activity.

The OMTs from *Citrus* and from *Arabidopsis thaliana* described above have the advantage of specifically methylating eriodictyol in position 4'.

During the design of the microorganism, the inventors observed that this methylation step constituted one of the limiting steps. Surprisingly, despite the presence of the cofactor S-adenosyl-L-methionine in the microorganism, in particular the yeast, the addition of an enzyme which increases the synthesis of this cofactor made it possible to dispel the limiting aspect of this step. Thus, in a preferred embodiment, the microorganism also comprises a heterologous or endogenous sequence coding for an enzyme which synthesizes S-adenosyl-L-methionine, an S-adenosylmethionine synthetase (SAMT). This enzyme belongs to the class EC 2.5.1.6.

In one embodiment, the microorganism comprises a heterologous nucleic acid sequence coding for an O-methyltransferase (OMT), which is in particular capable of methylating eriodictyol and/or luteolin in position 4' and a heterologous or endogenous nucleic acid sequence coding for an S-adenosylmethionine synthetase (SAMT).

In one embodiment, the SAMT originates from a yeast, in particular from *Saccharomyces cerevisiae*, most particularly when the microorganism is a yeast.

In a particular embodiment, the S-adenosylmethionine synthetase is an enzyme comprising a sequence chosen from SEQ ID NO: 81 and a polypeptide comprising a sequence having at least 60, 70, 80, 85, 90 or 95% identity with this sequence and having S-adenosylmethionine synthetase activity.

For example, the S-adenosylmethionine synthase may be from *Saccharomyces cerevisiae*.

It is described in the GenBank database from NCBI under the number NM_001180810.3 for the nucleic acid sequence and under the number NP_010790.3 for the protein sequence. The protein is described in UniProtKB/Swiss Prot under the reference number P19358.

In one embodiment, a new copy of a sequence coding for SAMT as defined above is introduced into the microorganism. In another embodiment, when the microorganism is *Saccharomyces cerevisiae*, the promoter of the endogenous gene coding for SAMT is replaced with a strong promoter. Thus, the expression of the SAMT is increased relative to the wild-type microorganism; the SAMT is thus overexpressed in the modified microorganism.

Thus, in a preferred embodiment, the microorganism comprises a heterologous nucleic acid sequence coding for an O-methyltransferase which is capable of methylating eriodictyol and/or luteolin in position 4' and a heterologous or endogenous nucleic acid sequence coding for an S-adenosylmethionine synthetase (SAMT) which is capable of producing S-adenosyl-L-methionine.

F3'H: Flavonoid 3'-monooxygenase

Several biosynthetic strategies were possible for preparing hesperetin and/or diosmetin from naringenin/apigenin. Indeed, it is necessary to make two modifications: methylation of the hydroxyl in position 4' and hydroxylation of position 3'. Thus, to increase the specificity of methylation of the hydroxyl in position 4', it appears logical to first perform methylation of the hydroxyl group already present before adding a second hydroxyl group in position 3'. On the contrary, the inventors arrived at the conclusion that it was necessary first to perform the hydroxylation and then the methylation, despite the risk of the problem of methylation specificity due to the introduction of the second hydroxyl.

To do this, the inventors had to identify and select enzymes that are capable of accepting naringenin and/or apigenin as substrate and of adding a hydroxyl group in position 3' of these compounds. Preferably, the enzyme is selected so as to have a preference for hydroxylation in position 3' of naringenin and/or apigenin. In a preferred embodiment, the enzyme is specific for the 3' position of naringenin and/or apigenin, in particular so as to avoid a double hydroxylation in positions 3' and 5', and preferably also to avoid hydroxylation in position 5'.

Flavonoid 3'-monooxygenase (F3'H) is an enzyme which performs the addition of a hydroxyl group in position 3' of naringenin and/or apigenin. This enzyme belongs to the class EC 1.14.14.82. It is also known as flavonoid 3'-hydroxylase.

The term "flavonoid 3'-monooxygenase activity" means the transformation of a flavonoid into a 3'-hydroxylated flavonoid by a CPR-dependent F3'H enzyme. To determine whether there is flavonoid 3'-monooxygenase activity, an enzymatic test may be performed, which consists of the in vitro incubation of the flavonoid 3'-monooxygenase enzyme in the presence of NAD(P)H, $O_2$, and of a flavonoid, under optimum conditions (pH, ions, etc.), and observation by UPLC-MS and comparison with the standard expected for the appearance of a 3'-hydroxylated flavonoid. Preferably, the flavonoid is naringenin or apigenin and the 3'-hydroxylated flavonoid is the 3'-hydroxylated form thereof, i.e. eriodictyol or luteolin.

The microorganism may thus comprise a heterologous nucleic acid sequence coding for a flavonoid 3'-monooxygenase (F3'H) which is capable of adding a hydroxyl in position 3' of naringenin and/or apigenin.

In one embodiment, the F3'H is a plant enzyme, notably from plants of the genus *Allium, Arabidopsis, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa, Arabidopsis thaliana, Brassica napus, Columnea hybrida, Callistephus chinensis, Citrus sinensis, Citrus clementina, Dianthus caryophyllus, Fragaria vesca, Fragaria x ananassa, Gerbera hybrida, Glycine max, Gentiana triflora, Ipomoea nil, Ipomoea purpurea, Ipomoea tricolor, Matthiola incana, Malus domestica, Osteospermum* hybrid cultivar, *Oryza sativa, Phanerochaete chrysosporium, Pilosella officinarum, Petroselinum crispum, Pelargonium* x *hortorum, Perilla frutescens* var. *crispa, Petunia* x *hybrida, Sinningia cardinalis, Sorghum bicolor, Torenia* sp, *Torenia* hybrid cultivar, *Vitis vinifera* or *Zea mays*. In a more specific embodiment, the F3'H is an enzyme from plants of the genus *Allium, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa, Brassica napus, Columnea hybrida, Callistephus chinensis,*

*Citrus sinensis, Citrus clementina, Dianthus caryophyllus, Fragaria vesca, Fragaria × ananassa, Gerbera hybrida, Glycine max, Gentiana triflora, Ipomoea nil, Ipomoea purpurea, Ipomoea tricolor, Matthiola incana, Malus domestica, Osteospermum* hybrid cultivar, *Oryza sativa, Phanerochaete chrysosporium, Pilosella officinarum, Petroselinum crispum, Pelargonium × hortorum, Perilla frutescens* var. *crispa, Petunia × hybrida, Sinningia cardinalis, Sorghum bicolor, Torenia* sp, *Torenia* hybrid cultivar, *Vitis vinifera* or *Zea mays*.

Preferably, the F3'H is an enzyme from *Perilla frutescens* var. *crispa, Petunia × hybrida, Callistephus chinensis, Gerbera hybrida, Citrus clementina, Osteospermum* cultivar, *Phanerochaete chrysosporium, Streptomyces avermitilis, Citrus sinensis, Arabidopsis thaliana* or *Pilosella officinarum*. In particular, the F3'H may be an enzyme from *Perilla frutescens* var. *crispa, Petunia × hybrida, Callistephus chinensis, Gerbera hybrida, Citrus sinensis* and *Pilosella officinarum*.

In a particular embodiment, the F3'H is selected from enzymes comprising a sequence chosen from SEQ ID NOs: 1, 3, 5, 7, 9, 11, 13, 15, 17, 19, 21 and 95, in particular from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 95, in particular from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, notably with naringenin and/or apigenin as substrate and with hydroxylation in position 3'. In a particular embodiment, the F3'H is an enzyme comprising a sequence selected from SEQ ID NOs: 5, 7 and 17 and polypeptides comprising a sequence having at least 60, 70, 80, 85, 90 or 95% identity with one of these sequences and having flavonoid 3'-monooxygenase activity. In a preferred embodiment, the F3'H is an enzyme comprising a sequence selected from SEQ ID NOs: 7, 11, 17 and 95 and polypeptides comprising a sequence having at least 60, 70, 80, 85, 90 or 95% identity with one of these sequences and having flavonoid 3'-monooxygenase activity. Most particularly preferably, the F3'H may be an enzyme comprising a sequence selected from SEQ ID NOs: 7, 17 and 95 and polypeptides comprising a sequence having at least 60, 70, 75, 80, 85, 90 or 95% identity with one of these sequences and having flavonoid 3'-monooxygenase activity.

Thus, the F3'H may be from *Perilla frutescens* var. *crispa*. The nucleic acid sequences coding for this enzyme and protein sequences are described in NCBI under the reference numbers AB045593.1 and BAB59005.1, respectively, and more particularly in SEQ ID NOs: 2 and 1.

The F3'H may be from *Phanerochaete chrysosporium*. The nucleic acid sequences coding for this enzyme and protein sequences are described in NCBI under the reference numbers AB597870.1 and BAL05157.1, respectively, and more particularly in SEQ ID NOs: 4 and 3.

The F3'H may be from *Petunia × hybrida*. The nucleic acid sequences coding for this enzyme and protein sequences are described in NCBI under the reference numbers AF155332.1 and AAD56282.1, respectively, and more particularly in SEQ ID NOs: 6 and 5.

The F3'H may be from *Callistephus chinensis*. In one embodiment, the nucleic acid sequences coding for this enzyme and protein sequences are described in NCBI under the reference numbers AF313488.1 and AAG49298.1, respectively, and more particularly in SEQ ID NOs: 8 and 7. In another embodiment, the nucleic acid sequences coding for this enzyme and protein sequences are described in NCBI under the reference numbers AF313489.1 and AAG49299.1, respectively, and more particularly in SEQ ID NOs: 10 and 9. The F3'H may be from *Gerbera hybrida*. The nucleic acid sequences coding for this enzyme and protein sequences are described in NCBI under the reference numbers DQ218417.1 and ABA64468.1, respectively, and more particularly in SEQ ID NOs: 12 and 11.

The F3'H may be from *Osteospermum* hybrid cultivar. The nucleic acid sequences coding for this enzyme and protein sequences are described in NCBI under the reference numbers DQ250711.1 and ABB29899.1, respectively, and more particularly in SEQ ID NOs: 14 and 13. The F3'H may be from *Citrus clementina*. The nucleic acid sequences coding for this enzyme and protein sequences are described in NCBI under the reference numbers XM_006440673.1 and XP_006440736.1, respectively, and more particularly in SEQ ID NOs: 16 and 15.

The F3'H may be from *Citrus sinensis*. The nucleic acid sequences coding for this enzyme and protein sequences are described in NCBI under the reference numbers XM_006477592.2 and XP_006477655.1, respectively, and more particularly in SEQ ID NOs: 18 and 17.

The F3'H may be from *Pilosella officinarum*. The nucleic acid sequences coding for this enzyme and protein sequences are described in NCBI under the reference numbers DQ319866.2 and ABC47161.1, respectively, and more particularly in SEQ ID NOs: 20 and 19.

The F3'H may be from *Streptomyces avermitilis*. The nucleic acid sequences coding for this enzyme and protein sequences are described in NCBI under the reference numbers SAV_4539 and WP_010985964.1, respectively, and more particularly in SEQ ID NOs: 22 and 21.

The F3'H may be from *Arabidopsis thaliana*. A nucleic acid sequence coding for this enzyme and the protein sequence are described in NCBI under the reference numbers NM_120881.2 and NP_196416.1, respectively, and more particularly in SEQ ID NOs: 96 and 95.

Preferably, the F3'H is an enzyme comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity. Most particularly preferably, the F3'H is an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity.

According to a preferred embodiment, the F3'H is an enzyme comprising a sequence chosen from SEQ ID NO: 7 and polypeptides comprising a sequence having at least 75%, at least 80%, at least 85%, at least 90% or at least 95% sequence identity with the sequence SEQ ID NO: 7 and having flavonoid 3'-monooxygenase activity.

According to another particular embodiment, the F3'H is an enzyme comprising a sequence chosen from SEQ ID NO: 17 and polypeptides comprising a sequence having at least 75%, at least 80%, at least 85%, at least 90% or at least 95% sequence identity with the sequence SEQ ID NO: 17 and having flavonoid 3'-monooxygenase activity.

According to another particular embodiment, the F3'H is an enzyme comprising a sequence chosen from SEQ ID NO: 95 and polypeptides comprising a sequence having at least 70%, at least 75%, at least 80%, at least 85%, at least 90% or at least 95% sequence identity with the sequence SEQ ID NO: 95 and having flavonoid 3'-monooxygenase activity.

According to another particular embodiment, the F3'H is an enzyme comprising a sequence chosen from SEQ ID NO: 11 and polypeptides comprising a sequence having at least 75%, at least 80%, at least 85%, at least 90% or at least 95% sequence identity with the sequence SEQ ID NO: 11 and having flavonoid 3'-monooxygenase activity.

Thus, in one embodiment, the microorganism comprises a heterologous nucleic acid sequence coding for an O-methyltransferase (OMT), in particular which is capable of methylating eriodictyol and/or luteolin in position 4' and a heterologous nucleic acid sequence coding for a flavonoid 3'-monooxygenase (F3'H), in particular which is capable of adding a hydroxyl in position 3' of naringenin and/or apigenin.

CPR: Cytochrome P450 Reductase

Flavonoid 3'-monooxygenase (F3'H) requires the presence of NADPH to perform the addition of the hydroxyl group.

Thus, in a preferred embodiment, the microorganism comprises a heterologous or endogenous nucleic acid coding for a cytochrome P450 reductase, an NADPH-cytochrome P450 reductase. This enzyme belongs to the class EC 1.6.2.4.

Thus, in a particular embodiment, the microorganism comprises a heterologous nucleic acid sequence coding for a flavonoid 3'-monooxygenase (F3'H), which is in particular capable of adding a hydroxyl in position 3' of naringenin and/or apigenin; and a heterologous or endogenous nucleic acid coding for a cytochrome P450 reductase.

Cytochrome P450 reductase originates from a eukaryote, notably from a yeast, for example of the genus *Saccharomycetales*, or from a plant, for example a plant of the genus *Arabidopsis, Ammi, Avicennia, Camellia, Camptotheca, Catharanthus, Citrus, Glycine, Helianthus, Lotus, Mesembryanthemum, Phaseolus, Physcomitrella, Pinus, Populus, Ruta, Saccharum, Solanum, Vigna, Vitis* or *Zea*.

In a preferred embodiment, the cytochrome P450 reductase originates from a eukaryote, for example from yeast, in particular from *Saccharomyces cerevisiae*, or from a plant, for example from *Catharanthus roseus* or *Arabidopsis thaliana*.

In a particular embodiment, the cytochrome P450 reductase is selected from enzymes comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity. In a preferred embodiment, the cytochrome P450 reductase may be selected from enzymes comprising a sequence chosen from SEQ ID NO: 25 and polypeptides comprising a sequence having at least 60, 70, 80, 85, 90 or 95% sequence identity with this sequence and having cytochrome P450 reductase activity.

For example, the cytochrome P450 reductase may be from *Catharanthus roseus*. It is described in the GenBank database from NCBI under the number X69791.1 for the nucleic acid sequence and under the number CAA49446.1 for the protein sequence, and more particularly in SEQ ID NOs: 24 and 23, respectively. The protein is described in UniProtKB/Swiss Prot under the reference number Q05001.

The cytochrome P450 reductase may be from *Saccharomyces cerevisiae*. It is described in the GenBank database from NCBI under the number NM_001179172.1 for the nucleic acid sequence and under the number NP_011908.1 for the protein sequence, and more particularly in SEQ ID NOs: 26 and 25, respectively. The protein is described in UniProtKB/Swiss Prot under the reference number P16603.

The cytochrome P450 reductase may be chimeric. It is described in the article by Aigrain et al. (2009, EMBO Reports, 10, 742-747). The nucleic acid sequence coding for this enzyme and the protein sequence are described in SEQ ID NOs: 28 and 27, respectively. Moreover, the cytochrome P450 reductase may be from *Arabidopsis thaliana*. When the cytochrome P450 originates from *Arabidopsis thaliana*, it may be named ATR. It is described in the GenBank database from NCBI under the number NM_118585.4 for the nucleic acid sequence and under the number NP_194183.1 for the protein sequence, and more particularly in SEQ ID NOs: 30 and 29, respectively. The protein is described in UniProtKB/Swiss Prot under the reference number Q9SB48.

In addition, the cytochrome P450 reductase may be from *Arabidopsis thaliana* and may be described in the GenBank database from NCBI under the number NM_179141.2 for the nucleic acid sequence and under the number NP_849472.2 for the protein sequence, and more particularly in SEQ ID NOs: 32 and 31, respectively. The protein is described in UniProtKB/Swiss Prot under the reference number Q9SUM3.

In one embodiment, a new copy of a sequence coding for CPR as defined above is introduced into the yeast. In another embodiment, when the yeast is *Saccharomyces cerevisiae* and when the CPR originates from the same yeast, the promoter of the endogenous gene coding for CPR is replaced with a strong promoter. Thus, the expression of the CPR is increased relative to the wild-type yeast; the CPR is thus overexpressed in the modified yeast.

In a particular embodiment, the F3'H and the CPR are from the same origin, the same species.

FNS: Flavone Synthase

Diosmetin may be produced from luteolin. It may also be obtained from eriodictyol, either by transforming it into luteolin and then preparing diosmetin from luteolin, or by transforming it into hesperetin and then preparing diosmetin from hesperetin. The enzyme that is capable of transforming eriodictyol into luteolin and/or hesperetin into diosmetin is a flavone synthase (FNS). In a particular embodiment, the flavone synthase is also capable of transforming eriodictyol into luteolin.

Thus, the microorganism may comprise a heterologous nucleic acid sequence coding for a flavone synthase, in particular a flavone synthase which is capable of producing luteolin from eriodictyol and/or diosmetin from hesperetin.

The term "flavone synthase activity" means the transformation of a flavanone into flavone by an FNSI enzyme (CPR-independent) or an FNSII enzyme (CPR-dependent).

To determine if there is flavone synthase activity, an enzymatic test may be performed, which consists of the in vitro incubation in the case of FNSI of a mixture composed of the flavone synthase enzyme (FNSI), a flavanone, 2-oxoglutarate and $O_2$, under optimum conditions (pH, temperature, ions, etc.) and in the case of FNSII of a mixture composed of the enzyme FNSII, a flavanone, NAD(P)H and $O_2$, under optimum conditions (pH, temperature, ions, etc.). After a certain incubation time, the appearance of the flavone corresponding to the flavanone is observed in UPLC-MS in comparison with the expected standard. Preferably, the flavanone is eriodictyol or hesperetin, which will be transformed, respectively, into their flavone form, i.e. into luteolin or diosmetin.

Thus, in a particular embodiment, the microorganism comprises a heterologous nucleic acid sequence coding for an O-methyltransferase (OMT), which is in particular capable of methylating eriodictyol and/or luteolin in position 4'; and a heterologous nucleic acid sequence coding for a flavone synthase, in particular a flavone synthase which is capable of producing luteolin from eriodictyol and/or diosmetin from hesperetin.

Preferably, the flavone synthase is an enzyme originating from a plant, for example of the genus *Aethusa, Angelica, Antirrhinum, Apium, Arabidopsis, Callistephus, Camellia, Conium, Cuminum, Cynara, Dahlia, Dorcoceras, Erythranthe, Lonicera, Medicago, Oryza, Perilla, Petroselinum, Plectranthus, Populus, Saussurea, Scutellaria* or *Zea*, in particular of the genus *Arabidopsis, Lonicera, Medicago, Oryza, Petroselinum, Populus* or *Zea*, notably of *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Petroselinum crispum*, or of the genus *Lonicera*, for instance *Lonicera japonica* and *Lonicera macranthoides*.

In a particular embodiment, the flavone synthase (FNS) is selected from enzymes comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity. In particular, the flavone synthase (FNS) is selected from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity. Preferably, the FNS is selected from enzymes comprising a sequence chosen from SEQ ID NO: 37 and polypeptides comprising a sequence having at least 60, 70, 80, 85, 90 or 95% sequence identity with this sequence and having flavone synthase activity.

There are two types of flavone synthase (FNS): flavone synthase 1 (FNSI) and flavone synthase 2 (FNSII). Starting with a flavanone and 2-oxoglutarate, FNSI is capable of producing the corresponding flavone. The enzyme FNSI belongs to the class EC 1.14.11.22. FNSII belongs to the P450 group and requires the presence of a cytochrome P450 reductase. The enzyme FNSII belongs to the class EC 1.14.13.

In one embodiment, the FNS is a type I flavone synthase. In another embodiment, the FNS is a type II flavone synthase. In an additional embodiment, the microorganism comprises a type I flavone synthase and a type II flavone synthase.

In a preferred embodiment, the microorganism comprises a heterologous nucleic acid sequence coding for a type I flavone synthase (FNSI). The advantage of FNSI is that it functions without cytochrome P450 reductase.

The FNSI may be a flavone synthase from a plant such as *Petroselinum crispum, Oryza sativa, Populus deltoides, Medicago truncatula, Apium graveolens, Cuminum cyminum, Aethusa cynapium, Angelica archangelica*, or *Conium maculatum*, in particular from *Petroselinum crispum, Oryza sativa, Populus deltoides* or *Medicago truncatula*, preferably from *Petroselinum crispum*.

The FNSI may be an enzyme comprising a sequence chosen from SEQ ID NOs: 37, 101, 111, 115, 117 and 119 and polypeptides comprising a sequence having at least 60, 70, 80, 85, 90 or 95% sequence identity with one of these sequences and having flavone synthase activity. In a particular aspect, the FNSI may be an enzyme comprising a sequence chosen from SEQ ID NO: 37 and a polypeptide comprising a sequence having at least 60, 70, 80, 85, 90 or 95% sequence identity with this sequence and having flavone synthase activity.

For example, the FNSI may be from *Petroselinum crispum*. It is described in the GenBank database from NCBI under the number AY817680.1 for the nucleic acid sequence and under the number AAX21541.1 for the protein sequence. The protein is described in UniProtKB/Swiss Prot under the reference number Q7XZQ8. The amino acid and nucleic acid sequences are described in SEQ ID NOs: 37 and 38, respectively.

The FNSI may also be from *Angelica archangelica*. It is described in the GenBank database from NCBI under the number DQ683352.1 for the nucleic acid sequence and under the number ABG78793.1 for the protein sequence. The amino acid and nucleic acid sequences are described in SEQ ID NOs: 101 and 102, respectively.

The FNSI may also be from *Apium graveolens*. It is described in the GenBank database from NCBI under the number AY817676.1 for the nucleic acid sequence and under the number AAX21537.1 for the protein sequence. The amino acid and nucleic acid sequences are described in SEQ ID NOs: 111 and 112, respectively.

The FNSI may also be from *Cuminum cyminum*. It is described in the GenBank database from NCBI under the number DQ683349.1 for the nucleic acid sequence and under the number ABG78790.1 for the protein sequence. The amino acid and nucleic acid sequences are described in SEQ ID NOs: 115 and 116, respectively.

The FNSI may also be from *Aethusa cynapium*. It is described in the GenBank database from NCBI under the number DQ683350.1 for the nucleic acid sequence and under the number DQ683350.1 for the protein sequence. The amino acid and nucleic acid sequences are described in SEQ ID NOs: 117 and 118, respectively.

The FNSI may also be from *Conium maculatum*. It is described in the GenBank database from NCBI under the number DQ683354.1 for the nucleic acid sequence and under the number ABG78795.1 for the protein sequence. The amino acid and nucleic acid sequences are described in SEQ ID NOs: 119 and 120, respectively.

In another embodiment, the microorganism comprises a heterologous nucleic acid sequence coding for a type II flavone synthase (FNSII).

The FNSII may be a flavone synthase from a plant, for example from *Arabidopsis thaliana, Zea mays*, of the genus *Lonicera*, for instance *Lonicera japonica* and *Lonicera macranthoides, Callistephus chinensis, Medicago truncatula, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular a flavone synthase from

*Arabidopsis thaliana* or *Zea mays* or of the genus *Lonicera*, for instance *Lonicera japonica* and *Lonicera macranthoides*.

In a particular embodiment, the flavone synthase (FNSII) is selected from enzymes comprising a sequence chosen from SEQ ID NOs: 33, 35, 103, 105, 107, 109, 113, 121, 123, 125, 127, 129, 131 and 133 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33 and 35 and polypeptides comprising a sequence having at least 60, 70, 80, 85, 90 or 95% sequence identity with one of these sequences and having flavone synthase activity.

In one embodiment, the flavone synthase FNS is an FNSII originating from *Lonicera japonica*. In this embodiment, the enzyme may be an enzyme described in the GenBank database from NCBI under the number KU127576.1 for the nucleic acid sequence and under the number AMQ91109.1 for the protein sequence, and more particularly in SEQ ID NOs: 34 and 33, respectively.

In another embodiment, the flavone synthase FNS is an FNSII originating from *Lonicera macranthoides*. The nucleic acid sequences coding for this enzyme and protein sequences are described in NCBI under the reference numbers KU127580.1 and AMQ91113.1, respectively, and more particularly in SEQ ID NOs: 36 and 35, respectively.

In another embodiment, the flavone synthase FNS is an FNSII originating from *Cynara cardunculus* var *scolymus*. The nucleic acid sequences coding for this enzyme and protein sequences are described in NCBI under the reference numbers JN825735.1 and AFG31000.1, respectively, and more particularly in SEQ ID NOs: 104 and 103, respectively.

In another embodiment, the flavone synthase FNS is an FNSII originating from *Perilla frutescens* var *crispa*. The nucleic acid sequences coding for this enzyme and protein sequences are described in NCBI under the reference numbers AB045592.1 and BAB59004.1, respectively, and more particularly in SEQ ID NOs: 106 and 105, respectively.

In another embodiment, the flavone synthase FNS is an FNSII originating from *Dahlia pinnata*. The nucleic acid sequences coding for this enzyme and protein sequences are described in NCBI under the reference numbers AB769842.1 and BAM72335.1, respectively, and more particularly in SEQ ID NOs: 108 and 107, respectively.

In another embodiment, the flavone synthase FNS is an FNSII originating from *Callistephus chinensis*. The nucleic acid sequences coding for this enzyme and protein sequences are described in NCBI under the reference numbers AF188612.1 and AAF04115.1, respectively, and more particularly in SEQ ID NOs: 110 and 109, respectively. In another embodiment, the flavone synthase FNS is an FNSII originating from *Medicago truncatula*. The nucleic acid sequences coding for this enzyme and protein sequences are described in NCBI under the reference numbers DQ354373.1 and ABC86159.1, respectively, and more particularly in SEQ ID NOs: 114 and 113, respectively.

In another embodiment, the flavone synthase FNS is an FNSII originating from *Camellia sinensis*. The nucleic acid sequences coding for this enzyme and protein sequences are described in NCBI under the reference numbers FJ169499.1 and ACH99109.1, respectively, and more particularly in SEQ ID NOs: 122 and 121, respectively.

In another embodiment, the flavone synthase FNS is an FNSII originating from *Saussurea medusa*. The nucleic acid sequences coding for this enzyme and protein sequences are described in NCBI under the reference numbers KF170286.1 and AGV40781.1, respectively, and more particularly in SEQ ID NOs: 124 and 123, respectively.

In another embodiment, the flavone synthase FNS is an FNSII originating from *Plectranthus barbatus*. The nucleic acid sequences coding for this enzyme and protein sequences are described in NCBI under the reference numbers KF606861.1 and AHJ89438.1, respectively, and more particularly in SEQ ID NOs: 126 and 125, respectively. In another embodiment, the flavone synthase FNS is an FNSII originating from *Scutellaria baicalensis*. The nucleic acid sequences coding for this enzyme and protein sequences are described in NCBI under the reference numbers KT963454.1 and AMW91729.1, respectively, and more particularly in SEQ ID NOs: 128 and 127, respectively.

In another embodiment, the flavone synthase FNS is an FNSII originating from *Dorcoceras hygrometricum*. The nucleic acid sequences coding for this enzyme and protein sequences are described in NCBI under the reference numbers KV013332.1 and KZV23934.1, respectively, and more particularly in SEQ ID NOs: 130 and 129, respectively.

In another embodiment, the flavone synthase FNS is an FNSII originating from *Antirrhinum majus*. The nucleic acid sequences coding for this enzyme and protein sequences are described in NCBI under the reference numbers AB028151.1 and BAA84071.1, respectively, and more particularly in SEQ ID NOs: 132 and 131, respectively.

In another embodiment, the flavone synthase FNS is an FNSII originating from *Erythranthe lewisii*. The nucleic acid sequences coding for this enzyme and protein sequences are described in NCBI under the reference numbers KX710102.1 and AOR81894.1, respectively, and more particularly in SEQ ID NOs: 134 and 133, respectively.

In a particular embodiment, the microorganism comprises a heterologous nucleic acid sequence coding for a type II flavone synthase (FNSII) and a type I flavone synthase, for example a sequence chosen from SEQ ID NOs: 33, 35, 103, 105, 107, 109, 113, 121, 123, 125, 127, 129, 131 and 133 and polypeptides comprising a sequence having at least 60, 70, 80, 85, 90 or 95% sequence identity with one of these sequences and having flavone synthase activity, and an enzyme comprising a sequence chosen from SEQ ID NOs: 37, 101, 111, 115, 117 and 119 and a polypeptide comprising a sequence having at least 60, 70, 80, 85, 90 or 95% sequence identity with one of these sequences and having flavone synthase activity, preferably a sequence chosen from SEQ ID NOs: 33 and 35 and polypeptides comprising a sequence having at least 60, 70, 80, 85, 90 or 95% sequence identity with one of these sequences and having flavone synthase activity and an enzyme comprising a sequence chosen from SEQ ID NO: 37 and a polypeptide comprising a sequence having at least 60, 70, 80, 85, 90 or 95% sequence identity with this sequence and having flavone synthase activity.

The type II FNSs, FNSII, require the presence of a cytochrome P450 reductase (CPR). If the microorganism does not comprise cytochrome P450 reductase, it will thus be necessary to introduce a heterologous cytochrome P450 reductase. If the microorganism already comprises one, it is possible to envisage either the overexpression of an endogenous cytochrome P450 reductase (for example by replacing the promoter with a strong promoter or by adding one or more copies of the coding sequence) or by also introducing a heterologous cytochrome P450 reductase.

In a particular embodiment, the type II FNS and the CPR are from the same origin, the same species.

Combination of Enzymes

Thus, the microorganism preferably comprises enzymes enabling the production of hesperetin and/or diosmetin from naringenin and/or apigenin.

In a first particular embodiment, the recombinant microorganism comprises:
- a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia* x *hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;
- optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity;
- a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity; and
- optionally, a heterologous nucleic acid sequence coding for a flavone synthase (FNS) which is capable of producing a flavone from a flavanone, in particular capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:
- a heterologous nucleic acid sequence coding for a flavonoid 3'-monooxygenase (F3'H) which is capable of hydroxylating naringenin and/or apigenin in position 3'; preferably from *Arabidopsis thaliana, Perilla frutescens* var. *crispa, Petunia* x *hybrida, Callistephus chinensis, Gerbera hybrida, Citrus sinensis, Citrus clementina, Osteospermum* hybrid cultivar, *Phanerochaete chrysosporium, Streptomyces avermitilis* or *Pilosella officinarum*, preferably an F3'H comprising a sequence chosen from SEQ ID NOs: 1, 3, 5, 7, 9, 11, 13, 15, 17, 19, 21 and 95 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 7, 11, 17 and 95 and polypeptides comprising a sequence having at least 60, 70, 80, 85, 90 or 95% sequence identity with one of these sequences and having flavonoid 3'-monooxygenase activity, and very particularly an F3'H comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;
- a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity; and
- optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:

a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Citrus clementina, Osteospermum* hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity; and a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity; and optionally, a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and very particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity; and optionally, a heterologous nucleic acid sequence coding for a cytochrome P450 reductase (CPR) and comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and very particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism also comprises a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

Each enzyme may be chosen from the enzymes described above.

Up to Naringenin and Apigenin

Various pathways for the biosynthesis of naringenin and apigenin are known in plants, in particular from glucose, tyrosine or phenylalanine. Microorganisms, notably *E. coli* and *Saccharomyces cerevisiae*, have been modified to produce naringenin and/or apigenin (Hwang E I, et al. 2003. Appl. Environ. Microbiol. 2003, 69(5): 2699-2706; Jiang H1, et al. 2005. Appl. Environ. Microbiol. 2005, 71(6): 2962-9; Pandey et al., 2016, Biotechnol. Adv., 34, 634-662).

For example, the pathway for the biosynthesis of naringenin and apigenin may be that described in FIG. 1.

In a first embodiment, the microorganism comprises the enzymes required for the synthesis of naringenin and/or apigenin from tyrosine.

In a second embodiment, the microorganism comprises the enzymes required for the synthesis of naringenin and/or apigenin from phenylalanine.

In a third embodiment, the microorganism comprises the enzymes required for the synthesis of naringenin and/or apigenin from tyrosine and phenylalanine.

TAL: Tyrosine Ammonia Lyase

TAL is a tyrosine ammonia lyase. This enzyme is capable of producing p-coumaric acid from tyrosine. This enzyme belongs to the class EC 4.3.1.23.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

A tyrosine ammonia lyase (TAL) may also have phenylalanine ammonia lyase (PAL) activity as defined above and/or dihydroxyphenylalanine ammonia-lyase (DAL) activity.

The microorganism may thus comprise a heterologous nucleic acid sequence coding for a tyrosine ammonia lyase.

Preferably, this enzyme is an enzyme produced by a bacterium of the genus *Rhodobacter* or a bacterium of the genus *Flavobacteriaceae*. In a particular embodiment, this enzyme is produced by a *Rhodobacter capsulatus* or *Rhodobacter sphaeroides* bacterium. In another particular embodiment, this enzyme is produced by a *Flavobacterium johnsoniae* bacterium. In another embodiment, this enzyme is an enzyme produced by a yeast, in particular a yeast of the genus *Rhodotorula*, for example *Rhodotorula glutinis*. Other organisms also produce such an enzyme, for example *Camellia sinensis, Fragaria x ananassa, Ralstonia metallidurans* or *Zea mays*.

In a particular embodiment, the tyrosine ammonia lyase is selected from enzymes comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity.

In a particular embodiment, the TAL is from *Flavobacterium johnsoniae*. It is described in the GenBank database from NCBI under the number KR095306.1 for the nucleic acid sequence and under the number AKE50827.1 for the protein sequence, and more particularly in SEQ ID NOs: 40 and 39.

In a particularly preferred embodiment, the TAL is from *Rhodotorula glutinis*. It is described in the GenBank database from NCBI under the number KF765779.1 for the nucleic acid sequence and under the number AGZ04575.1 for the protein sequence, and more particularly in SEQ ID NOs: 42 and 41, respectively.

In a particularly preferred embodiment, the tyrosine ammonia lyase is selected from the enzyme comprising a sequence chosen from SEQ ID NO: 41 and polypeptides comprising a sequence having at least 60, 70, 80, 85, 90 or 95% sequence identity with this sequence and having tyrosine ammonia lyase activity.

4CL: 4-Coumarate-CoA Ligase

4CL is a 4-coumarate-CoA ligase. This enzyme is capable of producing 4-coumaroyl-CoA from p-coumaric acid and Coenzyme A and of producing caffeoyl-CoA from caffeic acid and Coenzyme A. This enzyme belongs to the class EC 6.2.1.12.

The term "4-coumarate-CoA ligase activity" means the transformation of p-coumaric acid into p-coumaroyl-CoA or of caffeic acid into caffeoyl-CoA by the enzyme 4-coumarate CoA ligase. To determine whether there is 4-coumarate CoA ligase activity, an enzymatic test may be performed, which consists of the in vitro incubation of a mixture composed of the 4-coumarate CoA ligase enzyme, p-coumaric acid or caffeic acid, ATP and CoA under optimum conditions (pH, temperature, ions, etc.). After a certain incubation time, the appearance of p-coumaroyl-CoA or of caffeoyl-CoA is observed on the UV spectrophotometer at a wavelength of 333 nm and 346 nm, respectively, in comparison with the expected standard.

The microorganism may thus comprise a heterologous nucleic acid sequence coding for a 4-coumarate-CoA ligase.

Preferably, this enzyme is an enzyme produced by a plant, for example *Abies, Arabidopsis, Agastache, Amorpha, Brassica, Citrus, Cathaya, Cedrus, Crocus, Larix, Festuca, Glycine, Juglans, Keteleeria, Lithospermum, Lolium, Lotus, Lycopersicon, Malus, Medicago, Mesembryanthemum, Nicotiana, Nothotsuga, Oryza, Phaseolus, Pelargonium, Petroselinum, Physcomitrella, Picea, Prunus, Pseudolarix, Pseudotsuga, Rosa, Rubus, Ryza, Saccharum, Suaeda, Pinus, Populus, Solanum, Thellungiella, Triticum, Tsuga, Vitis* or *Zea*. Alternatively, this enzyme is an enzyme produced by a microorganism, for example *Aspergillus, Mycosphaerella, Mycobacterium, Neisseria, Neurospora, Streptomyces, Rhodobacter* or *Yarrowia*.

In a preferred embodiment, this enzyme is an enzyme produced by a plant, preferably *Arabidopsis thaliana, Citrus clementina* or *Petroselinum crispum*, in particular *Arabidopsis thaliana* or *Petroselinum crispum*, or by a bacterium, preferably of the genus *Streptomyces*, in particular *Streptomyces clavuligerus*.

In a particular embodiment, the 4-coumarate-CoA ligase is selected from enzymes comprising a sequence chosen from SEQ ID NOs: 43, 45, 47, 49, 97 and 99 and polypeptides comprising a sequence having at least 60, 70, 80, 85, 90 or 95% sequence identity with one of these sequences and having 4-coumarate-CoA ligase activity.

In another particular embodiment, the 4-coumarate-CoA ligase is an enzyme comprising a sequence selected from SEQ ID NOs: 43, 45, 47 and 49, preferably SEQ ID NOs: 45 and 49 and polypeptides comprising a sequence having at least 60, 70, 80, 85, 90 or 95% sequence identity with one of these sequences and having 4-coumarate-CoA ligase activity.

In a first particular embodiment, the 4CL is from *Arabidopsis thaliana*. It is described in the GenBank database from NCBI under the number AY099747.1 for the nucleic acid sequence and under the number AAM20598.1 for the protein sequence, and more particularly in SEQ ID NOs: 44 and 43, respectively.

In a second particular embodiment, the 4CL is from *Petroselinum crispum*. It is described in the GenBank database from NCBI under the number X13324.1 or X13325.1 for the nucleic acid sequence and under the number CAA31696.1 or CAA31697.1 for the protein sequence, respectively. The proteins are described in UniProtKB/Swiss Prot under the reference numbers P14912 and P14913, respectively, and more particularly in SEQ ID NOs: 46 and 45, and 48 and 47, respectively. Preferably, the 4CL is from *Petroselinum crispum* and is described in the GenBank database from NCBI under the number X13324.1 for the nucleic acid sequence and under the number CAA31696.1 for the protein sequence, and in UniProtKB/Swiss Prot under the reference number P14912, and more particularly in SEQ ID NOs: 46 and 45, respectively.

In a third particular embodiment, the 4CL is from *Streptomyces clavuligerus*. It is described in the GenBank database from NCBI under the number CP016559.1 for the nucleic acid sequence and under the number ANW18832.1 for the protein sequence, and more particularly in SEQ ID NOs: 50 and 49, respectively.

In a fourth particular embodiment, the 4CL is from *Citrus clementina*. A nucleotide sequence and the protein sequence of this enzyme are described, respectively, in SEQ ID NOs: 100 and 99.

In a fifth particular embodiment, the 4CL is from *Arabidopsis thaliana* and a nucleotide sequence and the protein sequence of this enzyme are described, respectively, in SEQ ID NOs: 98 and 97.

In a preferred embodiment, the 4CL is an enzyme comprising a sequence selected from SEQ ID NOs: 45, 97 and 99, preferably SEQ ID NOs: 97 and 45 and polypeptides comprising a sequence having at least 60, 70, 80, 85, 90 or 95% sequence identity with one of these sequences and having 4-coumarate-CoA ligase activity. Most particularly preferably, the 4CL is an enzyme comprising a sequence selected from SEQ ID NO: 45 and polypeptides comprising a sequence having at least 60, 70, 80, 85, 90 or 95% sequence identity with this sequence and having 4-coumarate-CoA ligase activity.

CHS: Chalcone Synthase

CHS is a chalcone synthase. This enzyme is capable of producing naringenin-chalcone from 4-coumaroyl-CoA and from malonyl-CoA and of producing eriodictyol-chalcone from caffeoyl-CoA and from malonyl-CoA. This enzyme belongs to the class EC 2.3.1.74.

The term "chalcone synthase activity" means the transformation of p-coumaroyl-CoA and of malonyl-CoA into naringenin chalcone or of caffeoyl-CoA and of malonyl-CoA into eriodictyol chalcone by means of the chalcone synthase enzyme. To determine whether there is chalcone synthase activity, an enzymatic test may be performed, which consists of the in vitro incubation of a mixture composed of the chalcone synthase enzyme, p-coumaroyl-CoA or caffeoyl-CoA and malonyl-CoA, under optimum conditions (pH, temperature, ions, etc.). After a certain incubation time, the appearance of naringenin chalcone or of eriodictyol chalcone, respectively, is observed in HPLC-MS in comparison with the expected standard.

The microorganism thus comprises a heterologous nucleic acid sequence coding for a chalcone synthase.

This enzyme may be an enzyme produced by a plant, notably of the genus *Arabidopsis, Avena, Cosmos, Citrus, Daucus, Fagopyrum, Freesia, Glycine, Glycyrrhiza, Humulus, Hypericum, Hordeum, Juglans, Medicago, Phaseolus, Physcomitrella, Plagiochasma, Petroselinum, Pueraria, Rubus, Secale, Scutellaria, Silene, Sinapis, Spinacia, Stellaria, Triticum, Tulipa, Verbena, Vitis* or *Xanthisma*, for example *Arabidopsis thaliana, Avena sativa, Cosmos sulphureus, Citrus sinensis, Daucus carota, Fagopyrum esculentum, Freesia* hybrid cultivar, *Glycine max, Glycyrrhiza echinata, Humulus lupulus, Hypericum androsaemum, Hordeum vulgare, Juglans* sp., *Medicago sativa, Phaseolus vulgaris, Physcomitrella patens, Plagiochasma appendiculatum, Petroselinum crispum, Pueraria montana* var. *lobata, Rubus idaeus, Secale cereale, Scutellaria baicalensis, Silene* sp., *Sinapis alba, Spinacia oleracea, Stellaria longipes, Triticum aestivum, Tulipa* hybrid cultivar, *Verbena* sp., *Vitis vinifera* or *Xanthisma gracile*.

Preferably, this enzyme is an enzyme produced by a plant, for example of the genus *Citrus*, in particular *Citrus sinensis*, or *Hordeum vulgare* or by a bacterium, preferably of the genus *Streptomyces*, in particular *Streptomyces clavuligerus*.

In a particular embodiment, the chalcone synthase is selected from enzymes comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity.

In a particularly preferred embodiment, the chalcone synthase is an enzyme comprising a sequence chosen from SEQ ID NO: 53 and polypeptides comprising a sequence having at least 60, 70, 80, 85, 90 or 95% sequence identity with this sequence and having chalcone synthase activity.

In a first particular embodiment, the CHS is from *Hordeum vulgare*. It is described in the GenBank database from NCBI under the number Y09233.1 for the nucleic acid sequence and under the number CAA70435.1 for the protein sequence, and more particularly in SEQ ID NOs: 52 and 51, respectively. The protein is described in UniProtKB/Swiss Prot under the reference number Q96562.

In a second particular embodiment, the CHS is from *Citrus sinensis*. It is described in the GenBank database from NCBI under the number AB009351.1 for the nucleic acid sequence and under the number BAA81664.1 for the protein sequence, and more particularly in SEQ ID NOs: 54 and 53, respectively.

In a third particular embodiment, the CHS is from *Citrus sinensis*. It is described in the GenBank database from NCBI under the number XM_006489733.1 for the nucleic acid sequence and under the number XP_006489796.1 for the protein sequence, and more particularly in SEQ ID NOs: 56 and 55, respectively.

In a fourth particular embodiment, the CHS is from *Streptomyces clavuligerus*. It is described in the GenBank database from NCBI under the number CP016559.1 for the nucleic acid sequence and under the number ANW16917.1 for the protein sequence, and more particularly in SEQ ID NOs: 58 and 57, respectively.

Since the reaction catalyzed by chalcone synthase requires the presence of malonyl-CoA, the microorganism can be modified to increase the synthesis of malonyl-CoA.

CHI: Chalcone Isomerase

CHI is a chalcone isomerase. It is capable of producing naringenin from naringenin chalcone and of producing eriodictyol from eriodictyol chalcone. This enzyme belongs to the class EC 5.5.1.6.

The term "chalcone isomerase activity" means the transformation of naringenin chalcone or of eriodictyol chalcone into naringenin or eriodictyol by a chalcone isomerase enzyme. To determine whether there is chalcone isomerase activity, an enzymatic test may be performed, which consists of the in vitro incubation of a mixture composed of the chalcone isomerase enzyme, naringenin chalcone or eriodictyol chalcone under optimum conditions (pH, temperature, ions, etc.). After a certain incubation time, the appearance of naringenin or of eriodictyol, respectively, is observed in HPLC-MS in comparison with the expected standard.

The microorganism thus comprises a heterologous nucleic acid sequence coding for a chalcone isomerase.

This enzyme may originate from a plant, notably of the genus *Arabidopsis, Ginkgo, Oncidium, Perilla, Citrus* or *Trigonella*, for example *Arabidopsis thaliana, Ginkgo biloba, Oncidium Gower Ramsey, Perilla frutescens, Citrus Sinensis* or *Trigonella foenum-graecum*.

Preferably, this enzyme is an enzyme produced by a plant, for example *Arabidopsis thaliana* or by a bacterium, preferably of the genus *Streptomyces*, in particular *Streptomyces clavuligerus*.

In a particular embodiment, the chalcone isomerase is selected from enzymes comprising a sequence chosen from SEQ ID NOs: 59 and 61 and polypeptides comprising a sequence having at least 60, 70, 80, 85, 90 or 95% sequence identity with one of these sequences and having chalcone isomerase activity.

In a preferred embodiment, the chalcone isomerase is selected from enzymes comprising a sequence chosen from SEQ ID NO: 61 and polypeptides comprising a sequence having at least 60, 70, 80, 85, 90 or 95% sequence identity with this sequence and having chalcone isomerase activity.

In a first particular embodiment, the CHI is from *Streptomyces clavuligerus*. It is described in the GenBank database from NCBI under the number CP016559.1 for the nucleic acid sequence and under the number ANW16918.1 for the protein sequence, and more particularly in SEQ ID NOs: 60 and 59, respectively.

In a second particular embodiment, the CHI is from *Arabidopsis thaliana*. It is described in the GenBank database from NCBI under the number NM_115370.4 for the nucleic acid sequence and under the number NP_191072.1 for the protein sequence, and more particularly in SEQ ID NOs: 62 and 61, respectively.

FNS: Flavone Synthase

Apigenin may be prepared from naringenin using a flavone synthase (FNS). It is capable of producing apigenin from naringenin.

The microorganism may thus comprise a heterologous nucleic acid sequence coding for a flavone synthase, which is in particular capable of producing apigenin from naringenin and/or a heterologous nucleic acid sequence coding for a flavone synthase, which is in particular capable of producing luteolin from eriodictyol, and/or a heterologous nucleic acid sequence coding for a flavone synthase, which is in particular capable of producing diosmetin from hesperetin.

The FNS may be chosen from those described previously.

Starting with Phenylalanine

Alternatively or in addition, the microorganism may also comprise the enzymes required for the synthesis of p-coumaric acid from phenylalanine.

In this context, the microorganism may also comprise a heterologous nucleic acid sequence coding for a phenylalanine ammonia lyase (PAL) and a heterologous nucleic acid sequence coding for a cinnamate 4-hydroxylase (C4H).

PAL belongs to the class EC 4.3.1.24. It is capable of producing cinnamic acid from phenylalanine.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

Several enzymes have already been described in the prior art. Preferably, the enzyme originates from a plant, for example a plant of the genus *Arabidopsis, Agastache, Ananas, Asparagus, Brassica, Bromheadia, Barnbusa, Beta, Betula, Citrus, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Phaseolus, Pinus, Populus, Pisum, Persea, Petroselinum, Phalaenopsis, Phyllostachys, Physcomitrella, Picea, Pyrus, Prunus, Quercus, Raphanus, Rehmannia, Rubus, Solanum, Sorghum, Sphenostylis, Stellaria, Stylosanthes, Triticum, Trifolium, Vaccinium, Vigna, Vitis, Zea* or *Zinnia*. For example, mention may be made of those from *Arabidopsis thaliana* or from *Petroselinum crispum*.

In addition, phenylalanine ammonia lyase (PAL) may also have tyrosine ammonia lyase (TAL) activity and/or dihydroxyphenylalanine ammonia-lyase (DAL) activity as defined below.

In a preferred embodiment, the PAL is from *Citrus sinensis*.

In a particular embodiment, the phenylalanine ammonia lyase (PAL) is selected from enzymes comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity.

In a preferred embodiment, the PAL is selected from enzymes comprising a sequence chosen from SEQ ID NOs: 65 and 77 and polypeptides comprising a sequence having at least 60, 70, 80, 85, 90 or 95% sequence identity with one of these sequences and having phenylalanine ammonia lyase activity. Most particularly preferably, the PAL is selected from enzymes comprising a sequence chosen from SEQ ID NO: 65 and polypeptides comprising a sequence having at least 60, 70, 80, 85, 90 or 95% sequence identity with this sequence and having phenylalanine ammonia lyase activity.

In a particular embodiment, the PAL from *Citrus sinensis* is described in the GenBank database from NCBI under the number XM_006481431.2 for the nucleic acid sequence and under the number XP_006481494.1 for the protein sequence, and more particularly in SEQ ID NOs: 64 and 63, respectively.

In another particular embodiment, the PAL from *Citrus sinensis* is described in the GenBank database from NCBI under the number XM_006488000.2 for the nucleic acid sequence and under the number XP_006488063.1 for the protein sequence, and more particularly in SEQ ID NOs: 66 and 65, respectively.

In another particular embodiment, the PAL from *Arabidopsis thaliana* is described in the GenBank database from NCBI under the number NM_115186.4 for the nucleic acid sequence and under the number NP_190894.1 for the protein sequence, and more particularly in SEQ ID NOs: 78 and 77, respectively.

Optionally, if biosynthesis starting with tyrosine and phenylalanine is envisaged, the PAL and the TAL may be replaced or supplemented with a phenylalanine/tyrosine ammonia lyase (PTAL). PTAL belongs to the class EC 4.3.1.25.

C4H belongs to the class EC 1.14.13.11. It is capable of producing p-coumaric acid from cinnamic acid.

The term "trans-cinnamate 4-monooxygenase activity" means the transformation of trans-cinnamic acid into p-coumaric acid by a trans-cinnamate 4-monooxygenase enzyme (CPR-dependent). To determine whether there is trans-cinnamate 4-monooxygenase activity, an enzymatic test may be performed, which consists of the in vitro incubation of a mixture composed of the trans-cinnamate 4-monooxygenase enzyme, cinnamic acid, NADPH, $H^+$ and $O_2$, under optimum conditions (pH, temperature, ions, etc.). After a certain incubation time, the appearance of the 4-hydroxycinnamate (p-coumaric acid) is observed in UPLC-MS in comparison with the expected standard.

Several enzymes have already been described in the prior art. Preferably, the enzyme originates from a plant, for example a plant of the genus *Arabidopsis, Ammi, Avicennia, Camellia, Camptotheca, Catharanthus, Citrus, Glycine, Helianthus, Lotus, Mesembryanthemum, Physcomitreila, Phaseolus, Pinus, Populus, Ruta, Saccharum, Solanum, Vitis, Vigna* or *Zea*.

In a preferred embodiment, the cinnamate 4-hydroxylase (C4H) is from *Citrus sinensis* or from *Arabidopsis thaliana*.

In a particular embodiment, the cinnamate 4-hydroxylase (C4H) is selected from enzymes comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity.

In a preferred embodiment, the C4H is selected from enzymes comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a particular embodiment, the C4H from *Citrus sinensis* is described in the GenBank database from NCBI under the number NM_001288840.1 for the nucleic acid sequence and under the number NP_001275769.1 for the protein sequence, and more particularly in SEQ ID NOs: 68 and 67, respectively.

In another particular embodiment, the C4H from *Citrus sinensis* is described in the GenBank database from NCBI under the number NM_001288895.1 for the nucleic acid sequence and under the number NP_001275824.1 for the protein sequence, and more particularly in SEQ ID NOs: 70 and 69, respectively.

In another particular embodiment, the C4H from *Arabidopsis thaliana* is described in the GenBank database from NCBI under the number NM_128601.3 for the nucleic acid sequence and under the number NP_180607.1 for the protein sequence, and more particularly in SEQ ID NOs: 80 and 79, respectively.

Proceeding Via Caffeic Acid

In an additional embodiment, the biosynthesis of eriodictyol may also comprise the synthesis of L-DOPA (3,4-dihydroxy-L-phenylalanine) from tyrosine and then of caffeic acid from L-DOPA (3,4-dihydroxy-L-phenylalanine). To do this, the following enzymes are necessary. To convert tyrosine into L-DOPA (3,4-dihydroxy-L-phenylalanine), two subunits are necessary, HpaB and HpaC.

HpaB is a 4-hydroxyphenylacetate 3-monooxygenase oxygenase subunit (HpaB).

Preferably, this enzyme is an enzyme produced by a bacterium, preferably *Escherichia coli*.

In a particular embodiment, the 4-hydroxyphenylacetate 3-monooxygenase oxygenase (HpaB) is an enzyme comprising a sequence chosen from SEQ ID NO: 83 and polypeptides comprising a sequence having at least 60, 70, 80, 85, 90 or 95% sequence identity with this sequence and having 4-hydroxyphenylacetate 3-monooxygenase activity.

In a particular embodiment, the HpaB is from *Escherichia coli*. It is described in the GenBank database from NCBI under the number CAQ34705.1 for the protein sequence, and more particularly in SEQ ID NO: 83. A nucleic acid sequence coding for this enzyme is described in SEQ ID NO: 84. The protein is described in UniProtKB/Swiss Prot under the reference number A0A140NG21.

HpaC is a 4-hydroxyphenylacetate 3-monooxygenase reductase subunit. The microorganism may thus comprise a heterologous nucleic acid sequence coding for a 4-hydroxyphenylacetate 3-monooxygenase reductase subunit (HpaC).

The term "p-coumarate 3-hydroxylase activity" means the transformation of p-coumaric acid into caffeic acid and/or of L-tyrosine into L-DOPA using an enzymatic complex composed of HpaB (4-hydroxyphenylacetate 3-hydroxylase oxidase) and HpaC (4-hydroxyphenylacetate 3-hydroxylase reductase). To determine whether there is p-coumarate 3-hydroxylase activity, an enzymatic test may be performed, which consists of the in vitro incubation of a mixture composed of the enzymes HpaB, HpaC, p-coumaric acid or L-tyrosine, FAD and NADH under optimum conditions (pH, temperature, ions, etc.). After a certain incubation time, the appearance of caffeic acid or of L-DOPA is observed in HPLC-MS in comparison with the expected standard.

Preferably, this enzyme is an enzyme produced by a bacterium, preferably *Escherichia coli*.

In a particular embodiment, the 4-hydroxyphenylacetate 3-monooxygenase reductase (HpaC) is an enzyme comprising a sequence chosen from SEQ ID NO: 85 and polypeptides comprising a sequence having at least 60, 70, 80, 85, 90 or 95% sequence identity with this sequence and having 4-hydroxyphenylacetate 3-monooxygenase activity.

In a particular embodiment, the HpaC is from *Escherichia coli*. It is described in the GenBank database from NCBI under the number CAQ34704.1 for the protein sequence, and more particularly in SEQ ID NO: 85. A nucleic acid sequence coding for this enzyme is described in SEQ ID NO: 86. The protein is described in UniProtKB/Swiss Prot under the reference number A0A140NG67.

Together, HpaB and HpaC are capable of producing L-DOPA (3,4-dihydroxy-L-phenylalanine) from tyrosine.

Thus, the microorganism may comprise a heterologous nucleic acid sequence coding for a 4-hydroxyphenylacetate 3-monooxygenase oxygenase (HpaB) and a heterologous nucleic acid sequence coding for 4-hydroxyphenylacetate 3-monooxygenase reductase (HpaC).

Moreover, this pathway also requires the presence of an enzyme that is capable of synthesizing caffeic acid from L-DOPA (3,4-dihydroxy-L-phenylalanine), a dihydroxyphenylalanine ammonia-lyase (DAL). This enzyme belongs to the class EC 4.3.1.11.

The term "dihydroxyphenylalanine ammonia lyase activity" means the transformation of L-DOPA into trans-caffeic acid by means of a dihydroxyphenylalanine ammonia lyase enzyme. To determine whether there is dihydroxyphenylalanine ammonia lyase activity, an enzymatic test may be performed, which consists of the in vitro incubation of a mixture composed of the dihydroxyphenylalanine ammonia lyase enzyme and L-DOPA (levodopa) under optimum conditions (pH, temperature, ions, etc.). After a certain incubation time, the appearance of trans-caffeic acid is observed in UPLC-MS in comparison with the expected standard.

In addition, dihydroxyphenylalanine ammonia lyase (DAL) may also have tyrosine ammonia lyase (TAL) activity and/or phenylalanine ammonia-lyase (PAL) activity.

The microorganism may thus comprise a heterologous nucleic acid sequence coding for a 4-hydroxyphenylacetate 3-monooxygenase oxygenase subunit (HpaB), a heterologous nucleic acid sequence coding for a 4-hydroxyphenylacetate 3-monooxygenase reductase subunit (HpaC) and a heterologous nucleic acid sequence coding for a dihydroxyphenylalanine ammonia-lyase (DAL).

As an alternative to the use of HpaB and HpaC or in combination therewith, it is possible to use an enzyme for converting tyrosine into L-DOPA and an enzyme for converting p-coumaric acid into caffeic acid.

These are, respectively, a 4-methoxybenzoate O-demethylase, also known as 4-methoxybenzoate monooxygenase (O-demethylating) which has L-tyrosine hydroxylase activity, belonging to the class EC 1.14.99.15, and a p-coumarate 3-hydroxylase having p-coumarate 3-hydroxylase activity, belonging to the class EC 1.14.13.

These various enzymes both form part of the cytochrome P450 (CYP) family.

The term "L-tyrosine hydroxylase activity" means the transformation of p-coumaric acid into caffeic acid and/or of L-tyrosine into L-DOPA using a p-coumarate 3-hydroxylase enzyme (CPR-dependent). To determine whether there is L-tyrosine hydroxylase activity, an enzymatic test may be performed, which consists of the in vitro incubation of a mixture composed of the p-coumarate 3-hydroxylase enzyme, p-coumaric acid or L-tyrosine and the necessary cofactors, under optimum conditions (pH, temperature, ions, etc.). After a certain incubation time, the appearance of caffeic acid or of L-DOPA is observed in HPLC-MS in comparison with the expected standard.

The term "p-coumarate 3-hydroxylase activity" means the transformation of p-coumaric acid into caffeic acid and/or of L-tyrosine into L-DOPA using a p-coumarate 3-hydroxylase enzyme (CPR-dependent). To determine whether there is p-coumarate 3-hydroxylase activity, an enzymatic test may be performed, which consists of the in vitro incubation of a mixture composed of the p-coumarate 3-hydroxylase enzyme, p-coumaric acid or L-tyrosine under optimum conditions (pH, temperature, ions, etc.). After a certain incubation time, the appearance of caffeic acid or of L-DOPA is observed in HPLC-MS in comparison with the expected standard.

The recombinant microorganism may thus comprise a heterologous nucleic acid sequence coding for a 4-methoxybenzoate O-demethylase (CYP) which is capable of converting tyrosine into L-DOPA and also p-coumaric acid into caffeic acid.

In one embodiment, the 4-methoxybenzoate O-demethylase is a bacterial enzyme, notably from *Rhodopseudomonas palustris*, *Pseudomonas putida* or *Escherichia coli*, a plant enzyme, notably from *Beta vulgaris*, a mammalian enzyme, notably from *Oryctolagus cuniculus* or a fungal enzyme, notably from *Rhodotorula glutinis*. In a particular embodiment, the 4-methoxybenzoate O-demethylase is an enzyme from *Rhodopseudomonas palustris*, *Saccharothrix espanaensis* or *Beta vulgaris*.

In a particular embodiment, the 4-methoxybenzoate O-demethylase is selected from enzymes comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity.

The 4-methoxybenzoate O-demethylase may also be from *Beta vulgaris*. The nucleic acid sequences coding for this enzyme and the protein sequences are described in SEQ ID NOs: 74 and 73, respectively. The protein is described in UniProtKB/Swiss Prot under the reference number P0DKI2.

In addition, the 4-methoxybenzoate O-demethylase may be from *Saccharothrix espanaensis*. The nucleic acid sequences coding for this enzyme and protein sequences are described in NCBI under the reference numbers NC_005296.1 and WP_011157377.1, respectively, and more particularly in SEQ ID NOs: 76 and 75. The protein is described in UniProtKB/Swiss Prot under the reference number Q6N8N2.

In one embodiment, the microorganism may comprise a heterologous nucleic acid sequence coding for a 4-methoxybenzoate O-demethylase and a heterologous nucleic acid sequence coding for a dihydroxyphenylalanine ammonia-lyase (DAL).

The recombinant microorganism may thus comprise a heterologous nucleic acid sequence coding for a coumarate 3-hydroxylase (Coum3H) which is capable of converting p-coumaric acid into caffeic acid.

In one embodiment, the coumarate 3-hydroxylase is a bacterial enzyme, notably from *Saccharothrix*.

In a particular embodiment, the 4-methoxybenzoate O-demethylase is selected from the enzyme comprising a sequence chosen from SEQ ID NO: 71 and polypeptides comprising a sequence having at least 60, 70, 80, 85, 90 or 95% sequence identity with one of these sequences and having coumarate 3-hydroxylase activity.

The nucleic acid sequence coding for this enzyme and the protein sequence are described in NCBI under the reference numbers DQ357071.1 and ABC88666.1, respectively, and more particularly in SEQ ID NOs: 72 and 71.

In one embodiment, the microorganism may comprise a heterologous nucleic acid sequence coding for a coumarate 3-hydroxylase and a heterologous nucleic acid sequence coding for a dihydroxyphenylalanine ammonia-lyase (DAL).

Additional Combination of Enzymes

Thus, besides the enzymes required for the biosynthesis of eriodictyol and/or luteolin from naringenin and/or apigenin as described previously, the microorganism preferably comprises enzymes for producing naringenin and/or apigenin from tyrosine and/or phenylalanine, preferably from tyrosine.

Thus, according to particular embodiments, the microorganism comprises a heterologous nucleic acid sequence coding for an O-methyltransferase (OMT) which is capable of methylating eriodictyol and/or luteolin in position 4', a heterologous nucleic acid sequence coding for an F3'H enzyme, and optionally a heterologous nucleic acid sequence coding for an FNS enzyme and a heterologous nucleic acid sequence coding for a CPR enzyme, and also comprises a heterologous nucleic acid sequence coding for a tyrosine ammonia lyase (TAL), a heterologous nucleic acid sequence coding for a 4-coumaroyl-CoA ligase (4CL), a heterologous nucleic acid sequence coding for a chalcone synthase (CHS) and a heterologous nucleic acid sequence coding for a chalcone isomerase (CHI).

In one embodiment, the microorganism comprises:
- a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;
- a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 97, 99, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 97, 99 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and
- a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and
- a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes OMT and F3'H, and optionally FNS and CPR described above, in particular:
- a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 91 and polypeptides comprising a sequence having at least 60, 70, 80, 85, 90 or 95% sequence identity with this sequence and having O-methyltransferase activity; and a heterologous nucleic acid sequence coding for a flavonoid
- 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and
- optionally, a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, in particular a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

Preferably, in this embodiment, the microorganism also comprises:
- a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and
- a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another embodiment, the microorganism comprises:
a heterologous nucleic acid sequence coding for a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity;
a heterologous nucleic acid sequence coding for a 4-coumaroyl-CoA ligase (4CL) comprising a sequence selected from SEQ ID NOs: 97, 99 and 45 and polypeptides comprising a sequence having at least 60, 70, 80, 85, 90 or 95% sequence identity with these sequences and having 4-coumarate-CoA ligase activity, most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity; and
a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity; and
a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes OMT and F3'H, and optionally FNS and CPR described above, in particular:
- a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 91 and polypeptides comprising a sequence having at least 60, 70, 80, 85, 90 or 95% sequence identity with this sequence and having O-methyltransferase activity; and
- a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and
- optionally, a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, in particular for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

Preferably, in this embodiment, the microorganism also comprises:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another particular embodiment, the microorganism comprises:

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana*, *Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, and preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia* x *hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, preferably an F3'H comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity;

optionally, a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity; and optionally, a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In a particular embodiment, the microorganism comprises heterologous nucleic acid sequences coding for the enzymes 4CL, CHS, CHI, F3'H, CPR and OMT, and optionally for the enzymes SAMT and FNS, as described in the preceding embodiment and also comprises:

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity, and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another particular embodiment, the microorganism comprises heterologous nucleic acid sequences coding for the enzymes 4CL, CHS, CHI, F3'H, CPR and OMT, and optionally for the enzymes SAMT and FNS, as described in the preceding embodiment, and also comprises:

a heterologous nucleic acid sequence coding for a dihydroxyphenylalanine ammonia-lyase (DAL) which is capable of producing caffeic acid from L-DOPA (3,4-dihydroxy-L-phenylalanine);

a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydroxylase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity.

In another particular embodiment, the microorganism comprises heterologous nucleic acid sequences coding for the enzymes 4CL, CHS, CHI, F3'H, CPR and OMT, and optionally for the enzymes SAMT and FNS, as described in the preceding embodiment, and also comprises:

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

optionally, a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine;

optionally, a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity;

optionally, a heterologous nucleic acid sequence coding for a dihydroxyphenylalanine ammonia-lyase (DAL) which is capable of producing caffeic acid from L-DOPA (3,4-dihydroxy-L-phenylalanine).

In another particular embodiment, the microorganism comprises:

a heterologous nucleic acid sequence coding for a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity;

a heterologous nucleic acid sequence coding for a cinnamate 4-hydroxylase (C4H), comprising a sequence chosen from SEQ ID NO: 79 and polypeptides comprising a sequence having at least 60, 70, 80, 85, 90 or 95% sequence identity with this sequence and having cinnamate 4-hydroxylase activity;

a heterologous nucleic acid sequence coding for a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) comprising a sequence selected from SEQ ID NO: 45 or 97 and polypeptides comprising a sequence having at least 60, 70, 80, 85, 90 or 95% sequence identity with one of these sequences and having 4-coumarate-CoA ligase activity;

a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a flavonoid 3'-monooxygenase (F3'H) comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

a heterologous nucleic acid sequence coding for a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a cytochrome P450 reductase (CPR) comprising a sequence chosen from SEQ ID NO: 25 and polypeptides comprising a sequence having at least 60, 70, 80, 85, 90 or 95% sequence identity with one of these sequences and having cytochrome P450 reductase activity; and a heterologous nucleic acid sequence coding for an O-methyltransferase (OMT) which is capable of methylating eriodictyol and/or luteolin in position 4' and comprising a sequence chosen from SEQ ID NOs: 91 and 93 and polypeptides comprising a sequence having at least 60, 70, 80, 85, 90 or 95% sequence identity with one of these sequences and having O-methyltransferase activity, and preferably an OMT comprising a sequence chosen from SEQ ID NO: 91 and polypeptides comprising a sequence having at least 60, 70, 80, 85, 90 or 95% sequence identity with this sequence and having O-methyltransferase activity.

Preferably, the microorganism also comprises a heterologous or endogenous nucleic acid sequence coding for an S-adenosylmethionine synthetase (SAMT), in particular an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

The origin of the enzymes or of a set of enzymes may be chosen so that their origin is the same or is similar. For example, the enzymes or the set of enzymes may be obtained from bacteria, for example from bacteria of the same genus or of the same species. In another example, the enzymes or the set of enzymes may be obtained from plants, for example from plants of the same genus or of the same species. The reason for this is that these common origins enable the enzymes to function together optimally.

In one embodiment, the microorganisms comprise a metabolic pathway for the biosynthesis of tyrosine. Notably, the microorganisms may have been modified to have increased production of tyrosine relative to a wild-type strain. Notably, the microorganisms may have been modified so that the carbon flow is redirected toward tyrosine biosynthesis. In addition, the microorganisms may have been modified to reduce or suppress the tyrosine biosynthesis feedback inhibitions.

In another embodiment, the microorganisms comprise a metabolic pathway for the biosynthesis of phenylalanine. Notably, the microorganisms may have been modified to have increased production of phenylalanine relative to a wild-type strain. Notably, the microorganisms may have been modified so that the carbon flow is redirected toward phenylalanine biosynthesis. In addition, the microorganisms may have been modified to reduce or suppress the phenylalanine biosynthesis feedback inhibitions.

In another embodiment, the microorganisms comprise a metabolic pathway for the biosynthesis of phenylalanine and tyrosine. Notably, the microorganisms may have been modified to have increased production of phenylalanine and tyrosine relative to a wild-type strain. Notably, the microorganisms may have been modified so that the carbon flow is redirected toward phenylalanine and tyrosine biosynthesis. In addition, the microorganisms may have been modified to reduce or suppress the phenylalanine and tyrosine biosynthesis feedback inhibitions.

Recombinant Nucleic Acid and Expression Cassette

Each nucleic acid sequence coding for an enzyme as described previously is included in an expression cassette. Preferably, the coding nucleic acid sequences have been optimized for expression in the host microorganism. The coding nucleic acid sequence is operatively linked to the elements required for the expression of the gene, notably for transcription and translation. These elements are chosen so as to be functional in the host recombinant microorganism. These elements may include, for example, transcription promoters, transcription activators, terminator sequences, and start and stop codons. The methods for selecting these elements as a function of the host cell in which expression is desired are well known to those skilled in the art.

Preferably, the promoter is a strong promoter. The promoter may optionally be inducible. For example, if the microorganism is prokaryotic, the promoter may be selected from the following promoters: LacI, LacZ, pLacT, ptac, pARA, pBAD, the RNA polymerase promoters of bacteriophage T3 or T7, the polyhedrin promoter, the PR or PL promoter of lambda phage. In one particular embodiment, the promoter is pLac. If the microorganism is eukaryotic and in particular a yeast, the promoter may be selected from the following promoters: the promoter pTDH3, the promoter pTEF1, the promoter pTEF2, the promoter pCCW12, the promoter pHHF2, the promoter pHTB2 and the promoter pRPL18B. Examples of inducible promoters that may be used in yeast are the promoters tetO-2, GAL10, GAL10-CYC1 and PHO5.

All or part of the expression cassettes comprising the nucleic acid sequences coding for the enzymes as described or a combination of some of them may be included in a common expression vector or in different expression vectors.

The present invention thus relates to a vector comprising a nucleic acid sequence coding for an OMT and at least one nucleic acid sequence chosen from: a nucleic acid sequence coding for an F3'H, a nucleic acid sequence coding for a CPR, a nucleic acid sequence coding for an FNS, a nucleic acid sequence coding for an SAMT, a nucleic acid sequence coding for a TAL, a nucleic acid sequence coding for a 4CL, a nucleic acid sequence coding for a CHS, a nucleic acid sequence coding for a CHI, a nucleic acid sequence coding for a PAL, a nucleic acid sequence coding for a C4H, a nucleic acid sequence coding for an HpaB, and a nucleic acid sequence coding for a DAL, each of these enzymes being as defined above, and also combinations thereof.

Preferably, the vector comprises a nucleic acid sequence coding for an OMT and at least one nucleic acid sequence chosen from: a nucleic acid sequence coding for an F3'H, a nucleic acid sequence coding for a CPR, a nucleic acid sequence coding for an FNS, a nucleic acid sequence coding for a TAL, a nucleic acid sequence coding for a 4CL, a nucleic acid sequence coding for a CHS, a nucleic acid sequence coding for a CHI, and optionally a nucleic acid sequence coding for a PAL and a nucleic acid sequence coding for a C4H.

According to one embodiment, the vector comprises:
a nucleic acid sequence coding for an O-methyltransferase (OMT) which is in particular capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity; and at least one nucleic acid sequence chosen from:

a nucleic acid sequence coding for a flavonoid 3'-monooxygenase (F3'H) which is capable of adding a hydroxyl in position 3' of naringenin and/or apigenin; in particular which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Citrus clementina, Osteospermum* hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

a nucleic acid sequence coding for a cytochrome P450 reductase;

preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27 and 29 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23 and 25 and polypeptides comprising a sequence having at least 60, 70, 80, 85, 90 or 95% sequence identity with one of these sequences and having cytochrome P450 reductase activity;

a nucleic acid sequence coding for a flavone synthase (FNS) which is in particular capable of transforming naringenin into apigenin, eriodictyol into luteolin and/or hesperetin into diosmetin, preferably of transforming eriodictyol into luteolin; preferably an FNS from *Arabidopsis thaliana, Petroselinum crispum, Zea mays, Lonicera japonica, Lonicera macranthoides, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a nucleic acid sequence coding for a tyrosine ammonia lyase (TAL) which is in particular capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a nucleic acid sequence coding for a 4-coumarate-CoA ligase (4CL) which is in particular capable of producing 4-coumaryl-CoA from p-coumaric acid and Coenzyme A and caffeoyl-CoA from caffeic acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, preferably an enzyme comprising a sequence selected from SEQ ID NOs: 45 and 49 and polypeptides comprising a sequence having at least 60, 70, 80, 85, 90 or 95% sequence identity with one of these sequences and having 4-coumarate-CoA ligase activity;

a nucleic acid sequence coding for a chalcone synthase (CHS) which is in particular capable of producing naringenin-chalcone from 4-coumaroyl-CoA and malonyl-CoA and eriodictyol-chalcone from caffeoyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity; preferably a CHS comprising a sequence chosen from SEQ ID NO: 53 and polypeptides comprising a sequence having at least 60, 70, 80, 85, 90 or 95% sequence identity with this sequence and having chalcone synthase activity;

a nucleic acid sequence coding for a chalcone isomerase (CHI) which is in particular capable of producing naringenin from naringenin chalcone and eriodictyol from eriodictyol-chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity;

a nucleic acid sequence coding for a phenylalanine ammonia lyase (PAL) which is in particular capable of producing cinnamic acid from phenylalanine, preferably a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity;

a nucleic acid sequence coding for a cinnamate 4-hydroxylase (C4H) which is in particular capable of producing p-coumaric acid from cinnamic acid, preferably a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity;

a nucleic acid sequence coding for a 4-hydroxyphenylacetate 3-monooxygenase oxygenase subunit (HpaB), preferably comprising a sequence SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

In a preferred embodiment, the vector comprises:

a nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 91 and polypeptides comprising a sequence having at least 60, 70, 80, 85, 90 or 95% sequence identity with this sequence and having O-methyltransferase activity; and and at least one nucleic acid sequence chosen from:

a nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, in particular a CPR comprising a sequence chosen from SEQ ID NO: 25 and polypeptides comprising a sequence having at least 60, 70, 80, 85, 90 or 95% sequence identity with one of these sequences and having cytochrome P450 reductase activity; and a heterologous nucleic acid sequence coding for a flavone synthase (FNS) and comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, and in particular a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) from *Arabidopsis thaliana*, *Citrus clementina*, *Petroselinum crispum* or *Streptomyces clavuligerus*; in particular a 4CL comprising a sequence chosen from SEQ ID NOs: 97, 99, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 97, 99 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis*, *Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the vector comprises each of these sequences.

Optionally, in this embodiment, the vector may also comprise:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another preferred embodiment, the vector comprises:

a heterologous nucleic acid sequence coding for an O-methyltransferase (OMT) which is capable of methylating eriodictyol and/or luteolin in position 4'; preferably an OMT from *Citrus clementina*, *Citrus sinensis*, *Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 91 and polypeptides comprising a sequence having at least 60, 70, 80, 85, 90 or 95% sequence identity with this sequence and having O-methyltransferase activity;

and at least one nucleic acid sequence chosen from:

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity;

a heterologous nucleic acid sequence coding for a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity; and a heterologous nucleic acid sequence coding for a 4-coumaroyl-CoA ligase (4CL) comprising a sequence selected from SEQ ID NOs: 97, 99 and 45 and polypeptides comprising a sequence having at least 60, 70, 80, 85, 90 or 95% sequence identity with one of these sequences and having 4-coumarate-CoA ligase activity; and a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity; a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, in particular a CPR comprising a sequence chosen from SEQ ID NO: 25 and polypeptides comprising a sequence having at least 60, 70, 80, 85, 90 or 95% sequence identity with one of these sequences and having cytochrome P450 reductase activity; and a heterologous nucleic acid sequence coding for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

Preferably, in this embodiment, the heterologous nucleic acid sequence coding for a 4-coumaroyl-CoA ligase (4CL) comprises a sequence selected from SEQ ID NO: 45 and polypeptides comprising a sequence having at least 60, 70, 80, 85, 90 or 95% sequence identity with this sequence and having 4-coumarate-CoA ligase activity. Preferably, in this embodiment, the vector also comprises a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a particular embodiment, the vector comprises:

a nucleic acid sequence coding for an O-methyltransferase, in particular which is capable of methylating eriodictyol and/or luteolin in position 4' and a heterologous nucleic acid sequence coding for a flavonoid 3'-monooxygenase (F3'H), in particular which is capable of adding a hydroxyl in position 3' of naringenin and/or apigenin; or a heterologous nucleic acid sequence coding for an O-methyltransferase (OMT), in particular which is capable of methylating eriodictyol and/or luteolin in position 4'; a heterologous nucleic acid sequence coding for a flavonoid 3'-monooxygenase (F3'H), in particular which is capable of adding a hydroxyl in position 3' of naringenin and/or apigenin; and a heterologous nucleic acid sequence coding for a cytochrome P450 reductase; or a heterologous nucleic acid sequence coding for an O-methyltransferase (OMT), in particular which is capable of methylating eriodictyol and/or luteolin in position 4'; and a heterologous nucleic acid sequence coding for a flavone synthase (FNS), which is capable of transforming naringenin into apigenin, eriodictyol into luteolin and/or hesperetin into diosmetin, preferably of transforming eriodictyol into luteolin; or a heterologous nucleic acid sequence coding for an O-methyltransferase which is capable of methylating eriodictyol and/or luteolin in position 4'; a heterologous nucleic acid sequence coding for a flavonoid 3'-monooxygenase (F3'H) which is capable of hydroxylating naringenin and/or apigenin in position 3'; a heterologous nucleic acid sequence coding for a cytochrome P450 reductase; and a heterologous nucleic acid sequence coding for flavone synthase (FNS) which is capable of transforming naringenin into apigenin, eriodictyol into luteolin and/or hesperetin into diosmetin, preferably of transforming eriodictyol into luteolin.

The vector may thus comprise several nucleic acid sequences chosen therefrom, notably 1, 2, 3, 4, 5, 6, 7, 8, 9 or 10 nucleic acid sequences chosen therefrom.

The vector may notably comprise combinations of particular coding sequences as described above.

The vectors comprise coding sequences that are heterologous insofar as the coding sequences may be optimized for the host microorganism, may be under the control of a heterologous promoter and/or may combine coding sequences which do not originate from the same original organism and/or which are not present in the same arrangement.

The vector may be any DNA sequence in which it is possible to insert foreign nucleic acids, the vectors making it possible to introduce foreign DNA into the host microorganism. For example, the vector may be a plasmid, a phagemid, a cosmid, an artificial chromosome, notably a YAC, or a BAC.

The expression vectors may comprise nucleic acid sequences coding for selection markers. The selection markers may be genes for resistance to one or more antibiotics or auxotrophic genes. The auxotrophic gene may be, for example, URA3, LEU2, HISS or TRP1. The antibiotic-resistance gene may preferably be, for example, a gene for resistance to ampicillin, kanamycin, hygromycin, geneticin and/or nourseothricin.

The introduction of vectors into a host microorganism is a process that is widely known to those skilled in the art. Several methods are notably described in "Current Protocols in Molecular Biology", 13.7.1-13.7.10; or in Ellis T. et al., Integrative Biology, 2011, 3(2), 109-118.

The host microorganism may be transiently or stably transformed/transfected and the nucleic acid, the cassette or the vector may be contained therein in episomal form or in a form incorporated into the genome of the host microorganism.

The expression vector may also comprise one or more sequences allowing the targeted insertion of the vector, of the expression cassette or of the nucleic acid into the genome of the host microorganism.

All or part of the expression cassettes comprising the nucleic acid sequences coding for the enzymes as described above or a combination of some of them may be inserted into the/a chromosome of the recombinant microorganism.

Conversely, all or part of the expression cassettes comprising the nucleic acid sequences coding for the enzymes as described or a combination of some of them may be conserved in episomal form, notably in plasmid form.

Optionally, the microorganism may comprise several copies of nucleic acid sequences coding for an enzyme as described previously. Notably, it may comprise 2 to 10 copies, for example 2, 3, 4, 5, 6, 7, 8, 9 or 10 copies of a nucleic acid sequence coding for an enzyme as described previously.

The present invention relates to a method for preparing a microorganism according to the present invention, comprising the introduction of a vector as defined previously into the microorganism and the selection of microorganisms comprising said vector. The invention also relates to a method for preparing a microorganism according to the present invention, comprising the introduction of a nucleic acid sequence coding for an O-methyltransferase, in particular which is capable of methylating eriodictyol and/or luteolin in position 4' into the microorganism, and the selection of microorganisms comprising said nucleic acid sequences. The method may also comprise the introduction of one or more nucleic acid sequences chosen from:

a nucleic acid sequence coding for a flavonoid 3'-monooxygenase (F3'H) which is capable of adding a hydroxyl in position 3' of naringenin and/or apigenin; in particular which is capable of hydroxylating naringenin and/or apigenin in position 3'; preferably from *Perilla frutescens* var. *crispa*, *Petunia* x *hybrida*, *Callistephus chinensis*, *Gerbera hybrida*, *Citrus sinensis*, *Citrus clementina*, *Osteospermum* hybrid cultivar, *Phanerochaete chrysosporium*, *Streptomyces avermitilis* or *Pilosella officinarum*, in particular from *Perilla frutescens* var. *crispa*, *Petunia* x *hybrida*, *Callistephus chinensis*, *Gerbera hybrida*, *Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, preferably an F3'H comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

a nucleic acid sequence coding for a cytochrome P450 reductase; preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27 and 29 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23 and 25 and polypeptides comprising a sequence having at least 60, 70, 80, 85, 90 or 95% sequence identity with one of these sequences and having cytochrome P450 reductase activity, in particular a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a nucleic acid sequence coding for an O-methyltransferase (OMT) which is in particular capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 89 and polypeptides comprising a sequence having at least 60, 70, 80, 85, 90 or 95% sequence identity with this sequence and having O-methyltransferase activity;

a nucleic acid sequence coding for a flavone synthase (FNS) which is in particular capable of transforming naringenin into apigenin, eriodictyol into luteolin and/ or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 101, 103, 105, 107, 109, 111, 113, 115, 117, 119, 121, 123, 125, 127, 129, 131 and 133 and polypeptides comprising a sequence having at least 60, 70, 80, 85, 90 or 95% sequence identity with one of these sequences and having flavone synthase activity, in particular an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity; preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a nucleic acid sequence coding for a tyrosine ammonia lyase (TAL), in particular which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a nucleic acid sequence coding for a 4-coumarate-CoA ligase (4CL), in particular which is capable of producing 4-coumaryl-CoA from p-coumaric acid and Coenzyme A and caffeoyl-CoA from caffeic acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, preferably an enzyme comprising a sequence selected from SEQ ID NOs: 45 and 49 and polypeptides comprising a sequence having at least 60, 70, 80, 85, 90 or 95% sequence identity with one of these sequences and having 4-coumarate-CoA ligase activity, and preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a nucleic acid sequence coding for a chalcone synthase (CHS) which is in particular capable of producing naringenin-chalcone from 4-coumaroyl-CoA and malonyl-CoA and eriodictyol-chalcone from caffeoyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity; preferably a CHS comprising a sequence chosen from SEQ ID NO: 53 and polypeptides comprising a sequence having at least 60, 70, 80, 85, 90 or 95% sequence identity with this sequence and having chalcone synthase activity;

a nucleic acid sequence coding for a chalcone isomerase (CHI) which is in particular capable of producing naringenin from naringenin chalcone and eriodictyol from eriodictyol-chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a nucleic acid sequence coding for a phenylalanine ammonia lyase (PAL) which is in particular capable of producing cinnamic acid from phenylalanine, preferably a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity;

a nucleic acid sequence coding for a cinnamate 4-hydroxylase (C4H) which is in particular capable of producing p-coumaric acid from cinnamic acid, preferably a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

a nucleic acid sequence coding for a 4-hydroxyphenylacetate 3-monooxygenase oxygenase subunit (HpaB), preferably comprising a sequence SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity; and a nucleic acid sequence coding for a dihydroxyphenylalanine ammonia-lyase (DAL).

Preferably, the method comprises the introduction of combinations of particular coding sequences as described above.

According to a preferred embodiment, the method comprises the introduction of:

a heterologous nucleic acid sequence coding for an O-methyltransferase (OMT) which is capable of methylating eriodictyol and/or luteolin in position 4'; preferably an OMT from *Citrus clementina*, *Citrus sinensis*, *Arabidopsis thaliana* or *Homo sapiens*, preferably an OMT comprising a sequence chosen from SEQ ID NOs: 91, 93, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 91 and 93 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 91 and polypeptides comprising a sequence having at least 60, 70, 80, 85, 90 or 95% sequence identity with this sequence and having O-methyltransferase activity;

and of at least one nucleic acid sequence chosen from:

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 95 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 95 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, in particular a CPR comprising a sequence chosen from SEQ ID NO: 25 and polypeptides comprising a sequence having at least 60, 70, 80, 85, 90 or 95% sequence identity with this sequence and having cytochrome P450 reductase activity; and a heterologous nucleic acid sequence coding for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity, and a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 97, 99, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 97, 99 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the method comprises the introduction of all these sequences.

Preferably, the method also comprises the introduction of:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

Production of Diosmetin and/or Hesperetin

The present invention relates to the use of a microorganism according to the present invention for producing diosmetin and/or hesperetin. In a first preferred embodiment, the invention relates to the use of a microorganism according to the present invention for producing diosmetin. In a second preferred embodiment, the invention relates to the use of a microorganism according to the present invention for producing hesperetin. In a preferred embodiment, the invention relates to the use of a microorganism according to the present invention for producing diosmetin and hesperetin.

The present invention also relates to a method for producing diosmetin and/or hesperetin, comprising the cultivation of a microorganism according to the present invention, notably under conditions allowing or that are favorable for the production of diosmetin and/or hesperetin and optionally the recovery and/or purification of the diosmetin and/or hesperetin produced.

Diosmetin and/or hesperetin may be either the final product or a synthetic or biosynthetic intermediate for the preparation of other products.

In an embodiment in which the production of hesperetin is sought, an O-methyltransferase (OMT) from *Citrus clementina, Citrus sinensis* or *Arabidopsis thaliana* or of mammalian origin, preferably human origin (*Homo sapiens*), will be preferred, preferably from *Citrus clementina, Citrus sinensis* or *Arabidopsis thaliana*, and even more preferably from *Citrus clementina*. In particular, in this embodiment, the OMT may be selected from the enzyme of SEQ ID NOs: 91, 93, 89 and 87 and polypeptides having at least 60, 70, 80, 85, 90 or 95% identity with one of these sequences and having O-methyltransferase activity, preferably from the enzyme of SEQ ID NOs: 91, 93 and 87 and polypeptides having at least 60, 70, 80, 85, 90 or 95% identity with one of these sequences and having O-methyltransferase activity, and most particularly preferably from the enzyme of SEQ ID NO: 91 and polypeptides having at least 60, 70, 80, 85, 90 or 95% identity with this sequence and having O-methyltransferase activity.

In an embodiment in which the production of hesperetin is sought, the presence of a flavone synthase, in particular a flavone synthase that is capable of producing luteolin from eriodictyol and/or diosmetin from hesperetin, is not necessary in the microorganism.

In an embodiment in which the production of diosmetin is sought, an O-methyltransferase (OMT) from *Arabidopsis thaliana* or *Citrus sinensis*, or of mammalian origin, preferably of human origin (*Homo sapiens*), will be preferred, preferably of human origin or from *Citrus sinensis*. In particular, in this embodiment, the OMT may be selected from the enzyme of SEQ ID NOs: 93, 89 and 87 and polypeptides having at least 60, 70, 80, 85, 90 or 95% identity with one of these sequences and having O-methyltransferase activity, preferably from the enzyme of SEQ ID NOs: 93 and 89 and polypeptides having at least 60, 70, 80, 85, 90 or 95% identity with one of these sequences and having O-methyltransferase activity, and most particularly preferably from the enzyme of SEQ ID NO: 93 and polypeptides having at least 60, 70, 80, 85, 90 or 95% identity with this sequence and having O-methyltransferase activity.

In an embodiment in which the production of diosmetin and hesperetin is sought, an O-methyltransferase (OMT) of mammalian origin, preferably of human origin (*Homo sapiens*), or from *Citrus clementina, Citrus sinensis* or *Arabi-*

*dopsis thaliana* will be preferred, preferably of human origin or from *Citrus sinensis*. In particular, in this embodiment, the OMT may be selected from the enzyme of SEQ ID NOs: 91, 93, 87 and 89 and polypeptides having at least 60, 70, 80, 85, 90 or 95% identity with one of these sequences and having O-methyltransferase activity, preferably from the enzyme of SEQ ID NOs: 93 and 91 and polypeptides having at least 60, 70, 80, 85, 90 or 95% identity with one of these sequences and having O-methyltransferase activity.

The conditions for cultivating the microorganism according to the invention may be adapted according to the conventional techniques that are well known to those skilled in the art.

The microorganism is cultivated in a suitable culture medium. The term "suitable culture medium" generally denotes a culture medium providing the nutrients that are essential for or beneficial to the maintenance and/or growth of said microorganism, such as carbon sources; nitrogen sources such as ammonium sulfate; phosphorus sources, for example monobasic potassium phosphate; trace elements, for example copper, iodide, iron, magnesium, zinc or molybdate salts; vitamins and other growth factors such as amino acids or other growth promoters. An antifoam may be added if need be. According to the invention, this suitable culture medium may be chemically defined or complex. The culture medium may thus be identical or similar in composition to that of a synthetic medium, as defined by Verduyn et al., (Yeast, 1992, 8: 501-17), adapted by Visser et al., (Biotechnology and Bioengineering, 2002, 79: 674-81), or commercially available such as the YNB medium (Yeast Nitrogen Base, MP Biomedicals or Sigma-Aldrich). Notably, the culture medium may comprise a simple carbon source, such as glucose, fructose, xylose, ethanol, glycerol, galactose, sucrose, cellulose, cellobiose, starch, glucose polymers, molasses, or byproducts of these sugars.

Preferably, the production of hesperetin and/or diosmetin by the microorganism according to the invention is obtained without supplying naringenin, apigenin, eriodictyol and/or luteolin to the culture medium, preferably without supplying naringenin, apigenin, eriodictyol and luteolin to the culture medium.

According to the invention, any cultivation method for the industrial-scale production of molecules of interest may be envisioned. Advantageously, the cultivation is performed in bioreactors, notably in batch, fed-batch, chemostat and/or continuous cultivation mode. Controlled feeding with vitamins during the process may also be beneficial to the productivity (Alfenore et al., Appl. Microbiol. Biotechnol. 2002, 60: 67-72).

The cultivation is generally performed in bioreactors, with possible solid and/or liquid preculturing steps in Erlenmeyer flasks, with a suitable culture medium.

In general, the conditions for cultivating the microorganisms according to the invention are readily adaptable by a person skilled in the art, as a function of the microorganism. For example, the cultivation temperature is notably, for yeasts, between 20° C. and 40° C., preferably between 28° C. and 35° C., and more particularly about 30° C. for *S. cerevisiae*.

The microorganism according to the present invention may be cultivated for 1 to 30 days and preferably for 1 to 10 days.

A microorganism according to the present invention is preferably capable of producing diosmetin and/or hesperetin in a minimum amount of 1 mg/l of culture medium, preferably 10, 20, 25, 30, 35, 40, 45, 50, 55, 60, 65, 70, 75, 80, 85, 90, 95 or 100 mg/l of culture medium, optionally 150, 200, 250, 300, 350, 400, 450, 500, 600, 700, 800, 900 or 1000 mg/l of culture medium.

DESCRIPTION OF THE FIGURES

FIG. 1: Description of the metabolic pathways for producing hesperetin and diosmetin.

FIG. 2: Production of eriodictyol from naringenin by the strain FL_405 (F3'H4+CPR2). Control strain: CF235. Observation of disappearance of the naringenin peak and appearance of an eriodictyol peak in the strain FL-405.

FIG. 3: Production of luteolin from apigenin by the strain FL_405 (F3'H4+CPR2). Control strain: CF235. Observation of disappearance of the apigenin peak and appearance of a luteolin peak in the strain FL-405.

FIG. 4: Production of apigenin from naringenin by the strain SC744 (FNSII1+CPR2). Control strain: CF234. Observation of disappearance of the naringenin peak and appearance of an apigenin peak in the strain.

FIG. 5: Production of luteolin from eriodictyol SC744 (FNSII1+CPR2). Control strain: CF234. Observation of disappearance of the eriodictyol peak and appearance of a luteolin peak in the strain.

FIG. 6: Production of eriodictyol and luteolin by the strain SC1500. Control strain: CF237. Observation of the eriodictyol and luteolin peaks.

FIG. 7: Production of hesperetin from eriodictyol by the strains SC 1612 (MET+SAM) and SC 1614 (MET+SAM). Control strain: CF235. Observation of disappearance of the eriodictyol peak and appearance of a hesperetin peak in the strains.

FIG. 8: Production of diosmetin from luteolin by the strains SC 1612 (MET+SAM) and SC 1614 (MET+SAM). Control strain: CF235. Observation of disappearance of the luteolin peak and appearance of a diosmetin peak in the strains.

FIG. 9: Production of diosmetin from hesperetin by the strain SC744 (FNSII+CPR). Control strain: CF234. Observation of disappearance of the hesperetin peak and appearance of a diosmetin peak in the strain.

FIG. 10: Production of hesperetin from eriodictyol by *E. coli* EC26 (MET+SAM). Control strain: *E. coli* MH1. Observation of disappearance of the eriodictyol peak and appearance of a hesperetin peak in the strain.

FIG. 11: Production of diosmetin from luteolin by *E. coli* EC26 (MET+SAM). Control strain: *E. coli* MH1. Observation of disappearance of the luteolin peak and appearance of a diosmetin peak in the strain.

FIG. 12: Production of diosmetin from hesperetin by *E. coli* EC30 (FNSII). Control strain: *E. coli* MH1. Observation of disappearance of the hesperetin peak and appearance of a diosmetin peak in the strain.

FIG. 13: Production of hesperetin and diosmetin by the strain SC1508. Control strain: CF237. Observation of the hesperetin and diosmetin peaks.

FIG. 14: Production of hesperetin from eriodictyol by *E. coli* EC41 (MET+SAM). Control strain: *E. coli* MH1. Observation of disappearance of the eriodictyol peak and appearance of a hesperetin peak in the strain.

FIG. 15: Production of hesperetin from eriodictyol by *E. coli* EC43 (MET+SAM). Control strain: *E. coli* MH1. Observation of disappearance of the eriodictyol peak and appearance of a hesperetin peak in the strain.

FIG. 16: Production of diosmetin from luteolin by *E. coli* EC43 (MET+SAM). Control strain: *E. coli* MH1. Observation of disappearance of the luteolin peak and appearance of a diosmetin peak in the strain.

FIG. 17: Production of hesperetin and diosmetin by the strain SC2408. Control strain: CF237. Observation of the hesperetin and diosmetin peaks.

FIG. 18: Production of hesperetin and diosmetin by the strain SC2409. Control strain: CF237. Observation of the hesperetin and diosmetin peaks.

FIG. 19: Production of hesperetin and homoeriodictyol by the strains SC2147, SC2151, SC1612 and SC1614. Control strain: CF235.

FIG. 20: Production of diosmetin and chrysoeriol by the strains SC2147, SC2151, SC1612 and SC1614. Control strain: CF235.

FIG. 21: Production of hesperetin and diosmetin by the strains SC2408, SC2409 and SC1508. Control strain: CF237.

FIG. 22: Production of eriodictyol and luteolin by the strains SC2424, SC2425, SC2426, SC2427, SC2428 and SC1500. Control strain: CF237.

FIG. 23: Production of diosmetin from naringenin by the strains SC2429 to SC2434, SC2436 to SC2444, SC2446 to SC2454, SC2456 to SC2464 and SC2466.

TABLE 1

| SEQUENCE DESCRIPTION | |
|---|---|
| SEQ ID NO. | Description |
| 39 | Amino acid sequence of tyrosine ammonia lyase from *Flavobacterium johnsoniae* |
| 40 | Nucleic acid sequence coding for tyrosine ammonia lyase from *Flavobacterium johnsoniae* |
| 41 | Amino acid sequence of tyrosine ammonia lyase from *Rhodotorula glutinis* |
| 42 | Nucleic acid sequence coding for tyrosine ammonia lyase from *Rhodotorula glutinis* |
| 43 | Amino acid sequence of 4-coumarate-CoA ligase from *Arabidopsis thaliana* |
| 44 | Nucleic acid sequence coding for 4-coumarate-CoA ligase from *Arabidopsis thaliana* |
| 45 | Amino acid sequence of 4-coumarate-CoA ligase from *Petroselinum crispum* |
| 46 | Nucleic acid sequence coding for 4-coumarate-CoA ligase from *Petroselinum crispum* |
| 47 | Amino acid sequence of 4-coumarate-CoA ligase from *Petroselinum crispum* |
| 48 | Nucleic acid sequence coding for 4-coumarate-CoA ligase from *Petroselinum crispum* |
| 49 | Amino acid sequence of 4-coumarate-CoA ligase from *Streptomyces clavuligerus* |
| 50 | Nucleic acid sequence coding for 4-coumarate-CoA ligase from *Streptomyces clavuligerus* |
| 51 | Amino acid sequence of chaicone synthase from *Hordeum vulgare* |
| 52 | Nucleic acid sequence coding for chaicone synthase from *Hordeum vulgare* |
| 53 | Amino acid sequence of chaicone synthase from *Citrus sinensis* |
| 54 | Nucleic acid sequence coding for chaicone synthase from *Citrus sinensis* |
| 55 | Amino acid sequence of chaicone synthase from *Citrus sinensis* |
| 56 | Nucleic acid sequence coding for chaicone synthase from *Citrus sinensis* |
| 57 | Amino acid sequence of chaicone synthase from *Streptomyces clavuligerus* |
| 58 | Nucleic acid sequence coding for chaicone synthase from *Streptomyces clavuligerus* |
| 59 | Amino acid sequence of chaicone isomerase from *Streptomyces clavuligerus* |
| 60 | Nucleic acid sequence coding for chaicone isomerase from *Streptomyces clavuligerus* |
| 61 | Amino acid sequence of chaicone isomerase from *Arabidopsis thaliana* |
| 62 | Nucleic acid sequence coding for chaicone isomerase from *Arabidopsis thaliana* |
| 33 | Amino acid sequence of flavone synthase from *Lonicera japonica* |
| 34 | Nucleic acid sequence coding for flavone synthase from *Lonicera japonica* |
| 35 | Amino acid sequence of flavone synthase from *Lonicera macranthoides* |
| 36 | Nucleic acid sequence coding for flavone synthase from *Lonicera macranthoides* |
| 37 | Amino acid sequence of flavone synthase from *Petroselinum crispum* |
| 38 | Nucleic acid sequence coding for flavone synthase from *Petroselinum crispum* |

TABLE 1-continued

SEQUENCE DESCRIPTION

| SEQ ID NO. | Description |
|---|---|
| 1 | Amino acid sequence of flavonoid 3'-monooxygenase from *Perilla frutescens* var. *crispa* |
| 2 | Nucleic acid sequence coding for flavonoid 3'-monooxygenase from *Perilla frutescens* var. *crispa* |
| 3 | Amino acid sequence of flavonoid 3'-monooxygenase from *Phanerochaete chrysosporium* |
| 4 | Nucleic acid sequence coding for flavonoid 3'-monooxygenase from *Phanerochaete chrysosporium* |
| 5 | Amino acid sequence of flavonoid 3'-monooxygenase from *Petunia × hybrida* |
| 6 | Nucleic acid sequence coding for flavonoid 3'-monooxygenase from *Petunia × hybrida* |
| 7 | Amino acid sequence of flavonoid 3'-monooxygenase from *Callistephus chinensis* |
| 8 | Nucleic acid sequence coding for flavonoid 3'-monooxygenase from *Callistephus chinensis* |
| 9 | Amino acid sequence of flavonoid 3'-monooxygenase from *Callistephus chinensis* |
| 10 | Nucleic acid sequence coding for flavonoid 3'-monooxygenase from *Callistephus chinensis* |
| 11 | Amino acid sequence of flavonoid 3'-monooxygenase from *Gerbera hybrida* |
| 12 | Nucleic acid sequence coding for flavonoid 3'-monooxygenase from *Gerbera hybrida* |
| 13 | Amino acid sequence of flavonoid 3'-monooxygenase from *Osteospermum hybrid cultivar* |
| 14 | Nucleic acid sequence coding for flavonoid 3'-monooxygenase from *Osteospermum hybrid cultivar* |
| 15 | Amino acid sequence of flavonoid 3'-monooxygenase from *Citrus Clementina* |
| 16 | Nucleic acid sequence coding for flavonoid 3'-monooxygenase from *Citrus Clementina* |
| 17 | Amino acid sequence of flavonoid 3'-monooxygenase from *Citrus sinensis* |
| 18 | Nucleic acid sequence coding for flavonoid 3'-monooxygenase from *Citrus sinensis* |
| 19 | Amino acid sequence of flavonoid 3'-monooxygenase from *Pilosella officinarum* |
| 20 | Nucleic acid sequence coding for flavonoid 3'-monooxygenase from *Pilosella officinarum* |
| 21 | Amino acid sequence of flavonoid 3'-monooxygenase from *Streptomyces avermitilis* |
| 22 | Nucleic acid sequence coding for flavonoid 3'-monooxygenase from *Streptomyces avermitilis* |
| 23 | Amino acid sequence of cytochrome P450 reductase from *Catharanthus roseus* |
| 24 | Nucleic acid sequence coding for cytochrome P450 reductase from *Catharanthus roseus* |
| 25 | Amino acid sequence of cytochrome P450 reductase from *Saccharomyces cerevisiae* |
| 26 | Nucleic acid sequence coding for cytochrome P450 reductase from *Saccharomyces cerevisiae* |
| 27 | Amino acid sequence of chimeric cytochrome P450 reductase |
| 28 | Nucleic acid sequence coding for chimeric cytochrome P450 reductase |
| 29 | Amino acid sequence of cytochrome P450 reductase from *Arabidopsis thaliana* |
| 30 | Nucleic acid sequence coding for cytochrome P450 reductase from *Arabidopsis thaliana* |
| 31 | Amino acid sequence of cytochrome P450 reductase from *Arabidopsis thaliana* |
| 32 | Nucleic acid sequence coding for cytochrome P450 reductase from *Arabidopsis thaliana* |
| 63 | Amino acid sequence of phenylalanine ammonia lyase from *Citrus sinensis* |
| 64 | Nucleic acid sequence coding for phenylalanine ammonia lyase from *Citrus sinensis* |
| 65 | Amino acid sequence of phenylalanine ammonia lyase from *Citrus sinensis* |
| 66 | Nucleic acid sequence coding for phenylalanine ammonia lyase from *Citrus sinensis* |
| 67 | Amino acid sequence of cinnamate 4-hydroxylase from *Citrus sinensis* |
| 68 | Nucleic acid sequence coding for cinnamate 4-hydroxylase from *Citrus sinensis* |

TABLE 1-continued

SEQUENCE DESCRIPTION

| SEQ ID NO. | Description |
|---|---|
| 69 | Amino acid sequence of cinnamate 4-hydroxylase from *Citrus sinensis* |
| 70 | Nucleic acid sequence coding for cinnamate 4-hydroxylase from *Citrus sinensis* |
| 71 | Amino acid sequence of coumarate 3-hydroxylase from *Saccharothrix espanaensis* |
| 72 | Nucleic acid sequence coding for coumarate 3-hydroxylase from *Saccharothrix espanaensis* |
| 73 | Amino acid sequence of 4-methoxybenzoate O-demethylase from *Beta vulgaris* |
| 74 | Nucleic acid sequence coding for 4-methoxybenzoate O-demethylase from *Beta vulgaris* |
| 75 | Amino acid sequence of 4-methoxybenzoate O-demethylase from *Rhodopseudomonas palustris* |
| 76 | Nucleic acid sequence coding for 4-methoxybenzoate O-demethylase from *Rhodopseudomonas palustris* |
| 77 | Amino acid sequence of phenylalanine ammonia lyase from *Arabidopsis thaliana* |
| 78 | Nucleic acid sequence coding for phenylalanine ammonia lyase from *Arabidopsis thaliana* |
| 79 | Amino acid sequence of cinnamate 4-hydroxylase from *Arabidopsis thaliana* |
| 80 | Nucleic acid sequence coding for cinnamate 4-hydroxylase from *Arabidopsis thaliana* |
| 81 | Amino acid sequence of S-adenosylmethionine synthetase from *Saccharomyces cerevisiae* |
| 82 | Nucleic acid sequence coding for S-adenosylmethionine synthetase from *Saccharomyces cerevisiae* |
| 83 | Amino acid sequence of 4-hydroxyphenylacetate 3-monooxygenase oxygenase from *Escherichia coli* |
| 84 | Nucleic acid sequence coding for 4-hydroxyphenylacetate 3-monooxygenase oxygenase from *Escherichia coli* |
| 85 | Amino acid sequence of 4-hydroxyphenylacetate 3-monooxygenase reductase from *Escherichia coli* |
| 86 | Nucleic acid sequence coding for 4-hydroxyphenylacetate 3-monooxygenase reductase from *Escherichia coli* |
| 87 | Amino acid sequence of O-methyltransferase from *Arabidopsis thaliana* |
| 88 | Nucleic acid sequence coding for O-methyltransferase from *Arabidopsis thaliana* |
| 89 | Amino acid sequence of O-methyltransferase from *Homo sapiens* |
| 90 | Nucleic acid sequence coding for O-methyltransferase from *Homo sapiens* |
| 91 | Amino acid sequence of O-methyltransferase from *Citrus Clementina* |
| 92 | Nucleic acid sequence coding for O-methyltransferase from *Citrus Clementina* |
| 93 | Amino acid sequence of O-methyltransferase from *Citrus sinensis* |
| 94 | Nucleic acid sequence coding for O-methyltransferase from *Citrus sinensis* |
| 95 | Amino acid sequence of flavonoid 3'-monooxygenase from *Arabidopsis thaliana* |
| 96 | Nucleic acid sequence coding for flavonoid 3'-monooxygenase from *Arabidopsis thaliana* |
| 97 | Amino acid sequence of a 4-coumarate-CoA ligase from *Arabidopsis thaliana* |
| 98 | Nucleic acid sequence coding for a 4-coumarate-CoA ligase from *Arabidopsis thaliana* |
| 99 | Amino acid sequence of a 4-coumarate-CoA ligase from *Citrus Clementina* |
| 100 | Nucleic acid sequence coding for 4-coumarate-CoA ligase from *Citrus Clementina* |
| 101 | Amino acid sequence of flavone synthase from *Angelica archangelica* |
| 102 | Nucleic acid sequence coding for flavone synthase from *Angelica archangelica* |
| 103 | Amino acid sequence of flavone synthase from *Cynara cardunculus* var. *scolymus* |
| 104 | Nucleic acid sequence coding for flavone synthase from *Cynara cardunculus* var. *scolymus* |
| 105 | Amino acid sequence of flavone synthase from *Perilla frutescens* var. *crispa* |

TABLE 1-continued

SEQUENCE DESCRIPTION

| SEQ ID NO. | Description |
|---|---|
| 106 | Nucleic acid sequence coding for flavone synthase from *Perilla frutescens* var. *crispa* |
| 107 | Amino acid sequence of flavone synthase from *Dahlia pinnata* |
| 108 | Nucleic acid sequence coding for flavone synthase from *Dahlia pinnata* |
| 109 | Amino acid sequence of flavone synthase from *Callistephus chinensis* |
| 110 | Nucleic acid sequence coding for flavone synthase from *Callistephus chinensis* |
| 111 | Amino acid sequence of flavone synthase from *Apium graveolens* |
| 112 | Nucleic acid sequence coding for flavone synthase from *Apium graveolens* |
| 113 | Amino acid sequence of flavone synthase from *Medicago truncatula* |
| 114 | Nucleic acid sequence coding for flavone synthase from *Medicago truncatula* |
| 115 | Amino acid sequence of flavone synthase from *Cuminum cyminum* |
| 116 | Nucleic acid sequence coding for flavone synthase from *Cuminum cyminum* |
| 117 | Amino acid sequence of flavone synthase from *Aethusa cynapium* |
| 118 | Nucleic acid sequence coding for flavone synthase from *Aethusa cynapium* |
| 119 | Amino acid sequence of flavone synthase from *Conium maculatum* |
| 120 | Nucleic acid sequence coding for flavone synthase from *Conium maculatum* |
| 121 | Amino acid sequence of flavone synthase from *Camellia sinensis* |
| 122 | Nucleic acid sequence coding for flavone synthase from *Camellia sinensis* |
| 123 | Amino acid sequence of flavone synthase from *Saussurea medusa* |
| 124 | Nucleic acid sequence coding for flavone synthase from *Saussurea medusa* |
| 125 | Amino acid sequence of flavone synthase from *Plectranthus barbatus* |
| 126 | Nucleic acid sequence coding for flavone synthase from *Plectranthus barbatus* |
| 127 | Amino acid sequence of flavone synthase from *Scutellaria baicalensis* |
| 128 | Nucleic acid sequence coding for flavone synthase from *Scutellaria baicalensis* |
| 129 | Amino acid sequence of flavone synthase from *Dorcoceras hygrometricum* |
| 130 | Nucleic acid sequence coding for flavone synthase from *Dorcoceras hygrometricum* |
| 131 | Amino acid sequence of flavone synthase from *Antirrhinum majus* |
| 132 | Nucleic acid sequence coding for flavone synthase from *Antirrhinum majus* |
| 133 | Amino acid sequence of flavone synthase from *Erythranthe lewisii* |
| 134 | Nucleic acid sequence coding for flavone synthase from *Erythranthe lewisii* |

EXAMPLES

Materials and Methods

Strains

The yeasts used in the examples were obtained from *Saccharomyces cerevisiae* FY1679-28A (Tettelin et al., 1995 https://doi.org/10.1016/S1067-2389(06)80008-7). This yeast is quadruply auxotrophic for uracil, tryptophan, histidine and leucine.

The bacterial strains used in the examples were obtained from *Escherichia coli* MH1.

Standards

The standards were acquired from the supplier Extrasynthèse, France (naringenin, apigenin, eriodictyol, luteolin, hesperetin and diosmetin).

Gene Cloning

The genes optimized to express in the yeast were synthesized by Eurofins Genomics, Ebersberg, Germany or Biomatik, Cambridge, Canada or Twist Biosciences, San Francisco, USA or DC Biosciences, Dundee, UK. By PCR, the gene cpr2 (SEQ ID NO: 26) from *S. cerevisiae* was amplified from the genomic DNA.

The genes obtained by synthesis or by PCR comprise at the 5' and 3' ends a BbsI (GAAGAC) or BsaI (GGTCTC) restriction site.

All the genes, promoters and terminators were restriction-cloned in the vector pSBK for expression in the yeast or in the vector pSB1K3 for expression in *E. coli*. The promoters and terminators (Wargner et al., 2015 DOI: 10.1016/j.fgb.2015.12.001) were recovered by PCR from the genomic DNA of the yeast *S. cerevisiae* or of *E. coli*.

The vector pSBK comprises a URA or LEU or TRP or HIS selection marker for the yeast and the vector pSB1K3 comprises a kanamycin-resistance marker.

Culture Conditions

The strains were cultivated in 1 ml of minimum nitrogen base medium (Dutscher, Brumath, Fr) supplemented with glucose at 20 g/l for the yeasts and in 1 ml of M9 supplemented with glucose at 4 g·l$^{-1}$ for *E. coli* in 24-well plates (Starlab, Orsay, Fr) at 30° C. for 72 hours with continuous stirring at 200 rpm. In certain cases, naringenin or apigenin was added at a concentration of 100 mg·l$^{-1}$ to determine the activity of the F3'Hs, naringenin or eriodictyol was added at a concentration of 100 mg·l$^{-1}$ to determine the activity of the FNSIIs, eriodictyol or luteolin was added at a concentration of 100 mg·l$^{-1}$ to determine the activity of the METs. Each strain was inoculated at an OD of 0.2 using a 24-hour preculture cultivated under the same conditions.

Analytical Method:

Preparation of the samples: The 1 mL cultures are frozen at −80° C. and then lyophilized for 12 hours at 0.10 mbar. The samples are then taken up in 1 mL of dimethyl sulfoxide (DMSO), stirred for 30 seconds at 1000 rpm and then centrifuged for 5 minutes at 3000 rpm at room temperature. After centrifugation, a known volume of supernatant is added to a known volume of a mixture of internal standards dissolved in methanol.

The final concentrations of the internal standards are:

| | |
|---|---|
| Diosmin C13 | 0.5 mg/L |
| Diosmetin C13 | 0.015 mg/L |

Analysis by UHPLC-TQ: The samples were analyzed using a Vanquish-H UHPLC machine (Thermo) coupled to a Quantis triple-quadrupole MS (Thermo). The column is a Waters Acquity UPLC@ USST3 column (8 μm 2.1×100 mm) combined with an HSST3 1.8 μm 2.1×5 mm precolumn.

The mobile phase A is a 0.1% solution of formic acid in LC/MS-grade water and the mobile phase B is a 0.1% solution of formic acid in pure LC/MS-grade acetonitrile. The column temperature is 50° C. and the temperature of the sample changer is 10° C.

Two chromatographic conditions were used for detecting the flavonoids of interest:

TABLE 2

Chromatographic conditions method 1

| Time (min) | Flow rate (ml/min) | Mobile phase A (%) | Mobile phase B (%) |
|---|---|---|---|
| 0 | 0.5 | 73 | 27 |
| 8 | 0.5 | 73 | 27 |

TABLE 3

Chromatographic conditions method 2

| Time (min) | Flow rate (ml/min) | Mobile phase A (%) | Mobile phase B (%) |
|---|---|---|---|
| 0 | 0.5 | 83 | 17 |
| 3.75 | 0.5 | 83 | 17 |
| 4 | 0.5 | 73 | 27 |
| 8.5 | 0.5 | 73 | 27 |
| 11.0 | 0.5 | 50 | 50 |
| 13.0 | 0.5 | 0 | 100 |
| 13.5 | 0.5 | 83 | 17 |
| 15.0 | 0.5 | 83 | 17 |

The ions monitored and the fragmentation conditions for the molecules of interest are:

TABLE 4

For method 1

| Molecules | Retention time (min) | Polarity | Precursor ion | Daughter ion | Collision energy | Lens RF (V) | Reference internal standard |
|---|---|---|---|---|---|---|---|
| Naringenin | 3.3 | Negative | 271.0 | 119.0 | 27 | 169 | Diosmetin C13 |
| | | | | 150.9 | 18 | 169 | |
| Apigenin | 3.5 | Negative | 269.0 | 117.1 | 35 | 201 | Diosmetin C13 |
| | | | | 150.9 | 24 | 201 | |
| Eriodictyol | 1.9 | Negative | 287.1 | 135.1 | 26 | 147 | Diosmetin C13 |
| | | | | 150.9 | 14 | 147 | |
| Luteolin | 2.1 | Negative | 285.0 | 133.0 | 34 | 213 | Diosmetin C13 |

TABLE 5

For method 2

| Molecules | Retention time (min) | Polarity | Precursor ion | Daughter ion | Collision energy | Lens RF (V) | Reference internal standard |
|---|---|---|---|---|---|---|---|
| Naringenin | 7.8 | Negative | 271.0 | 119.0 | 27 | 169 | Diosmetin C13 |
| | | | | 150.9 | 18 | 169 | |
| Apigenin | 8.2 | Negative | 269.0 | 117.1 | 35 | 201 | Diosmetin C13 |
| | | | | 150.9 | 24 | 201 | |

TABLE 5-continued

For method 2

| Molecules | Retention time (min) | Polarity | Precursor ion | Daughter ion | Collision energy | Lens RF (V) | Reference internal standard |
|---|---|---|---|---|---|---|---|
| Eriodictyol | 6.2 | Negative | 287.1 | 135.1 | 26 | 147 | Diosmetin |
| | | | | 150.9 | 14 | 147 | C13 |
| Luteolin | 6.6 | Negative | 285.0 | 133.0 | 34 | 213 | Diosmetin |
| | | | | 150.9 | 25 | 213 | C13 |
| Hesperetin | 8.7 | Negative | 301.0 | 164.0 | 24 | 169 | Diosmetin |
| | | | | 150.9 | 17 | 169 | C13 |
| Diosmetin | 9.1 | Negative | 299.0 | 256.0 | 30 | 192 | Diosmetin |
| | | | | 284.1 | 21 | 192 | C13 |

F3'H

Constructs for each of the F3'Hs were made in a vector bearing the URA selection marker (Table 6). Constructs including each SAM2 and only one of the various CPRs were created in a vector bearing the LEU selection marker (Table 7). Two vectors including only the URA or LEU selection marker were also created as controls. The marker genes make it possible to detect and to select the cells that have incorporated the gene of interest.

TABLE 6

List of the various F3'H constructs tested

| Names | Assembled genes | Markers |
|---|---|---|
| FL 23 | F3'H from *Perilla frutescens* var. *crispa* (SEQ ID NO: 2) | URA |

TABLE 6-continued

List of the various F3'H constructs tested

| Names | Assembled genes | Markers |
|---|---|---|
| FL 24 | F3'H from *Phanerochaete chrysosporium* (SEQ ID NO: 4) | URA |
| FL 25 | F3'H from *Petunia* × *hybrida* (SEQ ID NO: 6) | URA |
| FL 26 | F3'H from *Callistephus chinensis* (SEQ ID NO: 8) | URA |
| FL 27 | F3'H from *Callistephus chinensis* (SEQ ID NO: 10) | URA |
| FL 28 | F3'H from *Gerbera hybrida* (SEQ ID NO: 12) | URA |
| FL 29 | F3'H from *Osteospermum hybrid cultivar* (SEQ ID NO: 14) | URA |
| FL 30 | F3'H from *Citrus Clementina* (SEQ ID NO: 16) | URA |
| FL 31 | F3'H from *Citrus sinensis* (SEQ ID NO: 18) | URA |
| FL 32 | F3'H from *Pilosella officinarum* (SEQ ID NO: 20) | URA |
| FL 1031 | F3'H from *Arabidopsis thaliana* (SEQ ID NO: 96) | URA |
| TT URA | — | URA |

TABLE 7

List of constructs made with the various CPRs

| Names | Assembled genes | Markers |
|---|---|---|
| FL 121 (CPR + SAM) | CPR from *Catharanthus roseus* (SEQ ID NO: 24), SAM from *Saccharomyces cerevisiae* (SEQ ID NO: 82) | LEU |
| FL 274 (CPR + SAM) | Chimeric CPR (SEQ ID NO: 28), SAM from *Saccharomyces cerevisiae* (SEQ ID NO: 82) | LEU |
| FL 275 (ATR + SAM) | ATR from *Arabidopsis thaliana* (SEQ ID NO: 30), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 463 (ATR + SAM) | ATR from *Arabidopsis thaliana* (SEQ ID NO: 32), SAM from *Saccharomyces cerevisiae* (SEQ ID NO: 82) | LEU |
| TT LEU | — | LEU |

Several strains were created with, respectively, all the F3'Hs listed in Table 6 so that they could each be tested with the constructs of Table 7.

These various assemblies make it possible to check the enzymatic activity of the F3'Hs and also make it possible to determine the most efficient F3'H-CPR pairs.

For example, the strain FL 405 contains the constructs FL 26 and FL 401.

The control strain (without the genes) containing the constructs TT URA and TT LEU is called CF235.

FNSII

For each of the following FNSIIs, constructs in a TRP vector were prepared (Table 8). The same vectors with the LEU selection marker each containing SAM2 and a different CPR were used to test the FNSIIs (Table 9).

TABLE 8

Constructs including the various FNSIIs tested

| Names | Assembled genes | Markers |
|---|---|---|
| FL 620<br>(TAL + 4CL + CHS + CHI + FNSII) | TAL from *Rhodotorula glutinis* (SEQ ID NO: 42),<br>4CL from *Petroselinum crispum* (SEQ ID NO: 46),<br>CHS from *Citrus sinensis* (SEQ ID NO: 54),<br>CHI from *Arabidopsis thaliana* (SEQ ID NO: 62)<br>FNSII from *Lonicera japonica* (SEQ ID NO: 34) | TRP |
| FL 621<br>(TAL + 4CL + CHS + CHI + FNSII) | TAL from *Rhodotorula glutinis* (SEQ ID NO: 42),<br>4CL from *Petroselinum crispum* (SEQ ID NO: 46),<br>CHS from *Citrus sinensis* (SEQ ID NO: 54),<br>CHI from *Arabidopsis thaliana* (SEQ ID NO: 62)<br>FNSII from *Lonicera macranthoides* (SEQ ID NO: 36) | TRP |
| FL 112<br>(TAL + 4CL + CHS + CHI + FNSII) | TAL from *Flavobacterium jonhsoniae* (SEQ ID NO: 40),<br>4CL from *Petroselinum crispum* (SEQ ID NO: 46),<br>CHS from *Citrus sinensis* (SEQ ID NO: 54),<br>CHI from *Arabidopsis thaliana* (SEQ ID NO: 62)<br>FNSII from *Petroselinum crispum* (SEQ ID NO: 38) | TRP |
| TT TRP | — | TRP |

TABLE 9

List of constructs made with the various CPRs

| Names | Assembled genes | Markers |
|---|---|---|
| FL 121<br>(CPR + SAM) | CPR from *Catharanthus roseus* (SEQ ID NO: 24),<br>SAM from *Saccharomyces cerevisiae* (SEQ ID NO: 82) | LEU |
| FL 274<br>(CPR + SAM) | Chimeric CPR (SEQ ID NO: 28),<br>SAM from *Saccharomyces cerevisiae* (SEQ ID NO: 82) | LEU |
| FL 275<br>(ATR + SAM) | ATR from *Arabidopsis thaliana* (SEQ ID NO: 30),<br>SAM from *Saccharomyces cerevisiae* (SEQ ID NO: 82) | LEU |
| FL 401<br>(CPR + SAM) | CPR from *Saccharomyces cerevisiae* (SEQ ID NO: 26),<br>SAM from *Saccharomyces cerevisiae* (SEQ ID NO: 82) | LEU |
| FL 463<br>(ATR + SAM) | ATR from *Arabidopsis thaliana* (SEQ ID NO: 32),<br>SAM from *Saccharomyces cerevisiae* (SEQ ID NO: 82) | LEU |
| TT LEU | — | LEU |

Several strains were created with, respectively, each of the constructs of the FNSIIs listed in Table 8 and each of the constructs of the CPRs of Table 9.

These various assemblies make it possible to check the enzymatic activity of the FNSIIs and also make it possible to determine the most efficient FNSIIs.

For example, the strain SC 744 contains the constructs FL 620 and FL 401.

The control strain (without the genes) containing the constructs TT TRP and TT LEU is called CF234.

Similar constructs were made to test the FNSIIs of SEQ ID NOs: 101, 103, 105, 107, 109, 111, 113, 115, 117, 119, 121, 123, 125, 127, 129, 131 and 133.

Yeast Up to Eriodictyol/Luteolin

Strains including the pathway up to eriodictyol and luteolin were also tested:

the strain SC1500 comprises the constructs FL 26, FL 602, FL 808 and FL 822; and the strain SC2424 comprising the constructs FL 1031+FL 602+FL 822+TT HIS;

the strain SC2425 comprising the constructs FL 26+FL 602+FL 822+TT HIS;

the strain SC2426 comprising the constructs FL 31+FL 602+FL 822+TT HIS;

the strain SC2427 comprises the constructs FL 1031, FL 602, FL 808 and FL 822; and the strain SC2428 comprising the constructs FL 31+FL 602+FL 808+FL 822.

TABLE 10

Lists of constructs used for the strains including the pathway up to eriodictyol and luteolin

| Names | Assembled genes | Markers |
|---|---|---|
| FL 26<br>(F3'H) | F3'H from *Callistephus chinensis* (SEQ ID NO: 8) | URA |
| FL 1031<br>(F3'H) | F3'H from *Arabidopsis thaliana* (SEQ ID NO: 96) | URA |
| FL 31 (F3'H) | F3'H from *Citrus sinensis* (SEQ ID NO: 18) | URA |
| FL 602<br>(TAL + 4CL + CHS + | TAL from *Rhodotorula glutinis* (SEQ ID NO: 42),<br>4CL from *Petroselinum crispum* (SEQ ID NO: 46), | TRP |

TABLE 10-continued

Lists of constructs used for the strains including the pathway up to eriodictyol and luteolin

| Names | Assembled genes | Markers |
| --- | --- | --- |
| CHI + FNS) | CHS from *Citrus sinensis* (SEQ ID NO: 54), CHI from *Arabidopsis thaliana* (SEQ ID NO: 62) FNSII from *Petroselinum crispum* (SEQ ID NO: 38) | |
| FL 808 (PAL + C4H) | PAL from *Arabidopsis thaliana* (SEQ ID NO: 78), C4H from *Arabidopsis thaliana* (SEQ ID NO: 80), | HIS |
| FL 822 (CPR + CAF) | CPR from *Catharanthus roseus* (SEQ ID NO: 24), CAF from *Rhodopseudomonas palustris* (SEQ ID NO: 76) | LEU |
| TT HIS | | HIS |

The control strain (without the genes) containing the constructs TT URA, TT TRP, TT HIS and TT LEU is called CF237.

MET:

In order to test each of the METs, constructs were made and are presented in Table 11. The marker genes make it possible to detect and to select the cells that have incorporated the gene of interest.

TABLE 11

List of constructs made to test the various METs

| Names | Assembled genes | Markers |
| --- | --- | --- |
| FL 121 (CPR + SAM) | CPR from *Catharanthus roseus* (SEQ ID NO: 24), SAM from *Saccharomyces cerevisiae* (SEQ ID NO: 82) | LEU |
| FL 266 (F3'H + MET) | F3'H from *Callistephus chinensis* (SEQ ID NO: 8), MET from *Arabidopsis thaliana* (SEQ ID NO: 88) | URA |
| FL 268 (F3'H + MET) | F3'H from *Callistephus chinensis* (SEQ ID NO: 8), MET from *Homo sapiens* (SEQ ID NO: 90) | URA |
| FL 469 (F3'H + MET) | F3'H from *Callistephus chinensis* (SEQ ID NO: 8), MET from *Citrus Clementina* (SEQ ID NO: 92) | URA |
| FL 475 (F3'H + MET) | F3'H from *Callistephus chinensis* (SEQ ID NO: 8), MET from *Citrus sinensis* (SEQ ID NO: 94) | URA |

Four strains SC 1612, SC 1614, SC 2147 and SC 2151 were created, with FL 121 and FL 266 for SC 1612, FL 121 and FL 268 for SC 1614, FL 475 and FL 121 for SC 2147 and FL 469 and FL 121 for SC 2151 for the conversion of eriodictyol into hesperetin in order to determine which MET is the most efficient.

The control strain (without the genes) containing the constructs TT LEU and TT URA is called CF235.

F3'H, MET, FNS, CPR: Production of Diosmetin from Naringenin

TABLE 12

List of constructs used to test the enzymes in *Saccharomyces cerevisiae* (SC)

| Names | Assembled genes | Markers |
| --- | --- | --- |
| FL 121 (CPR + SAM) | CPR from *Catharanthus roseus* (SEQ ID NO: 24), SAM from *Saccharomyces cerevisiae* (SEQ ID NO: 82) | LEU |
| TT LEU | — | LEU |
| FL_26 (F3'H) | F3'H from *Callistephus chinensis* (SEQ ID NO: 8), | URA |
| FL 1031 (F3'H) | F3'H from *Arabidopsis thaliana* (SEQ ID NO: 96), | URA |
| FL 1111 (FNS + MET) | FNSII from *Petroselinum crispum* (SEQ ID NO: 33) MET from *Citrus Clementina* (SEQ ID NO: 92) | TRP |
| FL 1112 (FNS + MET) | FNSII from *Angelica archangelica* (SEQ ID NO: 102) MET from *Citrus Clementina* (SEQ ID NO: 92) | TRP |
| FL 1113 (FNS + MET) | FNSII from *Cynara cardunculus* var. *scolymus* (SEQ ID NO: 104) MET from *Citrus Clementina* (SEQ ID NO: 92) | TRP |
| FL 1114 (FNS + MET) | FNSII from *Perilla frutescens* var. crispa (SEQ ID NO: 106) MET from *Citrus Clementina* (SEQ ID NO: 92) | TRP |
| FL 1115 (FNS + MET) | FNSII from *Dahlia pinnata* (SEQ ID NO: 108) MET from *Citrus Clementina* (SEQ ID NO: 92) | TRP |
| FL 1116 (FNS + MET) | FNSII from *Petroselinum crispum* (SEQ ID NO: 33) MET from *Citrus sinensis* (SEQ ID NO: 94) | TRP |
| FL 1118 | FNSII from *Cynara cardunculus* var. *scolymus* (SEQ ID NO: 104) | TRP |

TABLE 12-continued

List of constructs used to test the enzymes in *Saccharomyces cerevisiae* (SC)

| Names | Assembled genes | Markers |
|---|---|---|
| (FNS + MET) | MET from *Citrus sinensis* (SEQ ID NO: 94) | |
| FL 1119 | FNSII from *Perilla frutescens* var. *crispa* (SEQ ID NO: 106) | TRP |
| (FNS + MET) | MET from *Citrus sinensis* (SEQ ID NO: 94) | |
| FL 1120 | FNSII from *Dahlia pinnata* (SEQ ID NO: 108) | TRP |
| (FNS + MET) | MET from *Citrus sinensis* (SEQ ID NO: 94) | |

The following strains were constructed:
SC2429: FL 1111+FL 1031+FL 121 SC2443: FL 1115+FL 1031+TT LEU
SC2430: FL 1112+FL 1031+FL 121 SC2434: FL 1116+FL 1031+FL 121
SC2431: FL 1113+FL 1031+FL 121 SC2436: FL 1118+FL 1031+FL 121
SC2432: FL 1114+FL 1031+FL 121 SC2437: FL 1119+FL 1031+FL 121
SC2433: FL 1115+FL 1031+FL 121 SC2438: FL 1120+FL 1031+FL 121
SC2439: FL 1111+FL 1031+TT LEU SC2444: FL 1116+FL 1031+TT LEU
SC2440: FL 1112+FL 1031+TT LEU SC2446: FL 1118+FL 1031+TT LEU
SC2441: FL 1113+FL 1031+TT LEU SC2447: FL 1119+FL 1031+TT LEU
SC2449: FL 1111+FL 26+FL 121 SC2463: FL 1115+FL 26+TT LEU
SC2450: FL 1112+FL 26+FL 121 SC2454: FL 1116+FL 26+FL 121
SC2451: FL 1113+FL 26+FL 121 SC2456: FL 1118+FL 26+FL 121
SC2452: FL 1114+FL 26+FL 121 SC2457: FL 1119+FL 26+FL 121
SC2453: FL 1115+FL 26+FL 121 SC2458: FL 1120+FL 26+FL 121
SC2459: FL 1111+FL 26+TT LEU SC2464: FL 1116+FL 26+TT LEU
SC2460: FL 1112+FL 26+TT LEU SC2466: FL 1118+FL 26+TT LEU
SC2461: FL 1113+FL 26+TT LEU SC2467: FL 1119+FL 26+TT LEU
SC2462: FL 1114+FL 26+TT LEU SC2468: FL 1120+FL 26+TT LEU The control strain (without the genes) containing the constructs TT URA, TT TRP, TT HIS and TT LEU is called CF237.

*E. Coli* Up to Hesperetin/Diosmetin

TABLE 13

List of constructs used to test the enzymes in *E. coli*

| Names | Assembled genes |
|---|---|
| EC26 | SAM from *Saccharomyces cerevisiae* (SEQ ID NO: 82) |
| (SAM + MET) | MET from *Homo sapiens* (SEQ ID NO: 90) |
| EC41 | SAM from *Saccharomyces cerevisiae* (SEQ ID NO: 82) |
| (SAM + MET) | MET from *Citrus Clementina* (SEQ ID NO: 92) |
| EC43 | SAM from *Saccharomyces cerevisiae* (SEQ ID NO: 82) |
| (SAM + MET) | MET from *Citrus sinensis* (SEQ ID NO: 94) |
| EC30 (FNSII) | FNSII from *Petroselinum crispum* (SEQ ID NO: 38) |

Yeast Up to Hesperetin/Diosmetin

Three strains including the pathway up to hesperetin/diosmetin were also tested. The strain SC 1508 comprises the constructs FL 121+FL 268+FL 602+FL 808 of Table 14. The strain SC 2408 comprises the constructs FL 121+FL 469+FL 602+FL 808 of Table 14. The strain SC 2409 comprises the constructs FL 121+FL 475+FL 602+FL 808 of Table 14.

TABLE 14

List of constructs used in the examples

| Names | Assembled genes | Markers |
|---|---|---|
| FL 121 | CPR from *Catharanthus roseus* (SEQ ID NO: 24), | LEU |
| (CPR + SAM) | SAM from *Saccharomyces cerevisiae* (SEQ ID NO: 82) | |
| FL 268 | F3'H from *Callistephus chinensis* (SEQ ID NO: 8), | URA |
| (F3'H + MET) | MET from *Homo sapiens* (SEQ ID NO: 90) | |
| FL 469 | F3'H from *Callistephus chinensis* (SEQ ID NO: 8), | URA |
| (F3'H + MET) | MET from *Citrus Clementina* (SEQ ID NO: 92) | |
| FL 475 | F3'H from *Callistephus chinensis* (SEQ ID NO: 8), | URA |
| (F3'H + MET) | MET from *Citrus sinensis* (SEQ ID NO: 94) | |
| FL 602 | TAL from *Rhodotorula glutinis* (SEQ ID NO: 42), | TRP |
| (TAL + 4CL + CHS + CHI + FNSII) | 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Petroselinum crispum* (SEQ ID NO: 38) | |
| FL 808 | PAL from *Arabidopsis thaliana* (SEQ ID NO: 78), | HIS |
| (PAL + C4H) | C4H from *Arabidopsis thaliana* (SEQ ID NO: 80), | |
| TT LEU | — | LEU |
| TT URA | — | URA |
| TT TRP | — | TRP |
| TT HIS | — | HIS |

The control strain (without the genes) containing the constructs TT LEU, TT URA, TT TRP and TT HIS is called CF237.

Results

F3'H

Tables 15 and 16 below show the production of eriodictyol (Table 15) and of luteolin (Table 16) obtained by cultivating the strains comprising the F3'Hs listed in Table 6 and the constructs of Table 7, in the presence of naringenin and apigenin, respectively.

TABLE 15

| | Concentration of eriodictyol (in mg · l$^{-1}$) | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 35.5 ± 2.9 | 42.1 ± 4.3 | 49.9 ± 4.2 | 43.6 ± 4.2 | 38.8 ± 4.1 | 43.3 ± 5.1 |
| 4 (FL24) | 1 ± 0.8 | 6.4 ± 0.5 | 4.0 ± 0.5 | 4.7 ± 0.3 | 5.1 ± 0.4 | 5.3 ± 0.4 |
| 6 (FL25) | 115.2 ± 3.2 | 76.8 ± 4.2 | 42.3 ± 2.6 | 70.2 ± 8.6 | 71.1 ± 8.7 | 71.3 ± 7.4 |
| 8 (FL26) | 108.3 ± 4.0 | 71.1 ± 7.1 | 89.2 ± 9.5 | 87.4 ± 5.0 | 75.8 ± 5.2 | 90.0 ± 6.1 |
| 10 (FL27) | 28.8 ± 1.2 | 57.7 ± 2.6 | 69.3 ± 10.6 | 79.1 ± 4.2 | 52.3 ± 0.5 | 69.7 ± 2.3 |
| 12 (FL28) | 108.0 ± 2.0 | 7.0 ± 1.4 | 9.1 ± 5.9 | 4.6 ± 0.3 | 7.4 ± 2.8 | 9.2 ± 0.6 |
| 14 (FL29) | 119.9 ± 1.1 | 39.9 ± 4.7 | 56.1 ± 16.3 | 64.8 ± 4.1 | 36.8 ± 4.4 | 46.1 ± 5.5 |
| 16 (FL30) | <QL | 76.3 ± 2.6 | 70.9 ± 6.2 | 70.4 ± 4.4 | 58.5 ± 10.9 | 76.9 ± 1.7 |
| 18 (FL31) | 107.3 ± 8.0 | 82.3 ± 17.2 | 102.2 ± 7.1 | 98.8 ± 5.9 | 96.6 ± 4.7 | 101.3 ± 4.0 |
| 20 (FL32) | 33.7 ± 4.0 | 68.9 ± 2.7 | 81.5 ± 3.4 | 63.6 ± 3.7 | 69.5 ± 0.9 | 69.7 ± 1.1 |
| 96 (FL1031) | 4.8 ± 0.3 | 60.5 ± 3.4 | 34.4 ± 2.8 | 25.8 ± 5.8 | 59.0 ± 1.7 | 40.0 ± 9.5 |

QL: below the quantification limit

The various strains are indeed capable of producing eriodictyol from naringenin, in different concentrations according to the F3'Hs and the CPR used (see FIG. 2).

TABLE 16

| | Concentration of luteolin (in mg · l$^{-1}$) | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 3.5 ± 0.1 | 11.7 ± 0.7 | 9.1 ± 2.1 | 11.01 ± 0.4 | 10.8 ± 1.7 | 10.2 ± 1.4 |
| 4 (FL24) | <QL | <QL | <QL | <QL | <QL | <QL |
| 6 (FL25) | 10.2 ± 0.9 | 12.8 ± 0.7 | 7.8 ± 1.4 | 11.9 ± 0.8 | 10.1 ± 1.2 | 12.9 ± 1.4 |
| 8 (FL26) | 9.5 ± 0.4 | 13.2 ± 1.1 | 8.2 ± 0.7 | 10.9 ± 0.7 | 12.2 ± 0.4 | 12.1 ± 0.7 |
| 10 (FL27) | <QL | 2.5 ± 0.3 | <QL | 0.5 ± 0 | 2.7 ± 0.1 | 2.77 ± 0.4 |
| 12 (FL28) | 12.1 ± 0.4 | 13.3 ± 1.2 | 14.7 ± 1.8 | 14.1 ± 1.7 | 12.5 ± 3.8 | 15.3 ± 0.9 |
| 14 (FL29) | 1.5 ± 0.1 | 0.6 ± 0.04 | 1.1 ± 0.2 | 0.8 ± 0.03 | 0.7 ± 0.06 | 1.0 ± 0.08 |
| 16 (FL30) | 0.5 ± 0.02 | 1.3 ± 0.1 | 2.5 ± 1.5 | 1.6 ± 0.1 | 1.5 ± 0.5 | 2.0 ± 0.1 |
| 18 (FL31) | 12.2 ± 0.7 | 13.2 ± 0.8 | 13.7 ± 1.2 | 12.7 ± 0.4 | 14.0 ± 1.8 | 12.7 ± 0.6 |
| 20 (FL32) | 1.2 ± 0.2 | 9.9 ± 1.4 | 2.8 ± 0.4 | 4.3 ± 0.1 | 11.0 ± 0.9 | 9.3 ± 1.8 |
| 96 (FL1031) | 0.4 ± 0.1 | 10.9 ± 0.1 | 3.0 ± 0.6 | 3.0 ± 0.9 | 11.4 ± 0.4 | 9.5 ± 1.6 |

QL: below the quantification limit

The various strains are indeed capable of producing luteolin from apigenin, in different concentrations according to the F3'Hs and the CPR used (see FIG. 3).

FNS

Tables 17 and 18 below show the production of apigenin (Table 17) and of luteolin (Table 18) obtained by cultivating the strains comprising the FNSIIs listed in Table 8 and the constructs of Table 9, in the presence of naringenin and eriodictyol, respectively.

TABLE 17

| | Concentration of apigenin (in mg · l$^{-1}$) | | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 11.6 ± 0.3 | 34.7 ± 1.0 | 47.6 ± 5.7 | 37.7 ± 1.6 | 50.5 ± 1.5 | 51.3 ± 3.4 |
| 36 (FL621) | 3.5 ± 0.1 | 35.6 ± 0.2 | 14.9 ± 1.3 | 16.4 ± 1.4 | 29.8 ± 3.9 | 33.2 ± 1.5 |
| 38 (FL112) | 2.9 ± 0.1 | 40.7 ± 1.2 | 41.4 ± 1.5 | 34.2 ± 1.7 | 38.0 ± 0.9 | 43.5 ± 0.0 |

TABLE 18

| | | Concentration of luteolin (in mg · l⁻¹) | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 2.5 ± 0.2 | 1.4 ± 0.3 | 7.8 ± 1.4 | 4.5 ± 0.9 | 4.5 ± 2.9 | 8.5 ± 0.8 |
| 36 (FL621) | 0.2 ± 0.2 | 1.5 ± 0.1 | 1.3 ± 0.2 | 0.9 ± 0.1 | 1.3 ± 0.3 | 1.2 ± 0.2 |
| 38 (FL112) | 0.2 ± 0.0 | 4.5 ± 1.9 | 2.3 ± 0.5 | 2.6 ± 1.2 | 1.4 ± 0.0 | 1.6 ± 0.0 |

The various strains are indeed capable of producing apigenin and luteolin from naringenin and eriodictyol, in different concentrations according to the FNS used (FIGS. 4 and 5). Similar results were obtained with the FNSIIs of SEQ ID NOs: 101, 103, 105, 107, 109, 111, 113, 115, 117, 119, 121, 123, 125, 127, 129, 131 and 133.

F3'H, MET, FNS, CPR: Production of Diosmetin from Naringenin

The results for the production of diosmetin from naringenin by the strains SC2429 to SC2434, SC2436 to SC2444, SC2446 to SC2454, SC2456 to SC2464 and SC2466 to SC2468 are presented in FIG. 23.

All the strains are capable of producing diosmetin from naringenin. The production of diosmetin is largely increased by adding a CPR.

Strain Up to Eriodictyol/Luteolin

The strains SC2424, SC2425, SC2426, SC2427, SC1500 and SC2428 contain all the enzymes of the pathway and are capable of producing luteolin and eriodictyol from glucose.

The results for the strain SC1500 correspond to FIG. 6, in which the eriodictyol and luteolin peaks are observed. Similar results are obtained for the strains SC2424, SC2425, SC2426, SC2427 and SC2428. The production of eriodictyol and of luteolin for each of the strains SC2424, SC2425, SC2426, SC2427, SC1500 and SC2428 is presented in FIG. 22.

It should be noted that the addition of the enzymes PAL and C4H to the biosynthetic pathway makes it possible to obtain markedly higher eriodictyol and luteolin concentrations. These concentrations may be up to six times higher than the concentrations obtained with the strains containing the same enzymes with the exception of PAL and C4H (cf. FIG. 22, for example by comparing the strain SC2425 without PAL/C4H and the strain SC1500 with PAL/C4H or the strain SC2426 without PAL/C4H and the strain SC2428 with PAL/C4H).

MET

The results for the production of hesperetin and diosmetin from eriodictyol and luteolin by the strains SC1612, SC1614, SC2147 and SC2151 are presented, respectively, in FIGS. 7, 8, 19 and 20.

The yeast strains SC1612, SC1614, SC2147 and SC2151 are indeed capable of producing hesperetin and/or diosmetin.

Starting with eriodictyol, the strains SC2147, SC2151 and SC1612 are capable of specifically producing hesperetin, i.e. of specifically methylating the hydroxyl in position 4' of eriodictyol (FIG. 19). The strain SC1614 produces, for its part, a mixture of hesperetin and of homoeriodictyol.

In a noteworthy manner, the strain SC2151 is moreover capable of producing about 40 mg/L of hesperetin (FIG. 19). The strains SC2147, SC1612 and SC1614, for their part, are capable of producing diosmetin from luteolin (FIG. 20).

FNSII

The results for the production of diosmetin from hesperetin by the strain SC744 are presented in FIG. 9.

The yeast strain SC744 is indeed capable of producing diosmetin from hesperetin.

E. Coli

The results for the production of hesperetin from eriodictyol by the strains EC26, EC41 and EC43 are presented in FIGS. 10, 14 and 15 and the production of diosmetin from luteolin by the strains EC26 and EC43 are presented in FIGS. 11 and 16.

The E. coli strains EC26, EC41 and EC43 are indeed capable of producing hesperetin and/or diosmetin.

The results for the production of diosmetin from hesperetin by the strain EC30 are presented in FIG. 12.

The E. coli strain EC30 is indeed capable of producing diosmetin from hesperetin.

Strain Up to Hesperetin/Diosmetin

The results for the production of hesperetin and diosmetin from glucose by the yeast strains SC1508, SC2408 and SC2409 are presented in FIGS. 13, 17 and 18.

The yeast strains SC1508, SC2408 and SC2409 containing all the enzymes of the pathway are capable of producing hesperetin and/or diosmetin from glucose (FIG. 21). In a noteworthy manner, the strain SC 2408 produces about 25 mg/L of hesperetin and about 5 mg/L of diosmetin.

The invention claimed is:

1. A recombinant microorganism comprising a heterologous nucleic acid sequence coding for an O-methyltransferase (OMT) which methylates eriodictyol and/or luteolin in position 4', wherein the O-methyltransferase (OMT) is selected from an enzyme comprising a sequence selected from the group consisting of SEQ ID NOs: 87, 89, 91 and 93 or comprising a sequence having at least 90% identity with a sequence selected from the group consisting of SEQ ID NOs: 87, 89, 91 and 93 and having O-methyltransferase activity, and wherein the microorganism is a yeast.

2. The microorganism as claimed in claim 1, wherein said microorganism comprises a heterologous nucleic acid sequence coding for an O-methyltransferase (OMT) which methylates eriodictyol and/or luteolin in position 4', said O-methyltransferase (OMT) being selected from an enzyme comprising a sequence selected from the group consisting of SEQ ID NOs: 87, 89, 91 and 93 or comprising a sequence having at least 95% identity with a sequence selected from the group consisting of SEQ ID NOs: 87, 89, 91 and 93 and having O-methyltransferase activity.

3. The microorganism as claimed in claim 1, wherein the microorganism also comprises a heterologous or endogenous nucleic acid sequence coding for an S-adenosylmethionine synthetase (SAMT).

4. The microorganism as claimed in claim 1, wherein the microorganism also comprises an endogenous or heterologous nucleic acid sequence coding for a flavone synthase (FNS).

5. The microorganism as claimed in claim 4, wherein the flavone synthase (FNS) is selected from enzymes comprising a sequence selected from the group consisting of SEQ ID NOs: 37, 33, 35, 101, 103, 105, 107, 109, 111, 113, 115, 117, 119, 121, 123, 125, 127, 129, 131 and 133 or comprising a sequence having at least 90% identity with a sequence selected from the group consisting of SEQ ID NOs: 37, 33, 35, 101, 103, 105, 107, 109, 111, 113, 115, 117, 119, 121, 123, 125, 127, 129, 131 and 133 and having flavone synthase activity.

6. The microorganism as claimed in claim 1, wherein the microorganism also comprises:
  a heterologous nucleic acid sequence coding for a tyrosine ammonia lyase (TAL);
  a heterologous nucleic acid sequence coding for a 4-coumaroyl-CoA ligase (4CL);
  a heterologous nucleic acid sequence coding for a chalcone synthase (CHS); and
  a heterologous nucleic acid sequence coding for a chalcone isomerase (CHI).

7. The microorganism as claimed in claim 6, wherein the microorganism comprises:
  a heterologous nucleic acid sequence coding for a tyrosine ammonia lyase (TAL) comprising a sequence selected from the group consisting of SEQ ID NOs: 41 and 39 or comprising a sequence having at least 90% identity with a sequence selected from the group consisting of SEQ ID NOs: 41 and 39 and having tyrosine ammonia lyase activity;
  a heterologous nucleic acid sequence coding for a 4-coumaroyl-CoA ligase (4CL) comprising a sequence selected from the group consisting of SEQ ID NOs: 97, 99, 43, 45, 47 and 49 or comprising a sequence having at least 90% identity with a sequence selected from the group consisting of SEQ ID NOs: 97, 99, 43, 45, 47 and 49 and having 4-coumarate-CoA ligase activity;

a heterologous nucleic acid sequence coding for a chalcone synthase (CHS) comprising a sequence selected from the group consisting of chosen from SEQ ID NOs: 53, 51, 55 and 57 or comprising a sequence having at least 90% identity with a sequence selected from the group consisting of SEQ ID NOs: 53, 51, 55 and 57 and having chalcone synthase activity; and a heterologous nucleic acid sequence coding for a chalcone isomerase (CHI) comprising a sequence selected from the group consisting of SEQ ID NOs: 61 and 59 or comprising a sequence having at least 90% identity with a sequence selected from the group consisting of 61 and 59 and having chalcone isomerase activity.

8. The microorganism as claimed in claim 7, wherein the microorganism comprises:

a heterologous nucleic acid sequence coding for a tyrosine ammonia lyase (TAL) comprising SEQ ID NO: 41 or a TAL comprising a sequence having at least 90% identity with SEQ ID NO: 41 and having tyrosine ammonia lyase activity; and a heterologous nucleic acid sequence coding for a 4-coumaroyl-CoA ligase (4CL) comprising SEQ ID NO: 45 or a 4CL comprising a sequence having at least 90% identity with SEQ ID NO: 45 and having 4-coumarate-CoA ligase activity;

a heterologous nucleic acid sequence coding for a chalcone synthase (CHS) comprising SEQ ID NO: 53 or a CHS comprising a sequence having at least 90% identity with SEQ ID NO: 53 and having chalcone synthase activity; and a heterologous nucleic acid sequence coding for a chalcone isomerase (CHI) comprising SEQ ID NO: 61 or a CHI comprising a sequence having at least 90% identity with SEQ ID NO: 61 and having chalcone isomerase activity.

9. The microorganism as claimed in claim 1, wherein the microorganism also comprises a heterologous nucleic acid sequence coding for a flavonoid 3'-monooxygenase (F3'H) comprising a sequence selected from the group consisting of SEQ ID NOs: 7, 1, 3, 5, 9, 11, 13, 15, 17, 19, 21 and 95 or comprising a sequence having at least 90% sequence identity with a sequence selected from the group consisting of SEQ ID NOs: 7, 1, 3, 5, 9, 11, 13, 15, 17, 19, 21 and 95 and having flavonoid 3'-monooxygenase activity.

10. The microorganism as claimed in claim 9, wherein the microorganism comprises a heterologous nucleic acid sequence coding for a flavonoid 3'-monooxygenase (F3'H) comprising a sequence selected from the group consisting of SEQ ID NOs: 7, 1, 3, 5, 9, 11, 13, 15, 17, 19, 21 and 95 or comprising a sequence having at least 95% sequence identity with a sequence selected from the group consisting of SEQ ID NOs: 7, 1, 3, 5, 9, 11, 13, 15, 17, 19, 21 and 95 and having flavonoid 3'-monooxygenase activity.

11. The microorganism as claimed in claim 1, wherein the microorganism also comprises a heterologous or endogenous nucleic acid sequence coding for a cytochrome P450 reductase (CPR).

12. The microorganism as claimed in claim 11, wherein the microorganism comprises a heterologous nucleic acid sequence coding for a cytochrome P450 reductase (CPR) comprising a sequence selected from the group consisting of SEQ ID NOs: 25, 23, 27, 29 and 31 or a CPR comprising a sequence having at least 90% identity with a sequence selected from the group consisting of SEQ ID NOs: 25, 23, 27, 29 and 31 and having cytochrome P450 reductase activity.

13. The microorganism as claimed in claim 1, wherein the microorganism also comprises a heterologous nucleic acid sequence coding for a 4-methoxybenzoate O-demethylase which converts tyrosine into L-DOPA and also p-coumaric acid into caffeic acid, comprising a sequence selected from the group consisting of SEQ ID NOs: 73 and 75 or comprising a sequence having at least 90% identity with a sequence selected from the group consisting of SEQ ID NOs: 73 and 75 and having L-tyrosine hydroxylase activity; or a heterologous nucleic acid sequence coding for a p-coumarate 3-hydroxylase which converts p coumaric acid into caffeic acid, comprising SEQ ID NO: 71 or a sequence having at least 90% identity with SEQ ID NO: 71 and having p-coumarate 3-hydroxylase activity.

14. The microorganism as claimed in claim 1, wherein the microorganism also comprises:

a heterologous nucleic acid sequence coding for a phenylalanine ammonia lyase (PAL), comprising a sequence selected from the group consisting of SEQ ID NOs: 63, 65 and 77 or comprising a sequence having at least 90% identity with a sequence selected from the group consisting of SEQ ID NOs: 63, 65 and 77 and having phenylalanine ammonia lyase activity; and a heterologous nucleic acid sequence coding for a cinnamate 4-hydroxylase (C4H) comprising a sequence selected from the group consisting of SEQ ID NOs: 67, 69 and 79 or comprising a sequence having at least 90% identity with a sequence selected from the group consisting of SEQ ID NOs: 67, 69 and 79 and having cinnamate 4-hydroxylase activity.

15. The microorganism as claimed in claim 1, wherein the microorganism comprises:

a heterologous nucleic acid sequence coding for a phenylalanine ammonia lyase (PAL) comprising SEQ ID NO: 65 or a PAL comprising a sequence having at least 90% identity with SEQ ID NO: 65 and having phenylalanine ammonia lyase activity;

a heterologous nucleic acid sequence coding for a cinnamate 4-hydroxylase (C4H), comprising SEQ ID NO: 79 or a C4H comprising a sequence having at least 90% identity with SEQ ID NO: 79 and having cinnamate 4-hydroxylase activity;

a heterologous nucleic acid sequence coding for a tyrosine ammonia lyase (TAL) comprising SEQ ID NO: 41 or a TAL comprising a sequence having at least 90% identity with SEQ ID NO: 41 and having tyrosine ammonia lyase activity;

a heterologous nucleic acid sequence coding for a 4-coumaroyl-CoA ligase (4CL) comprising SEQ ID NO: 45 or 97 or a 4CL comprising a sequence having at least 90% identity with SEQ ID NO: 45 or 97 and having 4-coumarate-CoA ligase activity;

a heterologous nucleic acid sequence coding for a chalcone synthase (CHS) comprising SEQ ID NO: 53 or a CHS comprising a sequence having at least 90% identity with SEQ ID NO: 53 and having chalcone synthase activity;

a heterologous nucleic acid sequence coding for a chalcone isomerase (CHI) comprising SEQ ID NO: 61 or a CHI comprising a sequence having at least 90% identity with SEQ ID NO: 61 and having chalcone isomerase activity;

a heterologous nucleic acid sequence coding for a flavonoid 3'-monooxygenase (F3'H) comprising SEQ ID NO: 7 or a F3'H comprising a sequence having at least 90% identity with SEQ ID NO: 7 and having flavonoid 3'-monooxygenase activity;

a heterologous nucleic acid sequence coding for a flavone synthase (FNS) comprising SEQ ID NO: 37 or a FNS comprising a sequence having at least 90% identity with SEQ ID NO: 37 and having flavone synthase activity; and a heterologous nucleic acid sequence coding for a cytochrome P450 reductase (CPR) comprising SEQ ID NO: 25 or a CPR comprising a sequence having at least 90% identity with SEQ ID NO: 25 and having cytochrome P450 reductase activity; and a heterologous nucleic acid sequence coding for an O-methyltransferase (OMT) comprising SEQ ID NO: 91 or 93 or an OMT comprising a sequence having at least 90% identity with SEQ ID NO: 91 or 93 and having O-methyltransferase activity.

16. The microorganism as claimed in claim 1, wherein the microorganism is a yeast of the genus *Saccharomyces*.

17. A method for producing diosmetin and/or hesperetin, comprising the cultivation of a microorganism as claimed in claim 1 and optionally the harvesting of the diosmetin and/or hesperetin.

18. The method as claimed in claim 17, wherein no naringenin, apigenin, eriodictyol and/or luteolin is supplied to the culture medium.

19. The microorganism as claimed in claim 2, wherein the microorganism also comprises a heterologous nucleic acid sequence coding for a flavonoid 3'-monooxygenase (F3'H) comprising a sequence selected from the group consisting of SEQ ID NOs: 7, 1, 3, 5, 9, 11, 13, 15, 17, 19, 21 and 95 or comprising a sequence having at least 95% sequence identity with a sequence selected from the group consisting of SEQ ID NOs: 7, 1, 3, 5, 9, 11, 13, 15, 17, 19, 21 and 95 and having flavonoid 3'-monooxygenase activity.

\* \* \* \* \*